US012351650B2

(12) United States Patent
De Goeij et al.

(10) Patent No.: US 12,351,650 B2
(45) Date of Patent: Jul. 8, 2025

(54) ANTIBODIES BINDING TO FIBROBLAST ACTIVATION PROTEIN ALPHA AND DEATH RECEPTOR 4

(71) Applicant: GENMAB A/S, Valby (DK)

(72) Inventors: Bart E.C.G. De Goeij, Maarssen (NL); Ilse Jongerius, De Bilt (NL); Grietje Andringa, Utrecht (NL); Madelon Paauwe, The Hague (NL); Theodorus Sjouke Plantinga, Duiven (NL); David Satijn, Nieuwegein (NL); Jamila Laoukili, Zeist (NL); Onno Wouter Kranenburg, Zeist (NL); Marije Overdijk, Utrecht (NL)

(73) Assignee: GENMAB A/S, Valby (DK)

( * ) Notice: Subject to any disclaimer, the term of this patent is extended or adjusted under 35 U.S.C. 154(b) by 0 days.

(21) Appl. No.: 18/755,457

(22) Filed: Jun. 26, 2024

(65) Prior Publication Data

US 2025/0002610 A1    Jan. 2, 2025

(30) Foreign Application Priority Data

Jun. 30, 2023   (EP) .................................. 23182845

(51) Int. Cl.
| A61P 35/04 | (2006.01) |
| C07K 16/46 | (2006.01) |
| G01N 33/68 | (2006.01) |
| A61K 39/00 | (2006.01) |

(52) U.S. Cl.
CPC ............ *C07K 16/468* (2013.01); *A61P 35/04* (2018.01); *G01N 33/6854* (2013.01); *A61K 2039/505* (2013.01); *C07K 2317/31* (2013.01); *C07K 2317/524* (2013.01); *C07K 2317/526* (2013.01); *C07K 2317/53* (2013.01); *C07K 2317/565* (2013.01); *G01N 2800/32* (2013.01)

(58) Field of Classification Search
CPC .............................. C07K 16/468; A61P 35/04
USPC ........................................................ 424/136.1
See application file for complete search history.

(56) References Cited

U.S. PATENT DOCUMENTS

| 4,699,880 | A | 10/1987 | Goldstein |
| 5,589,466 | A | 12/1996 | Felgner et al. |
| 5,731,168 | A | 3/1998 | Carter et al. |
| 5,973,972 | A | 10/1999 | Kwon et al. |
| 6,077,835 | A | 6/2000 | Hanson et al. |
| 7,262,028 | B2 | 8/2007 | Van Berkel et al. |
| 7,361,341 | B2 | 4/2008 | Salcedo et al. |
| 7,612,181 | B2 | 11/2009 | Wu et al. |
| 7,951,918 | B2 | 5/2011 | Glaser et al. |
| 9,150,663 | B2 | 10/2015 | Labrijn et al. |
| 9,212,230 | B2 | 12/2015 | Schuurman et al. |
| 9,926,379 | B2 | 3/2018 | Bruenker et al. |
| 10,195,156 | B2 | 2/2019 | Benenato et al. |
| 10,344,050 | B2 | 7/2019 | Gramer et al. |
| 10,590,206 | B2 | 3/2020 | Labrijn et al. |
| 10,597,464 | B2 | 3/2020 | Labrijn et al. |
| 10,906,991 | B2 | 2/2021 | Schuurman et al. |
| 11,017,533 | B2 * | 5/2021 | Gaire ................... G06T 7/0016 |
| 11,214,622 | B2 | 1/2022 | Bruenker et al. |
| 11,485,796 | B2 | 11/2022 | Labrijn et al. |
| 11,866,514 | B2 | 1/2024 | Labrijn et al. |
| 2009/0136503 | A1 | 5/2009 | Yu et al. |
| 2009/0304718 | A1 | 12/2009 | Adolf et al. |
| 2010/0105874 | A1 | 4/2010 | Schuurman et al. |
| 2010/0155133 | A1 | 6/2010 | Makwinski et al. |
| 2012/0184718 | A1 | 7/2012 | Bruenker et al. |
| 2013/0039913 | A1 | 2/2013 | Labrijn et al. |
| 2014/0303356 | A1 | 10/2014 | Gramer et al. |
| 2015/0274844 | A1 | 10/2015 | Blankenship et al. |
| 2015/0337049 | A1 | 11/2015 | Labrijn et al. |
| 2016/0046727 | A1 | 2/2016 | Labrijn et al. |
| 2016/0159930 | A1 | 6/2016 | Schuurman et al. |
| 2017/0233497 | A1 | 8/2017 | Labrijn et al. |
| 2018/0170866 | A1 | 6/2018 | Payne et al. |
| 2019/0022247 | A1 | 1/2019 | Ansell et al. |
| 2020/0048304 | A1 | 2/2020 | Gramer et al. |
| 2020/0190200 | A1 | 6/2020 | Alfonso Martin et al. |
| 2020/0262932 | A1 | 8/2020 | Labrijn et al. |
| 2020/0332022 | A1 | 10/2020 | Labrijn et al. |
| 2021/0269509 | A1 * | 9/2021 | Hibbert ............... C07K 16/2887 |
| 2023/0227495 | A1 | 7/2023 | Gramer et al. |

(Continued)

FOREIGN PATENT DOCUMENTS

| CN | 102250246 A | 11/2011 |
| EP | 1870459 A1 | 12/2007 |

(Continued)

OTHER PUBLICATIONS

Brunker et al. (Mol Cancer Ther (2016) 15 (5): 946-957).*
Koornstra et al (European Journal of Cancer 41 (2005) 1195-1202).*
Sykes, K, et al., "Linear expression elements: a rapid, in vivo, method to screen for gene functions," Nature Biotechology, vol. 17: 355-359 (1999).
Van Heeke, G, et al., "Expression of human asparagine synthetase in *Escherichia coli*," Journ of Bio-logical Chemistry, vol. 264(10): 5503-5509 (1989).

(Continued)

*Primary Examiner* — Lynn A Bristol
(74) *Attorney, Agent, or Firm* — Nelson Mullins Riley & Scarborough LLP; Jane E. Remillard, Esq.; Christopher L. Frank

(57) ABSTRACT

The present invention relates to a multispecific antibody comprising at least a FAPα binding region comprising a first heavy chain variable region and a first light chain variable region; and a DR4 binding region comprising a second heavy chain variable region and a second light chain variable region. The invention further provides pharmaceutical compositions comprising the antibodies and use of the antibodies for therapeutic and diagnostic procedures, in particular in cancer therapy.

34 Claims, 22 Drawing Sheets

Specification includes a Sequence Listing.

(56) References Cited

U.S. PATENT DOCUMENTS

| | | | |
|---|---|---|---|
| 2023/0322947 | A1 | 10/2023 | Labrijn et al. |
| 2024/0150484 | A1 | 5/2024 | De Kreuk et al. |
| 2024/0209117 | A1 | 6/2024 | Labrijn et al. |

FOREIGN PATENT DOCUMENTS

| | | | |
|---|---|---|---|
| EP | 2391343 | A2 | 12/2011 |
| EP | 2972360 | A1 | 1/2016 |
| ES | 2720433 | T3 * | 7/2019 |
| WO | 9850431 | A2 | 11/1998 |
| WO | 200046147 | A2 | 8/2000 |
| WO | 00/70087 | A1 | 11/2000 |
| WO | 2003074569 | A2 | 9/2003 |
| WO | 2005004809 | A2 | 1/2005 |
| WO | 2005061547 | A2 | 7/2005 |
| WO | 2007059782 | A1 | 5/2007 |
| WO | 2007110205 | A2 | 10/2007 |
| WO | 2008003116 | A2 | 1/2008 |
| WO | 2008119353 | A1 | 10/2008 |
| WO | 2008157379 | A2 | 12/2008 |
| WO | 2009040562 | A1 | 4/2009 |
| WO | 2009058383 | A2 | 5/2009 |
| WO | 2009089004 | A1 | 7/2009 |
| WO | 2010015792 | A1 | 2/2010 |
| WO | 2010026923 | A1 | 3/2010 |
| WO | 2010059315 | A1 | 5/2010 |
| WO | 2010080538 | A1 | 7/2010 |
| WO | 2010111625 | A1 | 9/2010 |
| WO | 2010129304 | A2 | 11/2010 |
| WO | 2010134666 | A1 | 11/2010 |
| WO | 2011028952 | A1 | 3/2011 |
| WO | 2011040972 | A1 | 4/2011 |
| WO | 2011069104 | A2 | 6/2011 |
| WO | 2011117329 | A1 | 9/2011 |
| WO | 2011131746 | A2 | 10/2011 |
| WO | 2011143545 | A1 | 11/2011 |
| WO | 2011147986 | A1 | 12/2011 |
| WO | 2012023053 | A2 | 2/2012 |
| WO | 2012025525 | A1 | 3/2012 |
| WO | 2012025530 | A1 | 3/2012 |
| WO | 2012058768 | A1 | 5/2012 |
| WO | 2013060867 | A2 | 5/2013 |
| WO | 2013157953 | A1 | 10/2013 |
| WO | 2014081202 | A1 | 5/2014 |
| WO | 2014152774 | A1 | 9/2014 |
| WO | 2018006052 | A1 | 1/2018 |
| WO | 2019178438 | A1 | 9/2019 |
| WO | 2022189667 | A1 | 9/2022 |

OTHER PUBLICATIONS

Ward, E. S. et al., "Binging activities of a repertoire of single immunoglobulin variable domains se-creted from *Escherichia coli*," Nature, vol. 641: 544-546 (1989).

Wigler, M. et al., "Biochemical transfer of single-copy eucaryotic genes using total cellular DNA as donor," Cell, vol. 14(3)725-731 (1978).

Wranik, B. et al., "LUZ-Y, a Novel Platform for the Mammalian Cell Production of Full-length IgG-bispecific Antibodies," Journ of Biological Chemistry, vol. 287(52): 43331-43339 (2012).

Wu, C., et al., "Generation and Characterization of a Dual Variable Domain Immunoglobin (DVD-Ig (TM)) Molecule," Springer, Chap. 19: 239-250 (2010).

Xin, L. et al., "Fibroblast Activation Protein-a as a Target in the Bench-to-Bedside Diagnosis and Treatment of Tumors: A Narrative Review," Frontiers Editorial Office, vol. 11:648187 (2021).

Zhu, X. et al., "COMBODY: one-domain antibody multimer with improved avidity," Immunology and Cell Biology, vol. 88(6): 667-675 (2010).

U.S. Appl. No. 12/593,759, filed Jan. 6, 2010, Janine Schuurman, U.S. Pat. No. 9,212,230.

U.S. Appl. No. 14/934,956, filed Nov. 6, 2015, Janine Schuurman, U.S. 10,906,991.

U.S. Appl. No. 16/777,053, filed Jan. 30, 2020, Aran Frank Labrijn, U.S. Pat. 11,866,514.

U.S. Appl. No. 15/414,122, filed Jan. 24, 2017, Aran Frank Labrijn, U.S. Pat. No. 10,597,464.

U.S. Appl. No. 14/830,336, filed Aug. 19, 2015, Aran Frank Labrijn, US 20160046727.

U.S. Appl. No. 13/642,253, filed Oct. 24, 2012, Aran Frank Labrijn, U.S. Pat. No. 9,150,663.

U.S. Appl. No. 18/507,869, filed Nov. 13, 2023, Aran Frank Labrijn, US 20240209117.

U.S. Appl. No. 17/939,736, filed Sep. 7, 2022, Michael Gramer, US 20230227495.

U.S. Appl. No. 16/426,647, filed May 30, 2019, Michael Gramer, U.S. Pat. No. 11,492,371.

U.S. Appl. No. 14/353,962, filed Apr. 24, 2014, Michael Gramer, U.S. Pat. No. 10,344,050.

U.S. Appl. No. 14/760,157, filed Jul. 9, 2015, Aran Frank Labrijn, U.S. Pat. No. 10,590,206.

U.S. Appl. No. 16/783,720, filed Feb. 6, 2020, Aran Frank Labrijn, U.S. Pat. No. 11,485,796.

U.S. Appl. No. 17/950,350, filed Sep. 22, 2022, Aran Frank Labrijn, US 20230322947.

U.S. Appl. No. 16/717,189, filed Dec. 17, 2019, Pedro Jose Alfonso Martin, US 20200190200.

U.S. Appl. No. 18/281,372, filed Sep. 11, 2023, Bart-Jan De Kreuk, US 20240150484.

Abdiche, Y. et al., "Exploring blocking assays using Octet, ProteOn, and Biacore biosensors," Anal Biochem., vol. 386(2):172-180 (2009).

Ausebel, F. et al., "Current Protocols in Molecular Biology," Wiley InterScience , 1 page (1987).

Barbas, et al., "Molecular Profile of an Antibody Response to HIV-1 as Probed by Combinatorial Li-braries," Academic Press, vol. 230(3): 812-823 (1993).

Benvenisty, N. et al., "Direct introduction of genes into rats and expression of the genes," PNAS, vol. 83: 9551-9555 (1986).

Betts, A. et al., "Linear pharmacokinetic parameters for monoclonal antibodies are similar within a species and across different pharmacological targets: A comparison between human, cynomolgus monkey and hFcRn Tg32 transgenic mouse using a population-modeling approach," MABS, vol. 10(5):751-764 (2018).

Bird, R. et al., "Single-Chain Antigen-Binding Proteins," Science, vol. 242:423-426 (1988).

Bitter, G.A., et al., "Expression and secretion vectors for yeast," Methods in Enxymology, vol. 153: 516-544 (1987).

Blankenship JW, et al., "Abstract #5465: CD79BxDR SCORPIONTM molecule: a single chain, bispecific immunotherapeutic with potent in vitro activity against B cell lymphoma," 4 pages (2009).

Bostrom, J. et al., "Variants of the Antibody Herceptin That Interact with HER2 and VEGF at the Antigen Binding Site," Science, vol. 323:1610-1614 (2009).

Brochet X, et al., "IMGT/V-QUEST: the highly customized and integrated system for IG and TR standardized V-J and V-D-J sequence analysis," Nucleic Acids Research, vol. 36: W503-W508 (2008).

Chiu, M. et al., "Antibody Structure and Function: The Basis for Engineering Therapeutics," Antibodies , vol. 8 (55): 80 pages (2019).

Corsaro, CM, et al., "Enhancing the efficiency of DNA-mediated gene transfer in mammalian cells," Somatic Cell Genetic, vol. 7(5),:603-611 (1981).

Denney, W.S. et al., "Simple, Automatic Noncompartmental Analysis: The PKNCA R," J Pharmacoki-net Pharmacodyn, T-51: S65 (2015).

Deo, Y. et al., "Bispecific molecules directed to the Fc receptor for IgA (Fc alpha RI, CD89) and tumor antigens efficiently promote cell-mediated cytotoxicity of tumor targets in whole blood," J Immunol vol. 160(4): 1677-1686 (1998).

Di Cristofano, F. et al., "Therapeutic targeting of TRAIL death receptors," Biochemical Society Transactions, vol. 51(1): 57-70 (2023).

Dick, L. et al., "C-terminal lysine variants in fully human monoclonal antibodies: investigation of test methods and possible causes," Biotechnology and Bioengineering, vol. 100(6):1132-1143 (2008).

(56) References Cited

OTHER PUBLICATIONS

Dimasi, N. et al., "The Design and Characterization of Oligospecific Antibodies for Simultaneous Tar-geting of Multiple Disease Mediators," J. Mol. Biol., vol. 393(3): 672-692 (2009).
Doppalapudi, V.R., et al., "Chemically programmed antibodies: Endothelin receptor targeting CovX-Bodies," Bioorganic & Medicinal Chemistry Letters, vol. 17: 501-506 vol. (2007).
Dubuisson, A. et al., "Antibodies and Derivatives Targeting DR4 and DR5 for Cancer Therapy," Antibodies, vol. 6(16) 31 pages (2017).
Engelberts, P. et al., "DuoBody-CD3xCD20 induces potent T-cell-mediated killing of malignant B cells in preclinical models and provides opportunities for subcutaneous dosing," EBioMedicine, vol. 52 (102625): 5 pages (2020).
Gramer, M.J., et al., "Production of stable bispecific IgG1 by controlled Fab-arm exchange: scalabil-ity from bench to large-scale manufacturing by application of standard approaches," MABS, vol. 5(6):962-973 (2013).
Hmila, A. et al., "A bispecfic nanobody to provide full protection againstlethal scorpion envenom-ing," The FASEB Journal, vol. 24: 3479-3489 (2010).
Holt, L. J. et al., "Domain antibodies: proteins for therapy," Trends in Biotechnology, vol. 21(11): 484-490 (2003).
International Search Report, PCT/EP2024/068031, dated Nov. 6, 2024, 7 pages.
Kabat, E. et al., "Sequences of proteins of Immunological interest," US Department of Health and Human Services, 1242 pages (1991).
Kontermann, R. et al., "Bispecific Antibodies," Drug Discovery Today, vol. 20(7): 838-847: (2015).
Kontermann, R., "Dual targeting strategies with bispecific antibodies," MABS, 4(2):182-197 (2012).
Labrijn, A. et al., "Bispecific antibodies: a mechanistic review of the pipeline," Nature Reviews, vol. 17: 585-608 (2019).
Labrijn, A.F., et al., "Efficient generation of stable bispecific IgG1 by controlled Fab-arm exchange," vol. 110(13): 5145-5150 (2013).
Lafleur, D. et al., "Monoclonal antibody therapeutics with up to five specificities: functional en-hancement through fusion of target-specific peptides," MABS, vol. 5(2): 208-218 (2013).
Lawrence, L. et al., "Orientation of antigen binding sites in dimeric and trimeric single chain Fv anti-body fragments," FEBS, vol. 425(3):479-484 (1998).
Le Gall, F. et al., "Effect of linker sequences between the antibody variable domains on the for-mation, stability and biological activity of a bispecific tandem diabody," Protein Engineering, Design & Selection, vol. 17(4): 357-366 (2004).
Lefranc MP. et al., " IMGT, the international ImMunoGene Tics database," Nucleic Acids Re-search, vol. 27 (1):209-212 (1999).
Lefranc, M. et al., "The IMGT Unique Numbering for Immuno-globulins, T-Cell Receptors, and Ig-like Domains, "The Immunologist, vol. 7(4):132-136 (1999).
Lefranc, M-P. et al., "IMGTR , the international ImMunoGeneTics information system R 25 years on," Nucleic Acids Research, vol. 43:D413-422 (2015).
Lewis, S. et al., "Generation of bispecific igG antibodies by structure-based design of an orthogonal Fab interface," Nature Biotechnology, vol. 32(2):191-198 (2014).
Lindhofer, H. et al., "Preferential species-restricted heavy/light chain pairing in rat/mouse quad-romas. Implications for a single-step purification of bispecific antibodies," J. Immunol., vol. 155(1):219-225 (1995).
Liu, R. et al., "Fc-Engineering for Modulated Effector Functions—Improving Antibodies for Cancer Treatment," Antibodies, vol. 9(4):457-66 (2020).
Lorusso, P. et al., "Eftozanermin alfa (ABBV-621) monotherapy in patients with previously treated solid tumors: findings of a phase 1, first-in-human study," Investigational New Drugs, vol. 40(4): 762-772 (2022).
Needleman, S. et al., "A general method applicable to the search for similarities in the amino acid sequence of two proteins," J. Mol. Biol., vol. 48(3): 443-453 (1970).
Papadopoulos, K. et al., "Unexpected hepatotoxicity in a phase I study of TAS266, a novel tetra-valent agonistic Nanobody targeting the DR5 receptor," Cancer Chenother Pharmacol., vol. 75(5): 887-895 (2015).
Patel, A. et al., "In Vivo Delivery of Synthetic Human DNA-Encoded Monoclonal Antibodies Protect against Ebolavirus Infection in a Mouse Model," Cell Reports, vol. 25(7):1982-1993(2018).
Pearce, L. et al., "Linear gene fusions of antibody fragments with streptavidin can be linked to bio-tin labelled secondary molecules to form bispecific reagents," Biochem and Molecular Biology Inter., vol. 42(6): 1179-1188 (1997).
Revets, H. et al., "Nanobodies as novel agents for cancer therapy," Expert Opinion on Biological Therapy, vol. 5 (1):111-124 (2005).
Rice, P. et al., "EMBOSS: The European Molecular Biology Open Software Suite," The European Mo-lecular Biology Open Software Suite, vol. 16(6): 276-277 (2000).
Schakowski, F. et al., "A novel minimal-size vector (MIDGE) improves transgene expression in co-lon carcinoma cells and avoids transfection of undesired DNA," vol. 3(5): 793-800 (2001).
Schoonjans, R. et al., "Fab chains as an efficient heterodimerization scaffold for the production of recombinant bispecific and trispecific antibody derivatives," Journ of Immunology, vol. 165(12): 7050-7057 (2000).
Shields, R. L. et al., "High Resolution Mapping of the Binding Site on Human IgG1 for FcgRI, FcgRII, FcgRIII, and FcRn and Design of IgG1 Variants with Improved Binding to the FcgR*," The Journal of Biological Chemistry, vol. 276 (9):6591-6604 (2001).
Snajdauf, M. et al., "The TRAIL in the Treatment of Human Cancer: An Update on Clinical Trials," Frontiers Media S.A, vol. 8: 628332 (2021).
Strating, E. et al., "Co-cultures of colon cancer cells and cancer-associated fibroblasts recapitulate the aggressive features of mesenchymal-like colon cancer," Frontiers Research Foundation, vol. 14: 1-16 (2023).

* cited by examiner

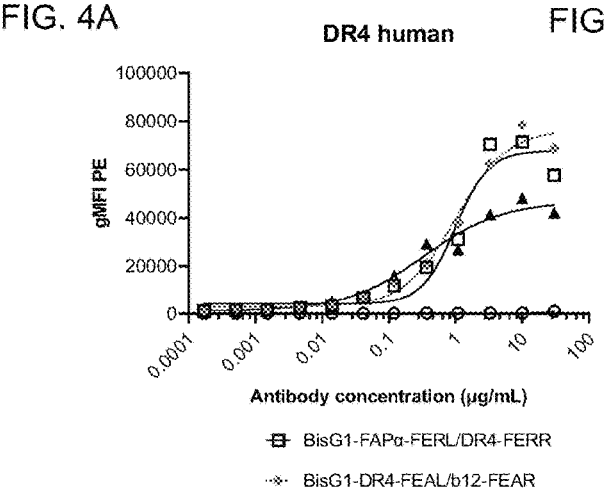
FIG. 4A DR4 human
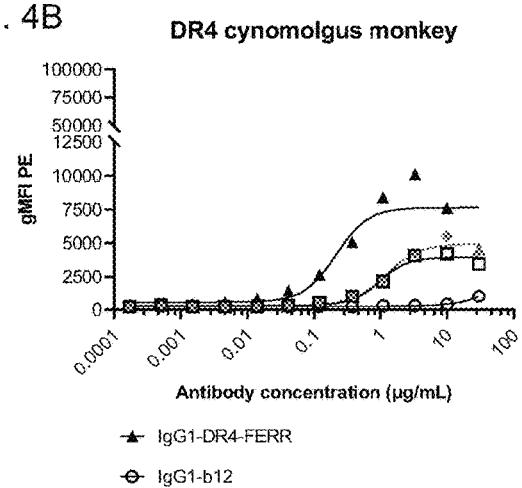
FIG. 4B DR4 cynomolgus monkey
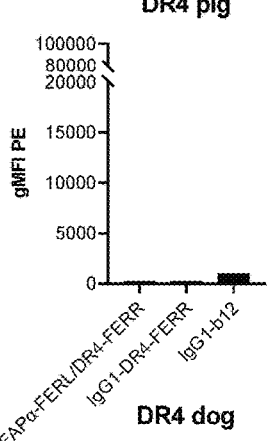
FIG. 4C DR4 pig
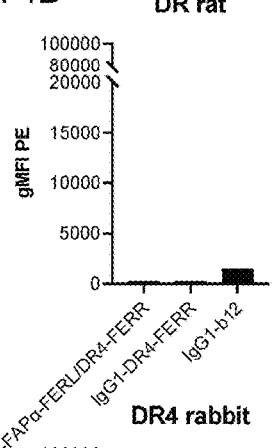
FIG. 4D DR rat
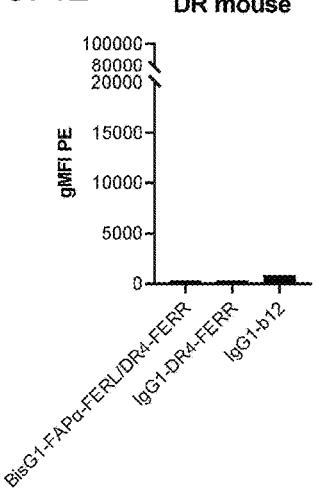
FIG. 4E DR mouse
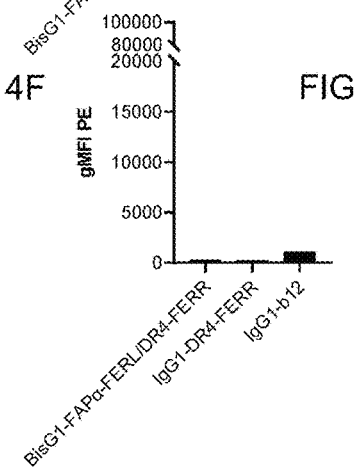
FIG. 4F DR4 dog
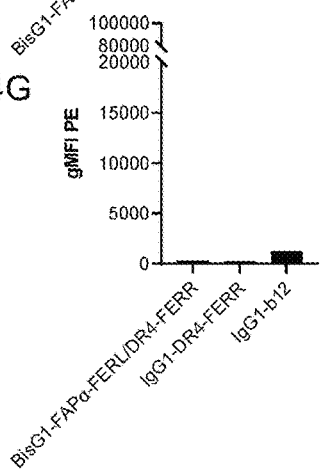
FIG. 4G DR4 rabbit FIG. 11F
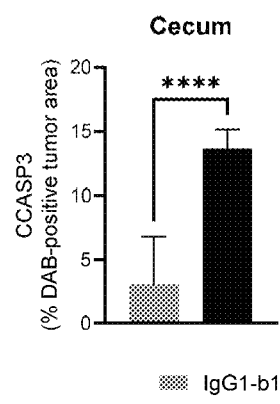
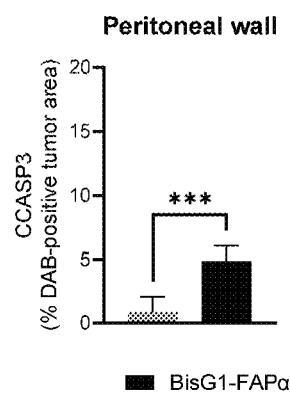
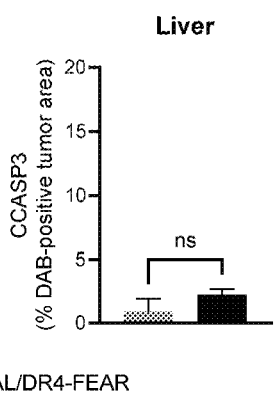

- ─□─ CAF#Scr + BisG1-FAPα-FERL/DR4-FERR
- ∙∙▒∙∙ CAF#34 + BisG1-FAPα-FERL/DR4-FERR
- ─○─ CAF#Scr + BisG1-b12-FERL/b12-FERR
- ∙∙▒∙∙ CAF#34 + BisG1-b12-FERL/b12-FERR

ANTIBODIES BINDING TO FIBROBLAST ACTIVATION PROTEIN ALPHA AND DEATH RECEPTOR 4

RELATED APPLICATIONS

This application claims priority to European Patent Application No. 23182845.0 filed Jun. 30, 2023. The contents of the aforementioned application are hereby incorporated by reference.

SEQUENCE LISTING

The instant application contains a Sequence Listing which has been submitted electronically in XML format and is hereby incorporated by reference in its entirety. Said XML copy, created on Jun. 23, 2024, is named GMI-235_SequenceListing.xml and is 85 kilobytes in size.

FIELD OF INVENTION

The present invention relates to antibodies binding to Fibroblast Activation Protein Alpha (FAPα) and Death Receptor 4 (DR4). The invention further provides pharmaceutical compositions comprising the antibodies and use of the antibodies for therapeutic and diagnostic procedures, such as treatment of cancer.

BACKGROUND

Therapeutic monoclonal antibodies are a promising type of immunotherapy due to their specific features which include target specificity, immune modulation, and generally low toxicity. Monoclonal antibodies are made of two distinct functional units: the antigen binding fragment Fab that binds to the targeted antigen, and the constant fragment (Fc) which mediates antibody-dependent immune effector functions. The main Fc domain-mediated mechanisms of action are complement dependent cytotoxicity (CDC) and binding to Fc-gamma receptors (specific for IgG) on various immune cells resulting in e.g. antibody-dependent cell-mediated cytotoxicity (ADCC). Additionally, Fab binding to the target can result in signaling perturbation.

The knowledge of antibody-based therapeutic strategies has advanced dramatically over recent years, delivering breakthroughs on target biology, mechanisms of action but also on antibody formats and developments. This has led to antibody-based therapies aimed at enhancing clinical effectiveness, as well as improving the target specificity (and therefore safety).

Apoptosis is a form of programmed cell death. Tumor necrosis factor (TNF)-related apoptosis-inducing ligand (TRAIL) can trigger apoptosis via binding to its agonist receptors that contain intracellular death domains (DD). DR4, also known as Tumor Necrosis Factor Receptor Superfamily member 10A (TNFRSF10A), TRAIL receptor 1 (TRAIL-R1) and CD261, is a cell surface receptor of the TNF receptor superfamily that binds TRAIL and mediates apoptosis. DR4 shares 60% homology with death receptor 5 (DR5), the other known TRAIL receptor capable of inducing apoptosis. DR4 is a single-pass type I membrane protein with at least three extracellular cysteine-rich domains (CRDs), a transmembrane Domain (TM) and a cytoplasmic DD. TRAIL binding leads to DR4 activation via receptor trimerization, resulting in clustering of the DD, followed by recruitment of the Fas-associated death domain (FADD) adaptor protein. Next, FADD recruits caspase-8 and -10 to form the death-inducing signaling complex (DISC). Active caspase-8 and -10 are then released in the cytosol, where they activate downstream effector caspases such as caspase-3. Activation of effector caspases culminates with apoptotic cell death.

FAPα is a type-II transmembrane (homodimer) serine protease, that is overexpressed in pathological conditions including fibrosis, arthritis, and cancer. FAPα is primarily expressed by activated stromal fibroblasts such as CAFs. FAPα can also be shed from the cell membrane forming soluble FAPα. FAPα is a member of the prolyl peptidase family and shares 70% amino acid sequence homology with the well-described dipeptidyl peptidase 4 (DPP4). Both peptidases contain dipeptidyl peptidase enzymatic activity, whilst endopeptidase activity is FAPα-specific and targets substrates including denatured collagen and α-2 anti-plasmin. While for most cancers elevated FAPα expression is associated with a worse outcome, the underlying biological mechanisms remain poorly understood.

Several first-generation DR agonist antibodies have been tested in the clinic showing limited antitumor efficacy, likely due to their inability to induce efficient receptor clustering which is essential to trigger apoptosis (Dubuisson and Micheau, Antibodies (Basel) 6(4), 2017). One such example is mapatumumab (HGS-ETR1), a DR4-specific agonist monoclonal antibody which showed limited clinical activity as explored in multiple phase 1/2 trials (Snajdauf et al., Front Mol Biosci 8: 628332, 2021). Next-generation agents, such as the TRAIL-R agonist Fc-fusion protein Eftozanermin alfa (ABBV-621), showed encouraging clinical activity but also induced side effects such as liver toxicity (Papadopoulos et al, Cancer Chemother Pharmacol 75(5): 887-895, 2015; LoRusso et al., Invest New Drugs 40(4): 762-772, 2022; Di Cristofano et al., Biochem Soc Trans 51(1): 57-70, 2023). The dual targeting of DR and FAPα has been explored with RG7386, an optimized tetravalent bispecific antibody targeting FAPα and DR5 (U.S. Pat. No. 9,926,379B2). However, clinical development for solid malignancies was stopped in 2018. Thus, there is a clear unmet need for development of novel therapeutics with improved safety and efficacy.

SUMMARY OF INVENTION

It is an object of the present invention to provide multispecific antibodies with improved safety and efficacy.

The multispecific antibodies according to the present invention comprise a DR4 binding region and a FAPα binding region. Thus, the proposed mechanism of action for the multispecific antibodies according to the present invention is a conditional transactivation of DR4 as a result of simultaneous binding to DR4-expressing tumor cells and FAPα on CAFs in the tumor microenvironment (TME). Furthermore, it has been found that some DR4 binding antibodies bind well to DR4-expressing cells and some FAPα binding antibodies bind well to FAPα-expressing cells in a bivalent (monoclonal) format but exhibit reduced binding in monovalent format. Thus, another object of the present invention relates to monoclonal antibodies capable of strong binding in either monovalent or bivalent format. This may form the basis for generation of e.g. bispecific antibodies showing strong monovalent binding to DR4 and FAPα.

As demonstrated in the present invention e.g. by examples 10-13 and 15, the trans-binding mechanism of the multispecific antibody is advantageous as the killing of the DR4-expressing tumor cell would be dependent on simultaneous binding of the multispecific antibody to a FAPα-expressing cell, such as CAFs. Thus, FAPα-dependent DR4 transactivation results in improved tumor-specific targeting due to the high expression of FAPα on CAFs in the TME. In addition, the multispecific antibody is showing an extended therapeutic window due to trans-binding dependent DR4 activation as opposed to cis-binding as DR4 is not expressed on fibroblasts, (e.g. example 9). As fibroblasts do not express DR4 they are not sensitive to induction of cell death through FAP-dependent DR4 agonism (e.g. example 9 and 11). In one aspect, the present invention relates to a multispecific antibody comprising at least (i) a FAPα binding region capable of binding to FAPα comprising a first heavy chain variable region and a first light chain variable region; and (ii) a DR4 binding region capable of binding to DR4 comprising a second heavy chain variable region and a second light chain variable region.

In a further aspect, the present invention relates to a nucleic acid construct, or a combination of nucleic acid constructs, encoding an antibody as defined herein.

In another aspect, the present invention relates to a composition comprising a nucleic acid construct or a combination of nucleic acid constructs as defined herein.

In yet another aspect, the present invention relates to a delivery vehicle comprising the nucleic acid construct(s) as described herein.

In still another aspect, the present invention relates to a recombinant host cell capable of producing the antibody as described herein, wherein the host cell comprises one or more nucleic acid constructs encoding the antibody as described herein.

In an even further aspect, the present invention relates to a pharmaceutical composition comprising a multispecific antibody as defined herein and a pharmaceutically-acceptable carrier.

In a still further aspect, the present invention relates to the multispecific antibody as described herein, the nucleic acid construct(s) as described herein, the delivery vehicle as described herein or the pharmaceutical composition as described herein for use in the treatment of cancer.

In an even further aspect, the present invention relates to methods for producing multispecific antibodies according to the invention.

Finally, the invention also provides monospecific antibodies targeting DR4 and FAPα, respectively.

These and other aspects and embodiments are described in more detail in the following sections.

BRIEF DESCRIPTION OF THE DRAWINGS

(FIGS. 1A and 1B) Binding of BisG1-FAPα-FERL/DR4-FERR, BisG1-FAPα-FERL/b12-FERR, BisG1-b12-FERL/b12-FERR and IgG1-FAPα-FERL to human lung fibroblasts (FIG. 1A) and CAFs (FIG. 1B) was assessed via flow cytometry. Data shown are geomean fluorescence intensity (gMFI) values for one representative experiment out of three. The concentration (µg/mL) at which 50% of the maximal effect was observed (EC$_{50}$) was derived from the fitted curves. For CAFs (FIG. 1B), IgG1-FAPα-FERL antibody was included with only the top four concentrations.

(FIGS. 2A-2F) Binding of BisG1-FAPα-FERL/DR4-FERR, BisG1-b12-FERL/DR4-FERR, IgG1-DR4-FERR and IgG1-b12 was assessed on six different cell lines: Colorectal adenocarcinoma cell lines DLD-1 and HCT-15, lung carcinoma A549, colorectal carcinoma HCT-116, breast adenocarcinoma MDA-MB-231 and pancreatic ductal adenocarcinoma PANC-1. Data shown are gMFI values as determined by flow cytometry, for one representative experiment out of three. (FIG. 2G) Binding of BisG1-b12-FEAL/DR4-T1014A04-FEAR, BisG1-b12-FEAL/DR4-chCTB007-FEAR, IgG1-DR4-chCTB007-FEAR, IgG1-DR4-T1014A04-FEAR and IgG1-b12-FEAL to DR4 was assessed on the multiple myeloma cell line OPM-2. Data shown are gMFI values as determined by flow cytometry, for one experiment. (FIG. 2H) Binding of IgG1-DR4-FERR, BisG1-b12-FERL/DR4-FERR, BisG1-FAPα-FERL/DR4-FERR, IgG1-DR4-chCTB007-FEAR, BisG1-b12-FEAL/DR4-chCTB007-FEAR, IgG1-DR4-T1014A04-FEAR, BisG1-b12-FEAL/DR4-T1014A04-FEAR and BisG1-b12-FERL/b12-FERR to DR4 was assessed on the breast adenocarcinoma cell line MDA-MB-231. Data is represented as mean (±SD) gMFI values as determined by flow cytometry of two independent experiments.

(FIGS. 3A-3F) Binding to Expi293F cells expressing human, cynomolgus monkey, mouse, rat, pig and dog FAPα, respectively. Data shown are gMFI values as determined by flow cytometry, for one representative experiment out of three.

FIGS. 4A-4G: Species cross reactivity to DR4 or mouse/rat DR orthologs. The antibodies BisG1-FAPα-FERL/DR4-FERR, BisG1-DR4-FEAL/b12-FEAR, IgG1-DR4-FERR and IgG1-b12 were tested. (FIG. 4A) Binding to ExpiCHO-S™ cells expressing human DR4. (FIG. 4B) Binding to ExpiCHO-S™ cells expressing cynomolgus DR4. Binding of BisG1-FAPα-FERL/DR4-FERR versus IgG1-DR4-FERR and IgG1-b12 to ExpiCHO-S™ cells expressing pig DR4 (FIG. 4C), rat DR (FIG. 4D), mouse DR (FIG. 4E), dog DR4 (FIG. 4F) or rabbit DR4 (FIG. 4G). Data shown are gMFI values as determined by flow cytometry, for one representative experiment out of three.

(FIGS. 5A and 5B) surface expression of DR4, DR5 and FAPα on human lung fibroblasts and CAFs. Summary data from two experiments (mean±SEM) are shown. The horizontal dotted line shows the lower limit of quantification (LLOQ). (FIG. 5C) Human lung fibroblasts cultured with BisG1-FAPα-FEAL/DR4-FEAR, BisG1-FAPα-FEAL/b12-FEAR, BisG1-b12-FEAL/DR4-FEAR, IgG1-FAPα-FEAL (negative control) or RG7386. The percentage of viable cells, normalized to a condition without antibodies, was plotted against antibody concentration and show mean±SEM of duplicates. (FIG. 5D) Human lung fibroblasts cultured with 10 µg/mL of BisG1-FAPα-FEAL/DR4-FEAR, BisG1-FAPα-FEAL/b12-FEAR, BisG1-b12-FEAL/DR4-FEAR or negative control IgG1-b12-FEAR. Staurosporine was used as positive control. The graph shows the fluorescence signal representative of the number of dead cells (±SEM of duplicates), plotted against time. (FIG. 5E) CAFs cultured with BisG1-FAPα-FEAL/DR4-FEAR. The graph shows the % viable tumor cells±SEM of duplicates, normalized to condition without antibody and plotted against the antibody concentration.

Figure 6A:
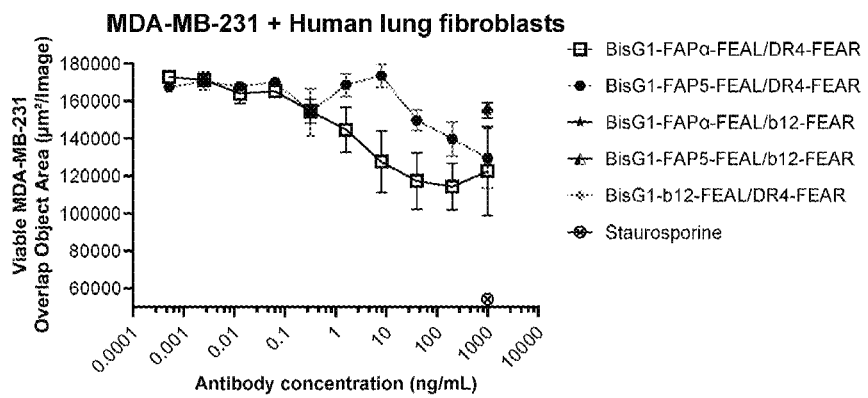
Figure 6B:
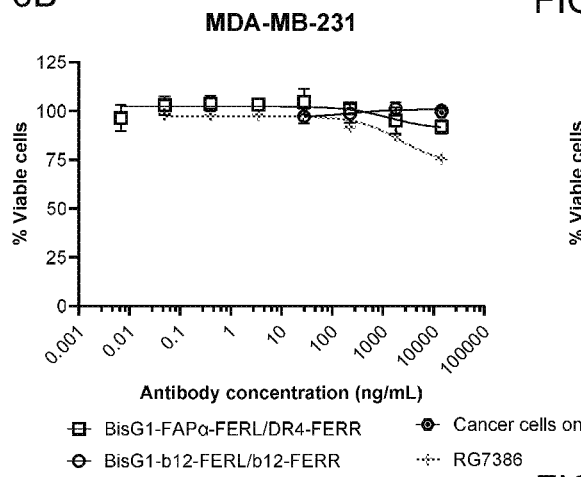
Figure 6C:
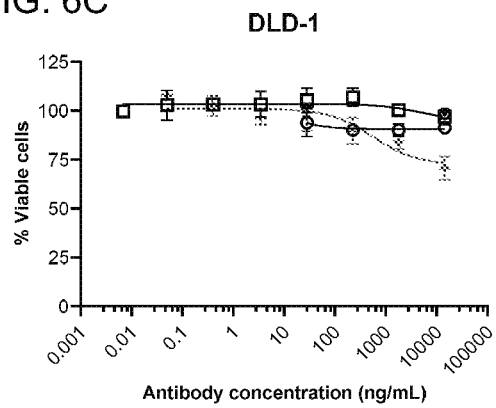
Figure 6D:
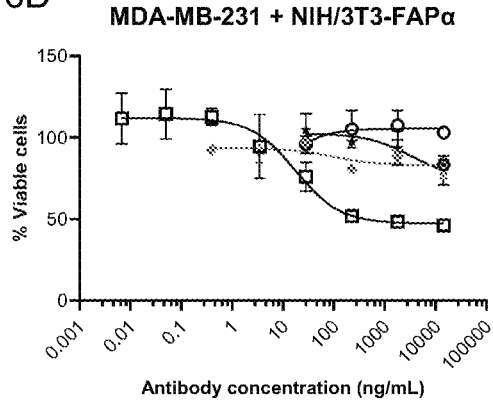

FIGS. 6A-6E: Transactivation potential of BisG1-FAPα-FEAL/DR4-FEAR. (FIG. 6A) Targeted cell death via DR4 transactivation was assessed on cancer cell line MDA-MB-231 cocultured with human lung fibroblasts using DR4-targeting bispecific antibodies containing FAPα or FAP5 binding arm. Negative control antibodies included were BisG1-FAPα-FEAL/b12-FEAR, BisG1-FAP5-FEAL/b12-FEAR and BisG1-b12-FEAL/DR4-FEAR. 1 μM Staurosporine was included as a positive control. Data shown are the mean viable tumor cell surface ($\mu m^2$/image)±SEM of duplicates and was plotted against the antibody concentration. (FIGS. 6B and 6C) To assess cell death via DR4 or DR5 in absence of fibroblasts, a monoculture of MDA-MB-231 (FIG. 6B) or DLD-1 (FIG. 6C) cells using BisG1-FAPα-FEAL/DR4-FEAR, BisG1-b12-FERL/b12-FERR (top 4 concentrations) or RG7386 was tested. (FIGS. 6D and 6E) DR4 transactivation-mediated cell death using BisG1-FAPα-FERL/DR4-FERR, BisG1-b12-FERL/DR4-FERR, BisG1-b12-FERL/b12-FERR (top 4 concentrations) and BisG1-FAPα-FERL/b12-FERR was assessed on MDA-MB-231 (FIG. 6D) and DLD-1 (FIG. 6E) cancer cell lines cocultured with FAPα-expressing cell line NIH/3T3-FAPα. Results from FIGS. 6B-6D show mean % viable cells±SEM of duplicates and were plotted against the antibody concentration, for one representative experiment out of three.

FIGS. 7A-7H: Caspase-8 activation in cocultures of tumor cells with NIH/3T3-FAPα cells Caspase-Glo® 8 luminescence signal for measurement of Caspase-8 activation in cocultures of DLD-1 (FIG. 7A), MDA-MB-231 (FIG. 7C), A549 (FIG. 7E) and SNU-1076 (FIG. 7G) tumor cells with NIH/3T3-FAPα cells or tumor cell monocultures (FIGS. 7B, 7D, 7F, and 7H) in presence of BisG1-FAPα-FERL/DR4-FERR, BisG1-b12-FERL/DR4-FERR or RG7386. As a positive control recombinant human TRAIL (the natural ligand of DR4) was included. Data presented are the mean±SEM luminescence (RLU) plotted against the antibody concentration of two or three independent experiments.

FIGS. 8A-8D: Targeted cell death of patient derived organoids (PDOs) via DR4 transactivation in the presence of CAFs. (FIGS. 8A-8C) The capacity of BisG1-FAPα-FEAL/DR4-FEAR and IgG1-FAPα-FEAL to induce DR4 transactivation-mediated cell death of three colorectal cancer (CRC) PDOs was explored in the presence and absence of CAFs. Data shows the viability of PDOs Hub096 (FIG. 8A), p18T (FIG. 8B) and p19B (FIG. 8C) cultured with (+CAF) or without CAFs in the presence of the indicated antibodies. Cell viability (%) was plotted against the antibody concentrations (mean t SEM of duplicates). (FIG. 8D) Apoptosis induction in cocultures of fluorescently labeled Hub096 (CellBrite® Blue) with CAFs (CellBrite® Orange) in the presence of BisG1-FAPα-FEAL/DR4-FEAR or IgG1-FAPα-FEAL was assessed in both cell populations separately using Annexin-V staining by flow cytometry. Data is presented as mean (±SD) percentage of Annexin-V-positive cells of two independent experiments.

FIGS. 9A-9I: Assessment of BisG1-FAPα-FEAL/DR4-FEAR antitumor activity in vivo. (FIG. 9A) FAPα staining in formalin fixed, paraffin embedded (FFPE) tissues obtained from PDX models. (FIG. 9A) CTG-1234 (gastric cancer), CTG-1150 (pancreatic cancer) and positive control (invasive ductal carcinoma) shown as percentage of tissue surface area, divided into categories from 1+ (low) to 3+ (high). (FIG. 9B) Mean (±SEM) tumor volume in gastric PDX tumor model CTG-1234 after treatment with BisG1-FAPα-FEAL/DR4-FEAR (0.5-8 mg/kg, one dose a week for three weeks) or BisG1-DR4-FEAL/b12-FEAR (8 mg/kg). (FIG. 9C) Kaplan Meier curves showing progression-free survival (PFS) of CTG-1234 tumor-bearing mice, for which PFS is defined as the percentage of mice with a tumor volume smaller than 1000 mm$^3$. (FIG. 9D) Tumor volumes in individual mice, and the mean t SEM for each treatment group, in the gastric cancer PDX CTG-1234 model at day 42, the last day all groups were complete. ***=p<0.001 vs control BisG1-DR4-FEAL/b12-FEAR treated group (Mann-Whitney). (FIG. 9E) Mean (±SEM) mouse body weights for all treatment groups. (FIG. 9F) Tumor volume for individual mice, and the mean±SEM for each treatment group, in the pancreatic PDX tumor model CTG-1150 on day 25, the last day all groups were complete. *=p<0.05 vs control BisG1-DR4-FEAL/b12-FEAR treated group (Mann-Whitney). (FIG. 9G) Kaplan-Meier curves showing PFS for CTG-1150 tumor-bearing mice, for which PFS is defined as the percentage of mice with a tumor volume smaller than 500 mm$^3$. (FIG. 9H) Mean (±SEM) tumor volume per treatment group against time, in the pancreatic PDX tumor model CTG-1150. (FIG. 9I) Mean (±SEM) body weights for all treatment groups.

Figure 10A:
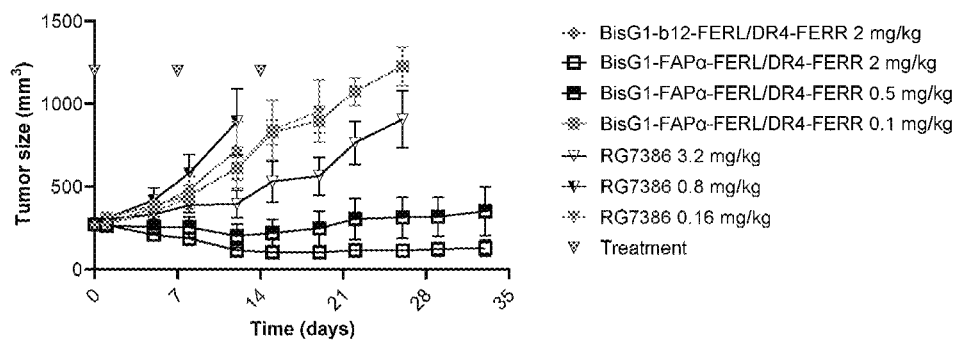
Figure 10B:
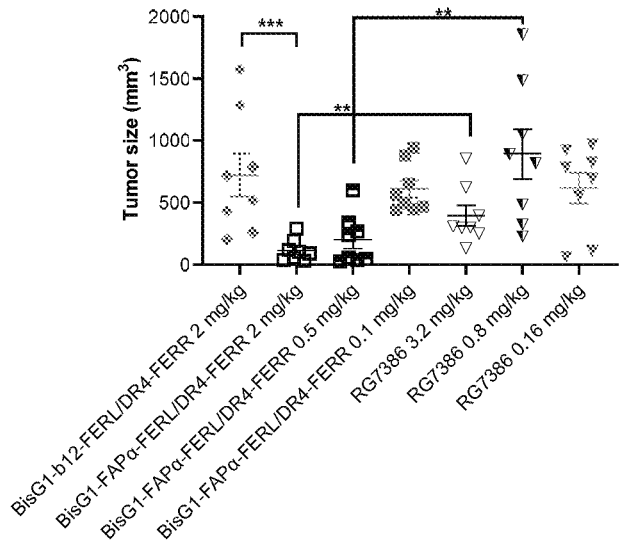
Figure 10C:
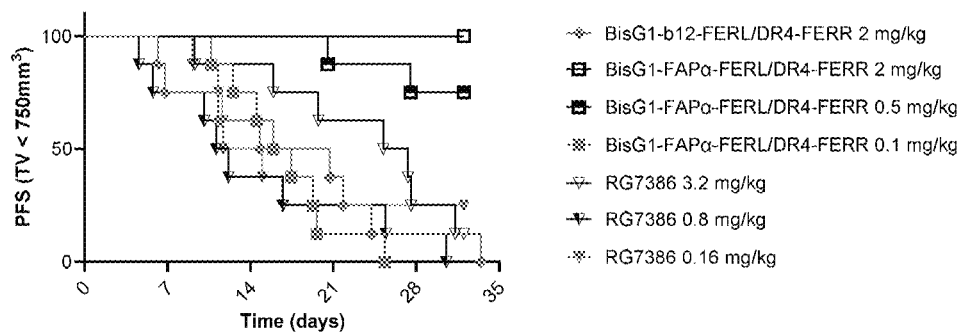
Figure 11A:
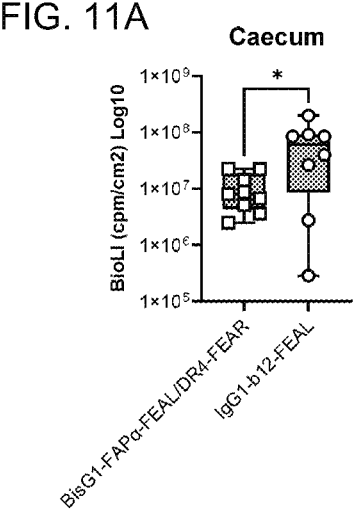
Figure 11B:
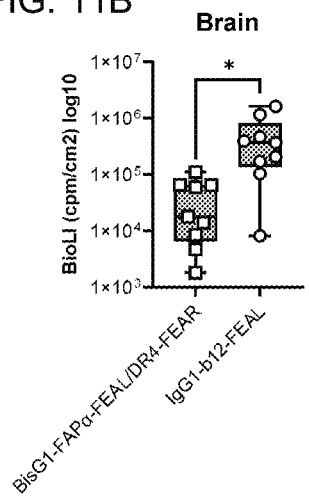
Figure 11C:
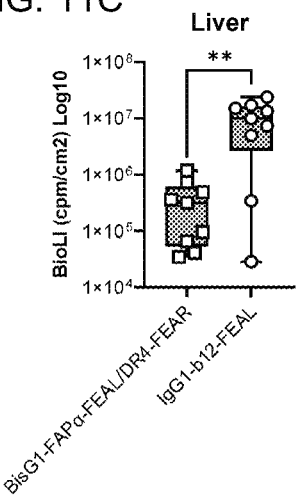
Figure 11D:
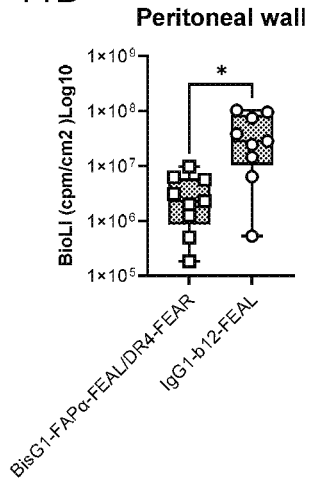
Figure 11E:
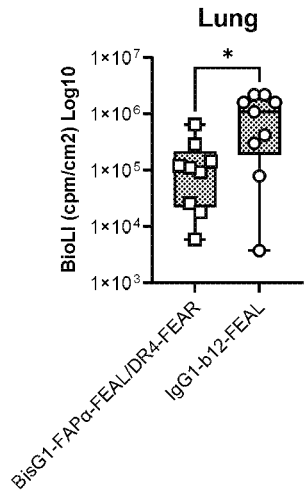

FIGS. 10A-10C: Assessment of BisG1-FAPα-FERL/DR4-FERR antitumor activity in vivo-follow up Mice with established tumors were dosed QW×3 by IV injection of the indicated antibody concentrations (n=8 mice per group). (FIG. 10A) Mean (±SEM) tumor volume in gastric PDX tumor model CTG-1234 after treatment with BisG1-b12-FERL/DR4-FERR (2 mg/kg), BisG1-FAPα-FERL/DR4-FERR (0.1, 0.5, or 2 mg/kg) or equimolar dose of RG7386 (0.16, 0.8, or 3.2 mg/kg). (FIG. 10B) Tumor volume in individual mice, and the mean±SEM for each group, in the gastric cancer PDX CTG-1234 model at day 12, the last day all groups were complete. *=p<0.001 vs control BisG1-b12-FERL/DR4-FERR treated group (Mann-Whitney) p<0.01 vs BisG1-FAPα-FERL/DR4-FERR 0.5 or 2 mg/kg treated group (Mann-Whitney) (FIG. 10C) Kaplan Meier curves showing progression-free survival (PFS) of CTG-1234 tumor-bearing mice, for which PFS is defined as the percentage of mice with a tumor volume smaller than 750 mm$^3$.

FIGS. 11A-11F: Antitumor activity in a multiorgan metastatic mouse model. (FIGS. 11A-11E) Ex vivo bioluminescence imaging (BioLI) measurement (counts per min (cpm)/cm$^2$, Log 10 scale) of tumor load from each mouse was plotted for indicated treatment groups, for each organ. For statistical analysis, paired t-test was performed and p<0.05 was considered statistically significant. Data shown are box plots including the individual data with the median of all animals per treatment group (n=9) with whiskers from minimum to maximum. *p≤0.05, p≤0.01 (FIG. 11F) DR4 activation as measured by cleaved caspase-3 IHC staining of FFPE sections from the excised primary tumors in cecum as well as metastatic tissue in the peritoneal wall and liver. Shown is the mean percentage (±SEM) annotated tumor area that was scored positive for cleaved caspase-3 of all sections analyzed per treatment group. ns=not significant, *P≤0.001 ****P≤0.0001 (Mann-Whitney).

FIGS. 12A-12D: Assessment of hepatocyte toxicity using human liver spheroids. Viability of the liver spheroids was determined by measuring the release of LDH (an indicator of plasma membrane damage) after 4 days of culture (FIGS. 12A and 12C), and intracellular ATP (an indicator of metabolically active cells) levels after 6 (FIG. 12B) or 7 (FIG. 12D) days of culture with BisG1-FAPα-FEAL/DR4-FEAR, ABBV-621-Fc fusion, RG7386, IgG1-b12-FEAR or IgG1-b12 antibodies. The dashed line represents the lower limit of detection (LLOD) for LDH. Data shown are mean t SEM of four technical replicates per condition of bioluminescence signal.

Figure 13A:
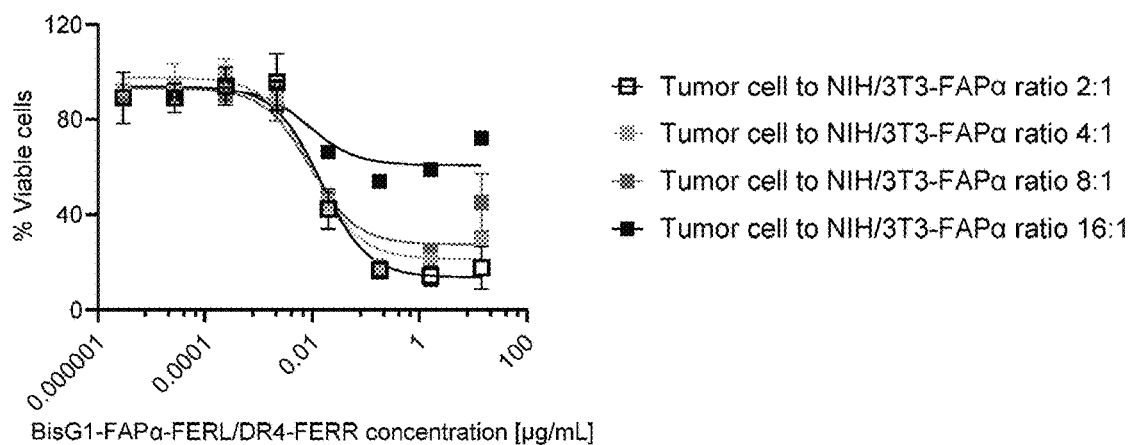
Figure 13B:
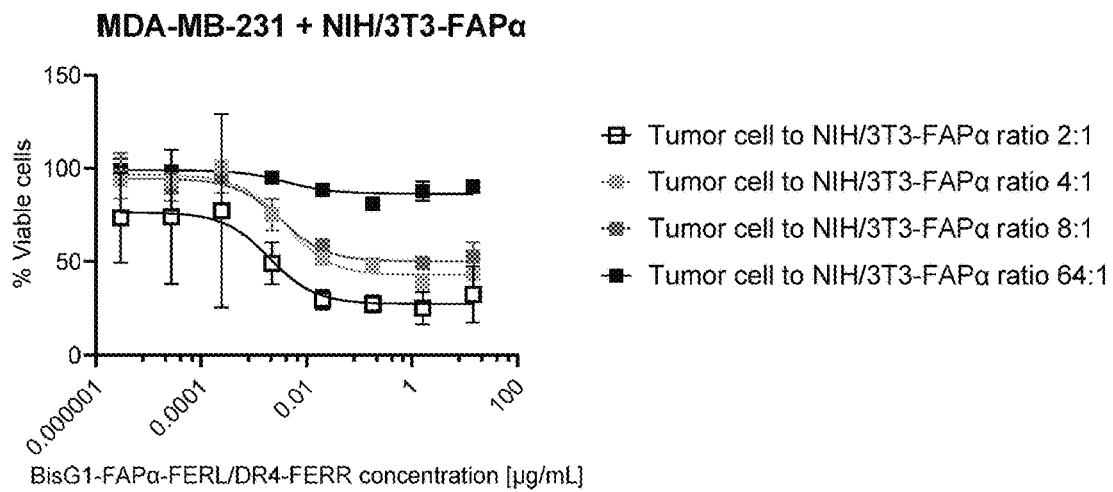
Figure 14A:
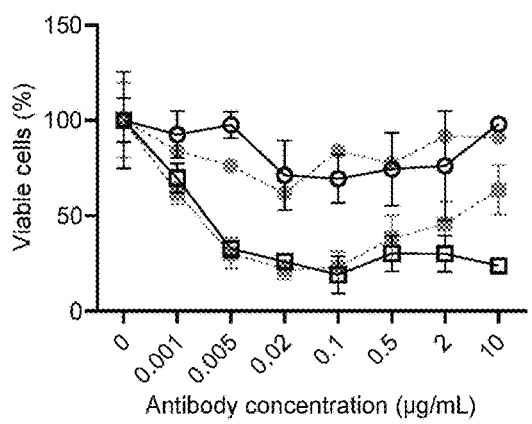
Figure 14B:
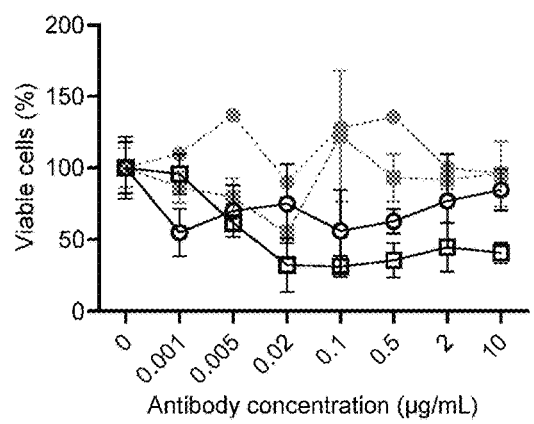
Figure 14C:
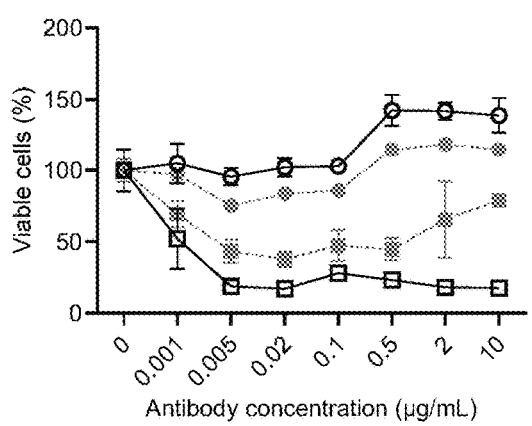
Figure 14D:
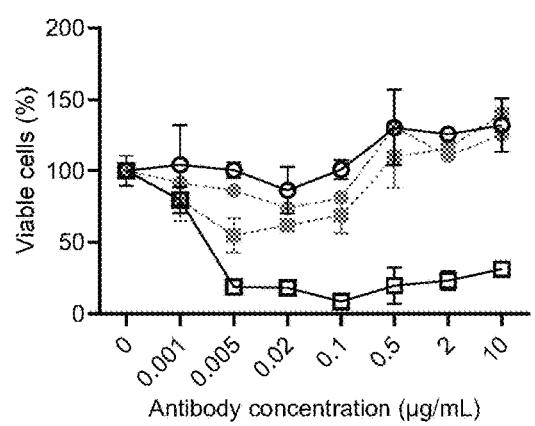

FIGS. 13A and 13B: Cytotoxicity in cocultures of tumor cells with different ratios of NIH/3T3-FAPα cells CellTiter-Glo® viability data of (FIG. 13A) DLD-1 or (FIG. 13B) MDA-MB-231 tumor cells cocultured with NIH/3T3-FAPα cells at different tumor cell to NIH/3T3-FAPα cell ratios in presence of BisG1-FAPα-FERL/DR4-FERR. Data are presented as the mean (±SD) % viable cells plotted against the antibody concentration, for duplicates from one representative out of three independent experiments.

FIGS. 14A-14D: Cytotoxicity in cocultures of PDOs with FAPα knockdown CAFs Cocultures of CRC-derived PDOs (FIG. 14A) Tor9, (FIG. 14B) p19B, (FIG. 14C) Hub096, and (FIG. 14D) Hub098 with CAFs transduced with FAPα shRNA (CAF #34) or non-target shRNA (CAF #Scr) were treated with BisG1-FAPα-FERL/DR4-FERR or negative control antibody BisG1-b12-FERL/b12-FERR. CellTiter-Glo® viability data are presented as the mean±SD cell viability (%) plotted against antibody concentration, for one experiment.

Figure 15A:
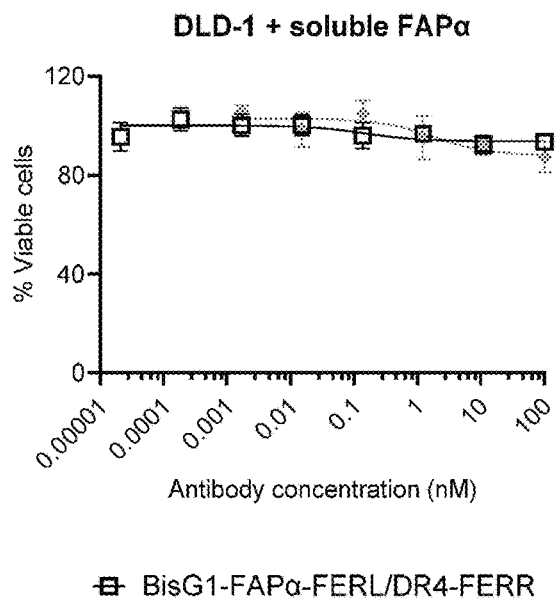
Figure 15B:
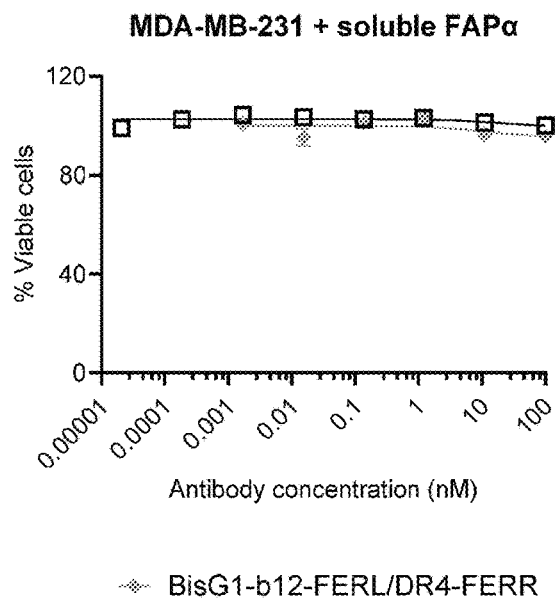

FIGS. 15A and 15B: Cytotoxicity and DR4 transactivation in presence of soluble FAPα

CellTiter-Glo® cytotoxicity data of (FIG. 15A) DLD-1 and (FIG. 15B) MDA-MB-231 tumor cell line monocultures in the presence of soluble FAPα (29.4 nM) and BisG1-FAPα-FERL/DR4-FERR. Data are presented as the mean±SEM % viable cells plotted against antibody concentration, for two-three independent experiments.

Figure 16:
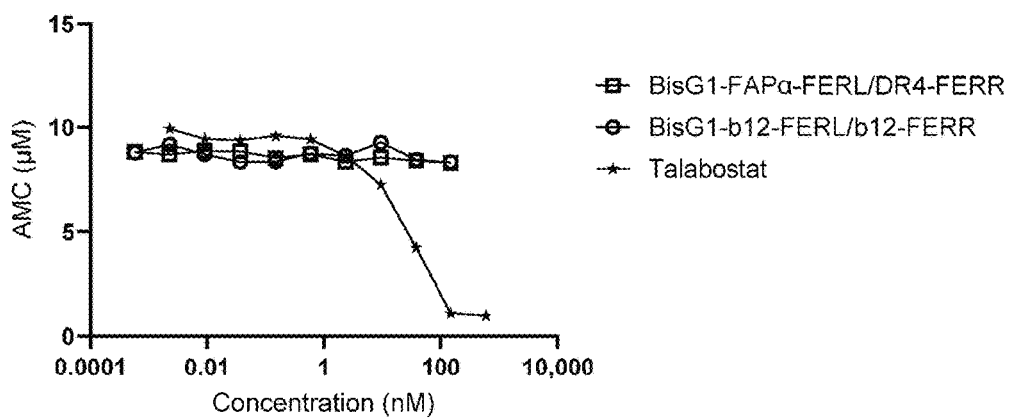

FIG. 16: Effect on FAPα enzymatic activity Fluorogenic dipeptidyl peptidase substrate was incubated with BisG1-FAPα-FERL/DR4-FERR, BisG1-b12-FERL/b12-FERR or the positive control, chemical dipeptidyl peptidase inhibitor Talabostat, in presence of recombinant human FAPα. Fluorescent 7-amino-4-methylcoumarin (AMC) was measured as a readout for FAPα dipeptidyl peptidase activity. Data shown are AMC concentrations plotted against antibody concentration for one representative out of two experiments.

Figure 17A:
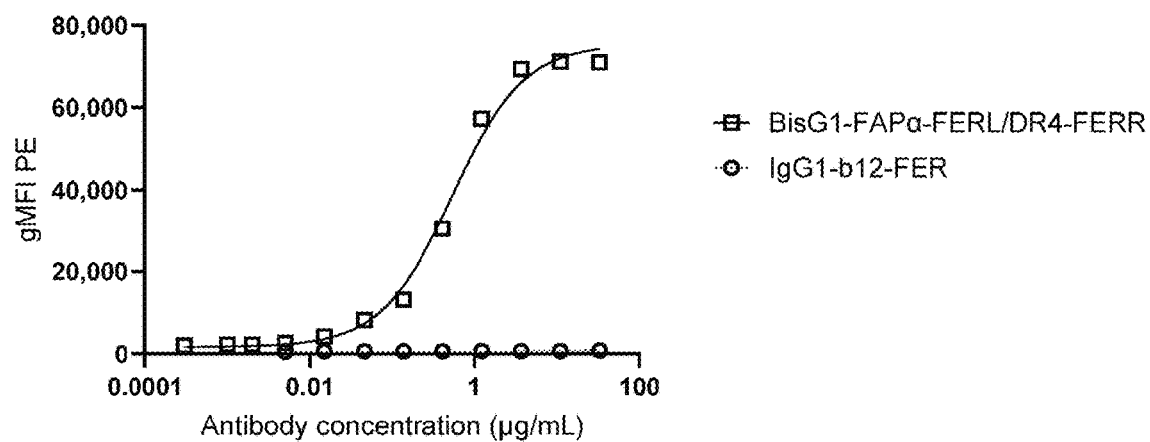
Figure 17B:
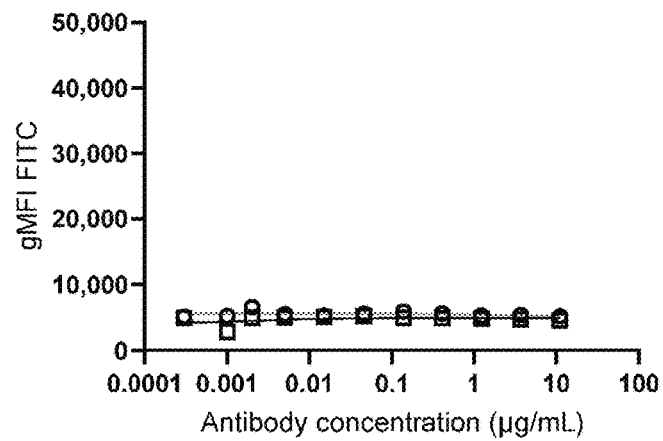

FIGS. 17A and 17B: C1q binding to cell membrane-bound BisG1-FAPα-FERL/DR4-FERR (FIG. 17A) Binding of BisG1-FAPα-FERL/DR4-FERR and IgG1-b12-FER nonbinding control antibody to MDA-MB-231 cells and (FIG. 17B) C1q binding to BisG1-FAPα-FERL/DR4-FERR bound to the cell surface was determined by flow cytometry using MDA-MB-231 cells in the presence of 20% NHS. Data shown are gMFI values as determined by flow cytometry, for one representative experiment out of three independent experiments.

Figure 18:
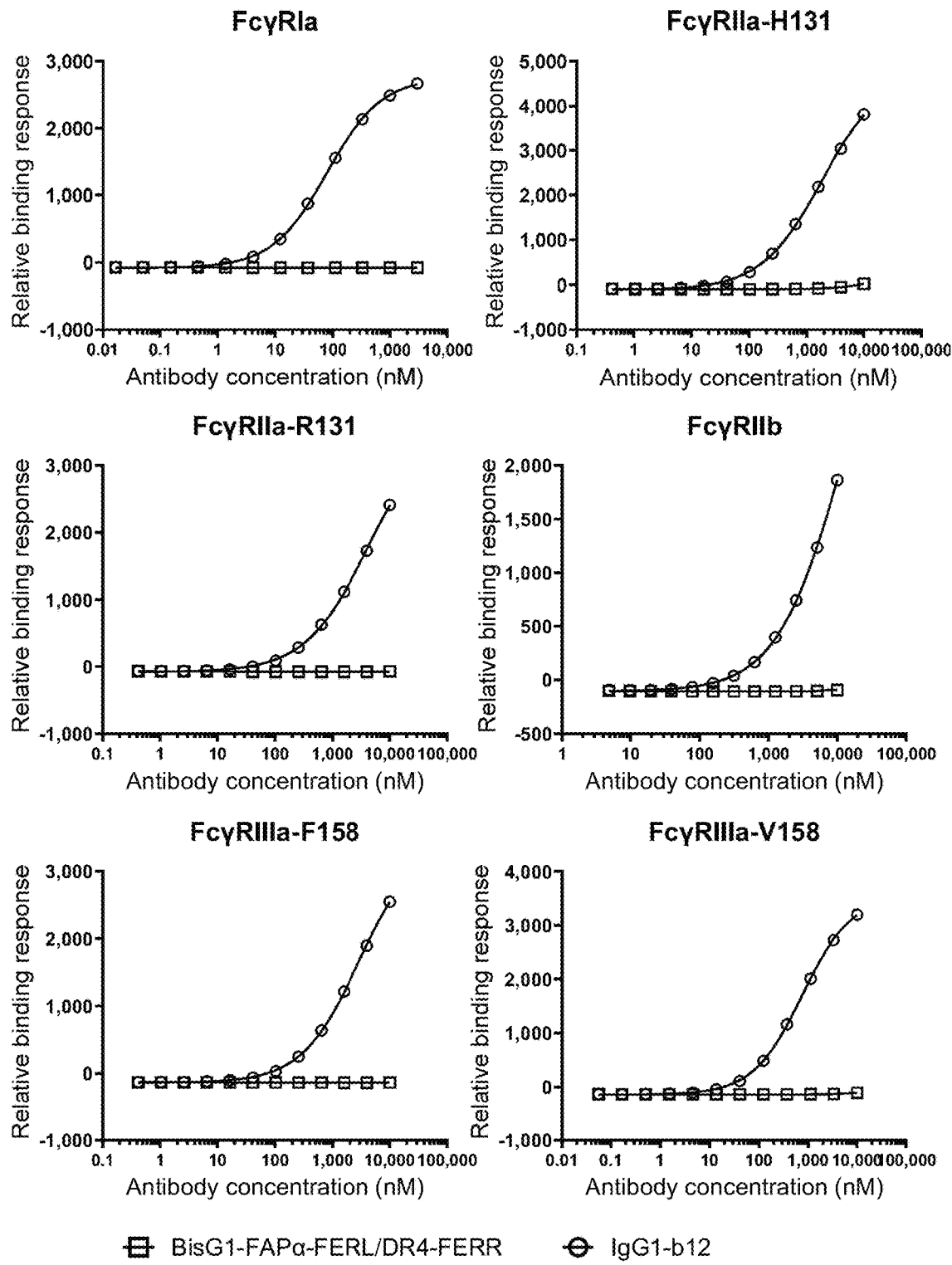

FIG. 18: Binding of BisG1-FAPα-FERL/DR4-FERR to immobilized FcγRs

Binding of BisG1-FAPα-FERL/DR4-FERR to immobilized recombinant human FcγRs (FcγRIa, FcγRIIa-H131, FcγRIIa-R131, FcγRIIb, FcγRIIIa-F158, FcγRIIIa-V158) was analyzed by SPR. Relative binding response is plotted against the antibody concentration for one experiment.

Figure 19A:
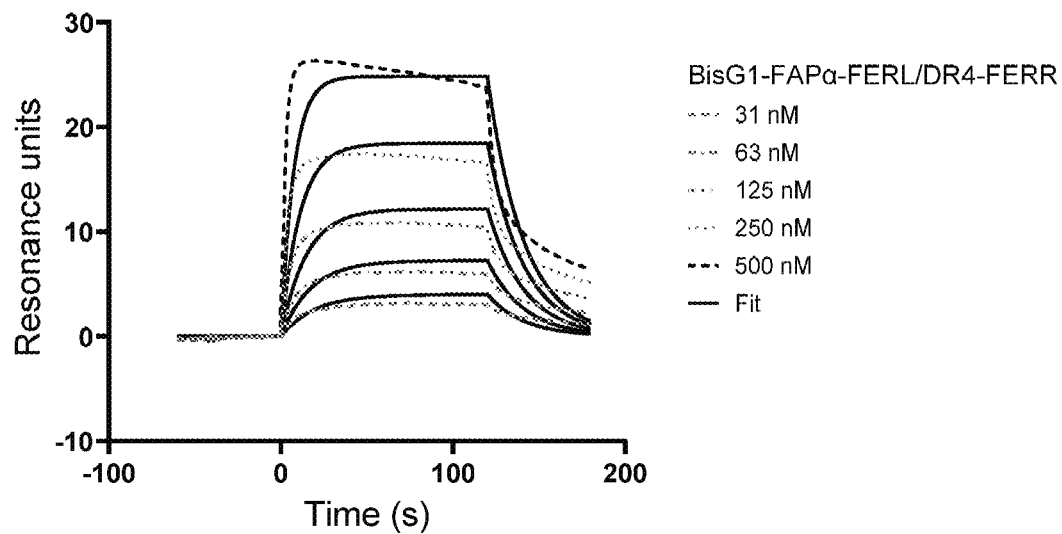
Figure 19B:
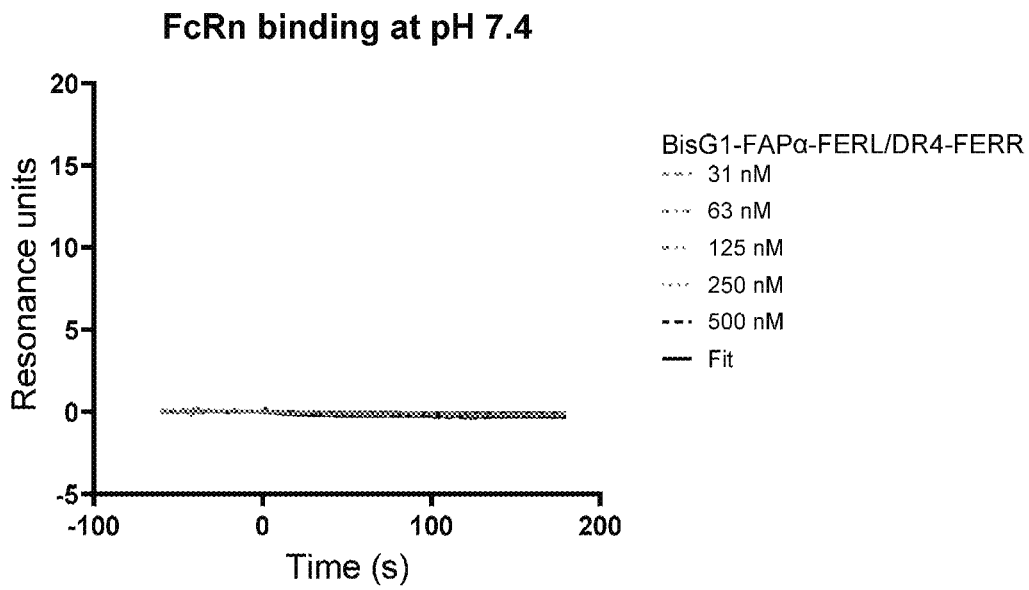

FIGS. 19A and 19B: Binding of BisG1-FAPα-FERL/DR4-FERR to immobilized FcRn

Binding of BisG1-FAPα-FERL/DR4-FERR to immobilized recombinant human FcRn at pH 6.0 (FIG. 19A) and pH 7.4 (FIG. 19B) was analyzed by SPR. Sensorgrams show raw data in dashed lines and curve fits in solid black lines from one representative run out of two runs (at pH 6.0) or four runs (at pH 7.4) performed.

Figure 20:
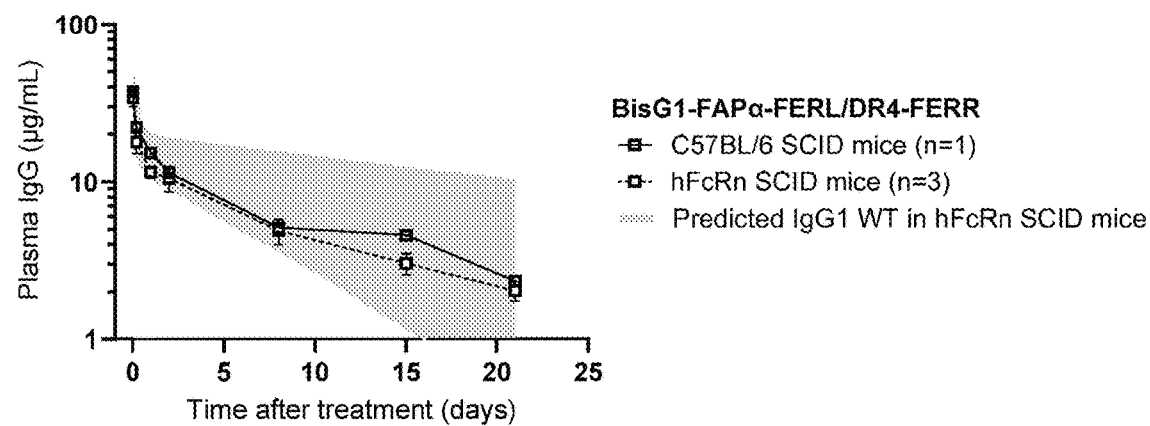

FIG. 20: Pharmacokinetic profile of BisG1-FAPα-FERL/DR4-FERR in non-tumor bearing mice Mice were injected IV with a single dose of 2 mg/kg BisG1-FAPα-FERL/DR4-FERR and total human IgG concentrations in plasma samples were determined by ECLIA. Data shown are the average concentration of plasma IgG over time after treatment for C57BL/6 SCID mice (n=1) and hFcRn SCID mice (n=3). 95% confidence interval for pharmacokinetic profile of wild-type IgG1 in hFcRn SCID mice is indicated in gray shaded area.

DETAILED DESCRIPTION

Definitions

The term "antibody" as used herein is intended to refer to an immunoglobulin molecule, a fragment of an immunoglobulin molecule, or a derivative of either thereof, which has the ability to specifically bind to an antigen under typical physiological and/or tumor-specific conditions with a half-life of significant periods of time, such as at least about 30 minutes, at least about 45 minutes, at least about one hour, at least about two hours, at least about four hours, at least about 8 hours, at least about 12 hours, at least about 24 hours or more, at least about 48 hours or more, at least about 3, 4, 5, 6, 7 or more days, etc., or any other relevant functionally-defined period such as a time sufficient to induce, promote, enhance, and/or modulate a physiological response associated with antibody binding to the antigen. The binding region (or binding domain which may be used herein, both having the same meaning) which interacts with an antigen, comprises variable regions of both the heavy and light chains of the immunoglobulin molecule. The constant regions of the antibodies (Abs) may mediate the binding of the immunoglobulin to host tissues or factors, including various cells of the immune system (such as effector cells) and components of the complement system such as C1q, the first component in the classical pathway of complement activation. Alternatively, the constant regions of the antibodies may be silenced e.g. by mutations, whereby they would not be able to or at least not as efficiently be able to activate the complement system. The term "antibody" includes a monoclonal antibody (mAb), an antibody-like polypeptide, such as a chimeric antibody and a humanized antibody, as well as an 'antibody fragment' or a 'fragment thereof' retaining the ability to specifically bind to the antigen (antigen-binding fragment) provided by any known technique, such as enzymatic cleavage, peptide synthesis, and recombinant techniques, and retaining the ability to be conjugated to a toxin. An antibody as defined according to the invention can possess any isotype unless the disclosure herein is otherwise limited. As indicated above, the term antibody as used herein, unless otherwise stated or clearly contradicted by context, includes fragments of an antibody that retain the ability to specifically interact, such as bind, to the antigen. It has been shown that the antigen-binding function of an antibody may be performed by fragments of a full-length antibody. Examples of binding fragments encompassed within the term "antibody" include (i) a Fab' or Fab fragment, a monovalent fragment consisting of the light chain variable domain (VL), heavy chain variable domain (VH), light chain constant region (CL) and heavy chain constant region domain 1 (CH1) domains, or a monovalent antibody as described in WO 2007/059782; (ii) F(ab')$_2$ fragments, bivalent fragments comprising two Fab fragments linked by a disulfide bridge at the hinge region; (iii) an Fd fragment consisting essentially of the VH and CH1 domains; (iv) an Fv fragment consisting essentially of the VL and VH domains of a single arm of an antibody, (v) a dAb fragment Ward et al., Nature 341, 544-546 (1989), which consists essentially of a VH domain and is also called domain antibody Holt et al; Trends Biotechnol. 2003 November; 21(11): 484-90; (vi) camelid or Nanobodies™ Revets et al; Expert Opin Biol Ther. 2005 January; 5(1): 111-24 and (vii) an isolated complementarity determining region (CDR).

Furthermore, although the two domains of the Fv fragment, VL and VH, are coded for by separate genes, they may be joined, using recombinant methods, by a synthetic linker that enables them to be made as a single protein chain in which the VL and VH regions pair to form monovalent molecules (known as single chain antibodies or single chain Fv (scFv), see for instance Revets et al; Expert Opin Biol Ther. 2005 January; 5(1): 111-24 and Bird et al., Science 242, 423-426 (1988). Such single chain antibodies are encompassed within the term antibody unless otherwise noted or clearly indicated by context. Although such fragments are generally included within the meaning of antibody, they collectively and each independently are unique features of the present invention, exhibiting different biological properties and utility. These and other useful antibody fragments in the context of the present invention are discussed further herein. An antibody can be produced in and collected from different in vitro or ex vivo expression or production systems, for example from recombinantly modified host cells, from hybridomas or systems that use cellular extracts supporting in vitro transcription and/or translation of nucleic acid sequences encoding the antibody. It is to be understood that a multitude of different antibodies, the antibodies being as defined in the context of the present invention, is one that can be provided by producing each antibody separately in a production system as mentioned above and thereafter mixing the antibodies, or by producing several antibodies in the same production system.

The term "immunoglobulin heavy chain" or "heavy chain of an immunoglobulin" as used herein is intended to refer to one of the heavy chains of an immunoglobulin. A heavy chain is typically comprised of a heavy chain variable region (abbreviated herein as VH) and a heavy chain constant region (abbreviated herein as CH) which defines the isotype of the immunoglobulin. The heavy chain constant region typically is comprised of three domains, CH1, CH2, and CH3. The term "immunoglobulin" as used herein is intended to refer to a class of structurally related glycoproteins consisting of two pairs of polypeptide chains, one pair of light (L) low molecular weight chains and one pair of heavy (H) chains, all four potentially inter-connected by disulfide bonds. The structure of immunoglobulins has been well characterized (see for instance Fundamental Immunology Ch. 7 (Paul, W., ed., 2nd ed. Raven Press, N.Y. (1989)). Within the structure of the immunoglobulin, the two heavy chains are inter-connected via disulfide bonds in the so-called "hinge region". Equally to the heavy chains, each light chain is typically comprised of several regions; a light chain variable region (abbreviated herein as VL) and a light chain constant region. The light chain constant region typically is comprised of one domain, CL. Furthermore, the VH and VL regions may be further subdivided into regions of hypervariability (or hypervariable regions which may be hypervariable in sequence and/or form of structurally defined loops), also termed complementarity determining regions (CDRs), interspersed with regions that are more conserved, termed framework regions (FRs). Each VH and VL is typically composed of three CDRs and four FRs, arranged from amino-terminus to carboxy-terminus in the following order: FR1, CDR1, FR2, CDR2, FR3, CDR3, FR4. CDR sequences are defined according to IMGT (see Lefranc M P. et al., Nucleic Acids Research, 27, 209-212, 1999] and Brochet X. Nucl. Acids Res. 36, W503-508 (2008)).

When used herein, the terms "half molecule", "Fab-arm" and "arm" refer to one heavy chain-light chain pair. When a bispecific antibody is described to comprise a half-molecule antibody "derived from" a first antibody, and a half-molecule antibody "derived from" a second antibody, the term "derived from" indicates that the bispecific antibody was generated by recombining, by any known method, said half-molecules from each of said first and second antibodies into the resulting bispecific antibody. In this context, "recombining" is not intended to be limited by any particular method of recombining and thus includes all of the methods for producing bispecific antibodies described herein below, including for example recombining by half-molecule exchange, as well as recombining at nucleic acid level and/or through co-expression of two half-molecules in the same cells.

The term "antigen-binding region" or "binding region" as used herein, refers to a region of an antibody which is capable of binding to the antigen, and which comprises the epitope. The antigen can be any molecule, such as a polypeptide, e.g. present on a cell, bacterium, or virion. The terms "antigen" and "target" may, unless contradicted by the context, be used interchangeably in the context of the present invention. The terms "antigen-binding region" and "antigen-binding site" may, unless contradicted by the context, be used interchangeably in the context of the present invention.

The term "epitope" means an antigenic determinant which is specifically bound by an antibody. Epitopes usually consist of surface groupings of molecules such as amino acids, sugar side chains or a combination thereof and usually have specific three-dimensional structural characteristics, as well as specific charge characteristics. Conformational and non-conformational epitopes are distinguished in that the binding to the former but not the latter is lost in the presence of denaturing solvents. The epitope may comprise amino acid residues which are directly involved in the binding, and other amino acid residues, which are not directly involved in the binding, such as amino acid residues which are effectively blocked or covered by the antibody when it is bound to the antigen (in other words, the amino acid residue is within or closely adjacent to the footprint of the specific antibody).

An antibody binding region may be determined by epitope binning using biolayer interferometry, by alanine scan, or by shuffle assays (using antigen constructs in which regions of the antigen are exchanged with that of another species and determining whether the antibody still binds to the antigen or not). The amino acids within the antibody binding region that are involved in the interaction with the antibody may be determined by hydrogen/deuterium exchange mass spectrometry and by crystallography of the antibody bound to its antigen.

The term "blocks binding" or "blocking the binding of an antibody" or "cross-blocking binding" or "cross-blocks binding" refers to the situation where one antibody bound to a specific antigen prevents binding of another second antibody to the same antigen. In the absence of the other antibody, each antibody has the ability to bind to the antigen as determined by a significant binding response, whereas one of the antibodies lacks a binding response when the other antibody is present. This type of behavior indicates binding of both antibodies to a substantially overlapping epitope on the antigen. The ability of one antibody to block the binding of another antibody may be determined by biolayer interferometry in a classical sandwich epitope binning assay format, for instance as described by Abdiche et al. (Abdiche Y N, Malashock D S, Pinkerton A, Pons J. Exploring blocking assays using Octet®, ProteOn™, and Biacore™ biosensors. Anal Biochem. 2009; 386(2): 172-180). Briefly, in a sandwich epitope binning assay, an antibody in solution is tested for binding to its specific antigen that is first captured via an immobilized antibody. In the context of the present invention, one antibody does not block the binding of another antibody if it is capable of "displacing" the other antibody, i.e. the one antibody dissociates from the antigen, when the other antibody binds to the antigen. The terms "blocks binding" and "blocking the binding of an antibody" and "cross-blocking binding" and "cross-blocks binding" may, unless contradicted by the context, be used interchangeably in the context of the present invention. Preferably, the ability of one antibody to block the binding of another antibody is determined using full-length antibodies.

The term "binding" as used herein refers to the binding of an antibody to a predetermined antigen or target, typically with a binding affinity corresponding to a $K_D$ of $1E^{-6}$ M or less, e.g. $5E^{-7}$ M or less, $1E^{-7}$ M or less, such as $5E^{-8}$ M or less, such as $1E^{-8}$ M or less, such as $5E^{-9}$ M or less, such as $1E^{-9}$ M or less, such as $5E^{-10}$ M or less, such as $1E^{-10}$ M or less, such as $5E^{-11}$ M or less, such as $1E^{-12}$ M or less, such as $5E^{-12}$ M or less or such as $1E^{-12}$ M or less, when determined by biolayer interferometry.

The term "$K_D$" (M), as used herein, refers to the dissociation equilibrium constant of a particular antibody-antigen interaction, and is obtained by dividing $k_d$ by $k_a$.

The term "$k_d$" (sec$^{-1}$), as used herein, refers to the dissociation rate constant of a particular antibody-antigen interaction. Said value is also referred to as the $k_{off}$ value or off-rate.

The term "$k_a$" (M$^{-1}$×sec$^{-1}$), as used herein, refers to the association rate constant of a particular antibody-antigen interaction. Said value is also referred to as the $k_{on}$ value or on-rate.

The term "cis-binding", as used herein, refers to the simultaneous binding of a multispecific antibody to distinct targets on the same cell. For example, a bispecific antibody may bind to its two targets on the same cell.

The term "trans-binding", as used herein, refers to the simultaneous binding of a multispecific antibody to distinct targets on different cells. For example, a bispecific antibody may bind to two cells by binding to one target on a first cell and another target on a second cell.

The term "FAPα" as used herein, refers to the protein entitled Fibroblast activation protein alpha, which is an enzyme encoded by the FAP gene and also referred to as surface-expressed protease (seprase), serine integral membrane protease (SIMP), dipeptidyl peptidase FAP, prolyl endopeptidase FAP and integral membrane serine protease. It is 170 kDa transmembrane protein. In humans (*Homo sapiens*), the FAPα protein has the amino acid sequence shown in SEQ ID NO: 33 ([Prolyl endopeptidase FAP]: Uniprot accession no. [Q12884]). In the amino acid sequence shown in SEQ ID NO: 33, amino acid residues [1-4] are a cytoplasmic peptide, amino acid residues [5-25] are transmembrane peptide and amino acid residues [26-760] are the extracellular polypeptide. In cynomolgus monkey (*Macaca fascicularis*), the FAPα protein has the amino acid sequence shown in SEQ ID NO: 39 (Uniprot accession no. A0A2K5VGF4), where amino acid residues [1-760] are the mature polypeptide. In mouse (*Mus musculus*), the FAPα protein has the amino acid sequence shown in SEQ ID NO: 35 (Uniprot accession no. P97321), where amino acid residues [1-761] are the mature polypeptide. In rat (*Rattus norvegicus*), the FAPα protein has the amino acid sequence shown in SEQ ID NO: 36 (Uniprot accession no. Q8R492), where amino acid residues [1-761] are the mature polypeptide. In dog (*Canis lupus familiaris*), the FAPα protein has the amino acid sequence shown in SEQ ID NO: 37 (Uniprot accession no. A0A8CONKP1), where amino acid residues [1-760] are the mature polypeptide. In pig (*Sus scrofa*), the FAPα protein has the amino acid sequence shown in SEQ ID NO: 38 (Uniprot accession no. K7GQN2), where amino acid residues [1-760] are the mature polypeptide.

The term "DR4" as used herein, refers to the protein entitled Death Receptor 4, which is a receptor for the cytotoxic ligand TNFSF10/TRAIL and also referred to as Tumor necrosis factor receptor superfamily member 10A, APO2, CD261 and TNF-related apoptosis-inducing ligand receptor 1 (TRAIL receptor 1; TRAIL-R1). It is 56 kDa transmembrane protein. In humans (*Homo sapiens*), the DR4 protein has the amino acid sequence shown in SEQ ID NO: 68 (Tumor necrosis factor receptor superfamily member 10A). In the amino acid sequence shown in SEQ ID NO: 68, amino acid residues [1-23] are a signal peptide and amino acid residues [24-468] are the mature polypeptide. In cynomolgus monkey (*Macaca fascicularis*), the DR4 protein has the amino acid sequence shown in SEQ ID NO: 69. In the amino acid sequence shown in SEQ ID NO: 69, amino acid residues [1-23] are a signal peptide, and amino acid residues [24-471] are the mature polypeptide.

The term "CAFs" as used herein refers to cancer-associated fibroblasts, which are present in the tumor microenvironment and is a heterogenous population of stromal cells with a mesenchymal cell lineage coexisting with the growing tumor mass. The CAFs are spindle-shaped cells that build up and remodel the extracellular matrix structure. The definition of CAFs is based on a combination of morphological features, biomarkers, and genetic mutations.

The term "tumor microenvironment" or "TME" as used herein refers to the ecosystem surrounding a tumor inside the body. The TME is a complex and dynamic environment, which influences the growth, invasion and metastasis of the tumor. The tumor and the TME constantly interact and influence one another both positively and negatively. The TME comprises immune cells, extracellular matrix, blood vessels and stromal cells.

The terms "monoclonal antibody", "monoclonal Ab", "monoclonal antibody composition", "mAb", or the like, as used herein refer to a preparation of antibody molecules of single molecular composition. A monoclonal antibody composition displays a single binding specificity and affinity for a particular epitope. Accordingly, the term "human monoclonal antibody" refers to antibodies displaying a single binding specificity which have variable and constant regions derived from human germline immunoglobulin sequences. The human monoclonal antibodies may be produced by a hybridoma which includes a B cell obtained from a transgenic or transchromosomal non-human animal, such as a transgenic mouse, having a genome comprising a human heavy chain transgene and a light chain transgene, fused to an immortalized cell. Monoclonal antibodies may also be produced from recombinantly modified host cells, or systems that use cellular extracts supporting in vitro transcription and/or translation of nucleic acid sequences encoding the antibody.

The term "isotype" as used herein refers to the immunoglobulin class (for instance IgG1, IgG2, IgG3, IgG4, IgD, IgA, IgE, or IgM) or any allotypes thereof, such as IgG1m (za) and IgG1m(f)) that is encoded by heavy chain constant region genes. Further, each heavy chain isotype can be combined with either a kappa (κ) or lambda (λ) light chain.

The term "allotype", as used herein, refers to the amino acid variation within one isotype class in the same species. The predominant allotype of an antibody isotype varies between ethnicity individuals. The known allotype variations within the IgG1 isotype of the heavy chain result from 4 amino acid substitutions in the antibody frame. In one embodiment the antibody of the invention is of the IgG1m(f) allotype as defined in SEQ ID NO: 21. In one embodiment of the invention the first and second antibody of the invention is of the IgG1m(f) allotype as defined in SEQ ID NO: 21, wherein at least one amino acid substitution has been introduced. In one embodiment of the invention the first and second antibody of the invention is of the IgG1m(f) allotype as defined in SEQ ID NO: 21, wherein at most five amino acid substitutions has been introduced, such as four amino acid substitutions, such as three amino acid substitutions, such as two amino acid substitutions.

The term "full-length" when used in the context of an antibody indicates that the antibody is not a fragment but contains all of the domains of the particular isotype normally found for that isotype in nature, e.g. the VH, CH1, CH2, CH3, hinge, VL and CL domains for an IgG1 antibody. In some embodiments, the term "full-length" when used herein in the context of an antibody, refers to an antibody (e.g., a parent or variant antibody) comprising one or two pairs of heavy and light chains, each containing all heavy and light chain constant and variable domains that are normally found in a heavy chain-light chain pair of a wild-type antibody of that isotype. In a full-length variant antibody, the heavy and light chain constant and variable domains may contain amino acid substitutions that improve the functional properties of the antibody when compared to the full-length parent or wild-type antibody. These include substitutions for the purpose of reducing antibody effector function and substitutions to facilitate assembly of multispecific antibodies, such as bispecific antibodies. A full-length antibody according to the present invention may be produced by a method comprising the steps of (i) cloning the CDR sequences into a suitable vector comprising complete heavy chain sequences and complete light chain sequence, and (ii) expressing the complete heavy and light chain sequences in suitable expression systems. It is within the knowledge of the skilled person to produce a full-length antibody when starting out from either CDR sequences or full variable region sequences.

The term "human antibody", as used herein, is intended to include antibodies having variable and framework regions derived from human germline immunoglobulin sequences and a human immunoglobulin constant domain. The human antibodies of the invention may include amino acid residues not encoded by human germline immunoglobulin sequences (e.g., mutations, insertions or deletions introduced by random or site-specific mutagenesis in vitro or by somatic mutation in vivo). However, the term "human antibody", as used herein, is not intended to include antibodies in which CDR sequences derived from the germline of another non-human species, such as a mouse, have been grafted onto human framework sequences.

The term "Fc-mediated effector functions," as used herein, is intended to refer to functions that are a consequence of binding a polypeptide or antibody to its target or antigen on a cell membrane wherein the Fc effector function is attributable to the Fc region of the polypeptide or antibody. Examples of Fc effector functions include (i) C1q-binding, (ii) complement activation, (iii) complement-dependent cytotoxicity (CDC), (iv) antibody-dependent cell-mediated cytotoxity (ADCC), (v) Fc-gamma receptor-binding, (vi) antibody-dependent cellular phagocytosis (ADCP), (vii) complement-dependent cellular cytotoxicity (CDCC), (viii) complement-enhanced cytotoxicity, (ix) binding to complement receptor of an opsonized antibody mediated by the antibody, (x) opsonisation, and (xi) a combination of any of (i) to (x).

The term "hinge region" as used herein refers to the hinge region of an immunoglobulin heavy chain. Thus, for example the hinge region of a human IgG1 antibody corresponds to amino acids 216-230 according to the Eu numbering as set forth in Kabat (Kabat, E. A. et al., Sequences of proteins of immunological interest. 5th Edition—US Department of Health and Human Services, NIH publication No. 91-3242, pp 662,680,689 (1991)). However, the hinge region may also be any of the other subtypes as described herein.

The term "CH1 region" or "CH1 domain" as used herein refers to the CH1 region of an immunoglobulin heavy chain. Thus, for example the CH1 region of a human IgG1 antibody corresponds to amino acids 118-215 according to the Eu numbering as set forth in Kabat (ibid). However, the CH1 region may also be any of the other subtypes as described herein.

The term "CH2 region" or "CH2 domain" as used herein refers to the CH2 region of an immunoglobulin heavy chain. Thus, for example the CH2 region of a human IgG1 antibody corresponds to amino acids 231-340 according to the Eu numbering as set forth in Kabat (ibid). However, the CH2 region may also be any of the other subtypes as described herein.

The term "CH3 region" or "CH3 domain" as used herein refers to the CH3 region of an immunoglobulin heavy chain. Thus for example the CH3 region of a human IgG1 antibody corresponds to amino acids 341-447 according to the Eu numbering as set forth in Kabat (ibid). However, the CH3 region may also be any of the other subtypes as described herein.

The term "inertness", "inert" or "non-activating" as used herein, refers to an Fc region which is at least not able to bind any Fc gamma receptors (FcgR), induce Fc-mediated cross-linking of FcgRs, or induce FcgR-mediated cross-linking of target antigens via two Fc regions of individual antibodies, or is not able to bind C1q. The inertness of an Fc region of an antibody may be tested using the antibody in a monospecific or bispecific format.

The term "monovalent antibody", in the context of the present invention, refers to an antibody molecule that can interact with a specific epitope on an antigen, with only one antigen binding domain (e.g. one Fab arm). In the context of a bispecific antibody, "monovalent antibody binding" refers to the binding of the bispecific antibody to one specific epitope on an antigen with only one antigen binding domain (e.g. one Fab arm).

The term "monospecific antibody" in the context of the present invention, refers to an antibody that has binding specificity to one epitope only. The antibody may be a monospecific, monovalent antibody (i.e. carrying only one antigen binding region) or a monospecifc, bivalent antibody (i.e. an antibody with two identical antigen binding regions). Thus, the antibody may be a monospecific antibody with monovalent binding (i.e. carrying only one antigen binding region) or a monospecifc antibody with bivalent binding (i.e. an antibody with two identical antigen binding regions).

The term "bispecific antibody" refers to an antibody having two non-identical antigen binding domains, e.g. two non-identical Fab-arms or two Fab-arms with non-identical CDR regions. In the context of this invention, bispecific antibodies have specificity for at least two different epitopes. Such epitopes may be on the same or different antigens or targets. If the epitopes are on different antigens, such antigens may be on the same cell or different cells, cell types or structures, such as extracellular matrix or vesicles and soluble protein. A bispecific antibody may thus be capable of crosslinking multiple antigens, e.g. two different cells.

The term "bivalent antibody" refers to an antibody that has two antigen binding regions, which bind to epitopes on one or two targets or antigens or binds to one or two epitopes on the same antigen. Hence, a bivalent antibody may be a monospecific, bivalent antibody or a bispecific, bivalent antibody i.e. a bivalent antibody may be a monospecific antibody with bivalent binding or a bispecific antibody with bivalent binding. In one embodiment, the bispecific antibody with bivalent binding is a bispecific antibody with monovalent binding to a first target and monovalent binding to a second target.

The term "multispecific antibody" refers to an antibody having two or more non-identical antigen binding domains, e.g. two or more non-identical Fab-arms or two or more Fab-arms with non-identical CDR regions. In the context of this invention, multispecific antibodies have specificity for at least two different epitopes. Such epitopes may be on the same or different antigens or targets. If the epitopes are on different antigens, such antigens may be on the same cell or different cells, cell types or structures, such as extracellular matrix or vesicles and soluble protein. A multispecific antibody may thus be capable of crosslinking multiple antigens, e.g., two different cells.

The term "amino acid" and "amino acid residue" may herein be used interchangeably, and are not to be understood limiting. Amino acids are organic compounds containing amine ($-NH_2$) and carboxyl ($-COOH$) functional groups, along with a side chain (R group) specific to each amino acid. In the context of the present invention, amino acids may be classified based on structure and chemical characteristics. Thus, classes of amino acids may be reflected in one or both of the following tables:

| Main classification based on structure and general chemical characterization of R group | |
|---|---|
| Class | Amino acid |
| Acidic Residues | D and E |
| Basic Residues | K, R, and H |
| Hydrophilic Uncharged Residues | S, T, N, and Q |
| Aliphatic Uncharged Residues | G, A, V, L, and I |
| Non-polar Uncharged Residues | C, M, and P |
| Aromatic Residues | F, Y, and W |

| Alternative Physical and Functional Classifications of Amino Acid Residues | |
|---|---|
| Class | Amino acid |
| Hydroxyl group containing residues | S and T |
| Aliphatic residues | I, L, V, and M |
| Cycloalkenyl-associated residues | F, H, W, and Y |
| Hydrophobic residues | A, C, F, G, H, I, L, M, R, T, V, W, and Y |
| Negatively charged residues | D and E |
| Polar residues | C, D, E, H, K, N, Q, R, S, and T |
| Positively charged residues | H, K, and R |
| Small residues | A, C, D, G, N, P, S, T, and V |
| Very small residues | A, G, and S |
| Residues involved in turn formation | A, C, D, E, G, H, K, N, Q, R, S, P, and T |
| Flexible residues | Q, T, K, S, G, P, D, E, and R |

Substitution of one amino acid for another may be classified as a conservative or non-conservative substitution. In the context of the invention, a "conservative substitution" is a substitution of one amino acid with another amino acid having similar structural and/or chemical characteristics, such substitution of one amino acid residue for another amino acid residue of the same class as defined in any of the two tables above: for example, leucine may be substituted with isoleucine as they are both aliphatic, branched hydrophobes. Similarly, aspartic acid may be substituted with glutamic acid since they are both small, negatively charged residues.

In the context of the present invention, a substitution in an antibody is indicated as:

Original amino acid—position—substituted amino acid;

Referring to the well-recognized nomenclature for amino acids, the three letter code, or one letter code, is used, including the codes "Xaa" or "X" to indicate any amino acid residue. Thus, Xaa or X may typically represent any of the 20 naturally occurring amino acids. The term "naturally occurring" as used herein refers to any one of the following amino acid residues; glycine, alanine, valine, leucine, isoleucine, serine, threonine, lysine, arginine, histidine, aspartic acid, asparagine, glutamic acid, glutamine, proline, tryptophan, phenylalanine, tyrosine, methionine, and cysteine. Accordingly, the notation "K409R" or "Lys409Arg" means, that the antibody comprises a substitution of Lysine with Arginine in amino acid position 409.

Substitution of an amino acid at a given position to any other amino acid is referred to as:

Original amino acid—position; or e.g. "K409"

For a modification where the original amino acid(s) and/or substituted amino acid(s) may comprise more than one, but not all amino acid(s), the more than one amino acid may be separated by "," or "/". E.g. the substitution of Lysine with Arginine, Alanine, or Phenylalanine in position 409 is: "Lys409Arg,Ala,Phe" or "Lys409Arg/Ala/Phe" or "K409R,A,F" or "K409R/A/F" or "K409 to R, A, or F".

Such designation may be used interchangeably in the context of the invention but have the same meaning and purpose.

Furthermore, the term "a substitution" embraces a substitution into any one or the other nineteen natural amino acids, or into other amino acids, such as non-natural amino acids. For example, a substitution of amino acid K in position 409 includes each of the following substitutions: 409A, 409C, 409D, 409E, 409F, 409G, 409H, 409I, 409L, 409M, 409N, 409Q, 409R, 409S, 409T, 409V, 409W, 409P, and 409Y. This is, by the way, equivalent to the designation 409X, wherein the X designates any amino acid other than the original amino acid. These substitutions may also be designated K409A, K409C, etc. or K409A,C, etc. or K409A/C/etc. The same applies by analogy to each and every position mentioned herein, to specifically include herein any one of such substitutions.

The term "amino acid corresponding to position . . . " as used herein refers to an amino acid position number in a human IgG1 heavy chain. Corresponding amino acid positions in other immunoglobulins may be found by alignment with human IgG1. Thus, an amino acid or segment in one sequence that "corresponds to" an amino acid or segment in another sequence is one that aligns with the other amino acid or segment using a standard sequence alignment program. It is considered well-known in the art how to align a sequence or segment in a sequence and thereby determine the corresponding position in a sequence to an amino acid position according to the present invention.

The term "host cell", as used herein, is intended to refer to a cell into which an expression vector has been introduced. It should be understood that such terms are intended to refer not only to the particular subject cell, but also to the progeny of such a cell. Because certain modifications may occur in succeeding generations due to either mutation or environmental influences, such progeny may not, in fact, be identical to the parent cell, but are still included within the scope of the term "host cell" as used herein. Recombinant host cells include, for example, transfectomas, such as CHO cells, HEK-293 cells, Expi293F cells, PER.C6 cells, NSO cells, and lymphocytic cells, and prokaryotic cells such as *E. coli* and other eukaryotic hosts such as plant cells and fungi.

The term "transfectoma", as used herein, includes recombinant eukaryotic host cells expressing the antibody or a target antigen, such as CHO cells, PER.C6 cells, NSO cells, HEK-293 cells, Expi293F cells, plant cells, or fungi, including yeast cells.

For purposes of the present invention, the "sequence identity" between two amino acid sequences is determined using the Needleman-Wunsch algorithm (Needleman and Wunsch, 1970, J. Mol. Biol. 48: 443-453) as implemented in the Needle program of the EMBOSS package (EMBOSS: The European Molecular Biology Open Software Suite, Rice et al., 2000, Trends Genet. 16: 276-277), preferably version 5.0.0 or later. The parameters used are gap open penalty of 10, gap extension penalty of 0.5, and the EBLOSUM62 (EMBOSS version of BLOSUM62) substitution matrix. The output of Needle labeled "longest identity" (obtained using the –nobrief option) is used as the percent identity and is calculated as follows:

(Identical Residues×100)/(Length of Alignment–
Total Number of Gaps in Alignment).

The retention of similar residues may also or alternatively be measured by a similarity score, as determined by use of a BLAST program (e.g., BLAST 2.2.8 available through the NCBI using standard settings BLOSUM62, Open Gap=11 and Extended Gap=1). Suitable variants typically exhibit at least about 45%, such as at least about 55%, at least about 65%, at least about 75%, at least about 85%, at least about 90%, at least about 95%, or more (e.g., about 99%) similarity to the parent sequence.

The term "internalized" or "internalization" as used herein, refers to a biological process in which molecules such as the antibody according to the present invention, are engulfed by the cell membrane and drawn into the interior of the cell. Internalization may also be referred to as "endocytosis".

Multispecific Antibodies

In a first aspect, the invention relates to a multispecific antibody comprising at least (i) a FAPα binding region comprising a first heavy chain variable region and a first light chain variable region; and (ii) a DR4 binding region comprising a second heavy chain variable region and a second light chain variable region. In one embodiment, the FAPα binding region is capable of binding to FAPα. In a further embodiment, the DR4 binding region is capable of binding to DR4.

In a further aspect, the invention relates to a multispecific antibody comprising at least: (i) a FAPα binding region capable of binding to FAPα comprising a first heavy chain variable region and a first light chain variable region; and (ii) a DR4 binding region capable of binding to DR4 comprising a second heavy chain variable region and a second light chain variable region.

The present invention further provides a multispecific antibody as described herein, wherein said multispecific antibody is a bispecific antibody with monovalent binding to FAPα and monovalent binding to DR4. In a further aspect, the present invention relates to a bispecific antibody having monovalent binding to FAPα (e.g. one Fab arm binding to FAPα) and monovalent binding to DR4 (e.g. one Fab arm binding to DR4).

As known to the skilled person, each antigen-binding region of an antibody generally comprise a heavy chain variable region (VH) and a light chain variable region (VL), and each of the variable regions comprises three CDR sequences, CDR1, CDR2 and CDR3, respectively, and may comprise four framework sequences, FR1, FR2, FR3 and FR4, respectively. This structure is preferably also found in the antibodies according to the present invention. In one embodiment, one, two, three or all of said four framework sequences are human framework sequences. CDR1, CDR2 and CDR3 regions can be identified from variable heavy and light chain regions using methods known in the art.

The FAPα binding region of the multispecific antibody may comprise a heavy chain variable region (VH) comprising the three complementarity determining regions, CDR1, CDR2, and CDR3, present within the amino acid sequence set forth in SEQ ID NO: 13. The FAPα binding region of the multispecific antibody may also comprise a light chain variable region (VL) comprising the three complementarity determining regions, CDR1, CDR2, and CDR3, present within the amino acid sequence set forth in SEQ ID NO: 14. In one embodiment, the FAPα binding region of the multispecific antibody as described herein comprises a heavy chain variable region (VH) comprising the three complementarity determining regions, CDR1, CDR2, and CDR3, present within the amino acid sequence set forth in SEQ ID NO: 13, and a light chain variable region (VL) comprising the three complementarity determining regions, CDR1, CDR2, and CDR3, present within the amino acid sequence set forth in SEQ ID NO: 14.

Further disclosed herein are multispecific antibodies, wherein the FAPα binding region comprises a heavy chain variable region (VH) comprising the CDR1, CDR2, and CDR3 sequences of SEQ ID NOs.: 1, 2 and 3, respectively. Also disclosed herein are multispecific antibodies, wherein the FAPα binding region comprises a light chain variable region (VL) comprising the CDR1, CDR2 and CDR3 sequences of SEQ ID NO: 4, the sequence VAS, and SEQ ID NO: 6, respectively. In one embodiment, the FAPα binding region of the multispecific antibody comprises a heavy chain variable region (VH) comprising the CDR1, CDR2, and CDR3 sequences of SEQ ID NOs.: 1, 2 and 3, respectively, and a light chain variable region (VL) comprising the CDR1, CDR2 and CDR3 sequences of SEQ ID NO: 4, the sequence VAS, and SEQ ID NO: 6, respectively. The CDR regions from said variable heavy and light chain regions have been annotated according to IMGT (see Lefranc, M.-P., The Immunologist, 7, 132-136 (1999); Lefranc, Developmental and Comparative Immunology, 27(1), 55-77 (2003)).

The present disclosure further provides a multispecific antibody, wherein the VH sequence of the FAPα binding region has at least 90%, at least 95%, at least 96%, at least 97%, at least 98%, or at least 99% amino acid sequence identity to the amino acid sequence as set forth in SEQ ID NO.: 13. Also, the present disclosure further provides a multispecific antibody, wherein said VL sequence of the FAPα binding region has at least 90%, at least 95%, at least 96%, at least 97%, at least 98%, or at least 99% amino acid sequence identity to the amino acid sequence as set forth in SEQ ID NO.: 14. In a further embodiment, the VH sequence of the FAPα binding region has at least 90%, at least 95%, at least 96%, at least 97%, at least 98%, or at least 99% amino acid sequence identity to the amino acid sequence as set forth in SEQ ID NO.: 13 and said VL sequence of the FAPα binding region has at least 90%, at least 95%, at least 96%, at least 97%, at least 98%, or at least 99% amino acid sequence identity to the amino acid sequence as set forth in SEQ ID NO.: 14.

Furthermore, the multispecific antibody may further comprise framework regions of the VH sequence of the FAPα binding region having at least 90%, at least 95%, at least 96%, at least 97%, at least 98%, or at least 99% amino acid sequence identity to the amino acid sequence as set forth in SEQ ID NO.: 13. Also, the multispecific antibody may further comprise framework regions of the VL sequence of the FAPα binding region having at least 90%, at least 95%, at least 96%, at least 97%, at least 98%, or at least 99% amino acid sequence identity to the amino acid sequence as set forth in SEQ ID NO.: 14. In a further embodiment, the framework regions of the VH sequence of the FAPα binding region has at least 90%, at least 95%, at least 96%, at least 97%, at least 98%, or at least 99% amino acid sequence identity to the amino acid sequence as set forth in SEQ ID NO.: 13 and said framework regions of the VL sequence of the FAPα binding region has at least 90%, at least 95%, at least 96%, at least 97%, at least 98%, or at least 99% amino acid sequence identity to the amino acid sequence as set forth in SEQ ID NO.: 14.

In a further embodiment, the framework regions of the VH sequence of the FAPα binding region of the multispecific antibody as described herein has at least 90%, at least 95%, at least 96%, at least 97%, at least 98%, or at least 99% amino acid sequence identity to the framework regions of the amino acid sequence as set forth in SEQ ID NO.: 13. In an even further embodiment, the framework regions of the VL sequence of the FAPα binding region of the multispecific antibody as described herein has at least 90%, at least 95%, at least 96%, at least 97%, at least 98%, or at least 99% amino acid sequence identity to the framework regions of the amino acid sequence as set forth in SEQ ID NO.: 14. In a still further embodiment, the framework regions of the VH sequence of the FAPα binding region has at least 90%, at least 95%, at least 96%, at least 97%, at least 98%, or at least 99% amino acid sequence identity to the framework regions of the amino acid sequence as set forth in SEQ ID NO.: 13 and said framework regions of the VL sequence of the FAPα binding region has at least 90%, at least 95%, at least 96%, at least 97%, at least 98%, or at least 99% amino acid sequence identity to the framework regions of the amino acid sequence as set forth in SEQ ID NO.: 14.

Furthermore in one embodiment, the multispecific antibody comprises outside the CDR regions, a VH sequence of the FAPα binding region having at least 90%, at least 95%, at least 96%, at least 97%, at least 98%, or at least 99% amino acid sequence identity to the amino acid sequence as set forth in SEQ ID NO.: 13. In a further embodiment, the multispecific antibody comprises outside the CDR regions, a VL sequence of the FAPα binding region having at least 90%, at least 95%, at least 96%, at least 97%, at least 98%, or at least 99% amino acid sequence identity to the amino acid sequence as set forth in SEQ ID NO.: 14. In a further embodiment, the multispecific antibody comprises outside the CDR regions a VH sequence of the FAPα binding region having at least 90%, at least 95%, at least 96%, at least 97%, at least 98%, or at least 99% amino acid sequence identity to the amino acid sequence as set forth in SEQ ID NO.: 13 and outside of the CFR regions a VL sequence of the FAPα binding region having at least 90%, at least 95%, at least 96%, at least 97%, at least 98%, or at least 99% amino acid sequence identity to the amino acid sequence as set forth in SEQ ID NO.: 14.

In a still further embodiment, said VH sequence of the FAPα binding region as set forth in SEQ ID NO.: 13 comprises at the most 10 substitutions, such as at the most 9 substitutions, like at the most 8 substitutions, such as at the most 7 substitutions, like at the most 6 substitutions, such as at the most 5 substitutions, like at the most 4 substitutions, such as at the most 3 substitutions, like at the most 2 substitutions, such as at the most 1 substitution. In a still further embodiment, said VL sequence of the FAPα binding region as set forth in SEQ ID NO.: 14 comprises at the most 10 substitutions, such as at the most 9 substitutions, like at the most 8 substitutions, such as at the most 7 substitutions, like at the most 6 substitutions, such as at the most 5 substitutions, like at the most 4 substitutions, such as at the most 3 substitutions, like at the most 2 substitutions, such as at the most 1 substitution.

Alternatively, said VH sequence of the FAPα binding region deviate from SEQ ID NO.: 13 by at the most 10 substitutions, such as at the most 9 substitution, like at the most 8 substitutions, such as at the most 7 substitutions, like at the most 6 substitutions, such as at the most 5 substitutions, like at the most 4 substitutions, such as at the most 3 substitutions, like at the most 2 substitutions, such as at the most 1 substitution. In a further embodiment, said VL sequence of the FAPα binding region deviate from SEQ ID NO.: 14 by at the most 10 substitutions, such as at the most 9 substitution, like at the most 8 substitutions, such as at the most 7 substitutions, like at the most 6 substitutions, such as at the most 5 substitutions, like at the most 4 substitutions, such as at the most 3 substitutions, like at the most 2 substitutions, such as at the most 1 substitution.

In a still further embodiment, said VH sequence of the FAPα binding region as set forth in SEQ ID NO.: 13 comprises 1-10 substitutions, such as 1-9 substitution, like 1-8 substitutions, such as 1-7 substitutions, like 1-6 substitutions, such as 1-5 substitutions, like 1-4 substitutions, such as 1-3 substitutions, like 1-2 substitutions. In a still further embodiment, said VL sequence of the FAPα binding region as set forth in SEQ ID NO.: 14 comprises 1-10 substitutions, such as 1-9 substitution, like 1-8 substitutions, such as 1-7 substitutions, like 1-6 substitutions, such as 1-5 substitutions, like 1-4 substitutions, such as 1-3 substitutions, like 1-2 substitutions.

In an even further embodiment, the VH and VL sequences of the FAPα binding region only deviate in the framework regions. In one embodiment, the FR1 is defined by amino acid residues 1-25, FR2 is defined by amino acid residues 34-50, FR3 is defined by amino acid residues 58-96 and FR4 is defined by amino acid residues 111-121 in the VH sequence according to SEQ ID NO.: 13. In another embodiment, the FR1 is defined by amino acid residues 1-26, FR2 is defined by amino acid residues 33-49, FR3 is defined by amino acid residues 53-88 and FR4 is defined by amino acid residues 98-107 in the VL sequence according to SEQ ID NO.: 14.

The present disclosure further provides a multispecific antibody, wherein the VH sequence of the FAPα binding region comprises or consists of a VH sequence as set forth in SEQ ID NO.: 13. The present disclosure further provides a multispecific antibody, wherein the VL sequence of the FAPα binding region comprises or consists of a VL sequence as set forth in SEQ ID NO.: 14. In a further embodiment the VH and VL sequences of the FAPα binding region comprise or consist of a VH sequence as set forth in SEQ ID NO.: 13 and a VL sequence as set forth in SEQ ID NO.: 14. In a further embodiment, the VH sequence of the FAPα binding region comprises, consists essentially of or consists of a VH sequence as set forth in SEQ ID NO.: 13. In an even further embodiment, the VL sequence of the FAPα binding region comprises, consists essentially of or consists of a VL sequence as set forth in SEQ ID NO.: 14. In a still further embodiment, the VH and VL sequences of the FAPα binding region comprise, consists essentially of or consist of a VH sequence as set forth in SEQ ID NO.: 13 and a VL sequence as set forth in SEQ ID NO.: 14.

An antibody in the context of the present invention may comprise a FAPα binding region capable of binding to FAPα, wherein FAPα is human FAPα such as the mature polypeptide of SEQ ID NO: 33 or a soluble FAPα of SEQ ID NO: 34; FAPα is mouse FAPα such as the mature polypeptide of SEQ ID NO: 35; FAPα is rat FAPα such as the mature polypeptide of SEQ ID NO: 36; FAPα is dog FAPα such as the mature polypeptide of SEQ ID NO: 37; FAPα is pig FAPα such as the mature polypeptide of SEQ ID NO: 38; or cynomolgus monkey FAPα, such as the mature polypeptide of SEQ ID NO: 39. In a further embodiment, FAPα is human FAPα such as the mature polypeptide of SEQ ID NO: 33 or soluble FAPα of SEQ ID NO: 34; or cynomolgus monkey FAPα, such as the mature polypeptide of SEQ ID NO: 39. In a preferred embodiment, wherein FAPα is human FAPα such as the mature polypeptide of SEQ ID NO: 33.

The antibody in accordance with the invention, may bind with an equilibrium dissociation constant $K_D$ between the antigen-binding region that binds to human FAPα, and human FAPα wherein the $K_D$ is 1000 µM or less, such as 900 µM or less, such as 800 µM or less, such as 700 µM or less, such as 600 µM or less, such as 500 µM or less, such as 400 µM or less, such as 300 µM or less, such as 200 µM or less, such as 100 µM or less, such as 90 µM or less, such as 80 µM or less, such as 70 µM or less, such as 60 µM or less, such as 50 µM or less, such as 40 µM or less, such as 30 µM or less; or within the range of 0.1 µM-1000 µM, such as 0.5-900 µM, such as 1 µM-800 µM, such as 2 µM-700 µM, such as 3 µM-600 µM, such as 4 µM-500 µM, such as 5 µM-400 µM, such as 6 µM-300 µM, such as 7 µM-200 µM, such as 8 µM-100 µM, such as 9 µM-75 µM, such as 10 µM-50 µM. The binding affinity can be determined by biolayer interferometry.

In a further embodiment, the equilibrium dissociation constant $K_D$ of the antigen-binding region for human FAPα is 1000 µM or less, such as 900 µM or less, such as 800 µM or less, such as 700 µM or less, such as 600 µM or less, such as 500 µM or less, such as 400 µM or less, such as 300 µM or less, such as 200 µM or less, such as 100 µM or less, such as 90 µM or less, such as 80 µM or less, such as 70 µM or less, such as 60 µM or less, such as 50 µM or less, such as 40 µM or less, such as 30 µM or less; or within the range of 0.1 µM-1000 µM, such as 0.5-900 µM, such as 1 µM-800 µM, such as 2 µM-700 µM, such as 3 µM-600 µM, such as 4 µM-500 µM, such as 5 µM-400 µM, such as 6 µM-300 µM, such as 7 µM-200 µM, such as 8 µM-100 µM, such as 9 µM-75 µM, such as 10 µM-50 µM, when binding monovalently. The binding affinity can be determined by biolayer interferometry.

Further disclosed herein are multispecific antibodies, wherein the $EC_{50}$ for FAPα binding is in the range of 0.01-0.5 µg/mL, such as in the range of 0.02-0.4 µg/mL, such as in the range of 0.03-0.3 µg/mL when binding to human lung fibroblast or CAFs, e.g. when assayed as described in Example 2 herein.

Further disclosed herein are multispecific antibodies, wherein the $EC_{50}$ for FAPα binding is in the range of 0.01-0.5 µg/mL, such as in the range of 0.02-0.1 µg/mL, such as in the range of 0.03-0.5 µg/mL when monovalently binding to human lung fibroblast, e.g. when assayed as described in Example 2 herein.

Further disclosed herein are multispecific antibodies, wherein the $EC_{50}$ for FAPα binding is in the range of 0.01-0.05 µg/mL, such as in the range of 0.01-0.03 µg/mL, such as in the range of 0.01-0.02 µg/mL when bivalently binding to human lung fibroblast, e.g. when assayed as described in Example 2 herein.

Further disclosed herein are multispecific antibodies, wherein the $EC_{50}$ for FAPα binding is in the range of 0.1-0.5 µg/mL, such as in the range of 0.15-0.4 µg/mL, such as in the range of 0.2-0.3 µg/mL when monovalently binding to CAFs, e.g. when assayed as described in Example 2 herein.

The DR4 binding region of the multispecific antibody may comprise a heavy chain variable region (VH) comprising the three complementarity determining regions, CDR1, CDR2, and CDR3, present within the amino acid sequence set forth in SEQ ID NO: 15.

The DR4 binding region of the multispecific antibody may comprise a light chain variable region (VL) comprising the three complementarity determining regions, CDR1, CDR2, and CDR3, present within the amino acid sequence set forth in SEQ ID NO: 16. In one embodiment, the DR4 binding region of the multispecific antibody comprises a heavy chain variable region (VH) comprising the three complementarity determining regions, CDR1, CDR2, and CDR3, present within the amino acid sequence set forth in SEQ ID NO: 15, and a light chain variable region (VL) comprising the three complementarity determining regions, CDR1, CDR2, and CDR3, present within the amino acid sequence set forth in SEQ ID NO: 16.

Further disclosed herein are multispecific antibodies, wherein the DR4 binding region comprises a heavy chain variable region (VH) comprising the CDR1, CDR2, and CDR3 sequences of SEQ ID NOs.: 7, 8 and 9, respectively. Also disclosed herein are multispecific antibodies, wherein the DR4 binding region comprises a light chain variable region (VL) comprising the CDR1, CDR2 and CDR3 sequences of SEQ ID NO: 10, the sequence EVT and SEQ ID NO: 12, respectively. In a further embodiment, the DR4 binding region of the multispecific antibody comprises a heavy chain variable region (VH) comprising the CDR1, CDR2, and CDR3 sequences of SEQ ID NOs.: 7, 8 and 9, respectively, and a light chain variable region (VL) comprising the CDR1, CDR2 and CDR3 sequences of SEQ ID NO: 10, the sequence EVT and SEQ ID NO: 12, respectively. The CDR regions from said variable heavy and light chain regions have been annotated according to IMGT (see Lefranc, M.-P., The Immunologist, 7, 132-136 (1999); Lefranc, Developmental and Comparative Immunology, 27(1), 55-77 (2003)).

The present disclosure further provides a multispecific antibody, wherein the VH sequence of the DR4 binding region has at least 90%, at least 95%, at least 96%, at least 97%, at least 98%, or at least 99% amino acid sequence identity to the amino acid sequence as set forth in SEQ ID NO.: 15. Also, the present disclosure further provides a multispecific antibody, wherein said VL sequence of the DR4 binding region has at least 90%, at least 95%, at least 96%, at least 97%, at least 98%, or at least 99% amino acid sequence identity to the amino acid sequence as set forth in SEQ ID NO.: 16. In a further embodiment, wherein the VH sequence of the DR4 binding region has at least 90%, at least 95%, at least 96%, at least 97%, at least 98%, or at least 99% amino acid sequence identity to the amino acid sequence as set forth in SEQ ID NO.: 15 and said VL sequence of the DR4 binding region has at least 90%, at least 95%, at least 96%, at least 97%, at least 98%, or at least 99% amino acid sequence identity to the amino acid sequence as set forth in SEQ ID NO.: 16.

Furthermore, the multispecific antibody may further comprise framework regions of the VH sequence of the DR4 binding region has at least 90%, at least 95%, at least 96%, at least 97%, at least 98%, or at least 99% amino acid sequence identity to the amino acid sequence as set forth in SEQ ID NO.: 15. Also, the multispecific antibody may further comprise framework regions of the VL sequence of the DR4 binding region has at least 90%, at least 95%, at least 96%, at least 97%, at least 98%, or at least 99% amino acid sequence identity to the amino acid sequence as set forth in SEQ ID NO.: 16. In a further embodiment, the framework regions of the VH sequence of the DR4 binding region has at least 90%, at least 95%, at least 96%, at least 97%, at least 98%, or at least 99% amino acid sequence identity to the amino acid sequence as set forth in SEQ ID NO.: 15 and said framework regions of the VL sequence of the DR4 binding region has at least 90%, at least 95%, at least 96%, at least 97%, at least 98%, or at least 99% amino acid sequence identity to the amino acid sequence as set forth in SEQ ID NO.: 16.

In a further embodiment, the framework regions of the VH sequence of the DR4 binding region of the multispecific antibody as described herein has at least 90%, at least 95%, at least 96%, at least 97%, at least 98%, or at least 99% amino acid sequence identity to the framework regions of the amino acid sequence as set forth in SEQ ID NO.: 15. In an even further embodiment, the framework regions of the VL sequence of the DR4 binding region as described herein has at least 90%, at least 95%, at least 96%, at least 97%, at least 98%, or at least 99% amino acid sequence identity to the framework regions of the amino acid sequence as set forth in SEQ ID NO.: 16. In a still further embodiment, the framework regions of the VH sequence of the DR4 binding region has at least 90%, at least 95%, at least 96%, at least 97%, at least 98%, or at least 99% amino acid sequence identity to the framework regions of the amino acid sequence as set forth in SEQ ID NO.: 15 and said framework regions of the VL sequence of the DR4 binding region has at least 90%, at least 95%, at least 96%, at least 97%, at least 98%, or at least 99% amino acid sequence identity to the framework regions of the amino acid sequence as set forth in SEQ ID NO.: 16.

In a further embodiment, said VH sequence of the DR4 binding region as set forth in SEQ ID NO.: 15 comprises at the most 10 substitutions, such as at the most 9 substitutions, like at the most 8 substitutions, such as at the most 7 substitutions, like at the most 6 substitutions, such as at the most 5 substitutions, like at the most 4 substitutions, such as at the most 3 substitutions, like at the most 2 substitutions, such as at the most 1 substitution. In a still further embodiment, said VL sequence of the DR4 binding region as set forth in SEQ ID NO.: 16 comprises at the most 10 substitutions, such as at the most 9 substitution, like at the most 8 substitutions, such as at the most 7 substitutions, like at the most 6 substitutions, such as at the most 5 substitutions, like at the most 4 substitutions, such as at the most 3 substitutions, like at the most 2 substitutions, such as at the most 1 substitution. In a further embodiment, said VH sequence of the DR4 binding region deviate from SEQ ID NO.: 15 by at the most 10 substitutions, such as at the most 9 substitution, like at the most 8 substitutions, such as at the most 7 substitutions, like at the most 6 substitutions, such as at the most 5 substitutions, like at the most 4 substitutions, such as at the most 3 substitutions, like at the most 2 substitutions, such as at the most 1 substitution. In a still further embodiment, said VL sequence of the DR4 binding region deviate from SEQ ID NO.: 16 by at the most 10 substitutions, such as at the most 9 substitution, like at the most 8 substitutions, such as at the most 7 substitutions, like at the most 6 substitutions, such as at the most 5 substitutions, like at the most 4 substitutions, such as at the most 3 substitutions, like at the most 2 substitutions, such as at the most 1 substitution.

In an even further embodiment, the VH and VL sequences of the DR4 binding region only deviate in the framework regions. In one embodiment, the FR1 is defined by amino acid residues 1-25, FR2 is defined by amino acid residues 35-51, FR3 is defined by amino acid residues 59-96 and FR4 is defined by amino acid residues 106-116 in the VH sequence according to SEQ ID NO.: 15. In another embodiment, the FR1 is defined by amino acid residues 1-25, FR2 is defined by amino acid residues 35-51, FR3 is defined by amino acid residues 55-90 and FR4 is defined by amino acid residues 101-110 in the VL sequence according to SEQ ID NO.: 16.

The present disclosure further provides a multispecific antibody, wherein the VH sequence of the DR4 binding region comprises or consists of a VH sequence as set forth in SEQ ID NO.: 15. The present disclosure further provides a multispecific antibody, wherein the VL sequence of the DR4 binding region comprises or consists of a VL sequence as set forth in SEQ ID NO.: 16. In a further embodiment, the VH and VL sequences of the DR4 binding region comprise or consist of a VH sequence as set forth in SEQ ID NO.: 15 and a VL sequence as set forth in SEQ ID NO.: 16. In a further embodiment, the VH sequence of the DR4 binding region comprises, consists essentially of or consists of a VH sequence as set forth in SEQ ID NO.: 15. In an even further embodiment, the VL sequence of the DR4 binding region comprises, consists essentially of or consists of a VL sequence as set forth in SEQ ID NO.: 16. In a still further embodiment, the VH and VL sequences of the DR4 binding region comprise, consists essentially of or consist of a VH sequence as set forth in SEQ ID NO.: 15 and a VL sequence as set forth in SEQ ID NO.: 16.

An antibody in the context of the present invention may comprise a DR4 binding region capable of binding to DR4, wherein DR4 is human DR4, such as the mature polypeptide of SEQ ID NO: 68 and is cynomolgus monkey DR4, such as the mature polypeptide of SEQ ID NO: 69. In a further embodiment, DR4 is human DR4, such as the mature polypeptide of SEQ ID NO: 68.

The antibody in accordance with the invention, may bind with an equilibrium dissociation constant $K_D$ between the antigen-binding region that binds to human DR4, and human DR4, wherein the $K_D$ is 100 nM or less, such as 90 nM or less, such as 80 nM or less, such as 70 nM or less, such as 60 nM or less, such as 50 nM or less, such as 40 nM or less, such as 30 nM or less, such as 20 nM or less, such as 10 nM or less, such as 9 nM or less, such as 8 nM or less, such as 7 nM or less, such as 6 nM or less, such as 5 nM or less, such as 4 nM or less, such as 3 nM or less, such as 2 nM or less, such as 1 nM or less, such as 0.5 nM or less; or within the range of 0.01 nM-10 nM, such as 0.02 nM-9 nM, such as 0.03 nM-8 nM, such as 0.04 nM-7 nM, such as 0.05 nM-6 nM, such as 0.075 nM-5 nM, such as 0.1 nM-4 nM, such as 0.15 nM-3 nM, such as 0.2 nM-2 nM, such as 0.25 nM-1 nM, such as 0.3 nM-0.75 nM (monovalent binding). The binding affinity can be determined by biolayer interferometry.

In a further embodiment, the equilibrium dissociation constant $K_D$ of the antigen-binding region to human DR4 is 100 nM or less, such as 90 nM or less, such as 80 nM or less, such as 70 nM or less, such as 60 nM or less, such as 50 nM or less, such as 40 nM or less, such as 30 nM or less, such as 20 nM or less, such as 10 nM or less, such as 9 nM or less, such as 8 nM or less, such as 7 nM or less, such as 6 nM or less, such as 5 nM or less, such as 4 nM or less, such as 3 nM or less, such as 2 nM or less, such as 1 nM or less, such as 0.5 nM or less; or within the range of 0.01 nM-10 nM, such as 0.02 nM-9 nM, such as 0.03 nM-8 nM, such as 0.04 nM-7 nM, such as 0.05 nM-6 nM, such as 0.075 nM-5 nM, such as 0.1 nM-4 nM, such as 0.15 nM-3 nM, such as 0.2 nM-2 nM, such as 0.25 nM-1 nM, such as 0.3 nM-0.75 nM, when binding monovalently. The binding affinity can be determined by biolayer interferometry.

Further disclosed herein are multispecific antibodies, wherein the $EC_{50}$ for binding to DR4 is in the range of 0.1-3.0 μg/mL, such as in the range of 0.2-2.5 μg/mL, such as in the range of 0.3-2.0 μg/mL when binding to DLD-1, A549, HCT-116, HCT-15, MDA-MB-231 or PANC-1, e.g. when assayed as described in Example 3 herein.

Further disclosed herein are multispecific antibodies, wherein the $EC_{50}$ for binding to DR4 is in the range of 0.1-3.0 μg/mL, such as in the range of 0.25-2.0 μg/mL, such as in the range of 0.3-1.75 μg/mL when monovalently binding to DLD-1, A549, HCT-116, HCT-15, MDA-MB-231 or PANC-1, e.g. when assayed as described in Example 3 herein.

Further disclosed herein are multispecific antibodies, wherein the $EC_{50}$ for binding to DR4 is in the range of 0.1-1.0 μg/mL, such as in the range of 0.1-0.75 μg/mL, such as in the range of 0.1-0.5 μg/mL when bivalently binding to DLD-1, A549, HCT-116, HCT-15, MDA-MB-231 or PANC-1, e.g. when assayed as described in Example 3 herein.

The present disclosure further provides a multispecific antibody being a bispecific antibody. In one embodiment, the antibody comprises (i) a FAPα binding region comprising a first heavy chain variable region and a first light chain variable region, wherein the heavy chain variable region (VH) comprises the CDR1, CDR2, and CDR3 sequences of SEQ ID NOs.: 1, 2 and 3, respectively, and the light chain variable region (VL) comprises the CDR1, CDR2 and CDR3 sequences of SEQ ID NO: 4, the sequence VAS and SEQ ID NO: 6, respectively; and (ii) a DR4 binding region comprising a second heavy chain variable region and a second light chain variable region, wherein the heavy chain variable region (VH) comprising the CDR1, CDR2, and CDR3 sequences of SEQ ID NOs.: 7, 8 and 9, respectively, and the light chain variable region (VL) comprises the CDR1, CDR2 and CDR3 sequences of SEQ ID NO: 10, the sequence EVT and SEQ ID NO: 12, respectively. In a further embodiment, the antibody comprises (i) a FAPα binding region comprising or consisting of a VH sequence as set forth in SEQ ID NO.: 13 and a VL sequence as set forth in SEQ ID NO.: 14, and (ii) a DR4 binding region comprising or consisting of a VH sequence as set forth in SEQ ID NO.: 15 and a VL sequence as set forth in SEQ ID NO.: 16. In another embodiment, said bispecific antibody comprises (i) a FAPα binding region comprising, consisting essentially of or consisting of a VH sequence as set forth in SEQ ID NO.: 13 and a VL sequence as set forth in SEQ ID NO.: 14, and (ii) a DR4 binding region comprising, consisting essentially of or consisting of a VH sequence as set forth in SEQ ID NO.: 15 and a VL sequence as set forth in SEQ ID NO.: 16.

The antibody in accordance with the invention, may bind with an equilibrium dissociation constant $K_D$ between the antigen-binding region that binds to human FAPα, and human FAPα, wherein the $K_D$ is 100 μM or less, and may bind with an equilibrium dissociation constant $K_D$ between the antigen-binding region that binds to human DR4, and human DR4, wherein the $K_D$ is 1 nM or less. The binding affinity can be determined by biolayer interferometry.

The antibody in accordance with the invention, may bind with an equilibrium dissociation constant $K_D$ between the antigen-binding region that binds to human FAPα, and human FAPα, wherein the $K_D$ is 100 μM or less (monovalent binding), and may bind with an equilibrium dissociation constant $K_D$ between the antigen-binding region that binds to human DR4, and human DR4, wherein the $K_D$ is 1 nM or less (monovalent binding). The binding affinity can be determined by biolayer interferometry.

The antibody in accordance with the invention, may bind with an equilibrium dissociation constant $K_D$ between the antigen-binding region that binds to human FAPα, and human FAPα, wherein the $K_D$ is 50 μM or less (monovalent binding), and may bind with an equilibrium dissociation constant $K_D$ between the antigen-binding region that binds to human DR4, and human DR4, wherein the $K_D$ is 0.5 nM or less (monovalent binding). The binding affinity can be determined by biolayer interferometry.

In a further aspect, the present invention relates to a multispecific antibody comprising at least one antigen-binding region capable of binding to FAPα, wherein the antibody is able to compete for binding to FAPα with antibody FAP-ESC11 comprising a heavy chain (HC) comprising the sequence set forth in SEQ ID NO: 50), and a light chain (LC) comprising the sequence set forth in SEQ ID NO: 51, e.g. as disclosed in WO2011040972, and/or to bind simultaneously to FAPα as antibody FAP5 comprising a heavy chain (HC) comprising the sequence set forth in SEQ ID NO: 48, and a light chain (LC) comprising the sequence set forth in SEQ ID NO: 49, e.g. as disclosed in US20090304718.

Antibody Formats

The multispecific antibody of the invention may have two or more specificities, such as two or three or more specificities. Furthermore, the multispecific antibody may have more than one copy of the antigen-binding region for FAPα and/or DR4. For example, in one embodiment, the antibody has two antigen-binding regions capable of binding FAPα, such as two identical binding regions that bind FAPα. For example, in another embodiment, the antibody has two antigen-binding regions that bind DR4, such as two identical binding regions that bind DR4. An additional antigen-binding region may e.g. be present in the form of a scFv covalently linked to the constant region.

In a preferred embodiment, the multispecific antibody of the invention is a bispecific antibody. Many different formats and uses of bispecific antibodies are known in the art, and were reviewed by Kontermann; Drug Discov Today, 2015 July; 20(7): 838-47 and; MAbs, 2012 March-April; 4(2): 182-97 and by Labrijn et al. 2019 Nat Rev Drug Discov 18(8) 585-608. A bispecific antibody according to the present invention may not be limited to any particular bispecific format or method of producing it.

Examples of bispecific antibody molecules which may be used in the present invention comprise (i) a single antibody that has two arms comprising different antigen-binding regions; (ii) a single chain antibody that has specificity to two different targets, e.g., via two scFvs linked in tandem by an extra peptide linker; (iii) a dual-variable-domain antibody (DVD-Ig), where each light chain and heavy chain contains two variable domains in tandem through a short peptide linkage (Wu et al., Generation and Characterization of a Dual Variable Domain Immunoglobulin (DVD-Ig™) Molecule, In: Antibody Engineering, Springer Berlin Heidelberg (2010)); (iv) a chemically-linked bispecific (Fab')2 fragment; (v) a Tandab, which is a fusion of two single chain diabodies resulting in a tetravalent bispecific antibody that has two binding sites for each of the target antigens; (vi) a flexibody, which is a combination of scFvs with a diabody resulting in a multivalent molecule; (vii) a so-called "dock and lock" molecule, based on the "dimerization and docking domain" in Protein Kinase A, which, when applied to Fabs, can yield a trivalent bispecific binding protein consisting of two identical Fab fragments linked to a different Fab fragment; (viii) a so-called Scorpion molecule, comprising, e.g., two scFvs fused to both termini of a human Fab-arm; and (ix) a diabody.

Further examples of different classes of bispecific antibodies include but are not limited to (i) IgG-like molecules with complementary CH3 domains to force heterodimerization; (ii) recombinant IgG-like dual targeting molecules, wherein the two sides of the molecule each contain the Fab fragment or part of the Fab fragment of at least two different antibodies; (iii) IgG fusion molecules, wherein full length IgG antibodies are fused to extra Fab fragment or parts of Fab fragment; (iv) Fc fusion molecules, wherein single chain Fv molecules or stabilized diabodies are fused to heavy-chain constant-domains, Fc-regions or parts thereof; (v) Fab fusion molecules, wherein different Fab-fragments are fused together, fused to heavy-chain constant-domains, Fc-regions or parts thereof; and (vi) scFv- and diabody-based and heavy chain antibodies (e.g., domain antibodies, Nanobodies™) wherein different single chain Fv molecules or different diabodies or different heavy-chain antibodies (e.g. domain antibodies, Nanobodies™) are fused to each other or to another protein or carrier molecule fused to heavy-chain constant-domains, Fc-regions or parts thereof.

Examples of IgG-like molecules with complementary CH3 domain molecules include but are not limited to the Triomab/Quadroma molecules (Trion Pharma/Fresenius Biotech; Roche, WO2011069104), the so-called Knobs-into-Holes molecules (Genentech, WO9850431), CrossMAbs (Roche, WO2011117329) and the electrostatically-matched molecules (Amgen, EP1870459 and WO2009089004; Chugai, US201000155133; Oncomed, WO2010129304), the LUZ-Y molecules (Genentech, Wranik et al. J. Biol. Chem. 2012, 287(52): 43331-9, doi: 10.1074/jbc.M112.397869. Epub 2012 November 1), DIG-body and PIG-body molecules (Pharmabcine, WO2010134666, WO2014081202), the Strand Exchange Engineered Domain body (SEEDbody) molecules (EMD Serono, WO2007110205), the Biclonics molecules (Merus, WO2013157953), FcAAdp molecules (Regeneron, WO201015792), bispecific IgG1 and IgG2 molecules (Pfizer/Rinat, WO11143545), Azymetric scaffold molecules (Zymeworks/Merck, WO2012058768), mAb-Fv molecules (Xencor, WO2011028952), bivalent bispecific antibodies (WO2009080254) and the DuoBody® molecules (Genmab A/S, WO2011131746).

Examples of recombinant IgG-like dual targeting molecules include but are not limited to Dual Targeting (DT)-Ig molecules (WO2009058383), Two-in-one Antibody (Genentech; Bostrom, et al 2009. Science 323, 1610-1614.), Cross-linked Mabs (Karmanos Cancer Center), mAb2 (F-Star, WO2008003116), Zybody molecules (Zyngenia; LaFleur et al. MAbs. 2013 March-April; 5(2): 208-18), approaches with common light chain (Crucell/Merus, U.S. Pat. No. 7,262,028), kappa/lambda Body™ molecules (NovImmune, WO2012023053) and CovX-body (CovX/Pfizer; Doppalapudi, V. R., et al 2007. Bioorg. Med. Chem. Lett. 17,501-506.).

Examples of IgG fusion molecules include but are not limited to Dual Variable Domain (DVD)-Ig molecules (Abbott, U.S. Pat. No. 7,612,181), Dual domain double head antibodies (Unilever; Sanofi Aventis, WO20100226923), IgG-like Bispecific molecules (ImClone/Eli Lilly, Lewis et al. Nat Biotechnol. 2014 February; 32(2): 191-8), Ts2Ab (MedImmune/AZ; Dimasi et al. J Mol Biol. 2009 October 30; 393(3): 672-92) and BsAb molecules (Zymogenetics, WO2010111625), HERCULES molecules (Biogen Idec, U.S. Ser. No. 00/795,1918), scFv fusion molecules (Novartis), scFv fusion molecules (Changzhou Adam Biotech Inc, CN 102250246) and TvAb molecules (Roche, WO2012025525, WO2012025530).

Examples of Fc fusion molecules include but are not limited to scFv/Fc Fusions (Pearce et al., Biochem Mol Biol Int. 1997 September; 42(6): 1179-88), SCORPION molecules (Emergent BioSolutions/Trubion, Blankenship J W, et al. AACR 100th Annual meeting 2009 (Abstract #5465); Zymogenetics/BMS, WO2010111625), Dual Affinity Retargeting Technology (Fc-based DART) molecules (MacroGenics, WO2008157379, WO2010080538) and Dual(scFv) 2-Fab molecules (National Research Center for Antibody Medicine—China).

Examples of Fab fusion bispecific antibodies include but are not limited to F(ab)2 molecules (Medarex/AMGEN; Deo et al J Immunol. 1998 Feb. 15; 160(4): 1677-86.), Dual-Action or Bis-Fab molecules (Genentech, Bostrom, et al 2009. Science 323, 1610-1614.), Dock-and-Lock (DNL) molecules (ImmunoMedics, WO2003074569, WO2005004809), Bivalent Bispecific molecules (Biotecnol, Schoonjans, J Immunol. 2000 December 15; 165(12): 7050-7.) and Fab-Fv molecules (UCB-Celltech, WO2009040562 A1).

Examples of scFv-, diabody-based and domain antibodies include but are not limited to Bispecific T Cell Engager (BiTE) molecules (Micromet, WO2005061547), Tandem Diabody molecules (TandAb) (Affimed) (Le Gall et al., Protein Eng Des Sel. 2004 April; 17(4): 357-66.), DART molecules (MacroGenics, WO2008157379, WO2010080538), Single-chain Diabody molecules (Lawrence, FEBS Lett. 1998 Apr. 3; 425(3): 479-84), TCR-like Antibodies (AIT, ReceptorLogics), Human Serum Albumin scFv Fusion (Merrimack, WO2010059315) and COMBODY molecules (Epigen Biotech, Zhu et al. Immunol Cell Biol. 2010 August; 88(6): 667-75.), dual targeting Nanobodies™ (Ablynx, Hmila et al., FASEB J. 2010) and dual targeting heavy chain only domain antibodies.

In one embodiment, the bispecific antibody of the present invention is a diabody, a cross-body, or a bispecific antibody obtained via a controlled Fab-arm exchange (such as described in WO2011131746 (Genmab)).

In one embodiment, the antibody of the present invention is a bispecific DuoBody® molecule (Genmab A/S, WO2011131746).

The multispecific, such as bispecific, antibody of the invention can be of any isotype. Exemplary isotypes include but are not limited to either of the human IgG1, IgG2, IgG3, and IgG4 isotypes. Preferably, the antibodies may be selected to be of the human IgG1 isotype, as shown in the examples. Thus, in one embodiment, the multispecific antibody is an IgG1 antibody. Either of the human light chain constant regions, kappa or lambda, or both may be used, e.g. the sequences set forth in SEQ ID NOs: 27 and 28. In one embodiment, the multispecific antibody comprises a kappa (κ) and a lambda (λ) light chain. For example, in one embodiment, the light chain involved in FAPα binding comprises a kappa constant region and the light chain involved in DR4 binding comprises a lambda constant region. In a further embodiment, said multispecific antibody comprises a heavy chain and a kappa (κ) light chain which comprise the FAPα binding region and a heavy chain and a lambda (λ) light chain which comprise the DR4 binding region. In one embodiment, both heavy chains of an antibody of the present invention are of the IgG1 isotype. In a further embodiment, the two heavy chains of a bispecific antibody are of the IgG1 and IgG4 isotypes, respectively. In a still further embodiment, said DR4 binding region is comprised in an heavy chain and a light chain, said heavy chain comprising said VH region and an IgG1 heavy chain constant region and said light chain comprising said VL region and a lambda light chain constant region; and wherein said FAPα binding region is comprised in a heavy chain and a light chain, said heavy chain comprising said VH region and an IgG1 heavy chain constant region and said light chain comprising said VL region and a kappa light chain constant region. In an even further embodiment, one IgG1 heavy chain constant region is as defined in SEQ ID NO.: 26 and the other is as defined in SEQ ID NO.: 70 and said kappa light chain constant region is as defined in SEQ ID NO.: 27 and said lambda light chain constant region is as defined in SEQ ID NO.: 28.

Preferably, bispecific antibodies may be selected to be of the human IgG1 isotype, as shown in the examples. Optionally, and preferably, the heavy chain and Fc region sequences thereof of the selected isotype, may be modified, preferably in the hinge, CH2 and/or CH3 region, to enable the generation of bispecific antibodies and/or introduce inertness.

In one embodiment, the multispecific antibody of the invention comprises an Fc region consisting of a first and second Fc polypeptide.

In one embodiment, the first Fc polypeptide and the first heavy chain variable region are comprised within the same polypeptide chain and the second Fc polypeptide and the second heavy chain variable region are comprised within the same polypeptide chain.

The first and second Fc polypeptide may each be of any isotype, including any human isotype, such as an IgG1, IgG2, IgG3, IgG4, IgE, IgD, IgM, or IgA isotype or a mixed isotype. Preferably, the Fc region is a human IgG1, IgG2, IgG3, IgG4 isotype or a mixed isotype. In one embodiment, said Fc region is a human IgG1 Fc region.

In a further embodiment, the multispecific antibody is a full-length antibody as defined herein. In a still further embodiment, the multispecific antibody is a full-length IgG1 antibody. In an even further embodiment, said first and second Fc regions, except for the specified mutations as defined herein, comprise the sequence of SEQ ID NO.: 21 (IgG1m(f)).

Antibodies according to the present invention may comprise modifications in the Fc region to render the antibody an inert, or non-activating, antibody. Hence, in the antibodies disclosed herein, one or both heavy chains may be modified so that the antibody induces Fc-mediated effector function to a lesser extent relative to an antibody which is identical, except that it does not comprise said modifications. Thus, in one embodiment, said antibody comprises a first heavy chain and a second heavy chain and wherein one or both heavy chains are modified so that the antibody induces Fc-mediated effector function to a lesser extent relative to an antibody which is identical, except for comprising non-modified first and second heavy chains. The Fc-mediated effector function may be measured by binding to Fcγ receptors, by binding to C1q, or by induction of Fc-mediated cross-linking of FcγRs. In particular, modifications of the heavy and light chain constant sequences may also result in reduced binding of C1q to said antibody. As compared to an unmodified antibody the reduction may be by at least 70%, at least 80%, at least 90%, at least 95%, at least 97%, or 100% and the C1q binding may be determined by ELISA. Further, the Fc region which may be modified so that said antibody mediates reduced Fc-mediated T-cell proliferation compared to an unmodified antibody by at least 50%, at least 60%, at least 70%, at least 80%, at least 90%, at least 99% or 100%, for example in a linear part of the curve, wherein said T-cell proliferation is measured in a PBMC-based functional assay. In one embodiment the multispecific antibody induces Fc-mediated effector function to less than 95%, such as less than 90%, like less than 85%, such as less than 80%, like less than 75%, such as less than 70%, like less than 65%, such as less than 60%, like less than 55%, such as less than 50% of an antibody which is identical, except for comprising non-modified first and second heavy chains.

A wide range of different non-activating antibody formats have been developed in which amino acid substitutions, and combinations thereof, have been introduced in the constant heavy chain region of an IgG1 isotype antibody to eliminate Fc-mediated effector functions (e.g. Chiu et al., Antibodies 2019 December; 8(4): 55; Liu et al., Antibodies, 2020 November 17; 9(4): 64; 29(10): 457-66; Shields et al., J Biol Chem. 2001 March 2; 276(9): 6591-604). In one embodiment, the multispecific antibody comprises a first heavy chain and a second heavy chain, wherein in at least one of said first and second heavy chains one or more amino acids in the positions corresponding to positions L234, L235, G236, D265, N297, and P331 in a human IgG1 heavy chain according to Eu numbering, are not L, L, G, D, N, and P, respectively.

Examples of amino acid positions that may be modified, e.g. in an IgG1 isotype antibody include positions L234 and L235. Thus, in one embodiment, the positions corresponding to positions L234 and L235 in a human IgG1 heavy chain according to Eu numbering are F and E, respectively, in said first and/or second heavy chains.

It is understood that in addition to modifications of amino acid positions L234 and L235, further positions may be modified. Thus, in a further embodiment, the first and second Fc polypeptides comprise substitutions of the amino acids corresponding to the amino acids at positions L234 and L235 to F and E, respectively, and the first and/or second Fc polypeptide further comprises a substitution of an amino acid corresponding to the amino acid at position G236 in a human IgG1 heavy chain, wherein the substitution preferably is to R.

In another embodiment, the first and second Fc polypeptides comprise substitutions of the amino acids corresponding to the amino acids at positions L234 and L235 to F and E, respectively, and the first and second Fc polypeptide further comprise a substitution of an amino acid corresponding to the amino acid at position G236 in a human IgG1 heavy chain, wherein the substitution preferably is to R.

In another embodiment, the first and second Fc polypeptides comprise substitutions of the amino acids corresponding to the amino acids at positions L234 and L235 to F and E, respectively, and the first and/or second Fc polypeptide further comprises a substitution of an amino acid corresponding to the amino acid at position D265 in a human IgG1 heavy chain, wherein the substitution preferably is to A.

In another embodiment, the first and second Fc polypeptides comprise substitutions of the amino acids corresponding to the amino acids at positions L234 and L235 to F and E, respectively, and the first and second Fc polypeptide further comprise a substitution of an amino acid corresponding to the amino acid at position D265 in a human IgG1 heavy chain, wherein the substitution preferably is to A.

In another embodiment, one of the first and second Fc polypeptides comprises substitutions of the amino acids corresponding to the amino acids at positions L234, L235 and G236 to F, E and R, respectively, and the other Fc polypeptide comprises substitutions of the amino acids corresponding to the amino acids at positions L234, L235E and D265 to F, E and A, respectively.

For example, constant regions having such Fc region substitutions are provided i.a. in SEQ ID NO. 22-23, which can be compared with SEQ ID NO. 21, which does not have such substitution(s). In one embodiment, the antibody of the invention comprises a sequence selected from the group consisting of SEQ ID NO: 22-23.

In one embodiment, the multispecific or bispecific antibody of the invention comprises an Fc region comprising first and second CH3 regions that are different and are such that the heterodimeric interaction between said first and second CH3 regions is stronger than each of the homodimeric interactions of said first and second CH3 regions. More details on these interactions and how they can be achieved are provided in WO2011131746 and WO2013060867 (Genmab), which are hereby incorporated by reference. Stable, heterodimeric antibodies can be obtained at high yield for instance by so-called Fab-arm exchange as provided in WO 2008/119353 and WO 2011/131746, on the basis of two homodimeric starting antibodies containing only a few, asymmetrical mutations in the CH3 regions.

Hence, in one embodiment, in the first Fc polypeptide, at least one of the amino acids in the positions corresponding to a position selected from the group consisting of: T366, L368, K370, D399, F405, Y407 and K409 in a human IgG1 heavy chain has been substituted, and in the second Fc polypeptide at least one of the amino acids in the positions corresponding to a position selected from the group consisting of: T366, L368, K370, D399, F405, Y407 and K409 in a human IgG1 heavy chain has been substituted, and wherein said substitutions in the first and second Fc polypeptides are not in the same positions, wherein the amino acid positions are as defined by Eu numbering. For example, constant regions having such Fc region substitutions are provided i.a. in SEQ ID NO. 24-25, which can be compared with SEQ ID NO. 21, which does not have such a substitution. In one embodiment, the antibody of the invention comprises a sequence selected from the group consisting of SEQ ID NO: 24-25.

Further disclosed herein are multispecific antibodies, (i) wherein the antibody comprises a first heavy chain and a second heavy chain, said first heavy chain comprising said FAPα binding region and said second heavy chain comprising said DR4 binding region; (ii) wherein each of said first heavy chain and said second heavy chain comprises at least a hinge region, a CH2 and a CH3 region, and (iii) wherein in said first heavy chain at least one of the amino acids in a position corresponding to a position selected from the group consisting of T366, L368, K370, D399, F405, Y407, and K409 (according to Eu numbering) has been substituted, and in said second heavy chain at least one of the amino acids in a position corresponding to a position selected from the group consisting of T366, L368, K370, D399, F405, Y407, and K409 (according to Eu numbering) has been substituted.

Further disclosed herein are multispecific antibodies, (i) wherein the antibody comprises a first heavy chain and a second heavy chain, said first heavy chain comprising said VH region of the FAPα binding region and said second heavy chain comprising said VH region of the DR4 binding region (ii) wherein each of said first heavy chain and said second heavy chain comprises at least a hinge region, a CH2 and a CH3 region, and (iii) wherein in said first heavy chain at least one of the amino acids in a position corresponding to a position selected from the group consisting of T366, L368, K370, D399, F405, Y407, and K409 (in a human IgG1 heavy chain according to Eu numbering) has been substituted, and in said second heavy chain at least one of the amino acids in a position corresponding to a position selected from the group consisting of T366, L368, K370, D399, F405, Y407, and K409 (in a human IgG1 heavy chain according to Eu numbering) has been substituted.

Further disclosed herein are a multispecific antibody, wherein said first heavy chain and said second heavy chain are not substituted at the same positions. Further disclosed are also multispecific antibodies, wherein (i) the amino acid in the position corresponding to F405 (according to Eu numbering) is L in said first heavy chain, and the amino acid in the position corresponding to K409 (according to Eu numbering) is R in said second heavy chain, or (ii) the amino acid in the position corresponding to K409 (according to Eu numbering) is R in said first heavy chain, and the amino acid in the position corresponding to F405 (according to Eu numbering) is L in said second heavy chain. Preferably, the amino acid in the position corresponding to F405 is L in the first Fc polypeptide and the amino acid in the position corresponding to K409 is R in the second Fc polypeptide, or vice versa. Thus, the invention provides an antibody, wherein the amino acid in the position corresponding to F405 in a human IgG1 heavy chain is L in said first Fc polypeptide, and the amino acid in the position corresponding to K409 in a human IgG1 heavy chain is R in said second Fc polypeptide, or vice versa. In a further embodiment, a multispecific antibody is disclosed wherein (i) the amino acid in the position corresponding to F405 (in a human IgG1 heavy chain according to Eu numbering) is L in said first heavy chain, and the amino acid in the position corresponding to K409 (in a human IgG1 heavy chain according to Eu numbering) is R in said second heavy chain, or (ii) the amino acid in the position corresponding to K409 (in a human IgG1 heavy chain according to Eu numbering) is R in said first heavy chain, and the amino acid in the position corresponding to F405 (in a human IgG1 heavy chain according to Eu numbering) is L in said second heavy chain.

Thus, in one embodiment, one of the first and second Fc polypeptides comprises substitutions of the amino acids corresponding to the amino acids at positions L234, L235, G236 and F405 to F, E, R and L, respectively, and the other Fc polypeptide comprises substitutions of the amino acids corresponding to the amino acids at positions L234, L235E, D265 and K409 to F, E, A and R, respectively.

In another embodiment, one of the first and second Fc polypeptides comprises substitutions of the amino acids corresponding to the amino acids at positions L234, L235, G236 and K409 to F, E, R and R, respectively, and the other Fc polypeptide comprises substitutions of the amino acids corresponding to the amino acids at positions L234, L235E, D265 and F405 to F, E, A and L, respectively.

In another embodiment, one of the first and second Fc polypeptides comprises substitutions of the amino acids corresponding to the amino acids at positions L234, L235, G236 and F405 to F, E, R and L, respectively, and the other Fc polypeptide comprises substitutions of the amino acids corresponding to the amino acids at positions L234, L235E, G236 and K409 to F, E, R and R, respectively.

In an even further embodiment, the first Fc polypeptide comprises substitutions of the amino acids corresponding to the amino acids at positions L234, L235, G236 and F405 to F, E, R and L, respectively, and the second Fc polypeptide comprises substitutions of the amino acids corresponding to the amino acids at positions L234, L235E, G236 and K409 to F, E, R and R, respectively.

In another embodiment, one of the first and second Fc polypeptides comprises substitutions of the amino acids corresponding to the amino acids at positions L234, L235, D265 and F405 to F, E, A and L, respectively, and the other Fc polypeptide comprises substitutions of the amino acids corresponding to the amino acids at positions L234, L235E, D265 and K409 to F, E, A and R, respectively.

In an even further embodiment, the first Fc polypeptide comprises substitutions of the amino acids corresponding to the amino acids at positions L234, L235, D265 and F405 to F, E, A and L, respectively, and the second Fc polypeptide comprises substitutions of the amino acids corresponding to the amino acids at positions L234, L235E, D265 and K409 to F, E, A and R, respectively.

In a further embodiment, a multispecific antibody is disclosed, wherein the antibody is a bispecific antibody comprising a first heavy chain and a second heavy chain and wherein the positions corresponding to positions L234, L235, and G236 in a human IgG1 heavy chain according to Eu numbering of both the first heavy chain and the second heavy chain are F, E, and R, respectively, and wherein the position corresponding to F405 in a human IgG1 heavy chain according to Eu numbering of the first heavy chain is L, and the position corresponding to K409 in a human IgG1 heavy chain according to Eu numbering of the second heavy chain is R.

In a further embodiment, one of the first and second heavy chains comprises substitutions of the amino acids corresponding to the amino acids at positions L234, L235 and G236 to F, E and R, respectively, and the other heavy chain comprises substitutions of the amino acids corresponding to the amino acids at positions L234, L235 and D265 to F, E and A, respectively, wherein the amino acid positions are as defined by Eu numbering.

In an even further embodiment, the antibody is a bispecific antibody comprising a first heavy chain and a second heavy chain and wherein one heavy chain comprises substitutions of the amino acids corresponding to the amino acids at positions L234, L235 and G236 to F, E and R, respectively, and the other heavy chain comprises substitutions of the amino acids corresponding to the amino acids at positions L234, L235 and D265 to F, E and A, respectively, and wherein (i) the position corresponding to F405 in a human IgG1 heavy chain according to Eu numbering of the first heavy chain is L, and the position corresponding to K409 in a human IgG1 heavy chain according to Eu numbering of the second heavy chain is R, or (ii) the position corresponding to K409 in a human IgG1 heavy chain according to Eu numbering of the first heavy chain is R, and the position corresponding to F405 in a human IgG1 heavy chain according to Eu numbering of the second heavy chain is L.

In one embodiment, the antibody of the invention comprises or consists of the heavy chain sequences set forth in SEQ ID NO: 17 and 19 and the light chain sequences set forth in SEQ ID NO: 18 and 20.

The present invention further discloses, a multispecific antibody as described herein, comprising a first heavy chain and a first light chain connected via disulfide bridges forming a first binding region that binds to FAPα and (ii) a second heavy chain and a second light chain connected via disulfide bridges forming a second binding region that binds to DR4, wherein i) the first heavy chain comprises the sequence set forth in SEQ ID NO.: 17 and the first light chain comprises the sequence set forth in SEQ ID NO.: 18; and ii) the second heavy chain comprises the sequence set forth in SEQ ID NO.: 19 and the second light chain comprises the sequence set forth in SEQ ID NO.: 20.

The constant region sequences listed in SEQ ID NOs: 21-26 and 70-72 do not include a C-terminal lysine (K). However, in naturally occurring sequences found in humans from which these Fc regions are derived, such a C-terminal lysine may be present as part of the open reading frame. During cell culture production of recombinant antibodies, this terminal lysine may be cleaved off by proteolysis by endogenous carboxypeptidase(s), resulting in a constant region having the same sequence but lacking the C-terminal lysine. For manufacturing purposes of antibodies, the DNA encoding this terminal lysine may be omitted from the sequence such that antibodies are produced without the lysine. Omission of the C-terminal lysine from the sequence encoding the antibody may increase the homogeneity of the antibody with respect to the presence of C-terminal lysine. Antibodies produced from nucleic acid sequences that either do, or do not encode a terminal lysine are substantially identical in sequence and in function since the degree of processing of the C-terminal lysine is typically high when e.g. using antibodies produced in CHO-based production systems (Dick, L. W. et al. Biotechnol. Bioeng. 2008; 100: 1132-1143). Hence, it is understood that antibodies in accordance with the invention can be generated without encoding or having a C-terminal lysine such as listed herein. For manufacturing purposes, antibodies can thus be generated without having a C-terminal lysine.

In one embodiment, the multispecific antibody is a bispecific antibody comprising a first heavy chain and a second heavy chain and wherein the positions corresponding to positions L234 and L235 in a human IgG1 heavy chain according to Eu numbering of both the first heavy chain and the second heavy chain are F and E, respectively, and wherein (i) the position corresponding to F405 in a human IgG1 heavy chain according to Eu numbering of the first heavy chain is L, and the position corresponding to K409 in a human IgG1 heavy chain according to Eu numbering of the second heavy chain is R, or (ii) the position corresponding to K409 in a human IgG1 heavy chain according to Eu numbering of the first heavy chain is R, and the position corresponding to F405 in a human IgG1 heavy chain according to Eu numbering of the second heavy chain is L.

In a further embodiment, the multispecific antibody is a bispecific antibody comprising a first heavy chain and a second heavy chain and wherein the positions corresponding to positions L234, L235, and D265 in a human IgG1 heavy chain according to Eu numbering of both the first heavy chain and the second heavy chain are F, E, and A, respectively, and wherein (i) the position corresponding to F405 in a human IgG1 heavy chain according to Eu numbering of the first heavy chain is L, and the position corresponding to K409 in a human IgG1 heavy chain according to Eu numbering of the second heavy chain is R, or (ii) the position corresponding to K409 in a human IgG1 heavy chain according to Eu numbering of the first heavy chain is R, and the position corresponding to F405 in a human IgG1 heavy chain according to Eu numbering of the second heavy chain is L.

In a still further embodiment, the multispecific antibody is a bispecific antibody comprising a first heavy chain and a second heavy chain and wherein the positions corresponding to positions L234, L235, and G236 in a human IgG1 heavy chain according to Eu numbering of both the first heavy chain and the second heavy chain are F, E, and R, respectively, and wherein (i) the position corresponding to F405 in a human IgG1 heavy chain according to Eu numbering of the first heavy chain is L, and the position corresponding to K409 in a human IgG1 heavy chain according to Eu numbering of the second heavy chain is R, or (ii) the position corresponding to K409 in a human IgG1 heavy chain according to Eu numbering of the first heavy chain is R, and the position corresponding to F405 in a human IgG1 heavy chain according to Eu numbering of the second heavy chain is L.

In an even further embodiment, the multispecific antibody is a bispecific antibody comprising a first heavy chain and a second heavy chain and wherein the positions corresponding to the amino acids at positions L234, L235 and G236 to F, E and R, respectively, and the other Fc polypeptide comprises substitutions of the amino acids corresponding to the amino acids at positions L234, L235 and D265 to F, E and A, respectively, and wherein (i) the position corresponding to F405 in a human IgG1 heavy chain according to Eu numbering of the first heavy chain is L, and the position corresponding to K409 in a human IgG1 heavy chain according to Eu numbering of the second heavy chain is R, or (ii) the position corresponding to K409 in a human IgG1 heavy chain according to Eu numbering of the first heavy chain is R, and the position corresponding to F405 in a human IgG1 heavy chain according to Eu numbering of the second heavy chain is L.

A multispecific antibody in the context of the present invention may comprise a bispecific antibody comprising (i) a first heavy chain and a first light chain comprising a FAPα binding region, wherein the FAPα binding region comprises a first heavy chain variable region and a first light chain variable region, wherein the first heavy chain variable region (VH) comprises the CDR1, CDR2, and CDR3 sequences of SEQ ID NOs.: 1, 2 and 3, respectively, and the first light chain variable region (VL) comprises the CDR1, CDR2 and CDR3 sequences of SEQ ID NO: 4, the sequence VAS and SEQ ID NO: 6, respectively; (ii) a second heavy chain and a second light chain comprising a DR4 binding region, wherein the DR4 binding region comprises a second heavy chain variable region and a second light chain variable region, wherein the second heavy chain variable region (VH) comprises the CDR1, CDR2, and CDR3 sequences of SEQ ID NOs.: 7, 8 and 9, respectively, and the second light chain variable region (VL) comprises the CDR1, CDR2 and CDR3 sequences of SEQ ID NO: 10, the sequence EVT and SEQ ID NO: 12, respectively; (iii) wherein the positions corresponding to positions L234, L235, and G236 in a human IgG1 heavy chain according to Eu numbering of both the first heavy chain and the second heavy chain are F, E, and R, respectively; and (iv) wherein the position corresponding to F405 in a human IgG1 heavy chain according to Eu numbering of the first heavy chain is L, and the position corresponding to K409 in a human IgG1 heavy chain according to Eu numbering of the second heavy chain is R.

A multispecific antibody in context of the present invention may comprise or consist of a bispecific antibody comprising (i) a FAPα heavy chain sequence as set forth in SEQ ID NO.: 17 and a FAPα light chain sequence as set forth in SEQ ID NO.: 18, and (ii) a DR4 heavy chain sequence as set forth in SEQ ID NO.: 19 and a DR4 light chain sequence as set forth in SEQ ID NO.: 20.

In one embodiment, the multispecific antibody as described herein is a bispecific, bivalent antibody. In a further embodiment, said multispecific antibody is a bispecific, bivalent antibody having monovalent binding to FAPα and monovalent binding to DR4.

In alternative embodiments, the multispecific antibody according to the invention in not a classical full-length antibody comprising an Fc region. For example, in one embodiment, the multispecific antibody is an antibody fragment. In further embodiments, (i) the FAPα binding region and/or the DR4 binding region is a Fab, (ii) the FAPα binding region and/or the DR4 binding region is an scFv, (iii) the FAPα binding region is Fab and the DR4 binding region is an scFv, or (iv) the FAPα binding region is an scFv and the DR4 binding region is a Fab.

Binding and Transactivation

Multispecific antibodies, such as bispecific antibodies, as described herein, that can bind to FAPα and DR4, such as human FAPα and human DR4, can advantageously target DR4 on tumor cells and FAPα positive cells, such as CAFs, thereby triggering apoptosis of the tumor cells specifically. In one embodiment, the multispecific antibody is a transactivating antibody. In a further embodiment, the multispecific antibody induces DR4-mediated activation e.g., leading to apoptosis, conditioned by binding to FAPα, such as transbinding to FAPα. Thus, the multispecific antibody is capable of FAPα-dependent DR4 transactivation. This means that the apoptotic effect induced by activation of DR4 upon binding of the multispecific antibody to DR4 is only observed by binding of the antibody to both DR4 and FAPα.

As said, preferably, the multispecific antibody in accordance with the invention is devoid of, or has reduced Fc-mediated effector function, and furthermore, the antibody:
i) is capable of binding to FAPα-expressing fibroblasts, like cancer associated fibroblasts (CAFs) such as described in Examples 2 herein,
ii) is capable of binding to DR4-expressing human tumor cell lines such as described in Examples 3 herein,
iii) is capable of binding in vitro in the presence of one or more DR4-expressing human tumor cell lines selected from the group consisting of DLD-1, A549, HCT-116, HCT-15, MDA-MB-231 and PANC-1; e.g. when assayed as described in Example 3 herein,
iv) is capable of mediating cell death in DR4-expressing human tumor cell lines when in the presence of FAPα-expressing cells, such as FAPα-expressing fibroblasts, when assayed as described in Examples 10 herein,
v) is capable of mediating concentration-dependent cell death in DR4-expressing human tumor cell lines when in the presence of FAPα-expressing cells, such as FAPα-expressing fibroblasts, when assayed as described in Examples 10 herein,
vi) is capable of mediating concentration-dependent cell death in one or more human DR4-expressing tumor cell lines selected from the group consisting of DLD-1 and MDA-MB-231 when in the presence of FAPα-expressing fibroblasts, when assayed as described in Example 10 herein,
vii) is capable of inducing caspase-8 activation in one or more human DR4-expressing tumor cell lines selected from the group consisting of DLD-1 and MDA-MB-231 when in the presence of FAPα-expressing fibroblasts, when assayed as described in Example 10 herein,
viii) is capable of killing CRC-derived organoids in the presence of FAPα-expressing CAFs, e.g. when assayed as described in Example 11 herein,
ix) is capable of anti-tumor activity against pancreatic and gastric tumors, e.g. when assayed as described in Example 12 herein,
x) is capable of anti-tumor and anti-metastatic activity, e.g. when assayed as described in Example 13 herein,
xi) is capable of anti-tumor and anti-metastatic activity against CRC, e.g. when assayed as described in Example 13 herein,
xii) does not exhibit any hepatocyte toxicity, e.g. when assayed as described in Example 14 herein,
xiii) is not capable of binding to C1q, e.g., when assayed as described in Example 18 herein,
xiv) is not capable of binding to FcγRs, such as FcγRIa, FcγRIIa, FcγRIIb, and/or FcγRIIIa, e.g., when assayed as described in Example 18 herein,
xv) is capable of binding FcRn, e.g., when assayed as described in Example 18 herein, and/or
xvi) show pharmacokinetic properties similar to wild-type IgG1, e.g. when assayed as described in Example 19 herein.

Furthermore, the antibody in accordance with the invention may be capable of inducing transactivation-mediated cell death, wherein cytotoxicity is assessed in an in vitro viability assay comprising:
i) providing NIH/3T3 cells transfected to express FAPα mature polypeptide,
ii) providing DR4-expressing tumor cells, such as MDA-MB-231 or DLD-1
iii) combining said NIH/3T3 with said DR4-expressing tumor cells, wherein the ratio of the number of NIH/3T3 cells to the selected tumor cell is 1:2;
iv) providing said antibody in a dilution series to said samples, ranging e.g. from 028 ng/mL to 14,400 ng/mL, and
v) incubating the samples obtained in step iv), e.g. for 72 hours at 37° C.; and subsequently,
vi) assessing the viability of the DR4-expressing tumor cells,
vii) determining the percentage of viable cells for each dilution sample e.g., using a luminescence readout, and
viii) determining the percentage of live cells.

In one embodiment, the antibody is capable of inducing cell death, e.g., transactivation-mediated cell death, of at least 20% at an antibody concentration of 28 ng/ml and/or at least 45%, such as at least 50% at an antibody concentration of 1800 ng/ml.

In a further embodiment, the multispecific antibody according to the present invention does not induce detectable hepatotoxicity. This may be monitored by measuring on liver spheroids consisting e.g. of primary human hepatocytes and non-parenchymal liver cell types, lactic acid dehydrogenase e.g. at day 4, and/or intracellular adenosine triphosphate e.g. at days 6 and/or 7, after exposure to the multispecific antibody.

Nucleic Acid Constructs and Expression Vectors

A further aspect of the invention provides a nucleic acid construct, or a combination of nucleic acid constructs, encoding an antibody as defined herein. For example, in one embodiment, said combination of nucleic acid constructs comprises a first construct encoding the first heavy chain, a second construct encoding the second heavy chain, a third construct encoding the first light chain and a fourth construct encoding the second light chain. Alternatively, said combination of nucleic acid constructs comprises a first construct encoding the first heavy chain and the first light chain and a second construct encoding the second heavy chain and the second light chain.

Another aspect of the invention provides an expression vector, or a combination of expression vectors, comprising the nucleic acid construct(s) as described herein. An expression vector in the context of the present invention may be any suitable vector, including chromosomal, non-chromosomal, and synthetic nucleic acid vectors (a nucleic acid sequence comprising a suitable set of expression control elements). Examples of such vectors include derivatives of SV40, bacterial plasmids, phage DNA, baculovirus, yeast plasmids, vectors derived from combinations of plasmids and phage DNA, and viral nucleic acid (RNA or DNA) vectors. In one embodiment, an anti-FAPα antibody-encoding nucleic acid and/or anti-DR4 antibody-encoding nucleic acid is comprised in a naked DNA or RNA vector, including, for example, a linear expression element (as described in for instance Sykes and Johnston, Nat Biotech 17, 355-59 (1997)), a compacted nucleic acid vector (as described in for instance U.S. Pat. No. 6,077,835 and/or WO 00/70087), a plasmid vector such as pBR322, pUC 19/18, or pUC 118/119, a "midge" minimally-sized nucleic acid vector (as described in for instance Schakowski et al., Mol Ther 3, 793-800 (2001)), or as a precipitated nucleic acid vector construct, such as a $CaPO_4$-precipitated construct (as described in for instance WO 00/46147, Benvenisty and Reshef, PNAS USA 83, 9551-55 (1986), Wigler et al., Cell 14, 725 (1978), and Coraro and Pearson, Somatic Cell Genetics 7, 603 (1981)). Such nucleic acid vectors and the usage thereof are well known in the art (see for instance U.S. Pat. Nos. 5,589,466 and 5,973,972).

In one embodiment, the vector is suitable for expression of the anti-FAPα antibody and/or anti-DR4 antibody in a bacterial cell. Examples of such vectors include expression vectors such as BlueScript (Stratagene), pIN vectors Van Heeke & Schuster, J Biol Chem 264, 5503 5509 (1989), pET vectors (Novagen, Madison WI) and the like).

An expression vector may also or alternatively be a vector suitable for expression in a yeast system. Any vector suitable for expression in a yeast system may be employed. Suitable vectors include, for example, vectors comprising constitutive or inducible promoters such as alpha factor, alcohol oxidase and PGH (reviewed in: F. Ausubel et al., ed. Current Protocols in Molecular Biology, Greene Publishing and Wiley InterScience New York (1987), and Grant et al., Methods in Enzymol 153, 516 544 (1987)).

A nucleic acid construct and/or vector may also comprise a nucleic acid sequence encoding a secretion/localization sequence, which can target a polypeptide, such as a nascent polypeptide chain, to the periplasmic space or into cell culture media. Such sequences are known in the art, and include secretion leader or signal peptides, organelle targeting sequences (e. g., nuclear localization sequences, ER retention signals, mitochondrial transit sequences, chloroplast transit sequences), membrane localization/anchor sequences (e. g., stop transfer sequences, GPI anchor sequences), and the like.

A nucleic acid and/or expression vector may also comprise a nucleic acid sequence encoding a secretion/localization sequence, which can target a polypeptide, such as a nascent polypeptide chain, to the periplasmic space or into cell culture media. Such sequences are known in the art and include secretion leader or signal peptides. The nucleic acid and/or expression vector may comprise any suitable elements facilitating expression, i.e. transcription and/or translation of the nucleic acid such that the components of the (bispecific) antibodies are expressed. The nucleic acid and/or vector be associated with any suitable promoter, enhancer, and other expression-facilitating elements. Examples of such elements include strong expression promoters (e. g., human CMV IE promoter/enhancer as well as RSV, SV40, SL3 3, MMTV, and HIV LTR promoters), effective poly (A) termination sequences, an origin of replication for plasmid product in *E. coli*, an antibiotic resistance gene as selectable marker, and/or a convenient cloning site (e.g., a polylinker). Nucleic acids may also comprise an inducible promoter as opposed to a constitutive promoter such as CMV IE.

In a further aspect, the invention provides a composition comprising a nucleic acid construct or a combination of nucleic acid constructs as defined herein.

Delivery Vehicle

In a further aspect, the invention relates to the administration of nucleic acid constructs encoding an antibody of the invention for in vivo expression. For in vivo expression of the nucleic acid encoding the antibody, said nucleic acid typically is administered in a form suitable for the nucleic acid to enter the cells of the subject. Different methods for delivering a nucleic acid for in vivo expression exist and include both methods involving mechanical and chemical means. For example, such methods may involve electroporation or tattooing the nucleic acid onto the skin (Patel et al., 2018, Cell Reports 25, 1982-1993). Other methods suitable for administration of the nucleic acid to a subject involve administration of the nucleic acid in a suitable formulation.

Thus, the present invention also relates to a delivery vehicle comprising the nucleic acid construct(s) as described herein. In one embodiment, the delivery vehicle may be a particle. In some embodiments said delivery vehicle may be a lipid formulation. The lipids of the formulation may be particle(s), such as a lipid nanoparticle(s) (LNPs). The nucleic acid or combination of nucleic acids of the present may be encapsulated within said particle, e.g. within said LNP. Different lipid formulations suitable for administration of a nucleic acid to a subject for in vivo expression are well known to a person skilled in the art. For example, said lipid formulation may typically comprise lipids, ionizable aminolipids, PEG-lipids, cholesterol or any combination thereof.

Various forms and methods for preparation of lipid formulations suitable for administration of a nucleic acid to a subject for expression of a therapeutic antibody are well known in the art. Examples of such lipid formulations include but are not limited to those described in US20180170866 (Arcturus), EP 2391343 (Arbutus), WO 2018/006052 (Protiva), WO2014152774 (Shire Human Genetics), EP 2 972 360 (Translate Bio), U.S. Ser. No. 10/195,156 (Moderna) and US20190022247 (Acuitas).

Accordingly, in a further aspect, the invention relates to (a) nucleic acid construct(s) according to the invention or a delivery vehicle according to the invention for use as a medicament, preferably for use in the treatment of cancer, such as in the treatment of solid cancers.

Cells and Host Cells

In a further aspect, the invention provides a recombinant host cell capable of producing the multispecific antibody as described herein comprising one or more nucleic acid constructs encoding the antibody as defined herein above, or an expression vector as defined herein above. It is to be understood that the cell may have been obtained by transfecting a host cell with said nucleic acid construct or expression vector, such as a recombinant host cell. In one embodiment, the host cell is an isolated host cell.

The host cell may be of human origin, such as a human embryonic kidney (HEK) cell, such as a HEK/Expi cell. Alternatively, it may be of rodent origin, such as a Chinese hamster ovary cell, such as a CHO/N50 cell or a CHO cell. Further, the host cell may be of bacterial origin.

The host cell may comprise a nucleic acid sequence encoding an antibody of the invention or parts thereof stably integrated into the cellular genome. Alternatively, the cell may comprise a non-integrated nucleic acid, such as a plasmid, cosmid, phagemid, or linear expression element, which comprises a sequence coding for expression of an anti-FAPα antibody and/or an anti-DR4 antibody of the invention or a part thereof. In particular, the host cell may comprise a non-integrated nucleic acid, such as a plasmid, cosmid, phagemid, or linear expression element, which comprises a sequence coding for expression of an anti-FAPα antibody and/or an anti-DR4 antibody or a part thereof.

Compositions, (medical) uses and therapeutical applications

Furthermore, the invention provides for a composition comprising an antibody as defined herein. Preferably, such a composition is a pharmaceutical composition i.e. the antibody is comprised in a pharmaceutically-acceptable carrier.

A pharmaceutical composition may be formulated in accordance with conventional techniques such as those disclosed in Remington: The Science and Practice of Pharmacy, 19th Edition, Gennaro, Ed., Mack Publishing Co., Easton, PA, 1995. A pharmaceutical composition of the present invention may e.g. include diluents, fillers, salts, buffers, detergents (e. g., a nonionic detergent, such as Tween® 20 or Tween® 80), stabilizers (e. g., sugars or protein-free amino acids), preservatives, tissue fixatives, solubilizers, and/or other materials suitable for inclusion in a pharmaceutical composition.

The pharmaceutical composition or the multispecific antibody may be administered by any suitable route and mode in a therapeutically effective amount. In one embodiment, the pharmaceutical composition and/or the multispecific antibody is administered by intravenous injection or infusion.

In a further aspect, the multispecific antibody, the nucleic acid construct(s), the delivery vehicle, the composition or the pharmaceutical composition as described herein is for use as a medicament.

In an even further aspect, the multispecific antibody, the nucleic acid construct(s), the delivery vehicle, the composition or the pharmaceutical composition is for use in the treatment of diseases, such as cancer.

In particular, the bispecific antibodies of the invention may be used for the treatment of various forms of cancer.

Further disclosed herein are multispecific antibodies, nucleic acid constructs, delivery vehicles, compositions or pharmaceutical compositions, which are for use in the treatment of a primary tumor and/or for use in the prevention and/or treatment of metastases.

In one aspect, the invention relates to the multispecific antibody, the nucleic acid construct(s), the delivery vehicle or the pharmaceutical composition for use in treating cancer, wherein the cancer is solid cancer. In one embodiment, the solid cancer is malignant solid cancer such as a malignant solid tumor. In a further embodiment, the malignant solid tumor is an advanced and/or a metastatic solid tumor. In a further embodiment, the malignant solid tumor is a metastatic solid tumor. In one embodiment, the solid cancer is a metastatic cancer. In a further aspect, the invention relates to the use of the multispecific antibody, the nucleic acid construct(s), the delivery vehicle or the pharmaceutical composition. In one embodiment, the cancer is a carcinoma. Examples of cancer, which may be treated are cancers selected from the group of colorectal cancer (CRC), such as colorectal adenocarcinoma; breast cancer, such as triple-negative breast cancer; pancreatic cancer, such as pancreatic ductal adenocarcinoma; gastric cancer and lung cancer, such as non-small cell lung cancer. In particular, cancers selected from the group of pancreatic cancer, gastric cancer and CRC. In a further embodiment, the cancer is selected from the group consisting of colorectal cancer [CRC]; breast cancer, such as triple negative breast cancer [TNBC]; pancreatic cancer, such as pancreatic ductal adenocarcinoma [PDAC]; esophagogastric cancer, such as gastric cancer and esophageal cancer; Head and neck squamous cell carcinoma [HNSCC]; cervical cancer; and lung cancer, such as non-small cell lung cancer [NSCLC].

In one aspect, the present invention provides a method for treating a cancer in a subject, which method comprises administration of a therapeutically effective amount of a multispecific antibody of the present invention. In a further embodiment, the present invention provides a method for treating a disorder involving cells expressing DR4 being in close proximity to cells expressing FAPα, in a subject, which method comprises administration of a therapeutically effective amount of a multispecific antibody of the present invention. DR4-expressing cells being in close proximity to FAPα-expressing cells enable the multispecific antibody according to the present invention of transbinding.

As said, suitable diseases that can be contemplated in methods and uses in accordance with the invention are cancer. Said cancer most preferably is characterized by expression of DR4. Expression of DR4 in a cancer can easily be determined using methods known in the art, such as PCR, immunostaining, or FACS analysis, i.e. detecting expression of DR4 transcript and/or protein. The antibodies as described herein that are capable of binding to human DR4 may be used e.g. in immunostaining and/or FACS analysis or the like. Furthermore, FAPα-expressing cells, such as CAFs, are preferably to be detected in the TME. Thus, in one embodiment, a TME comprises CAFs, and preferably the CAFs express FAPα. Expression of FAPα in the TME may easily be determined using methods known in the art such as PCR, immunostaining, or FACS analysis, i.e. detecting expression of DR4 transcript and/or protein. Preferably, the multispecific antibody, the nucleic acid construct(s), the delivery vehicle or the pharmaceutical composition are used for treatment when the cancer expresses DR4, a tumor microenvironment comprises CAFs, and the CAFs express FAPα.

In a further embodiment, a patient being diagnosed with cancer may be subjected to an assessment of DR4 expression in the cancer cells as well as an assessment of FAPα-expressing cells in the TME, and when DR4 and FAPα are detected, which may be in the range from low to high, such a patient may be selected for treatment with an antibody in accordance with the invention. However, it may not necessarily be a requirement to include such an assessment in selecting a patient for treatment.

In a further aspect the present invention relates to a method of treating cancer comprising administering to a subject in need thereof an effective amount of the multispecific antibody as defined herein, the nucleic acid construct(s) as described herein, the delivery vehicle as described herein, a composition as described herein or the pharmaceutical composition as described herein. In particular, the method may be for treating a solid cancer, a primary tumor and/or metastases. Examples of cancers to be treated may be selected from the group consisting of CRC, breast cancer, pancreatic cancer, gastric cancer and lung cancer. In particular, selected from the group consisting of pancreatic cancer, gastric cancer and colorectal cancer.

In an even further aspect, the present invention relates to the use of a multispecific antibody as described herein in the manufacture of a medicament for the treatment of cancer.

Kits

The invention further provides a kit-of-parts comprising an antibody as disclosed above, such as a kit for use as a companion diagnostic/for identifying within a population of patients, those patients which have a propensity to respond to treatment with an antibody as defined herein above, or for predicting efficacy or anti-tumor activity of said antibody when used in treatment of a patient, the kit comprising an antibody as defined above; and instructions for use of said kit.

In one embodiment, the present invention provides a kit for diagnosis of cancer comprising a container comprising a multispecific FAPαxDR4 antibody, and one or more reagents for detecting cross-linking of FAPα expressing cells and DR4 expressing cells. Reagents may include, for example, fluorescent tags, enzymatic tags, or other detectable tags. The reagents may also include secondary or tertiary antibodies or reagents for enzymatic reactions, wherein the enzymatic reactions produce a product that may be visualized.

In a further aspect, the present invention provides a diagnostic composition comprising an antibody as defined herein. The diagnostic composition may further comprise a dilution buffer.

In a further aspect, the invention relates to a method for detecting whether cross-linking between FAPα- and DR4-expressing cells occurs in a sample derived from a patient, upon administration of a multispecific antibody according to any one of the embodiments as disclosed herein, comprising the steps of: (i) contacting the sample with a multispecific antibody according to any one of the embodiments as disclosed herein under conditions that allow for formation of a complex between said bispecific antibody and the FAPα-expressing cells and the DR4-expressing cells; and (ii) analyzing whether a complex has been formed.

FAPα Antibodies

In a further aspect, the present invention relates to a monospecific antibody and provides an anti-FAPα antibody comprising at least one FAPα binding region, wherein the FAPα binding region comprises a heavy chain variable region (VH) comprising the three complementarity determining regions, CDR1, CDR2, and CDR3, present within the amino acid sequence set forth in SEQ ID NO: 13, and a light chain variable region (VL) comprising the three complementarity determining regions, CDR1, CDR2, and CDR3, present within the amino acid sequence set forth in SEQ ID NO: 14. In one embodiment, the FAPα binding region is capable of binding to FAPα.

In a further aspect, the present invention relates to a monospecific antibody and provides an anti-FAPα antibody comprising at least one FAPα binding region capable of binding to FAPα, wherein the FAPα binding region comprises a heavy chain variable region (VH) comprising the three complementarity determining regions, CDR1, CDR2, and CDR3, present within the amino acid sequence set forth in SEQ ID NO: 13, and a light chain variable region (VL) comprising the three complementarity determining regions, CDR1, CDR2, and CDR3, present within the amino acid sequence set forth in SEQ ID NO: 14.

An anti-FAPα antibody in the context of the present invention relates in a further aspect to an anti-FAPα antibody, wherein the apparent affinity of a monovalent binding anti-FAPα antibody to human FAPα, e.g., expressed by human lung fibroblast, is higher compared to a monovalent binding reference antibody anti-FAP5, such as at least fivefold higher, like at least tenfold higher, e.g., when measured as exemplified in example 2. As known to a person skilled in the art, a lower $EC_{50}$ indicates a higher apparent affinity.

In a further embodiment, maximal binding (max gMFI) of said anti-FAPα antibody, at a concentration of 10 μg/mL, is higher, such as at least 25% higher, like at least 40% higher, compared to the reference antibody anti-FAP5, when said anti-FAPα antibody and said anti-FAP5 antibody are monovalently binding to human FAPα, e.g., expressed by human lung fibroblast, and e.g., when measured as exemplified in example 2.

In a further embodiment, the apparent affinity of the bivalent binding anti-FAPα antibody to human FAPα, e.g., expressed by human lung fibroblast, is higher compared to bivalent binding reference antibody anti-FAP5, such as at least fivefold higher, like at least tenfold higher, e.g., when measured as exemplified in example 2. As known to a person skilled in the art, a lower $EC_{50}$ indicates a higher apparent affinity.

Further disclosed herein are an anti-FAPα antibody, wherein the anti-FAPα antibody comprises a heavy chain variable region (VH) comprising the CDR1, CDR2, and CDR3 sequences of SEQ ID NOs.: 1, 2 and 3, respectively. Further disclosed herein are also anti-FAPα antibodies, wherein the anti-FAPα antibody comprises a light chain variable region (VL) comprising the CDR1, CDR2 and CDR3 sequences of SEQ ID NO: 4, the sequence VAS and SEQ ID NO: 6, respectively. In one embodiment, the anti-FAPα antibody comprises a heavy chain variable region (VH) comprising the CDR1, CDR2, and CDR3 sequences of SEQ ID NOs.: 1, 2 and 3, respectively, and a light chain variable region (VL) comprising the CDR1, CDR2 and CDR3 sequences of SEQ ID NO: 4, the sequence VAS and SEQ ID NO: 6, respectively. The CDR regions from said variable heavy and light chain regions have been annotated according to IMGT (see Lefranc, M.-P., The Immunologist, 7, 132-136 (1999); Lefranc, Developmental and Comparative Immunology, 27(1), 55-77 (2003)).

The present disclosure further provides an anti-FAPα antibody, wherein the VH sequence of the FAPα binding region has at least 90%, at least 95%, at least 96%, at least 97%, at least 98%, or at least 99% amino acid sequence identity to the amino acid sequence as set forth in SEQ ID NO.: 13. Also, the present disclosure further provides an anti-FAPα antibody, wherein said VL sequence of the FAPα binding region has at least 90%, at least 95%, at least 96%, at least 97%, at least 98% or at least 99% amino acid sequence identity to the amino acid sequence as set forth in SEQ ID NO.: 14. In one embodiment, the VH sequence of the FAPα binding region has at least 90%, at least 95%, at least 96%, at least 97%, at least 98%, or at least 99% amino acid sequence identity to the amino acid sequence as set forth in SEQ ID NO.: 13 and said VL sequence of the FAPα binding region has at least 90%, at least 95%, at least 96%, at least 97%, at least 98%, or at least 99% amino acid sequence identity to the amino acid sequence as set forth in SEQ ID NO.: 14.

In a still further embodiment, said VH sequence of the FAPα binding region as set forth in SEQ ID NO.: 13 comprises at the most 10 substitutions, such as at the most 9 substitutions, like at the most 8 substitutions, such as at the most 7 substitutions, like at the most 6 substitutions, such as at the most 5 substitutions, like at the most 4 substitutions, such as at the most 3 substitutions, like at the most 2 substitutions, such as at the most 1 substitution. In a still further embodiment, said VL sequence of the FAPα binding region as set forth in SEQ ID NO.: 14 comprises at the most 10 substitutions, such as at the most 9 substitution, like at the most 8 substitutions, such as at the most 7 substitutions, like at the most 6 substitutions, such as at the most 5 substitutions, like at the most 4 substitutions, such as at the most 3 substitutions, like at the most 2 substitutions, such as at the most 1 substitution. In an even further embodiment, the VH and VL sequences of the anti-FAPα antibody only deviate in the framework regions. In an even further embodiment, said VH sequence of the FAPα binding region deviate from SEQ ID NO.: 13 by at the most 10 substitutions, such as at the most 9 substitution, like at the most 8 substitutions, such as at the most 7 substitutions, like at the most 6 substitutions, such as at the most 5 substitutions, like at the most 4 substitutions, such as at the most 3 substitutions, like at the most 2 substitutions, such as at the most 1 substitution. In a still further embodiment, said VL sequence of the FAPα binding region deviate from SEQ ID NO.: 14 by at the most 10 substitutions, such as at the most 9 substitution, like at the most 8 substitutions, such as at the most 7 substitutions, like at the most 6 substitutions, such as at the most 5 substitutions, like at the most 4 substitutions, such as at the most 3 substitutions, like at the most 2 substitutions, such as at the most 1 substitution.

The anti-FAPα antibody according to the present invention may either be monovalent or bivalent. In one embodiment, the anti-FAPα antibody is monovalent. In another embodiment, the anti-FAPα antibody is a bivalent antibody having two antigen-binding regions capable of binding to human FAPα, preferably said two antigen-binding regions have identical variable region sequences.

An anti-FAPα antibody in the context of the present invention may comprise one or more substitutions in the first and/or second heavy chains hereby comprising an Fc region comprising first and second CH3 regions that are different resulting in a heterodimeric interaction between said first and second CH3 regions or an Fc region comprising first and second CH3 regions that are similar resulting in homodimeric interactions of said first and second CH3 regions. The first and/or second heavy chains of the anti-FAPα antibody may as well comprise modifications in the Fc region to render the antibody an inert, or non-activating, antibody similar to the substitution and modifications described for the multispecific antibody above. Hence, the present disclosure further provides an anti-FAPα antibody, (i) wherein the anti-FAPα antibody comprises a first heavy chain and a second heavy chain, (ii) wherein each of said first heavy chain and a second heavy chain comprises at least a hinge region, a CH2 and a CH3 region, (iii) wherein in said first heavy chain at least one of the amino acids in a position corresponding to a position selected from the group consisting of T366, L368, K370, D399, F405, Y407, and K409 (according to Eu numbering) has been substituted, and in said second heavy chain at least one of the amino acids in a position corresponding to a position selected from the group consisting of T366, L368, K370, D399, F405, Y407, and K409 (according to Eu numbering) has been substituted. Also, the present disclosure further provides an anti-FAPα antibody as described herein, (i) wherein the anti-FAPα antibody comprises a first heavy chain and a second heavy chain, (ii) wherein each of said first heavy chain and said second heavy chain comprises at least a hinge region, a CH2 and a CH3 region, (iii) wherein in said first heavy chain at least one of the amino acids in a position corresponding to a position selected from the group consisting of T366, L368, K370, D399, F405, Y407, and K409 (in a human IgG1 heavy chain according to Eu numbering) has been substituted, and in said second heavy chain at least one of the amino acids in a position corresponding to a position selected from the group consisting of T366, L368, K370, D399, F405, Y407, and K409 (in a human IgG1 heavy chain according to Eu numbering) has been substituted. In a further embodiment, said first heavy chain and said second heavy chain are substituted in the same positions. In a still further embodiment, the anti-FAPα antibody provides (i) the amino acid in the position corresponding to F405 (according to Eu numbering) is L, or (ii) the amino acid in the position corresponding to K409 (according to Eu numbering) is R. In an even further embodiment, the anti-FAPα antibody provides (i) the amino acid in the position corresponding to F405 (according to Eu numbering) being L. In an even further embodiment, (i) the amino acid in the position corresponding to F405 (in a human IgG1 heavy chain according to Eu numbering) is L, or (ii) the amino acid in the position corresponding to K409 (in a human IgG1 heavy chain according to Eu numbering) is R.

The present disclosure further provides an anti-FAPα antibody, wherein said anti-FAPα antibody comprises a first heavy chain and a second heavy chain and wherein one or both heavy chains are modified so that the antibody induces Fc-mediated effector function to a lesser extent relative to an antibody which is identical, except for comprising non-modified first and second heavy chains.

The anti-FAPα antibody may comprise a first heavy chain and a second heavy chain, wherein in at least one of said first heavy chain and said second heavy chain one or more amino acids in the positions corresponding to positions L234, L235, G236, D265, N297, and P331 in a human IgG1 heavy chain according to Eu numbering, are not L, L, G, D, N, and P, respectively. In one embodiment, the anti-FAPα antibody comprises the positions corresponding to positions L234 and L235 in a human IgG1 heavy chain according to Eu numbering are F and E, respectively, in said first heavy chain and said second heavy chains. In a still further embodiment, the positions corresponding to positions L234, L235, and D265 in a human IgG1 heavy chain according to Eu numbering are F, E, and A, respectively, in said first heavy chain and said second heavy chain. In an even further embodiment, the positions corresponding to positions L234, L235, and G236 in a human IgG1 heavy chain according to Eu numbering are F, E, and R, respectively, in said first heavy chain and said second heavy chain.

The present disclosure further provides an anti-FAPα antibody, wherein the anti-FAPα antibody comprises a first heavy chain and a second heavy chain and wherein the positions corresponding to positions L234, L235, and G236 in a human IgG1 heavy chain according to Eu numbering of both the first heavy chain and the second heavy chain are F, E, and R, respectively, and wherein (i) the position corresponding to F405 in a human IgG1 heavy chain according to Eu numbering is L, or (ii) the position corresponding to K409 in a human IgG1 heavy chain according to Eu numbering of the first heavy chain is R.

An anti-FAPα antibody in the context of the present invention may comprise(i) a FAPα binding region, wherein the heavy chain variable region (VH) comprises the CDR1, CDR2, and CDR3 sequences of SEQ ID NOs.: 1, 2 and 3, respectively, and the light chain variable region (VL) comprises the CDR1, CDR2 and CDR3 sequences of SEQ ID NO: 4, the sequence VAS and SEQ ID NO: 6, respectively; (ii) wherein the anti-FAPα antibody comprises a first heavy chain and a second heavy chain and wherein the positions corresponding to positions L234, L235, and G236 in a human IgG1 heavy chain according to Eu numbering of both the first heavy chain and the second heavy chain are F, E, and R, respectively; and (iii) wherein the position corresponding to F405 in a human IgG1 heavy chain according to Eu numbering of the first heavy chain is L, or wherein the position corresponding to K409 in a human IgG1 heavy chain according to Eu numbering of the first heavy chain is R. In one embodiment, the antibody comprises (i) a FAPα binding region, wherein the heavy chain variable region (VH) comprises the CDR1, CDR2, and CDR3 sequences of SEQ ID NOs.: 1, 2 and 3, respectively, and the light chain variable region (VL) comprises the CDR1, CDR2 and CDR3 sequences of SEQ ID NO: 4, the sequence VAS and SEQ ID NO: 6, respectively; (ii) wherein the anti-FAPα antibody comprises a first heavy chain and a second heavy chain and wherein the positions corresponding to positions L234, L235, and G236 in a human IgG1 heavy chain according to Eu numbering of both the first heavy chain and the second heavy chain are F, E, and R, respectively; and (iii) wherein the position corresponding to F405 in a human IgG1 heavy chain according to Eu numbering of the first heavy chain is L.

An anti-FAPα antibody in the context of the present invention may comprise a heavy chain sequence as set forth in SEQ ID NO.: 17 and a light chain sequence as set forth in SEQ ID NO.: 18.

The present disclosure further provides an anti-FAPα antibody, wherein the $EC_{50}$ of the binding of said anti-FAPα antibody to FAPα is in the range of 0.005-0.1 µg/mL, such as in the range of 0.01-0.05 µg/mL, such as in the range of 0.012-0.2 µg/mL when binding to human lung fibroblast or CAFs, e.g. when assayed as described in Example 2 herein.

The present disclosure further provides an anti-FAPα antibody, wherein the $EC_{50}$ of the binding of said anti-FAPα antibody to FAPα is in the range of 0.005-0.1 µg/mL, such as in the range of 0.01-0.05 µg/mL, such as in the range of 0.012-0.2 µg/mL when bivalently binding to human lung fibroblast or CAFs, e.g. when assayed as described in Example 2 herein.

DR4 Antibodies

In a further aspect, the present invention relates to a monospecific antibody and provides an anti-DR4 antibody comprising at least one DR4 binding region, wherein the DR4 binding region comprises a heavy chain variable region (VH) comprising the three complementarity determining regions, CDR1, CDR2, and CDR3, present within the amino acid sequence set forth in SEQ ID NO: 15, and a light chain variable region (VL) comprising the three complementarity determining regions, CDR1, CDR2, and CDR3, present within the amino acid sequence set forth in SEQ ID NO: 16. In one embodiment, the DR4 binding region is capable of binding to DR4.

In a further aspect, the present invention relates to a monospecific antibody and provides an anti-DR4 antibody comprising at least one DR4 binding region capable of binding to DR4, wherein the DR4 binding region comprises a heavy chain variable region (VH) comprising the three complementarity determining regions, CDR1, CDR2, and CDR3, present within the amino acid sequence set forth in SEQ ID NO: 15, and a light chain variable region (VL) comprising the three complementarity determining regions, CDR1, CDR2, and CDR3, present within the amino acid sequence set forth in SEQ ID NO: 16.

An anti-DR4 antibody in the context of the present invention relates in a further aspect to an anti-DR4 antibody, wherein the apparent affinity of the monovalent binding anti-DR4 antibody to human DR4, e.g., expressed by human tumor cell line MDA-MB-231, is higher compared to
 (i) monovalent binding reference antibody IgG1-DR4-chCTB007, such as at least two-fold higher, like at least threefold higher, e.g., when measured as exemplified in example 3; and/or
 (ii) monovalent binding reference antibody IgG1-DR4-T1014A04, such as at least fivefold higher, like at least eightfold higher, e.g., when measured as exemplified in example 3.

As known to a person skilled in the art, a lower $EC_{50}$ indicates a higher apparent affinity.

In a further embodiment, maximal binding (max gMFI) of said anti-DR4 antibody, at a concentration of 90 µg/mL, is higher compared to
 (i) reference antibody IgG1-DR4-chCTB007, such as at least twofold higher, like at least threefold higher; when said anti-DR4 antibody and said IgG1-DR4-chCTB007 antibody are monovalent binding to human DR4, e.g., expressed by human tumor cell line MDA-MB-231, and e.g., when measured as exemplified in example 3; and/or
 (ii) reference antibody IgG1-DR4-T1014A04, such as at least fivefold higher, like at least ninefold higher; when said anti-DR4 antibody and said IgG1-DR4-T1014A04 antibody are monovalent binding to human DR4, e.g., expressed by human tumor cell line MDA-MB-231, and e.g., when measured as exemplified in example 3.

In a further embodiment, the apparent affinity of the bivalent binding anti-DR4 antibody to human DR4, e.g., expressed by human tumor cell line MDA-MB-231, is higher compared to bivalent binding reference antibody IgG1-DR4-T1014A04, such as at least twofold higher, like at least fivefold higher, e.g., when measured as exemplified in example 3. As known to a person skilled in the art, a lower $EC_{50}$ indicates a higher apparent affinity.

In a further embodiment, maximal binding (max gMFI) of said anti-DR4 antibody, at a concentration of 90 µg/mL, is higher, such as at least twofold higher, like at least threefold higher, compared to the reference antibody IgG1-DR4-T1014A04, when said anti-DR4 antibody and said IgG1-DR4-T1014A04 antibody are bivalent binding to human DR4, e.g., expressed by human tumor cell line MDA-MB-231, and e.g., when measured as exemplified in example 3.

Further disclosed herein are anti-DR4 antibodies, wherein the DR4 binding region comprises a heavy chain variable region (VH) comprising the CDR1, CDR2, and CDR3 sequences of SEQ ID NOs.: 7, 8 and 9, respectively. Further disclosed herein are also anti-DR4 antibodies, wherein the DR4 binding region comprises a light chain variable region (VL) comprising the CDR1, CDR2 and CDR3 sequences of SEQ ID NO: 10, the sequence EVT and SEQ ID NO: 12, respectively. In one embodiment, the DR4 binding region comprises a heavy chain variable region (VH) comprising the CDR1, CDR2, and CDR3 sequences of SEQ ID NOs.: 7, 8 and 9, respectively, and a light chain variable region (VL) comprising the CDR1, CDR2 and CDR3 sequences of SEQ ID NO: 10, the sequence EVT and SEQ ID NO: 12, respectively. The CDR regions from said variable heavy and light chain regions have been annotated according to IMGT (see Lefranc, M.-P., The Immunologist, 7, 132-136 (1999); Lefranc, Developmental and Comparative Immunology, 27(1), 55-77 (2003)).

The present disclosure further provides an anti-DR4 antibody, wherein the VH sequence of the DR4 binding region has at least 90%, at least 95%, at least 96%, at least 97%, at least 98%, or at least 99% amino acid sequence identity to the amino acid sequence as set forth in SEQ ID NO.: 15. Also, the present disclosure further provides an anti-DR4 antibody, wherein said VL sequence of the DR4 binding region has at least 90%, at least 95%, at least 96%, at least 97%, at least 98%, or at least 99% amino acid sequence identity to the amino acid sequence as set forth in SEQ ID NO.: 16. In one embodiment, the VH sequence of the DR4 binding region has at least 90%, at least 95%, at least 96%, at least 97%, at least 98%, or at least 99% amino acid sequence identity to the amino acid sequence as set forth in SEQ ID NO.: 15 and said VL sequence of the DR4 binding region has at least 90%, at least 95%, at least 96%, at least 97%, at least 98%, or at least 99% amino acid sequence identity to the amino acid sequence as set forth in SEQ ID NO.: 16.

In a still further embodiment, said VH sequence of the DR4 binding region as set forth in SEQ ID NO.: 15 comprises at the most 10 substitutions, such as at the most 9 substitution, like at the most 8 substitutions, such as at the most 7 substitutions, like at the most 6 substitutions, such as at the most 5 substitutions, like at the most 4 substitutions, such as at the most 3 substitutions, like at the most 2 substitutions, such as at the most 1 substitution. In a still further embodiment, said VL sequence of the DR4 binding region as set forth in SEQ ID NO.: 16 comprises at the most 10 substitutions, such as at the most 9 substitution, like at the most 8 substitutions, such as at the most 7 substitutions, like at the most 6 substitutions, such as at the most 5 substitutions, like at the most 4 substitutions, such as at the most 3 substitutions, like at the most 2 substitutions, such as at the most 1 substitution. In an even further embodiment, the VH and VL sequences only deviate in the framework regions. In an even further embodiment, the said VH sequence of the DR4 binding region deviate from SEQ ID NO.: 15 by at the most 10 substitutions, such as at the most 9 substitution, like at the most 8 substitutions, such as at the most 7 substitutions, like at the most 6 substitutions, such as at the most 5 substitutions, like at the most 4 substitutions, such as at the most 3 substitutions, like at the most 2 substitutions, such as at the most 1 substitution. In a still further embodiment, said VL sequence of the DR4 binding region deviate from SEQ ID NO.: 16 by at the most 10 substitutions, such as at the most 9 substitution, like at the most 8 substitutions, such as at the most 7 substitutions, like at the most 6 substitutions, such as at the most 5 substitutions, like at the most 4 substitutions, like at the most 3 substitutions, like at the most 2 substitutions, like at the most 1 substitution.

The anti-DR4 antibody according to the present invention may either be monovalent or bivalent. In one embodiment, the anti-DR4 antibody is monovalent. In another embodiment, the anti-DR4 antibody is a bivalent antibody having two antigen-binding regions capable of binding to human DR4, preferably wherein said two antigen-binding regions have identical variable region sequences.

An anti-DR4 antibody in the context of the present invention may comprise one or more substitutions in the first and/or second heavy chains hereby comprising an Fc region comprising first and second CH3 regions that are different resulting in a heterodimeric interaction between said first and second CH3 regions or an Fc region comprising first and second CH3 regions that are similar resulting in homodimeric interactions of said first and second CH3 regions. The first and/or second heavy chains of the anti-DR4 antibody may as well comprise modifications in the Fc region to render the antibody an inert, or non-activating, antibody similar to the substitution and modifications described for the multispecific antibody above. Hence, the present disclosure further provides, an anti-DR4 antibody, (i) wherein the anti-DR4 antibody comprises a first heavy chain and a second heavy chain, (ii) wherein each of said first heavy chain and a second heavy chains comprises at least a hinge region, a CH2 and a CH3 region, (iii) wherein in said first heavy chain at least one of the amino acids in a position corresponding to a position selected from the group consisting of T366, L368, K370, D399, F405, Y407, and K409 (according to Eu numbering) has been substituted, and in said second heavy chain at least one of the amino acids in a position corresponding to a position selected from the group consisting of T366, L368, K370, D399, F405, Y407, and K409 (according to Eu numbering) has been substituted. Also, the present disclosure further provides, an anti-DR4 antibody (i) wherein the anti-DR4 antibody comprises a first heavy chain and a second heavy chain, (ii) wherein each of said first heavy chain and said second heavy chain comprises at least a hinge region, a CH2 and a CH3 region, (iii) wherein in said first heavy chain at least one of the amino acids in a position corresponding to a position selected from the group consisting of T366, L368, K370, D399, F405, Y407, and K409 (in a human IgG1 heavy chain according to Eu numbering) has been substituted, and in said second heavy chain at least one of the amino acids in a position corresponding to a position selected from the group consisting of T366, L368, K370, D399, F405, Y407, and K409 (in a human IgG1 heavy chain according to Eu numbering) has been substituted. In a further embodiment, said first heavy chain and said second heavy chain are substituted at the same positions. In a still further embodiment, the anti-DR4 antibody provides (i) the amino acid in the position corresponding to F405 (according to Eu numbering) is L, or (ii) the amino acid in the position corresponding to K409 (according to Eu numbering) is R. In an even further embodiment, the anti-DR4 antibody provides (i) the amino acid in the position corresponding to F405 (in a human IgG1 heavy chain according to Eu numbering) is L, or (ii) the amino acid in the position corresponding to K409 (in a human IgG1 heavy chain according to Eu numbering) is R.

The present disclosure further provides an anti-DR4 antibody, wherein said anti-DR4 antibody comprises a first heavy chain and a second heavy chain and wherein one or both heavy chains are modified so that the antibody induces Fc-mediated effector function to a lesser extent relative to an antibody which is identical, except for comprising non-modified first and second heavy chains.

The anti-DR4 antibody may comprise a first heavy chain and a second heavy chain, wherein in at least one of said first heavy chain and said second heavy chain one or more amino acids in the positions corresponding to positions L234, L235, G236, D265, N297, and P331 in a human IgG1 heavy chain according to Eu numbering, are not L, L, G, D, N, and P, respectively. In one embodiment, the anti-DR4 antibody comprises the positions corresponding to positions L234 and L235 in a human IgG1 heavy chain according to Eu numbering are F and E, respectively, in said first heavy chain and said second heavy chain. In a further embodiment, the positions corresponding to positions L234, L235, and D265 in a human IgG1 heavy chain according to Eu numbering are F, E, and A, respectively, in said first heavy chain and said second heavy chain. In a still further embodiment, the positions corresponding to positions L234, L235, and G236 in a human IgG1 heavy chain according to Eu numbering are F, E, and R, respectively, in said first heavy chain and said second heavy chain.

The present disclosure further provides an anti-DR4 antibody, wherein the anti-DR4 antibody comprises a first heavy chain and a second heavy chain and wherein the positions corresponding to positions L234, L235, and G236 in a human IgG1 heavy chain according to Eu numbering of both the first heavy chain and the second heavy chain are F, E, and R, respectively, and wherein (i) the position corresponding to F405 in a human IgG1 heavy chain according to Eu numbering is L, or (ii) the position corresponding to K409 in a human IgG1 heavy chain according to Eu numbering of the first heavy chain is R.

An anti-DR4 antibody in the context of the present invention may comprise (i) a DR4 binding region, wherein the heavy chain variable region (VH) comprises the CDR1, CDR2, and CDR3 sequences of SEQ ID NOs.: 7, 8 and 9, respectively, and the light chain variable region (VL) comprises the CDR1, CDR2 and CDR3 sequences of SEQ ID NO: 10, the sequence EVT and SEQ ID NO: 12, respectively; (ii) wherein the anti-DR4 antibody comprises a first heavy chain and a second heavy chain and wherein the positions corresponding to positions L234, L235, and G236 in a human IgG1 heavy chain according to Eu numbering of both the first heavy chain and the second heavy chain are F, E, and R, respectively; and (iii) wherein the position corresponding to K409 in a human IgG1 heavy chain according to Eu numbering is R in the first and second heavy chains, or wherein the position corresponding to F405 in a human IgG1 heavy chain according to Eu numbering is L in the first and second heavy chains. In one embodiment, the antibody comprises (i) a DR4 binding region, wherein the heavy chain variable region (VH) comprises the CDR1, CDR2, and CDR3 sequences of SEQ ID NOs.: 7, 8 and 9, respectively, and the light chain variable region (VL) comprises the CDR1, CDR2 and CDR3 sequences of SEQ ID NO: 10, the sequence EVT and SEQ ID NO: 12, respectively; (ii) wherein the anti-DR4 antibody comprises a first heavy chain and a second heavy chain and wherein the positions corresponding to positions L234, L235, and G236 in a human IgG1 heavy chain according to Eu numbering of both the first heavy chain and the second heavy chain are F, E, and R, respectively; and (iii) wherein the position corresponding to K409 in a human IgG1 heavy chain according to Eu numbering is R in the first and second heavy chains.

An anti-DR4 antibody in the context of the present invention may comprise a heavy chain sequence as set forth in SEQ ID NO.: 19 and a light chain sequence as set forth in SEQ ID NO.: 20.

The present disclosure further provides an anti-DR4 antibody, wherein the $EC_{50}$ of the binding of said anti-DR4 antibody to DR4 is in the range of 0.01-1.0 μg/mL, such as in the range of 0.05-0.75 μg/mL, such as in the range of 0.1-0.5 μg/mL when binding to DLD-1, A549, HCT-116, HCT-15, MDA-MB-231 or PANC-1, e.g. when assayed as described in Example 3 herein.

The present disclosure further provides an anti-DR4 antibody, wherein the $EC_{50}$ of the binding of said anti-DR4 antibody to DR4 is in the range of 0.1-2.0 μg/mL, such as in the range of 0.25-1.75 μg/mL, such as in the range of 0.4-1.75 μg/mL, such as in the range of 0.5-1.5 μg/mL when monovalently binding to DLD-1, A549, HCT-116, HCT-15, MDA-MB-231 or PANC-1, e.g. when assayed as described in Example 3 herein.

The present disclosure further provides an anti-DR4 antibody, wherein the $EC_{50}$ of the binding of said anti-DR4 antibody to DR4 is in the range of 0.1-1.0 μg/mL, such as in the range of 0.15-0.75 μg/mL, such as in the range of 0.2-0.5 μg/mL, such as in the range of 0.25-0.4 μg/mL when bivalently binding to DLD-1, A549, HCT-116, HCT-15, MDA-MB-231 or PANC-1, e.g. when assayed as described in Example 3 herein.

Antibody Production

Traditional methods such as the hybrid hybridoma and chemical conjugation methods (Marvin and Zhu (2005) Acta Pharmacol Sin 26:649) can be used in the preparation of the antibodies of the invention including the multispecific and bispecific antibodies. Antibodies may be produced by a method comprising the steps of (a) culturing the recombinant host cell as described herein under conditions wherein the antibody is produced, and (b) isolating the produced antibody from the culture. Co-expression in a host cell of two antibodies, consisting of different heavy and light chains, leads to a mixture of possible antibody products in addition to the desired bispecific antibody, which can then be isolated by, e.g., affinity chromatography or similar methods.

As mentioned, strategies favoring the formation of a functional bispecific, product, upon co-expression of different antibody constructs can also be used, e.g., the method described by Lindhofer et al. (1995 J Immunol 155:219). Fusion of rat and mouse hybridomas producing different antibodies leads to a limited number of heterodimeric proteins because of preferential species-restricted heavy/light chain pairing. Another strategy to promote formation of heterodimers over homodimers is a "knob-into-hole" strategy in which a protuberance is introduced on a first heavy-chain polypeptide and a corresponding cavity in a second heavy-chain polypeptide, such that the protuberance can be positioned in the cavity at the interface of these two heavy chains so as to promote heterodimer formation and hinder homodimer formation. "Protuberances" are constructed by replacing small amino-acid side-chains from the interface of the first polypeptide with larger side chains. Compensatory "cavities" of identical or similar size to the protuberances are created in the interface of the second polypeptide by replacing large amino-acid side-chains with smaller ones (U.S. Pat. No. 5,731,168). EP1870459 (Chugai) and WO2009089004 (Amgen) describe other strategies for favoring heterodimer formation upon co-expression of different antibody domains in a host cell. In these methods, one or more residues that make up the CH3-CH3 interface in both CH3 domains are replaced with a charged amino acid such that homodimer formation is electrostatically unfavorable and heterodimerization is electrostatically favorable. WO2007110205 (Merck) describe yet another strategy, wherein differences between IgA and IgG CH3 domains are exploited to promote heterodimerization.

Another in vitro method for producing bispecific antibodies has been described in WO2008119353 (Genmab), wherein a bispecific antibody is formed by "Fab-arm" or "half-molecule" exchange (swapping of a heavy chain and attached light chain) between two monospecific IgG4- or IgG4-like antibodies upon incubation under reducing conditions. The resulting product is a bispecific antibody having two Fab arms which may comprise different sequences.

A preferred method for preparing the bispecific FAPaxDR4 antibodies of the present invention includes methods described in WO2011131746 and WO13060867 (Genmab) comprising the following steps:

a) providing a first antibody comprising an Fc region, said Fc region comprising a first CH3 region;
b) providing a second antibody comprising a second Fc region, said Fc region comprising a second CH3 region, wherein the first antibody is a FAPα antibody and the second antibody is a DR4 antibody, or vice versa;
wherein the sequences of said first and second CH3 regions are different and are such that the heterodimeric interaction between said first and second CH3 regions is stronger than each of the homodimeric interactions of said first and second CH3 regions;
c) incubating said first antibody together with said second antibody under reducing conditions; and
d) obtaining said bispecific FAPaxDR4 antibody.

Similarly, the invention relates to a method for producing a multispecific, such as a bispecific, antibody according to the invention, comprising a) providing a first homodimeric antibody comprising the FAPα binding region as described herein, and a second homodimeric antibody comprising the DR4 binding region as described herein, said antibodies comprise an Fc region and optionally contain further features described herein,
wherein the sequences of the first and second CH3 regions of the first and second antibodies are different and are such that the heterodimeric interaction between the first and second CH3 regions is stronger than each of the homodimeric interactions of the first and second CH3 regions;

b) incubating the first antibody together with the second antibody under reducing conditions sufficient to allow the cysteines in the hinge regions to undergo disulfide-bond isomerization; and c) obtaining a heterodimeric multispecific antibody of the invention as described herein, comprising the first immunoglobulin heavy chain and the first immunoglobulin light chain of the first antibody and the second immunoglobulin heavy chain and the second immunoglobulin light chain of the second antibody.

In one embodiment, the said first antibody together with said second antibody are incubated under reducing conditions sufficient to allow the cysteines in the hinge region to undergo disulfide-bond isomerization, wherein the heterodimeric interaction between said first and second antibodies in the resulting heterodimeric antibody is such that no Fab-arm exchange occurs at 0.5 mM GSH after 24 hours at 37° C.

Without being limited to theory, in step c), the heavy-chain disulfide bonds in the hinge regions of the parent antibodies are reduced and the resulting cysteines are then able to form inter heavy-chain disulfide bond with cysteine residues of another parent antibody molecule (originally with a different specificity). In one embodiment of this method, the reducing conditions in step c) comprise the addition of a reducing agent, e.g. a reducing agent selected from the group consisting of: 2-mercaptoethylamine (2-MEA), dithiothreitol (DTT), dithioerythritol (DTE), glutathione, tris(2-carboxyethyl)phosphine (TCEP), L-cysteine and beta-mercapto-ethanol, preferably a reducing agent selected from the group consisting of: 2-mercaptoethylamine, dithiothreitol and tris(2-carboxyethyl)phosphine. In a preferred embodiment, the reducing agent is 2-mercaptoethylamine. In a further embodiment, step c) comprises restoring the conditions to become non-reducing or less reducing, for example by removal of a reducing agent, e.g. by desalting.

In a further aspect, the invention relates to a method for producing a multispecific antibody, comprising (a) providing:
  (i) a first antibody being a monospecific anti-FAPα antibody as described herein and a second antibody comprising
     a DR4 binding region comprising a heavy chain variable region (VH) that comprises the CDR1, CDR2, and CDR3 sequences of SEQ ID NOs.: 7, 8 and 9, respectively, and a light chain variable region (VL) that comprises the CDR1, CDR2 and CDR3 sequences of SEQ ID NO: 10, the sequence EVT and SEQ ID NO: 12, respectively;
     wherein the antibody comprises a first heavy chain and a second heavy chain and wherein the positions corresponding to positions L234, L235, and G236 in a human IgG1 heavy chain according to Eu numbering of both the first heavy chain and the second heavy chain are F, E, and R, respectively;
  (ii) a second antibody being a monospecific anti-DR4 antibody as described herein and a first antibody comprising
     a FAPα binding region comprising a heavy chain variable region (VH) that comprises the CDR1, CDR2, and CDR3 sequences of SEQ ID NOs.: 1, 2 and 3, respectively, and a light chain variable region (VL) that comprises the CDR1, CDR2 and CDR3 sequences of SEQ ID NO: 4, the sequence VAS and SEQ ID NO: 6, respectively;
     wherein the antibody comprises a first heavy chain and a second heavy chain and wherein the positions corresponding to positions L234, L235, and G236 in a human IgG1 heavy chain according to Eu numbering of both the first heavy chain and the second heavy chain are F, E, and R, respectively; or
  (iii) a first antibody being a monospecific anti-FAPα antibody as described herein and a second antibody being a monospecific anti-DR4 antibody as described herein;

wherein the sequences of the first and second CH3 regions of the first and second antibodies are different and are such that the heterodimeric interaction between the first and second CH3 regions is stronger than each of the homodimeric interactions of the first and second CH3 regions; wherein preferably the amino acid in the position corresponding to F405 is L in the first CH3 region and the amino acid in the position corresponding to K409 is R in the second CH3 region, or vice versa, (b) incubating the first antibody together with the second antibody under reducing conditions sufficient to allow the cysteines in the hinge regions to undergo disulfide-bond isomerization; and (c) obtaining the multispecific antibody comprising the first immunoglobulin heavy chain and the first immunoglobulin light chain of the first antibody and the second immunoglobulin heavy chain and the second immunoglobulin light chain of the second antibody.

In a further aspect, the invention relates to a method for producing a multispecific antibody, comprising (a) providing
  (i) a first antibody being a monospecific anti-FAPα antibody as described herein and a second antibody comprising
     a DR4 binding region, wherein the heavy chain variable region (VH) comprises the CDR1, CDR2, and CDR3 sequences of SEQ ID NOs.: 7, 8 and 9, respectively, and the light chain variable region (VL) comprises the CDR1, CDR2 and CDR3 sequences of SEQ ID NO: 10, the sequence EVT and SEQ ID NO: 12, respectively;
     wherein the antibody comprises a first heavy chain and a second heavy chain and wherein the positions corresponding to positions L234, L235, and G236 in a human IgG1 heavy chain according to Eu numbering of both the first heavy chain and the second heavy chain are F, E, and R, respectively;
  (ii) a second antibody being a monospecific anti-DR4 antibody as described herein and a first antibody comprising
     a FAPα binding region, wherein the heavy chain variable region (VH) comprises the CDR1, CDR2, and CDR3 sequences of SEQ ID NOs.: 1, 2 and 3, respectively, and the light chain variable region (VL) comprises the CDR1, CDR2 and CDR3 sequences of SEQ ID NO: 4, the sequence VAS and SEQ ID NO: 6, respectively;
     wherein the antibody comprises a first heavy chain and a second heavy chain and wherein the positions corresponding to positions L234, L235, and G236 in a human IgG1 heavy chain according to Eu numbering of both the first heavy chain and the second heavy chain are F, E, and R, respectively; or
  (iii) a first antibody being a monospecific anti-FAPα antibody as described herein and a second antibody being a monospecific anti-DR4 antibody as described herein;

wherein the sequences of the first and second CH3 regions of the first and second antibodies are different and are such that the heterodimeric interaction between the first and second CH3 regions is stronger than each of the homodimeric interactions of the first and second CH3 regions; wherein preferably the amino acid in the position corresponding to F405 is L in the first CH3 region and the amino acid in the position corresponding to K409 is R in the second CH3 region, (b) incubating the first antibody together with the second antibody under reducing conditions sufficient to allow the cysteines in the hinge regions to undergo disulfide-bond isomerization; and (c) obtaining the multispecific antibody comprising the first immunoglobulin heavy chain and the first immunoglobulin light chain of the first antibody and the second immunoglobulin heavy chain and the second immunoglobulin light chain of the second antibody.

In a further aspect, the present invention relates to a method, comprising the steps of
(a) culturing a host cell comprising an expression vector comprising: (i) a nucleic acid sequence encoding a heavy chain sequence of a FAPα binding region as defined herein;
(ii) a nucleic acid sequence encoding a light chain sequence of a FAPα binding region as defined herein; and purifying a first antibody from the culture media;
(b) culturing a host cell comprising an expression vector comprising: (iii) a nucleic acid sequence encoding a heavy chain sequence of a DR4 binding region as defined herein;
(iv) a nucleic acid sequence encoding a light chain sequence of a DR4 binding region as defined herein; and purifying a second antibody from the culture media;
(c) incubating said first antibody with said second antibody under reducing conditions sufficient to allow the cysteines in the hinge region to undergo disulfide-bond isomerization, thereby obtaining a bispecific antibody.

In one embodiment, step c) comprises the addition of a reducing agent. In a further embodiment, step c) comprises the addition of a reducing agent selected from the group consisting of: 2-mercaptoethylamine (2-MEA), dithiothreitol (DTT), dithioerythritol (DTE), glutathione, tris(2-carboxyethyl)phosphine (TCEP), L-cysteine and beta-mercapto-ethanol. In a still further embodiment, step c) comprises the addition of a reducing agent selected from the group consisting of: 2-mercaptoethylamine, dithiothreitol and tris(2-carboxyethyl)phosphine. In an even further embodiment, step c) comprises restoring the conditions to become non-reducing or less reducing, for example by removal of a reducing agent. In a further embodiment, the reducing agent is removed by desalting.

In a further aspect the present invention relates to a multispecific antibody obtained by a method as described herein.

Anti-Idiotypic Antibodies

In a further aspect, the invention relates to an anti-idiotypic antibody which binds to an antibody comprising at least one antigen-binding region capable of binding to DR4 and/or FAPα, i.e. an antibody according to the invention as described herein. In particular embodiments, the anti-idiotypic antibody binds to the antigen-binding region capable of binding to DR4 and/or FAPα.

An anti-idiotypic (Id) antibody is an antibody which recognizes unique determinants generally associated with the antigen-binding site of an antibody. An anti-Id antibody may be prepared by immunizing an animal of the same species and genetic type as the source of the monoclonal antibody, with the monoclonal antibody against which an anti-Id is being prepared. The immunized animal typically can recognize and respond to the idiotypic determinants of the immunizing antibody by producing an antibody to these idiotypic determinants (the anti-Id antibody). Such antibodies are described in for instance U.S. Pat. No. 4,699,880. Such antibodies are further features of the present invention.

An anti-Id antibody may also be used as an "immunogen" to induce an immune response in yet another animal, producing a so-called anti-anti-Id antibody. An anti-anti-Id antibody may be epitopically identical to the original monoclonal antibody, which induced the anti-Id antibody. Thus, by using antibodies to the idiotypic determinants of a monoclonal antibody, it is possible to identify other clones expressing antibodies of identical specificity. Anti-Id antibodies may be varied (thereby producing anti-Id antibody variants) and/or derivatized by any suitable technique, such as those described elsewhere herein with respect to DR4 and/or FAPα-specific antibodies of the present invention. For example, a monoclonal anti-Id antibody may be coupled to a carrier such as keyhole limpet hemocyanin (KLH) and used to immunize BALB/c mice.

Sera from these mice typically will contain anti-anti-Id antibodies that have the binding properties similar, if not identical, to an original/parental antibody.

Sequences

| SEQ ID NO | Sequence Name | Domain | Sequence |
|---|---|---|---|
| 1 | IgG1-FAPα-FERL | VH_CDR1 | GFTFSSYA |
| 2 | IgG1-FAPα-FERL | VH_CDR2 | ISGSGGGR |
| 3 | IgG1-FAPα-FERL | VH_CDR3 | AKEGYSSSGTYWDH |
| 4 | IgG1-FAPα-FERL | VL_CDR1 | QGVSSW |
|  | IgG1-FAPα-FERL | VL_CDR2 | VAS |
| 6 | IgG1-FAPα-FERL | VL_CDR3 | QQANSFPPT |

-continued

| SEQ ID NO | Sequence Name | Domain | Sequence |
|---|---|---|---|
| 7 | IgG1-DR4-FERR | VH_CDR1 | GGSISSYSW |
| 8 | IgG1-DR4-FERR | VH_CDR2 | LYHSGST |
| 9 | IgG1-DR4-FERR | VH_CDR3 | VRGVATIDY |
| 10 | IgG1-DR4-FERR | VL_CDR1 | SSDVGGYNF |
| 11 | IgG1-DR4-FERR | VL_CDR2 | EVT |
| 12 | IgG1-DR4-FERR | VL_CDR3 | SSYAGSNNVM |
| 13 | IgG1-FAPα-FERL | VH | EVQLLESGGGLVQPGGSPRLSCEASGFTFSSYALSWVRQAP GKGLEWVSAISGSGGGRYYADSVKGRFTISRDNSKNTLFLQ MNSLRAEDTAVYYCAKEGYSSSGTYWDHWGQGTLVTVSS |
| 14 | IgG1-FAPα-FERL | VL | AIQMTQSPSSVSASVGDRVTITCRASQGVSSWLAWYQQKPG RAPKLLIYVASTLQSGVPSRFSGSGSGTDFTLTINSLQPED FATYYCQQANSFPPTFGQGTRLEMK |
| 15 | IgG1-DR4-FERR | VH | QVQLQESGPGLVKPSGTLSLTCAVSGGSISSYSWWSWIRQP PGKGLEWIGELYHSGSTNYNPSLKSRVTISVDKSKNQFSLK LRSVTAADTAVYYCVRGVATIDYWGQGTLVTVSS |
| 16 | IgG1-DR4-FERR | VL | QSALTQPPSASGSPGQSVTISCTGTSSDVGGYNFVSWYQQD PGKAPKLLIYEVTKRPSGVPDRFSGSKSGNTASLTVSGLQA EDEADYYCSSYAGSNNVMFGGGTKLTVL |
| 17 | IgG1-FAPα-FERL | Full heavy chain | EVQLLESGGGLVQPGGSPRLSCEASGFTFSSYALSWVRQAP GKGLEWVSAISGSGGGRYYADSVKGRFTISRDNSKNTLFLQ MNSLRAEDTAVYYCAKEGYSSSGTYWDHWGQGTLVTVSSAS TKGPSVFPLAPSSKSTSGGTAALGCLVKDYFPEPVTVSWNS GALTSGVHTFPAVLQSSGLYSLSSVVTVPSSSLGTQTYICN VNHKPSNTKVDKRVEPKSCDKTHTCPPCPAPEFERGPSVFL FPPKPKDTLMISRTPEVTCVVVDVSHEDPEVKFNWYVDGVE VHNAKTKPREEQYNSTYRVVSVLTVLHQDWLNGKEYKCKVS NKALPAPIEKTISKAKGQPREPQVYTLPPSREEMTKNQVSL TCLVKGFYPSDIAVEWESNGQPENNYKTTPPVLDSDGSFLL YSKLTVDKSRWQQGNVFSCSVMHEALHNHYTQKSLSLSPG |
| 18 | IgG1-FAPα-FERL | Full light chain | AIQMTQSPSSVSASVGDRVTITCRASQGVSSWLAWYQQKPG RAPKLLIYVASTLQSGVPSRFSGSGSGTDFTLTINSLQPED FATYYCQQANSFPPTFGQGTRLEMKRTVAAPSVFIFPPSDE QLKSGTASVVCLLNNFYPREAKVQWKVDNALQSGNSQESVT EQDSKDSTYSLSSTLTLSKADYEKHKVYACEVTHQGLSSPV TKSFNRGEC |
| 19 | IgG1-DR4-FERR | Full heavy chain | QVQLQESGPGLVKPSGTLSLTCAVSGGSISSYSWWSWIRQP PGKGLEWIGELYHSGSTNYNPSLKSRVTISVDKSKNQFSLK LRSVTAADTAVYYCVRGVATIDYWGQGTLVTVSSASTKGPS VFPLAPSSKSTSGGTAALGCLVKDYFPEPVTVSWNSGALTS GVHTFPAVLQSSGLYSLSSVVTVPSSSLGTQTYICNVNHKP SNTKVDKRVEPKSCDKTHTCPPCPAPEFERGPSVFLFPPKP KDTLMISRTPEVTCVVVDVSHEDPEVKFNWYVDGVEVHNAK TKPREEQYNSTYRVVSVLTVLHQDWLNGKEYKCKVSNKALP APIEKTISKAKGQPREPQVYTLPPSREEMTKNQVSLTCLVK GFYPSDIAVEWESNGQPENNYKTTPPVLDSDGSFFLYSRLT VDKSRWQQGNVFSCSVMHEALHNHYTQKSLSLSPG |
| 20 | IgG1-DR4-FERR | Full light chain | QSALTQPPSASGSPGQSVTISCTGTSSDVGGYNFVSWYQQD PGKAPKLLIYEVTKRPSGVPDRFSGSKSGNTASLTVSGLQA EDEADYYCSSYAGSNNVMFGGGTKLTVLGQPKAAPSVTLFP PSSEELQANKATLVCLISDFYPGAVTVAWKADSSPVKAGVE TTTPSKQSNNKYAASSYLSLTPEQWKSHRSYSCQVTHEGST VEKTVAPTECS |

Sequences

| SEQ ID NO | Sequence Name | Domain | Sequence |
|---|---|---|---|
| 21 | IgG1 constant region | | ASTKGPSVFPLAPSSKSTSGGTAALGCLVKDYFPEPVTVSW NSGALTSGVHTFPAVLQSSGLYSLSSVVTVPSSSLGTQTYI CNVNHKPSNTKVDKRVEPKSCDKTHTCPPCPAPELLGGPSV FLFPPKPKDTLMISRTPEVTCVVVDVSHEDPEVKFNWYVDG VEVHNAKTKPREEQYNSTYRVVSVLTVLHQDWLNGKEYKCK VSNKALPAPIEKTISKAKGQPREPQVYTLPPSREEMTKNQV SLTCLVKGFYPSDIAVEWESNGQPENNYKTTPPVLDSDGSF FLYSKLTVDKSRWQQGNVFSCSVMHEALHNHYTQKSLSLSP G |
| 22 | IgG1 constant region | with FER substitution (bold) | ASTKGPSVFPLAPSSKSTSGGTAALGCLVKDYFPEPVTVSW NSGALTSGVHTFPAVLQSSGLYSLSSVVTVPSSSLGTQTYI CNVNHKPSNTKVDKRVEPKSCDKTHTCPPCPAPEFERGPSV FLFPPKPKDTLMISRTPEVTCVVVDVSHEDPEVKFNWYVDG VEVHNAKTKPREEQYNSTYRVVSVLTVLHQDWLNGKEYKCK VSNKALPAPIEKTISKAKGQPREPQVYTLPPSREEMTKNQV SLTCLVKGFYPSDIAVEWESNGQPENNYKTTPPVLDSDGSF FLYSKLTVDKSRWQQGNVFSCSVMHEALHNHYTQKSLSLSP G |
| 23 | IgG1 constant region | with FEA substitution (bold) | ASTKGPSVFPLAPSSKSTSGGTAALGCLVKDYFPEPVTVSW NSGALTSGVHTFPAVLQSSGLYSLSSVVTVPSSSLGTQTYI CNVNHKPSNTKVDKRVEPKSCDKTHTCPPCPAPEFEGGPSV FLFPPKPKDTLMISRTPEVTCVVVAVSHEDPEVKFNWYVDG VEVHNAKTKPREEQYNSTYRVVSVLTVLHQDWLNGKEYKCK VSNKALPAPIEKTISKAKGQPREPQVYTLPPSREEMTKNQV SLTCLVKGFYPSDIAVEWESNGQPENNYKTTPPVLDSDGSF FLYSKLTVDKSRWQQGNVFSCSVMHEALHNHYTQKSLSLSP G |
| 24 | IgG1 constant region | with F405L substitution (bold) | ASTKGPSVFPLAPSSKSTSGGTAALGCLVKDYFPEPVTVSW NSGALTSGVHTFPAVLQSSGLYSLSSVVTVPSSSLGTQTYI CNVNHKPSNTKVDKRVEPKSCDKTHTCPPCPAPELLGGPSV FLFPPKPKDTLMISRTPEVTCVVVDVSHEDPEVKFNWYVDG VEVHNAKTKPREEQYNSTYRVVSVLTVLHQDWLNGKEYKCK VSNKALPAPIEKTISKAKGQPREPQVYTLPPSREEMTKNQV SLTCLVKGFYPSDIAVEWESNGQPENNYKTTPPVLDSDGSF LLYSKLTVDKSRWQQGNVFSCSVMHEALHNHYTQKSLSLSP G |
| 25 | IgG1 constant region | with K409R substitution (bold) | ASTKGPSVFPLAPSSKSTSGGTAALGCLVKDYFPEPVTVSW NSGALTSGVHTFPAVLQSSGLYSLSSVVTVPSSSLGTQTYI CNVNHKPSNTKVDKRVEPKSCDKTHTCPPCPAPELLGGPSV FLFPPKPKDTLMISRTPEVTCVVVDVSHEDPEVKFNWYVDG VEVHNAKTKPREEQYNSTYRVVSVLTVLHQDWLNGKEYKCK VSNKALPAPIEKTISKAKGQPREPQVYTLPPSREEMTKNQV SLTCLVKGFYPSDIAVEWESNGQPENNYKTTPPVLDSDGSF FLYSRLTVDKSRWQQGNVFSCSVMHEALHNHYTQKSLSLSP G |
| 26 | IgG1 constant region | with FER substitution and with F405L substitution (bold) | ASTKGPSVFPLAPSSKSTSGGTAALGCLVKDYFPEPVTVSW NSGALTSGVHTFPAVLQSSGLYSLSSVVTVPSSSLGTQTYI CNVNHKPSNTKVDKRVEPKSCDKTHTCPPCPAPEFERGPSV FLFPPKPKDTLMISRTPEVTCVVVDVSHEDPEVKFNWYVDG VEVHNAKTKPREEQYNSTYRVVSVLTVLHQDWLNGKEYKCK VSNKALPAPIEKTISKAKGQPREPQVYTLPPSREEMTKNQV SLTCLVKGFYPSDIAVEWESNGQPENNYKTTPPVLDSDGSF LLYSKLTVDKSRWQQGNVFSCSVMHEALHNHYTQKSLSLSP G |
| 27 | constant region | IgG1 kappa light chain constant region | RTVAAPSVFIFPPSDEQLKSGTASVVCLLNNFYPREAKVQW KVDNALQSGNSQESVTEQDSKDSTYSLSSTLTLSKADYEKH KVYACEVTHQGLSSPVTKSFNRGEC |
| 28 | constant region | IgG1 lambda light chain constant region | GQPKAAPSVTLFPPSSEELQANKATLVCLISDFYPGAVTVA WKADSSPVKAGVETTTPSKQSNNKYAASSYLSLTPEQWKSH RSYSCQVTHEGSTVEKTVAPTECS |
| 29 | IgG1-FAPα-FEAL | Full heavy chain | EVQLLESGGGLVQPGGSPRLSCEASGFTFSSYALSWVRQAP GKGLEWVSAISGSGGGRYYADSVKGRFTISRDNSKNTLFLQ MNSLRAEDTAVYYCAKEGYSSSGTYWDHWGQGTLVTVSSAS TKGPSVFPLAPSSKSTSGGTAALGCLVKDYFPEPVTVSWNS |

-continued

| SEQ ID NO | Sequence Name | Domain | Sequence |
|---|---|---|---|
| | | | GALTSGVHTFPAVLQSSGLYSLSSVVTVPSSSLGTQTYICN VNHKPSNTKVDKRVEPKSCDKTHTCPPCPAPEFEGGPSVFL FPPKPKDTLMISRTPEVTCVVVAVSHEDPEVKFNWYVDGVE VHNAKTKPREEQYNSTYRVVSVLTVLHQDWLNGKEYKCKVS NKALPAPIEKTISKAKGQPREPQVYTLPPSREEMTKNQVSL TCLVKGFYPSDIAVEWESNGQPENNYKTTPPVLDSDGSFLL YSKLTVDKSRWQQGNVFSCSVMHEALHNHYTQKSLSLSPG |
| 30 | IgG1-DR4-FEAR | Full heavy chain | QVQLQESGPGLVKPSGTLSLTCAVSGGSISSYSWWSWIRQP PGKGLEWIGELYHSGSTNYNPSLKSRVTISVDKSKNQFSLK LRSVTAADTAVYYCVRGVATIDYWGQGTLVTVSSASTKGPS VFPLAPSSKSTSGGTAALGCLVKDYFPEPVTVSWNSGALTS GVHTFPAVLQSSGLYSLSSVVTVPSSSLGTQTYICNVHKP SNTKVDKRVEPKSCDKTHTCPPCPAPEFEGGPSVFLFPPKP KDTLMISRTPEVTCVVVAVSHEDPEVKFNWYVDGVEVHNAK TKPREEQYNSTYRVVSVLTVLHQDWLNGKEYKCKVSNKALP APIEKTISKAKGQPREPQVYTLPPSREEMTKNQVSLTCLVK GFYPSDIAVEWESNGQPENNYKTTPPVLDSDGSFFLYSRLT VDKSRWQQGNVFSCSVMHEALHNHYTQKSLSLSPG |
| 31 | IgG1-FAPα-F405L | Full heavy chain | EVQLLESGGGLVQPGGSPRLSCEASGFTFSSYALSWVRQAP GKGLEWVSAISGSGGGRYYADSVKGRFTISRDNSKNTLFLQ MNSLRAEDTAVYYCAKEGYSSSGTYWDHWGQGTLVTVSSAS TKGPSVFPLAPSSKSTSGGTAALGCLVKDYFPEPVTVSWNS GALTSGVHTFPAVLQSSGLYSLSSVVTVPSSSLGTQTYIC NVNHKPSNTKVDKRVEPKSCDKTHTCPPCPAPELLGGPSVFL FPPKPKDTLMISRTPEVTCVVVDVSHEDPEVKFNWYVDGVE VHNAKTKPREEQYNSTYRVVSVLTVLHQDWLNGKEYKCKVS NKALPAPIEKTISKAKGQPREPQVYTLPPSREEMTKNQVSL TCLVKGFYPSDIAVEWESNGQPENNYKTTPPVLDSDGSFLL YSKLTVDKSRWQQGNVFSCSVMHEALHNHYTQKSLSLSPG |
| 32 | IgG1-DR4-FEAL | Full heavy chain | QVQLQESGPGLVKPSGTLSLTCAVSGGSISSYSWWSWIRQP PGKGLEWIGELYHSGSTNYNPSLKSRVTISVDKSKNQFSLK LRSVTAADTAVYYCVRGVATIDYWGQGTLVTVSSASTKGPS VFPLAPSSKSTSGGTAALGCLVKDYFPEPVTVSWNSGALTS GVHTFPAVLQSSGLYSLSSVVTVPSSSLGTQTYICNVNHKP SNTKVDKRVEPKSCDKTHTCPPCPAPEFEGGPSVFLFPPKP KDTLMISRTPEVTCVVVAVSHEDPEVKFNWYVDGVEVHNAK TKPREEQYNSTYRVVSVLTVLHQDWLNGKEYKCKVSNKALP APIEKTISKAKGQPREPQVYTLPPSREEMTKNQVSLTCLVK GFYPSDIAVEWESNGQPENNYKTTPPVLDSDGSFLLYSKLT VDKSRWQQGNVFSCSVMHEALHNHYTQKSLSLSPG |
| 33 | Human FAPα (Homo sapiens) | Full length FAPα | MKTWVKIVFGVATSAVLALLVMCIVLRPSRVHNSEENTMRA LTLKDILNGTFSYKTFFPNWISGQEYLHQSADNNIVLYNIE TGQSYTILSNRTMKSVNASNYGLSPDRQFVYLESDYSKLWR YSYTATYYIYDLSNGEFVRGNELPRPIQYLCWSPVGSKLAY VYQNNIYLKQRPGDPPFQITFNGRENKIFNGIPDWVYEEEM LATKYALWWSPNGKFLAYAEFNDTDIPVIAYSYYGDEQYPR TINIPYPKAGAKNPVVRIFIIDTTYPAYVGPQEVPVPAMIA SSDYYFSWLTWVTDERVCLQWLKRVQNVSVLSICDFREDWQ TWDCPKTQEHIEESRTGWAGGFFVSTPVFSYDAISYYKIFS DKDGYKHIHYIKDTVENAIQITSGKWEAINIFRVTQDSLFY SSNEFEEYPGRRNIYRISIGSYPPSKKCVTCHLRKERCQYY TASFSDYAKYYALVCYGPGIPISTLHDGRTDQEIKILEENK ELENALKNIQLPKEEIKKLEVDEITLWYKMILPPQFDRSKK YPLLIQVYGGPCSQSVRSVFAVNWISYLASKEGMVIALVDG RGTAFQGDKLLYAVYRKLGVYEVEDQITAVRKFIEMGFIDE KRIAIWGWSYGGYVSSLALASGTGLFKCGIAVAPVSSWEYY ASVYTERFMGLPTKDDNLEHYKNSTVMARAEYFRNVDYLLI HGTADDNVHFQNSAQIAKALVNAQVDFQAMWYSDQNHGLSG LSTNHLYTHMTHFLKQCFSLSD |
| 34 | Human FAPα (Homo sapiens) | Soluble polypeptide | LRPSRVHNSEENTMRALTLKDILNGTFSYKTFFPNWISGQE YLHQSADNNIVLYNIETGQSYTILSNRTMKSVNASNYGLSP DRQFVYLESDYSKLWRYSYTATYYIYDLSNGEFVRGNELPR PIQYLCWSPVGSKLAYVYQNNIYLKQRPGDPPFQITFNGRE NKIFNGIPDWVYEEEMLATKYALWWSPNGKFLAYAEFNDTD IPVIAYSYYGDEQYPRTINIPYPKAGAKNPVVRIFIIDTTY PAYVGPQEVPVPAMIASSDYYFSWLTWVTDERVCLQWLKRV QNVSVLSICDFREDWQTWDCPKTQEHIEESRTGWAGGFFVS TPVFSYDAISYYKIFSDKDGYKHIHYIKDTVENAIQITSGK WEAINIFRVTQDSLFYSSNEFEEYPGRRNIYRISIGSYPPS |

| SEQ ID NO | Sequence Name | Domain | Sequence |
|---|---|---|---|
| | | | KKCVTCHLRKERCQYYTASFSDYAKYYALVCYGPGIPISTL HDGRTDQEIKILEENKELENALKNIQLPKEEIKKLEVDEIT LWYKMILPPQFDRSKKYPLLIQVYGGPCSQSVRSVFAVNWI SYLASKEGMVIALVDGRGTAFQGDKLLYAVYRKLGVYEVED QITAVRKFIEMGFIDEKRIAIWGWSYGGYVSSLALASGTGL FKCGIAVAPVSSWEYYASVYTERFMGLPTKDDNLEHYKNST VMARAEYFRNVDYLLIHGTADDNVHFQNSAQIAKALVNAQV DFQAMWYSDQNHGLSGLSTNHLYTHMTHFLKQCFSLSD |
| 35 | Mouse FAPα (Mus musculus) | Mature polypeptide | MKTWLKTVFGVTTLAALALVVICIVLRPSRVYKPEGNTKRA LTLKDILNGTFSYKTYFPNWISEQEYLHQSEDDNIVFYNIE TRESYIILSNSTMKSVNATDYGLSPDRQFVYLESDYSKLWR YSYTATYYIYDLQNGEFVRGYELPRPIQYLCWSPVGSKLAY VYQNNIYLKQRPGDPPFQITYTGRENRIFNGIPDWVYEEEM LATKYALWWSPDGKFLAYVEFNDSDIPIIAYSYYGDGQYPR TINIPYPKAGAKNPVVRVFIVDTTYPHHVGPMEVPVPEMIA SSDYYFSWLTWVSSERVCLQWLKRVQNVSVLSICDFREDWH AWECPKNQEHVEESRTGWAGGFFVSTPAFSQDATSYYKIFS DKDGYKHIHYIKDTVENAIQITSGKWEAIYIFRVTQDSLFY SSNEFEGYPGRRNIYRISIGNSPPSKKCVTCHLRKERCQYY TASFSYKAKYYALVCYGPGLPISTLHDGRTDQEIQVLEENK ELENSLRNIQLPKVEIKKLKDGGLTFWYKMILPPQFDRSKK YPLLIQVYGGPCSQSVKSVFAVNWITYLASKEGIVIALVDG RGTAFQGDKFLHAVYRKLGVYEVEDQLTAVRKFIEMGFIDE ERIAIWGWSYGGYVSSLALASGTGLFKCGIAVAPVSSWEYY ASIYSERFMGLPTKDDNLEHYKNSTVMARAEYFRNVDYLLI HGTADDNVHFQNSAQIAKALVNAQVDFQAMWYSDQNHGISS GRSQNHLYTHMTHFLKQCFSLSD |
| 36 | Rat FAPα (Rattus norvegicus) | Mature polypeptide | MKTWLKTVFGVTTLVALALVVICIVLRPSRVYSPEGNTGRS LTLKDILNGTFSYKTYFPNWISEQEYLHQSEDDNIVFYNIE TRESYIILSNSTMKSVNATDYGLSPDRQFIYLESDYSKLWR YSYTATYYIYDLQNGEFVRGYELPRPIQYLCWSPVGSKLAY VYQNNIYLKQRPGDPPFQITYTGRENRIFNGIPDWVYEEEM LATKYALWWSPDGKYLAYVEFNDSDIPIIAYSYYGDGQYPR TINIPYPKAGAKNPIVRVFIVDTIYPHHVGPIEVPVPEMIA SSDYYFTWLTWVTNERVCLQWLKRVQNVSVLSICDFREDWH AWDCPKNQEHIEESRTGWAGGFFVSTPAFSQDAASYYKIFS DKDGYKHIHYIKDTVENAIQITSGKWEAIYIFRVTQDSLFY SSNEFEGYPGRRNIYRISIGNSPPSKKCVTCHLRKERCQYY TASFSYKAKYYALICYGPGLPISTLHDGRTDQEIQVLEENK ELENALRNIQLPAVEIKKLEDGGMTFWYKMILPPQFDRSKK YPLLIQVYGGPCSQSVKSVFSVNWITYLASKEGIVVALVDG RGTAFQGDKFLHAVYRKLGVYEVEDQLTAVRKFIEMGFIDE GRIAIWGWSYGGYVSSLALASGTGLFKCGIAVAPVSSWEYY ASIYTERFMGLPTKDDNLEHYKNSTVMARAEYFRNVDYLLI HGTADDNVHFQNSAQIAKALVNAQVDFQAMWYSDQNHGISS GRSQNHLYTHMTHFLKQCFSLSD |
| 37 | Dog FAPα (Canis lupus familiaris) | Mature polypeptide | MKTWLKIVFGVATSAVLALLVMCIVLRPSRVHDSEGGTTRA LTLEDILNGTFTYKTFFPNWISGQEYLHQSTDNDIVYYNIE TGESYTILSNATMKSVNASNYGLSPDRQFAYLESDYSKLWR YSYTATYHIYNLNNGEFIRRNELPRPIQYLCWSPVGSKLAY VYQNNIYLKQRPEDPPFQITYNGRENKIFNGIPDWVYEEEM LATKHALWWSPNGKFLAYAEFNDTEIPVIAYSYYGDEQYPR TINIPYPKAGAKNPVVRIFIIDTTYPQQTGPREVPVPAMIA SSDYYFSWLTWVTDERVCLQWLKRIQNVSVLSICDFREGWQ TWDCPKAQEHIEESRTGWAGGFFVSTPVFSYDAISYYKIFS DKDGYKHIHYIKDTVENAIQITSGKWEAINIFRVTQDSLFY SSNEFEDYPGRRNIYRISIGSSPPSKKCITCHLRKERCQYY TASFSDYAKYYALICYGPGLPISTLHDGHTDQEIKILEENK ELENALKNIQLPKEEIKKLEVDDITLWYKMMLPPRFDRSKK YPLLIQVYGGPCSQSVKSVFSINWISYLASKEGIVIALVDG RGTAYQGDKLLYAVYRKLGVYEVEDQITAVRKFIEMGFIDE KRIAIWGWSYGGYVSSLALASGTGLFKCGIAVAPVSSWEYY ASIYTERFMGLPTKNDNLEHYKNSTVMARAEYFRNVDYLLI HGTADDNVHFQNSAQIAKALVNAQVDFQAMWYSDQNHGIPG LSSKHLYTRMTHFLKQCFSLSD |
| 38 | Pig FAPα (Sus scrofa) | Mature polypeptide | MKTWLKIVFGVATSAVLALLVMCIVLRPSRVPNSEGSKTRA LTLKDILNGTFSYKTFFPNWISGQEYLHQSTDDNVIFYNIE TGESYTILSNTTMKSVNASSYGLSPDRQFAYLESDYSKLWR YSYTATYHIYDLRNGEFITRNELPRPIQYLCWSPVGSKLAY VYQNNIYLKQRPEDPPFQITYNGKENKIFNGIPDWVYEEEM |

-continued

| SEQ ID NO | Sequence Name | Domain | Sequence |
|---|---|---|---|
| | | | LATKYALWWSPNGRFLAYAEFNDTEIPVIAYSYYGDEQYPR<br>TINIPYPKAGAKNPFVRIFIIDTSYPGHVGPREVPVPAMIA<br>SSDYYFSWFTWVTDDRICLQWLKRIQNVSVLSICDFREDWQ<br>TWNCPKTQEHIEESRTGWAGGFFVSTPVFSYDAISYYKIFS<br>DKDGYKHIHYIKDSVENAIQITSGKWEAINIFRVTQDSLFY<br>SSNEFEGYPGRRNIYRISIGSHPPSKKCVTCHLREKRCQYY<br>TASFSDYAKYYALVCYGPGLPISTLHDGRTDQEIKILEENK<br>DLEYALKNIRLPKEEIKKLDVDDITLWYKMILPPQFDRSKK<br>YPLLIQVYGGPCSQSVRSVFSIRWISYLASKEGIVIALVDG<br>RGTAFQGDKLLYAVYRKLGVYEVEDQITAVRKFIEMGFIDE<br>KRIAIWGWSYGGYVSSLALASGTGLFKCGIAVAPVSSWEYY<br>ASIYTERFMGLPTKDDNLEHYKNSTVMARAEYFRNVDYLLI<br>HGTADDNVHFQNSAQIAKALVNAQVDFQAMWYSDQNHGISG<br>LSTKHLYTHMTHFLKQCFSLPD |
| 39 | Cynomolgus monkey FAPα (Macaca fascicularis) | Mature polypeptide | MKTWVKIVFGVATSSAVLALLVMCIVLRPPRVHNSEENTMRA<br>LTLKDILNGTFSYKTFFPNWISGQEYLHQSADNNIVLYNIE<br>TGQSYTILSNRTMKSVNASNYGLSPDRQFVYLESDYSKLWR<br>YSYTATYYIYDLSNGEFVRGNELPRPIQYLCWSPVGSKLAY<br>VYQNNIYLKQRPGDPPFQITFNGRENKIFNGIPDWVYEEEM<br>LATKYALWWSPNGKFLAYAEFNDTDIPVIAYSYYGDEQYPR<br>TINIPYPKAGAKNPFVRIFIIDTTYPAYVGPQEVPVPAMIA<br>SSDYYFSWLTWVTDERVCLQWLKRVQNVSVLSICDFREDWQ<br>TWDCPKTQEHIEESRTGWAGGFFVSTPVFSYDAISYYKIFS<br>DKDGYKHIHYIKDTVENAIQITSGKWEAINIFRVTQDSLFY<br>SSNEFEDYPGRRNIYRISIGSYPPSKKCVTCHLRKERCQYY<br>TASFSDYAKYYALVCYGPGIPISTLHDGRTDQEIKILEENK<br>ELENALKNIQLPKEEIKKLEVDEITLWYKMILPPQFDRSKK<br>YPLLIQVYGGPCSQSVRSVFAVNWISYLASKEGMVIALVDG<br>RGTAFQGDKLLYAVYRKLGVYEVEDQITAVRKFIEMGFIDE<br>KRIAIWGWSYGGYVSSLALASGTGLFKCGIAVAPVSSWEYY<br>ASVYTERFMGLPTKDDNLEHYKNSTVMARAEYFRNVDYLLI<br>HGTADDNVHFQNSAQIAKALVNAQVDFQAMWYSDQNHGLSG<br>LSTNHLYTHMTHFLKQCFSLSD |
| 40 | Human DR4 (Homo sapiens) with death domain deletion | Mature polypeptide | MAPPPARVHLGAFLAVTPNPGSAASGTEAAAATPSKVWGSS<br>AGRIEPRGGGRGALPTSMGQHGPSARARAGRAPGPRPAREA<br>SPRLRVHKTFKFVVVGVLLQVVPSSAATIKLHDQSIGTQQW<br>EHSPLGELCPPGSHRSEHPGACNRCTEGVGYTNASNNLFAC<br>LPCTACKSDEEERSPCTTTRNTACQCKPGTFRNDNSAEMCR<br>KCSRGCPRGMVKVKDCTPWSDIECVHKESGNGHNIWVILVV<br>TLVVPLLLVAVLIVCCCIGSGCGGDPKCMDRVCFWRLGLLR<br>GPGAEDNAHNEILSNADSLSTFVSEQQMESQEPADLTGVTV<br>QSPGEAQCLLGPAEAEGSQRRLLVPANGADPTETLVDSGK<br>FIYLEDGTGSAVSLEGASSGSSGSGSQKKPRYEIRWKVVVI<br>SAILALVVLTVISLIILIMLWGSDYKDDDDKGMQYPYDVPD<br>YA |
| 41 | Cynomolgus monkey DR4 (Macaca fascicularis) with death domain deletion | Mature polypeptide | MAPPPAGVKLGAFLAVTPNPGSAASGTEAATATPSKVWGSS<br>AGRIEPRGGGRGALPTSMGQQGPSAQARAGRVVGPRSAQGA<br>SPGLRVHKTLKFVVVGVLLQVVPGSAATIKVHDQSVGTQQW<br>EHSPLGELCPPGSHRSEHSGACNQCTEGVGYTSASNNLFSC<br>LPCTACKSDEEERSACTRTRNTACQCKPGTFRNDDSAEMCR<br>KCSTGCPRGKVKVKDCTPWSDIECVHNESGNGHNVWAILIV<br>IVVILVVLLLLVAVLMFCRRIGSGCGGNPKCMHRVFLWCLG<br>LLRGPGAEDNAHNMILNHGDSLSTFISEQQMESQEPADLTG<br>VTVQSPGEAQCLLGPAEPEGSQRRLLVPANGADPTETMML<br>IYVEDGTGSAVSLEGASSGSSGSGSQKKPRYEIRWKVVVIS<br>AILALVVLTVISLIILIMLWGSDYKDDDDKGMQYPYDVPDY<br>A |
| 42 | Mouse DR5 (Mus musculus) with death domain deletion | Mature polypeptide | MEPPGPSTPTASAAARADHYTPGLRPLPKRRLLYSFALLLA<br>VLQAVFVPVTANPAHNRPAGLQRPEESPSRGPCLAGQYLSE<br>GNCKPCREGIDYTSHSNHSLDSCILCTVCKEDKVVETRCNI<br>TTNTVCRCKPGTFEDKDSPEICQSCSNCTDGEEELTSCTPR<br>ENRKCVSKTAWASWHKLGLWIGLLVPVVLLIGALLVWKTGA<br>WRQWLLCIKRGCERDPESANSVHSSLLDRQTSSTTNDSNHN<br>TEPGKTQKTGKKLLVPVNGNDSADDLVKSGRFTYQNAAAQP<br>ETGPGGSQCVGASSGSSGSGSQKKPRYEIRWKVVVISAILA<br>LVVLTVISLIILIMLWGSDYKDDDDKGMQYPYDVPDYA |
| 43 | Rat DR5 (Rattus norvegicus) | Mature polypeptide | MLQAFLLLSFFVPVTAKLAQDRPADLQRLKQSPLECPAGQY<br>LSKEDGSCKACIDGENYTSGPNVLPSCLSCRVCKEDKVIKS<br>RCVKARNTECECKPGSFEDKDSTEICQTCSNCTDGEDEVIP |

| SEQ ID NO | Sequence Name | Domain | Sequence |
|---|---|---|---|
| | with death domain deletion | | CTPKANRKCVPKNTQIPQHNLGLLIGLLASVISVVLFVAVI WKTKAWESVCLFMARVYPGCEQDHENTVGLSLLDAQTSRKT NGSHHNTEPDRTQSSPLGRKLLVLANGNNPADALKLIFERC STEVPFNVKSGKFVYQNTTAGASSGSSGSGSQKKPRYEIRW KVVVISAILALVVLTVISLIILIMLWGSDYKDDDDKGMQYP YDVPDYA |
| 44 | Dog DR4 (Canis lupus familiaris) with death domain deletion | Mature polypeptide | MGWSCIILFLVATATGVHSLPEWRVLGRAWAVCPLLLLLKV RVPMAAIVSDCMEYEYKPEGLNLCCEKCPAGHYVSKHCDKN HGAGVCSPCEPGSYLPYRNGETNCRLCSRCREDQEVVSPCT ATRDQQCQCKPGYFCDSENCVENCFRCQSCPDHVSSPCNAT RDTVCNTQDTTDTSEKKPEGGSLQMFVLVVITITIIIVIVV VALIFLLVYCYKKKGMWLYQRLISLLKGRVDEQSSTVEILF PSNPENHQPALDIETLLLKEGLEESPRPRPLEETEEGIELQ DVVVRESPPAPEQVVQTPALAVSVSQNQNEVFPSLKSLEQE YAKRYFVKDTSNEGTTRLYYELGRHAETSDGASSGSSGSGS QKKPRYEIRWKVVVISAILALVVLTVISLIILIMLWGSDYK DDDDKGMQYPYDVPDYA |
| 45 | Pig DR4 (Sus scrofa) with death domain deletion | Mature polypeptide | MGWSCIILFLVATATGVHSRWPGQRAPLNRTGQWGQSAPTT SGAQAGCAPSRQSWLQDPRALIFVVFGVLWLVTAASAMPTR QERVHQQFNVPQGWRRNFWELCPPGYHVSEDGKNCTSCIHG VDFTIYWNVLPSCLPCTTCKSGEEEKTPCTATADTRCECKP GTFREENSPEFCQKCHTRCPDGMVMATPCTPSSDLKCMDQE SGNSELVVGIAVPCSILLLAVVIACLVCKCKVQGCGLHRKF MDKVLFWRSHPSRGPGAQDNKLMCGDSLSTLLTKKEQEDQE QEKPADVTVQSSREAEHLLEPAAAEGSQVRRRLLVPADGGD PTVCLRQVFKESEAGAAVSGASSGSSGSGSQKKPRYEIRWK VVVISAILALVVLTVISLIILIMLWGSDYKDDDDKGMQYPY DVPDYA |
| 46 | Rabbit DR4 (Orycto- lagus cuniculus) with death domain deletion | Mature polypeptide | MGWSCIILFLVATATGVHSIACEPDEYLVENYCCRFCPAGH FVSGLCSQNHSIGECEPCRPGTFMAYPSSEASCSPCSPCRP DQEVVANCTLTSNTRCQCRPGHFYCDSEDCVENCFRCSRCP KDKVTRRLCTPTRNTECADPTTGWWLLSLLAIPFVLVLILF IVRYCKSRGRSLGQACWGAKGLAGLSSPVPGVLRSLARIFK RKSSEPGSHALGPLEPTEALLSAETKGSEMDPGREDALLVM EEETSASAPGAGPCPAPTGPGGSPEPQAAASGTSPTGPGQA PHPDPAARGARNRTKAAASLEELEQEYAEQYVLMDTSGPGI SALGKRHGGDTPHAASGASSGSSGSGSQKKPRYEIRWKVVV ISAILALVVLTVISLIILIMLWGSDYKDDDDKGMQYPYDVP DYA |
| 47 | IgG1-FAP5- FEAL | Full heavy chain | QVQLQQSGAELARPGASVNLSCLASGYTFTNNGINWLKQRT GQGLEWIGEIYPRSTNTLYNEKFKGKATLTADRSSNTAYME LRSLTSEDSAVYFCARTLTAPFAFWGQGTLVTVSSASTKGP SVFPLAPSSKSTSGGTAALGCLVKDYFPEPVTVSWNSGALT SGVHTFPAVLQSSGLYSLSSVVTVPSSSLGTQTYICNVNHK PSNTKVDKRVEPKSCDKTHTCPPCPAPEFEGGPSVFLFPPK PKDTLMISRTPEVTCVVVAVSHEDPEVKFNWYVDGVEVHNA KTKPREEQYNSTYRVVSVLTVLHQDWLNGKEYKCKVSNKAL PAPIEKTISKAKGQPREPQVYTLPPSREEMTKNQVSLTCLV KGFYPSDIAVEWESNGQPENNYKTTPPVLDSDGSFLLYSKL TVDKSRWQQGNVFSCSVMHEALHNHYTQKSLSLSPG |
| 48 | IgG1-FAP5 | Full light chain | QIVLTQSPAIMSASPGELVTMTCSASSGVNFMHWYQQLSGT SPKRWIFDTSKLASGVPARFSGSGSGTSYSLTISSMEAEDA ATYYCQQWSFNPPTFGGGTKLEIKRTVAAPSVFIFPPSDEQ LKSGTASVVCLLNNFYPREAKVQWKVDNALQSGNSQESVTE QDSKDSTYSLSSTLTLSKADYEKHKVYACEVTHQGLSSPVT KSFNRGEC |
| 49 | IgG1-FAP5 | Full heavy chain | QVQLQQSGAELARPGASVNLSCLASGYTFTNNGINWLKQRT GQGLEWIGEIYPRSTNTLYNEKFKGKATLTADRSSNTAYME LRSLTSEDSAVYFCARTLTAPFAFWGQGTLVTVSSASTKGP SVFPLAPSSKSTSGGTAALGCLVKDYFPEPVTVSWNSGALT SGVHTFPAVLQSSGLYSLSSVVTVPSSSLGTQTYICNVNHK PSNTKVDKRVEPKSCDKTHTCPPCPAPELLGGPSVFLFPPK PKDTLMISRTPEVTCVVVDVSHEDPEVKFNWYVDGVEVHNA KTKPREEQYNSTYRVVSVLTVLHQDWLNGKEYKCKVSNKAL PAPIEKTISKAKGQPREPQVYTLPPSREEMTKNQVSLTCLV KGFYPSDIAVEWESNGQPENNYKTTPPVLDSDGSFFLYSKL TVDKSRWQQGNVFSCSVMHEALHNHYTQKSLSLSPG |

-continued

| SEQ ID NO | Sequence Name | Domain | Sequence |
|---|---|---|---|
| 50 | IgG1-FAP-ESC11-F405L | Full heavy chain | QVQLQESGPGLVKPSETLSLTCTVSGGSISSNNYYWGWIRQ TPGKGLEWIGSIYYSGSTNYNPSLKSRVTISVDTSKNQFSL KLSSVTAADTAVYYCARGARWQARPATRIDGVAFDIWGQGT MVTVSSASTKGPSVFPLAPSSKSTSGGTAALGCLVKDYFPE PVTVSWNSGALTSGVHTFPAVLQSSGLYSLSSVVTVPSSSL GTQTYICNVNHKPSNTKVDKRVEPKSCDKTHTCPPCPAPEL LGGPSVFLFPPKPKDTLMISRTPEVTCVVVDVSHEDPEVKF NWYVDGVEVHNAKTKPREEQYNSTYRVVSVLTVLHQDWLNG KEYKCKVSNKALPAPIEKTISKAKGQPREPQVYTLPPSREE MTKNQVSLTCLVKGFYPSDIAVEWESNGQPENNYKTTPPVL DSDGSFLLYSKLTVDKSRWQQGNVFSCSVMHEALHNHYTQK SLSLSPG |
| 51 | IgG1-FAP-ESC11-F405L | Full light chain | ETTLTQSPGTLSLSPGERATLSCRASQTVTRNYLAWYQQKP GQAPRLLMYGASNRAAGVPDRFSGSGSGTDFTLTISRLEPE DFAVYYCQQFGSPYTFGQGTKVEIKRTVAAPSVFIFPPSDE QLKSGTASVVCLLNNFYPREAKVQWKVDNALQSGNSQESVT EQDSKDSTYSLSSTLTLSKADYEKHKVYACEVTHQGLSSPV TKSFNRGEC |
| 52 | IgG1-DR4-T1014A04-FEAR | Full heavy chain | EVQLVQSGADVKRPGASVKVSCKISGDSFNAYFIHWVRQAP GQGLEWMGWFNPDSGTADSAQKFHGRVTMTRDTSSSTAFLE LSRLRSDDTAVYYCVRQHRGNTFAPWGRGTMVTVSSASTKG PSVFPLAPSSKSTSGGTAALGCLVKDYFPEPVTVSWNSGAL TSGVHTFPAVLQSSGLYSLSSVVTVPSSSLGTQTYICNVNH KPSNTKVDKRVEPKSCDKTHTCPPCPAPEFEGGPSVFLFPP KPKDTLMISRTPEVTCVVVAVSHEDPEVKFNWYVDGVEVHN AKTKPREEQYNSTYRVVSVLTVLHQDWLNGKEYKCKVSNKA LPAPIEKTISKAKGQPREPQVYTLPPSREEMTKNQVSLTCL VKGFYPSDIAVEWESNGQPENNYKTTPPVLDSDGSFFLYSR LTVDKSRWQQGNVFSCSVMHEALHNHYTQKSLSLSPG |
| 53 | IgG1-DR4-T1014A04-FEAR | Full light chain | QSVLTQPPSASGSPGQSVTISCTGTTSDVGGYNYVSWYQQH PGKAPKLMIYGVNQRPSGVPDRFSGSKSGNTASLTVSGLQA EDEADYYCSSYAGSNNWVFGGGTKLTVLGQPKAAPSVTLFP PSSEELQANKATLVCLISDFYPGAVTVAWKADSSPVKAGVE TTTPSKQSNNKYAASSYLSLTPEQWKSHRSYSCQVTHEGST VEKTVAPTECS |
| 54 | IgG1-DR4-chCTB007-FEAR | Full heavy chain | EVQLQQSGAELVKPGASVKLSCTASGFNIKDTYMHWVKQRP EQGLEWIGRIDPANGNTKYDPKFQGKATITADTSSNTAYLQ LSSLTSEDTAVYYCAYYYVSNAWFTYWGQGTLVTVSAASTK GPSVFPLAPSSKSTSGGTAALGCLVKDYFPEPVTVSWNSGA LTSGVHTFPAVLQSSGLYSLSSVVTVPSSSLGTQTYICNVN HKPSNTKVDKRVEPKSCDKTHTCPPCPAPEFEGGPSVFLFP PKPKDTLMISRTPEVTCVVVAVSHEDPEVKFNWYVDGVEVH NAKTKPREEQYNSTYRVVSVLTVLHQDWLNGKEYKCKVSNK ALPAPIEKTISKAKGQPREPQVYTLPPSREEMTKNQVSLTC LVKGFYPSDIAVEWESNGQPENNYKTTPPVLDSDGSFFLYS RLTVDKSRWQQGNVFSCSVMHEALHNHYTQKSLSLSPG |
| 55 | IgG1-DR4-chCTB007-FEAR | Full light chain | DIQMTQSPASLSVSVGETVTITCRASENIYSNLEWYQQKQG KSPQLLVYAATNLADGVPSRFSGSGSGTQYSLKINSLQSED FGSYYCQHFWGTWTFGGGTKLEIKRTVAAPSVFIFPPSDEQ LKSGTASVVCLLNNFYPREAKVQWKVDNALQSGNSQESVTE QDSKDSTYSLSSTLTLSKADYEKHKVYACEVTHQGLSSPVT KSFNRGEC |
| 56 | IgG1-b12 | Full heavy chain | QVQLVQSGAEVKKPGASVKVSCQASGYRFSNFVIHWVRQAP GQRFEWMGWINPYNGNKEFSAKFQDRVTFTADTSANTAYME LRSLRSADTAVYYCARVGPYSWDDSPQDNYYMDVWGKGTTV IVSSASTKGPSVFPLAPSSKSTSGGTAALGCLVKDYFPEPV TVSWNSGALTSGVHTFPAVLQSSGLYSLSSVVTVPSSSLGT QTYICNVNHKPSNTKVDKRVEPKSCDKTHTCPPCPAPELLG GPSVFLFPPKPKDTLMISRTPEVTCVVVDVSHEDPEVKFNW YVDGVEVHNAKTKPREEQYNSTYRVVSVLTVLHQDWLNGKE YKCKVSNKALPAPIEKTISKAKGQPREPQVYTLPPSREEMT KNQVSLTCLVKGFYPSDIAVEWESNGQPENNYKTTPPVLDS DGSFFLYSKLTVDKSRWQQGNVFSCSVMHEALHNHYTQKSL SLSPG |
| 57 | IgG1-b12 | Full light chain | EIVLTQSPGTLSLSPGERATFSCRSSHSIRSRRVAWYQHKP GQAPRLVIHGVSNRASGISDRFSGSGSGTDFTLTITRVEPE DFALYYCQVYGASSYTFGQGTKLERKRTVAAPSVFIFPPSD |

| SEQ ID NO | Sequence Name | Domain | Sequence |
|---|---|---|---|
| | | | EQLKSGTASVVCLLNNFYPREAKVQWKVDNALQSGNSQESV TEQDSKDSTYSLSSTLTLSKADYEKHKVYACEVTHQGLSSP VTKSFNRGEC |
| 58 | IgG1-b12-FEAL | Full heavy chain | QVQLVQSGAEVKKPGASVKVSCQASGYRFSNFVIHWVRQAP GQRFEWMGWINPYNGNKEFSAKFQDRVTFTADTSANTAYME LRSLRSADTAVYYCARVGPYSWDDSPQDNYYMDVWGKGTTV IVSSASTKGPSVFPLAPSSKSTSGGTAALGCLVKDYFPEPV TVSWNSGALTSGVHTFPAVLQSSGLYSLSSVVTVPSSSLGT QTYICNVNHKPSNTKVDKRVEPKSCDKTHTCPPCPAPEFEG GPSVFLFPPKPKDTLMISRTPEVTCVVVAVSHEDPEVKFNW YVDGVEVHNAKTKPREEQYNSTYRVVSVLTVLHQDWLNGKE YKCKVSNKALPAPIEKTISKAKGQPREPQVYTLPPSREEMT KNQVSLTCLVKGFYPSDIAVEWESNGQPENNYKTTPPVLDS DGSFLLYSKLTVDKSRWQQGNVFSCSVMHEALHNHYTQKSL SLSPG |
| 59 | IgG1-b12-FEAR | Full heavy chain | QVQLVQSGAEVKKPGASVKVSCQASGYRFSNFVIHWVRQAP GQRFEWMGWINPYNGNKEFSAKFQDRVTFTADTSANTAYME LRSLRSADTAVYYCARVGPYSWDDSPQDNYYMDVWGKGTTV IVSSASTKGPSVFPLAPSSKSTSGGTAALGCLVKDYFPEPV TVSWNSGALTSGVHTFPAVLQSSGLYSLSSVVTVPSSSLGT QTYICNVNHKPSNTKVDKRVEPKSCDKTHTCPPCPAPEFEG GPSVFLFPPKPKDTLMISRTPEVTCVVVAVSHEDPEVKFNW YVDGVEVHNAKTKPREEQYNSTYRVVSVLTVLHQDWLNGKE YKCKVSNKALPAPIEKTISKAKGQPREPQVYTLPPSREEMT KNQVSLTCLVKGFYPSDIAVEWESNGQPENNYKTTPPVLDS DGSFFLYSRLTVDKSRWQQGNVFSCSVMHEALHNHYTQKSL SLSPG |
| 60 | IgG1-b12-FERL | Full heavy chain | QVQLVQSGAEVKKPGASVKVSCQASGYRFSNFVIHWVRQAP GQRFEWMGWINPYNGNKEFSAKFQDRVTFTADTSANTAYME LRSLRSADTAVYYCARVGPYSWDDSPQDNYYMDVWGKGTTV IVSSASTKGPSVFPLAPSSKSTSGGTAALGCLVKDYFPEPV TVSWNSGALTSGVHTFPAVLQSSGLYSLSSVVTVPSSSLGT QTYICNVNHKPSNTKVDKRVEPKSCDKTHTCPPCPAPEFER GPSVFLFPPKPKDTLMISRTPEVTCVVVDVSHEDPEVKFNW YVDGVEVHNAKTKPREEQYNSTYRVVSVLTVLHQDWLNGKE YKCKVSNKALPAPIEKTISKAKGQPREPQVYTLPPSREEMT KNQVSLTCLVKGFYPSDIAVEWESNGQPENNYKTTPPVLDS DGSFLLYSKLTVDKSRWQQGNVFSCSVMHEALHNHYTQKSL SLSPG |
| 61 | IgG1-b12-FERR | Full heavy chain | QVQLVQSGAEVKKPGASVKVSCQASGYRFSNFVIHWVRQAP GQRFEWMGWINPYNGNKEFSAKFQDRVTFTADTSANTAYME LRSLRSADTAVYYCARVGPYSWDDSPQDNYYMDVWGKGTTV IVSSASTKGPSVFPLAPSSKSTSGGTAALGCLVKDYFPEPV TVSWNSGALTSGVHTFPAVLQSSGLYSLSSVVTVPSSSLGT QTYICNVNHKPSNTKVDKRVEPKSCDKTHTCPPCPAPEFER GPSVFLFPPKPKDTLMISRTPEVTCVVVDVSHEDPEVKFNW YVDGVEVHNAKTKPREEQYNSTYRVVSVLTVLHQDWLNGKE YKCKVSNKALPAPIEKTISKAKGQPREPQVYTLPPSREEMT KNQVSLTCLVKGFYPSDIAVEWESNGQPENNYKTTPPVLDS DGSFFLYSRLTVDKSRWQQGNVFSCSVMHEALHNHYTQKSL SLSPG |
| 62 | RG7386 | Full heavy chain | EVQLVQSGGGVERPGGSLRLSCAASGFTFDDYAMSWVRQAP GKGLEWVSGINWQGGSTGYADSVKGRVTISRDNAKNSLYLQ MNSLRAEDTAVYYCAKILGAGRGWYFDYWGKGTTVTVSSAS TKGPSVFPLAPSSKSTSGGTAALGCLVKDYFPEPVTVSWNS GALTSGVHTFPAVLQSSGLYSLSSVVTVPSSSLGTQTYICN VNHKPSNTKVDKKVEPKSCDKTHTCPPCPAPELLGGPSVFL FPPKPKDTLMISRTPEVTCVVVDVSHEDPEVKFNWYVDGVE VHNAKTKPREEQYNSTYRVVSVLTVLHQDWLNGKEYKCKVS NKALPAPIEKTISKAKGQPREPQVYTLPPSRDELTKNQVSL TCLVKGFYPSDIAVEWESNGQPENNYKTTPPVLDSDGSFFL YSKLTVDKSRWQQGNVFSCSVMHEALHNHYTQKSLSLSPGK SGGGGSGGGGSGGGGSGGGGSEVQLLESGGGLVQPGGSLRL SCAASGFTFSSHAMSWVRQAPGKGLEWVSAIWASGEQYYAD SVKGRFTISRDNSKNTLYLQMNSLRAEDTAVYYCAKGWLGN FDYWGQGTLVTVSSASVAAPSVFIFPPSDEQLKSGTASVVC LLNNFYPREAKVQWKVDNALQSGNSQESVTEQDSKDSTYSL SSTLTLSKADYEKHKVYACEVTHQGLSSPVTKSFNRGEC |

Sequences

| SEQ ID NO | Sequence Name | Domain | Sequence |
|---|---|---|---|
| 63 | RG7386 | Full light chain 1 | EIVLTQSPGTLSLSPGERATLSCRASQSVSRSYLAWYQQKP GQAPRLLIIGASTRATGIPDRFSGSGSGTDFTLTISRLEPE DFAVYYCQQGQVIPPTFGQGTKVEIKSSASTKGPSVFPLAP SSKSTSGGTAALGCLVKDYFPEPVTVSWNSGALTSGVHTFP AVLQSSGLYSLSSVVTVPSSSLGTQTYICNVNHKPSNTKVD KKVEPKSCD |
| 64 | RG7386 | Full light chain 2 | SSELTQDPAVSVALGQTVRITCSGDSLRSYYASWYQQKPGQ APVLVIYGANNRPSGIPDRFSGSSSGNTASLTITGAQAEDE ADYYCNSADSSGNHVVFGGGTKLTVLGQPKAAPSVTLFPPS SEELQANKATLVCLISDFYPGAVTVAWKADSSPVKAGVETT TPSKQSNNKYAASSYLSLTPEQWKSHRSYSCQVTHEGSTVE KTVAPTECS |
| 65 | ABBV-621-Fc fusion | Fc fusion polypeptide | QRVAAHITGTRGRSNTLSSPNSKNEKALGRKINSWESSRSG HSFLSNLHLRNGELVIHEKGFYYIYSQTYFRFQEEIKENTK NDKQMVQYIYKYTSYPDPILLMKSARNSCWSKDAEYGLYSI YQGGIFELKENDRIFVSVTNEHLIDMDHEASFFGAFLVGGS GSGNGSRVAAHITGTRGRSNTLSSPNSKNEKALGRKINSWE SSRSGHSFLSNLHLRNGELVIHEKGFYYIYSQTYFRFQEEI KENTKNDKQMVQYIYKYTSYPDPILLMKSARNSCWSKDAEY GLYSIYQGGIFELKENDRIFVSVTNEHLIDMDHEASFFGAF LVGGSGSGNGSRVAAHITGTRGRSNTLSSPNSKNEKALGRK INSWESSRSGHSFLSNLHLRNGELVIHEKGFYYIYSQTYFR FQEEIKENTKNDKQMVQYIYKYTSYPDPILLMKSARNSCWS KDAEYGLYSIYQGGIFELKENDRIFVSVTNEHLIDMDHEAS FFGAFLVGGPGSSSSSSSGSCDKTHTCPPCPAPELLGGPSV FLFPPKPKDTLMISRTPEVTCVVVDVSHEDPEVKFNWYVDG VEVHNAKTKPREEQYSSTYRVVSVLTVLHQDWLNGKEYKCK VSNKALPAPIEKTISKAKGQPREPQVYTLPPSREEMTKNQV SLTCLVKGFYPSDIAVEWESNGQPENNYKTTPPVLDSDGSF FLYSKLTVDKSRWQQGNVFSCSVMHEALHNHYTQKSLSLSP G |
| 66 | Human DR4HsECD-FcHisCtag | | MAPPPARVHLGAFLAVTPNPGSAASGTEAAAATPSKVWGSS AGRIEPRGGGRGALPTSMGQHGPSARARAGRAPGPRPAREA SPRLRVHKTFKFVVVGVLLQVVPSSAATIKLHDQSIGTQQW EHSPLGELCPPGSHRSEHPGACNRCTEGVGYTNASNNLFAC LPCTACKSDEEERSPCTTTRNTACQCKPGTFRNDNSAEMCR KCSRGCPRGMVKVKDCTPWSDIECVHKESGNGHNPKSCDKT HTCPPCPAPEAEGAPSVFLFPPKPKDTLMISRTPEVTCVVV DVSHEDPEVKFNWYVDGVEVHNAKTKPREEQYNSTYRVVSV LTVLHQDWLNGKEYKCKVSNKALPAPIEKTISKAKGQPREP QVYTLPPSREEMTKNQVSLTCLVKGFYPSDIAVEWESNGQP ENNYKTAPPVLDSDGSFFLYSKLTVDKSRWQQGNVFSCSVM HEALHNHYTQKSLSLSPGKHHHHHHHEPEA |
| 67 | Cynomolgus monkey DR4MfECD-FcHisCtag | | MAPPPAGVKLGAFLAVTPNPGSAASGTEAATATPSKVWGSS AGRIEPRGGGRGALPTSMGQQGPSAQARAGRVVGPRSAQGA SPGLRVHKTLKFVVVGVLLQVVPGSAATIKVHDQSVGTQQW EHSPLGELCPPGSHRSEHSGACNQCTEGVGYTSASNNLFSC LPCTACKSDEEERSACTRTRNTACQCKPGTFRNDDSAEMCR KCSTGCPRGKVKVKDCTPWSDIECVHNESGNGHNPKSCDKT HTCPPCPAPEAEGAPSVFLFPPKPKDTLMISRTPEVTCVVV DVSHEDPEVKFNWYVDGVEVHNAKTKPREEQYNSTYRVVSV LTVLHQDWLNGKEYKCKVSNKALPAPIEKTISKAKGQPREP QVYTLPPSREEMTKNQVSLTCLVKGFYPSDIAVEWESNGQP ENNYKTAPPVLDSDGSFFLYSKLTVDKSRWQQGNVFSCSVM HEALHNHYTQKSLSLSPGKHHHHHHHEPEA |
| 68 | Full length Human DR4 | Mature polypeptide | MAPPPARVHLGAFLAVTPNPGSAASGTEAAAATPSKVWGSS AGRIEPRGGGRGALPTSMGQHGPSARARAGRAPGPRPAREA SPRLRVHKTFKFVVVGVLLQVVPSSAATIKLHDQSIGTQQW EHSPLGELCPPGSHRSEHPGACNRCTEGVGYTNASNNLFAC LPCTACKSDEEERSPCTTTRNTACQCKPGTFRNDNSAEMCR KCSRGCPRGMVKVKDCTPWSDIECVHKESGNGHNIWVILVV TLVVPLLLVAVLIVCCCIGSGCGGDPKCMDRVCFWRLGLLR GPGAEDNAHNEILSNADSLSTFVSEQQMESQEPADLTGVTV QSPGEAQCLLGPAEAEGSQRRRLLVPANGADPTETLMLFFD KFANIVPFDSWDQLMRQLDLTKNEIDVVRAGTAGPGDALYA MLMKWVNKTGRNASIHTLLDALERMEERHAREKIQDLLVDS GKFIYLEDGTGSAVSLE |

| SEQ ID NO | Sequence Name | Domain | Sequence |
|---|---|---|---|
| 69 | Full length Cynomolgus monkey DR4 | Mature polypeptide | MAPPPAGVKLGAFLAVTPNPGSAASGTEAATATPSKVWGSS AGRIEPRGGGRGALPTSMGQQGPSAQARAGRVVGPRSAQGA SPGLRVHKTLKFVVVGVLLQVVPGSAATIKVHDQSVGTQQW EHSPLGELCPPGSHRSEHSGACNQCTEGVGYTSASNNLFSC LPCTACKSDEEERSACTRTRNTACQCKPGTFRNDDSAEMCR KCSTGCPRGKVKVKDCTPWSDIECVHNESGNGHNVWAILIV IVVILVVLLLLVAVLMFCRRIGSGCGGNPKCMHRVFLWCLG LLRGPGAEDNAHNMILNHGDSLSTFISEQQMESQEPADLTG VTVQSPGEAQCLLGPAEPEGSQRRRLLVPANGADPTETMML FFDNFADIVPFNSWDQLMRQLGLTNNEIHMVRADTAGPGDA LYAMLMKWVNKTGQDASIHTLLDALERIGERHAKERIQDLL VDSGKFIYVEDGTGSAVSLE |
| 70 | IgG1 constant region | with FER substitution and with K409R substitution (bold) | ASTKGPSVFPLAPSSKSTSGGTAALGCLVKDYFPEPVTVSW NSGALTSGVHTFPAVLQSSGLYSLSSVVTVPSSSLGTQTYI CNVNHKPSNTKVDKRVEPKSCDKTHTCPPCPAPEFERGPSV FLFPPKPKDTLMISRTPEVTCVVVDVSHEDPEVKFNWYVDG VEVHNAKTKPREEQYNSTYRVVSVLTVLHQDWLNGKEYKCK VSNKALPAPIEKTISKAKGQPREPQVYTLPPSREEMTKNQV SLTCLVKGFYPSDIAVEWESNGQPENNYKTTPPVLDSDGSF FLYSRLTVDKSRWQQGNVFSCSVMHEALHNHYTQKSLSLSP G |
| 71 | IgG1 constant region | with FEA substitution and with F405L substitution (bold) | ASTKGPSVFPLAPSSKSTSGGTAALGCLVKDYFPEPVTVSW NSGALTSGVHTFPAVLQSSGLYSLSSVVTVPSSSLGTQTYI CNVNHKPSNTKVDKRVEPKSCDKTHTCPPCPAPEFEGGPSV FLFPPKPKDTLMISRTPEVTCVVVAVSHEDPEVKFNWYVDG VEVHNAKTKPREEQYNSTYRVVSVLTVLHQDWLNGKEYKCK VSNKALPAPIEKTISKAKGQPREPQVYTLPPSREEMTKNQV SLTCLVKGFYPSDIAVEWESNGQPENNYKTTPPVLDSDGSF LLYSKLTVDKSRWQQGNVFSCSVMHEALHNHYTQKSLSLSP G |
| 72 | IgG1 constant region | with FEA substitution and with K409R substitution (bold) | ASTKGPSVFPLAPSSKSTSGGTAALGCLVKDYFPEPVTVSW NSGALTSGVHTFPAVLQSSGLYSLSSVVTVPSSSLGTQTYI CNVNHKPSNTKVDKRVEPKSCDKTHTCPPCPAPEFEGGPSV FLFPPKPKDTLMISRTPEVTCVVVAVSHEDPEVKFNWYVDG VEVHNAKTKPREEQYNSTYRVVSVLTVLHQDWLNGKEYKCK VSNKALPAPIEKTISKAKGQPREPQVYTLPPSREEMTKNQV SLTCLVKGFYPSDIAVEWESNGQPENNYKTTPPVLDSDGSF FLYSRLTVDKSRWQQGNVFSCSVMHEALHNHYTQKSLSLSP G |
| 73 | IgG1-b12-FER | Full heavy chain | QVQLVQSGAEVKKPGASVKVSCQASGYRFSNFVIHWVRQAP GQRFEWMGWINPYNGNKEFSAKFQDRVTFTADTSANTAYME LRSLRSADTAVYYCARVGPYSWDDSPQDNYYMDVWGKGTTV IVSSASTKGPSVFPLAPSSKSTSGGTAALGCLVKDYFPEPV TVSWNSGALTSGVHTFPAVLQSSGLYSLSSVVTVPSSSLGT QTYICNVNHKPSNTKVDKRVEPKSCDKTHTCPPCPAPEFER GPSVFLFPPKPKDTLMISRTPEVTCVVVDVSHEDPEVKFNW YVDGVEVHNAKTKPREEQYNSTYRVVSVLTVLHQDWLNGKE YKCKVSNKALPAPIEKTISKAKGQPREPQVYTLPPSREEMT KNQVSLTCLVKGFYPSDIAVEWESNGQPENNYKTTPPVLDS DGSFFLYSKLTVDKSRWQQGNVFSCSVMHEALHNHYTQKSL SLSPG |

Additional Items of the Present Disclosure

The present invention is further illustrated by the following examples which should not be construed as further limiting.

EXAMPLES

Example 1: Generation of Antibodies a. FAPα Antibodies

Immunization and hybridoma generation were performed at Aldevron GmbH (Freiburg, Germany). The construct used for immunization was cDNA encoding for full length human FAPα (SEQ ID NO: 33) cloned into an Aldevron proprietary immunization vector. Anti-FAPα antibodies were generated by genetic (DNA) immunization of OmniRat™ animals (transgenic rats expressing a diversified repertoire of antibodies with fully human idiotypes; Ligand Pharmaceuticals Inc.) using gene gun. Serum samples were collected after a series of immunizations and tested by flow cytometry using mammalian cells transiently transfected with an expression plasmid to stably express human FAPα (SEQ ID NO: 33). Antibody-producing cells were isolated from rat spleen and fused with mouse myeloma cells (Ag8) according to standard procedures. RNA from hybridomas producing FAPα-specific antibody was extracted for sequencing. The variable regions of heavy and light chains (VH and VL domains) of interest were gene synthesized and cloned into expression vectors containing the backbone sequences for a human IgG1 heavy chain constant region of the human IgG1m(f) allotype (SEQ ID NO: 21) or the constant region of the human kappa light chain (LC) (SEQ ID NO: 27), as appropriate for the selected binding domains. A FAPα-specific IgG1 kappa antibody IgG1-FAPα was selected, with the variable domain sequences as in SEQ ID NO: 14 (VL) and SEQ ID NO: 13 (VH).

Other FAPα-targeting antibodies used in the examples: FAP5 as disclosed in US20090304718A1, ESC11 as disclosed in WO2011040972A1 and RG7386 as disclosed in U.S. Pat. No. 9,926,379B2. Antibodies were generated according to standard procedures (described in sections d-f).

b. DR4 Antibodies

Immunization and hybridoma generation were performed at Aldevron GmbH (Freiburg, Germany). The constructs used for immunization were cDNA encoding for full length human DR4 (SEQ ID NO: 68) cloned into an Aldevron proprietary immunization vector, and cDNA encoding the extracellular domain (ECD) of human DR4 (aa 24-239 of SEQ ID NO: 68) cloned into an Aldevron proprietary immunization vector having a vector-derived N-terminal tag-sequence. Anti-DR4 antibodies were generated by genetic (DNA) immunization of OmniRat™ animals using gene gun. Serum samples were collected after a series of immunizations and tested by flow cytometry using mammalian cells transiently transfected with the expression plasmid for human DR4 expression. Antibody-producing cells were isolated from rat spleen and fused with mouse myeloma cells (Sp2.0) according to standard procedures. RNA from hybridomas producing DR4-specific antibody was extracted for sequencing. The variable regions of heavy and light chains (VH and VL domains) of interest were gene synthesized and cloned into expression vectors containing the backbone sequences for a human IgG1 heavy chain constant region of the human IgG1m(f) allotype (SEQ ID NO: 21) or the constant region of the human lambda light chain (LC) (SEQ ID NO: 28), as appropriate for the selected binding domains. DR4-specific IgG1 lambda antibody IgG1-DR4 was selected, with the variable domain sequences as in SEQ ID NO: 16 (VL) and SEQ ID NO: 15 (VH).

Other DR4-targeting antibodies used in the experiments: T1014A04 as disclosed in U.S. Pat. No. 7,361,341B2, chCTB007 as disclosed in US20090136503A1, and ABBV-621, a TRAIL-R fusion agonist, as disclosed in WO2019178438A1. Antibodies were generated according to standard procedures (described in sections d-f).

c. Control Antibodies

Human IgG1 antibodies with antigen-binding domains identical to HIV1 gp120-specific antibody b12 were used as negative nonbinding controls in several experiments (Barbas et al., J Mol Biol. 1993 Apr. 5; 230(3): 812-2). VH and VL domains of b12 were generated by de novo gene synthesis (GeneArt Gene Synthesis; ThermoFisher Scientific, Germany) and cloned into expression vectors containing the backbone sequences for a human IgG1 heavy chain constant region of the human IgG1m(f) allotype. The sequence of the heavy chain and the sequence of the light chain for the b12 control antibodies are included below in section g.

d. Antibody Expression

Antibodies were obtained by transfection of heavy and light chain expression vectors in production cell lines and purified from the culture supernatant by Protein A affinity chromatography for functional characterization. IgG concentration was measured by absorbance at 280 nm. Purified antibodies were stored in phosphate-buffered saline (PBS) at 4° C.

e. Generation of Bispecific Antibodies

Bispecific antibodies were obtained by controlled Fab arm exchange (DuoBody® platform technology), i.e. 2-MEA-induced controlled Fab-arm exchange (cFAE) as described in WO2011147986, WO2011131746 and WO2013060867 (Genmab) and Labrijn et al. (Labrijn et al., PNAS 2013, 110: 5145-50; Gramer et al., MAbs 2013, 5: 962-973). Briefly, two parental antibodies, containing single matched point mutations in the CH3 domain (F405L in one and K409R in the other [Eu numbering (Kabat, NIH publication no 91-3242, 5th edition ed. National Institutes of Public Health, Bethesda, MD, USA. 662, 680, 689)]), were produced separately, mixed, and subjected to controlled reducing conditions. The reducing conditions break down the inter-chain disulfide bonds of the molecule, while the matched CH3 domains (containing the F405L and K409R) drive heterodimerization of the Fab arms and formation of bispecific molecules. Subsequent reoxidation of the disulfide bonds yields highly pure bispecific antibody preparations with a regular IgG1 architecture.

f. Fc Mutations

To minimize interaction with Fcγ receptors and complement system component C1q, mutations L234F, L235E and D265A (FEA; Engelberts et al. EBiomedicine 2020; SEQ ID NO: 23) or L234F, L235E and G236R (FER, WO2022/189667, SEQ ID NO: 22) were introduced in the heavy chain constant domain according to Eu numbering.

Antibodies with introduction of both FEA and F405L or K409R mutations are referred to as FEAL or FEAR, respectively, in indicated experiments. Antibodies with introduction of both FER and F405L or K409R mutations are referred to as FERL or FERR in indicated experiments.

To generate bispecific antibodies, the two parental antibodies were mixed in equal mass amounts in PBS buffer (Phosphate Buffered Saline; 8.7 mM $HPO_4^{2-}$, 1.8 mM $H_2PO_4^-$, 163.9 mM $Na^+$, 140.3 mM $Cl^-$, pH 7.4). 2-mercaptoethylamine-HCl (2-MEA) was added to a final concentration of 75 mM and the reaction mixture was incubated at 31° C. for 5 h. The 2-MEA was removed by dialysis into PBS buffer using 10 kDa molecular-weight cutoff Slide-A-Lyzer™ carriages (Thermo Fisher Scientific) according to the manufacturer's protocol in order to allow re-oxidation of the inter-chain disulfide bonds and formation of intact bispecific antibodies.

q. Overview of Antibodies Used in the Examples

The amino acid sequences of the antibodies such as the parental antibodies of bispecific antibodies and/or monospecific antibodies used in the following experiments are set forth in the following SEQ ID NOs:

| | |
|---|---|
| IgG1-FAPα-FERL: | SEQ ID NO: 17 (HC) and SEQ ID NO: 18 (LC). |
| IgG1-FAPα-FEAL: | SEQ ID NO: 29 (HC) and SEQ ID NO: 18 (LC). |
| IgG1-DR4-FERR: | SEQ ID NO: 19 (HC) and SEQ ID NO: 20 (LC). |
| IgG1-DR4-FEAR: | SEQ ID NO: 30 (HC) and SEQ ID NO: 20 (LC). |

| | |
|---|---|
| IgG1-DR4-FEAL: | SEQ ID NO: 32 (HC) and SEQ ID NO: 20 (LC). |
| IgG1-b12-FERL: | SEQ ID NO: 60 (HC) and SEQ ID NO: 57 (LC). |
| IgG1-b12-FEAL: | SEQ ID NO: 58 (HC) and SEQ ID NO: 57 (LC). |
| IgG1-b12-FERR: | SEQ ID NO: 61 (HC) and SEQ ID NO: 57 (LC). |
| IgG1-b12-FEAR: | SEQ ID NO: 59 (HC) and SEQ ID NO: 57 (LC). |
| IgG1-b12: | SEQ ID NO: 56 (HC) and SEQ ID NO: 57 (LC). |
| IgG1-FAP5-FEAL: | SEQ ID NO: 47 (HC) and SEQ ID NO: 48 (LC). |
| IgG1-FAP5: | SEQ ID NO: 49 (HC) and SEQ ID NO: 48 (LC). |
| IgG1-FAPα-F405L: | SEQ ID NO: 31 (HC) and SEQ ID NO: 18 (LC). |
| IgG1-FAP-ESC11-F405L: | SEQ ID NO: 50 (HC) and SEQ ID NO: 51 (LC). |
| IgG1-DR4-T1014A04-FEAR: | SEQ ID NO: 52 (HC) and SEQ ID NO: 53 (LC). |
| IgG1-DR4-chCTB007-FEAR: | SEQ ID NO: 54 (HC) and SEQ ID NO: 55 (LC). |
| ABBV-621-Fc fusion: | SEQ ID NO: 65. |
| RG7386: | SEQ ID NO: 62 (HC) and SEQ ID NOs: 63-64 (LCs). |
| IgG1-b12-FER: | SEQ ID NO: 73 (HC) and SEQ ID NO: 57 (LC). |

Example 2: Binding to Human Lung Fibroblasts and CAFs a. Binding of BisG1-FAPα-FERL/DR4-FERR to Cell Surface Expressed FAPα.

Binding of bispecific or monoclonal antibodies carrying the anti-FAPα arm derived from IgG1-FAPα-FERL (BisG1-FAPα-FERL/DR4-FERR, BisG1-FAPα-FERL/b12-FERR, and IgG1-FAPα-FERL) to cell surface expressed human FAPα was analyzed by flow cytometry using human lung fibroblasts and CAFs, which endogenously express FAPα. BisG1-b12-FERL/b12-FERR was used as negative control.

Human lung fibroblasts (Coriell Institute, Cat #GM05389) and CAFs (expanded from a primary human CRC biopsy; Starting et al., Front. Immunol. 2023, 16:14: 1053920) cell viability was measured using Acridine Orange/Propidium Iodide (AO/PI; Nexcelom, Cat #CS2-0106). Human lung fibroblasts and CAFs (50,000 cells/well) were seeded in 96-Well round bottom plates (Greiner Bio-one, Cat #650101). Antibody dilutions were prepared using fluorescence-activated cell sorting (FACS) buffer, consisting of phosphate buffer saline (PBS, Lonza, Cat #BE17-517Q)+ 1% Bovine Serum Albumin (BSA, Roche, Cat #10735086001)+0.02% Sodium Azide (Bio-World, Cat #41920044-3). Plates were centrifuged, supernatant was removed, cells were resuspended in 50 µL of human Fc Block (BD, Cat #564220, diluted 1:100 in FACS buffer) and 50 µL of viability stain TO-PRO®-3 Iodide (Thermo Fisher, Cat #T3605, diluted 1:25,000 in FACS buffer), and incubated for 15 min at 4° C. Plates were washed three times with FACS buffer. Plates were centrifuged, supernatant was removed, cells were resuspended in 50 µL of antibody dilutions (concentration range 90-0.0005 µg/mL, three-fold dilution steps using FACS buffer) of BisG1-FAPα-FERL/DR4-FERR, BisG1-FAPα-FERL/b12-FERR, BisG1-b12-FERL/b12-FERR (top six concentrations only for CAFs culture) or IgG1-FAPα-FERL (top four concentrations only for CAFs culture) and incubated for 30 min at 4° C. Cells were washed three times with FACS buffer and resuspended in 50 µL of Fluorescein isothiocyanate (FITC)-labeled polyclonal antibody goat anti-mouse IgG1 (Jackson Immuno Research, Cat #109-096-097, diluted 1:100 in FACS buffer). After 30 min incubation at 4° C., cells were washed twice with FACS buffer and resuspended in FACS buffer. Antibody binding to viable cells (TO-PRO®-3 negative) was analyzed by flow cytometry on a FACSCelesta™ (BD biosciences) and data were processed using FlowJo_v10.8.1 (FlowJo LLC). Geomean fluorescence intensity, gMFI, was determined and visualized using GraphPad Prism. Binding curves were analyzed using nonlinear regression analysis. The concentration (µg/mL) at which 50% of the maximal effect was observed ($EC_{50}$) was derived from the fitted curves.

Results

Figure 1A:
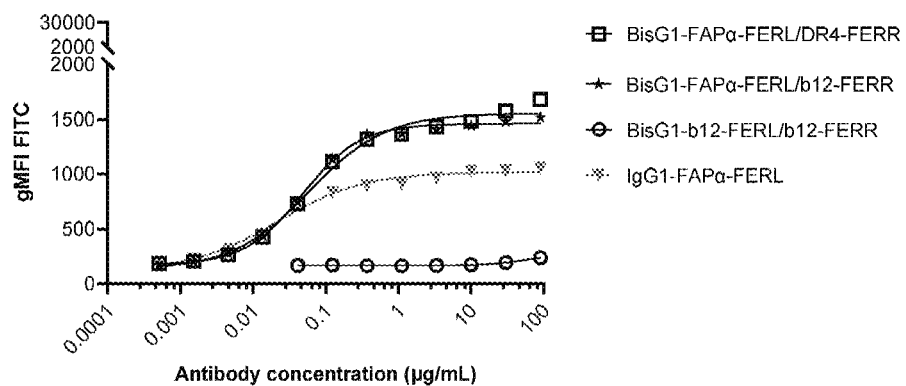
FIGS. 1A-IC: Binding to human lung fibroblasts and CAFs.
Figure 1B:
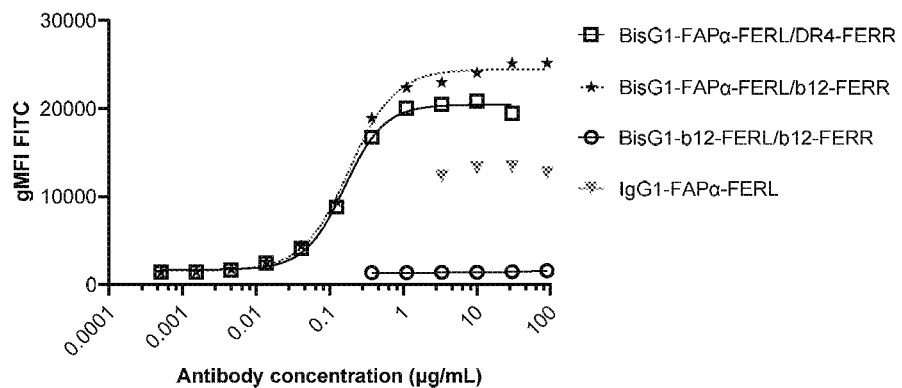

Similar dose-dependent human FAPα binding profiles were observed for both bispecific antibodies containing a FAPα-specific arm (i.e., BisG1-FAPα-FERL/DR4-FERR and BisG1-FAPα-FERL/b12-FERR) on human lung fibroblasts and CAFs (FIGS. 1A-B and Table 1 for $EC_{50}$ from three experiments). Lower maximal binding was observed for the bivalent monoclonal antibody IgG1-FAPα-FERL. No binding was observed for the negative control BisG1-b12-FERL/b12-FERR antibody.

TABLE 1

EC$_{50}$ values (μg/mL) of FAPα-specific arm binding to human lung fibroblasts and CAFs.

| Target cells | Antibody | EC$_{50}$ (μg/mL) n = 1 | n = 2 | n = 3 | Average ± SEM |
|---|---|---|---|---|---|
| Human lung fibroblasts | BisG1-FAPα-FERL/DR4-FERR | 0.046 | 0.047 | 0.059 | 0.051 ± 0.004 |
|  | BisG1- FAPα-FERL/b12-FERR | 0.043 | 0.034 | 0.048 | 0.041 ± 0.004 |
|  | IgG1-FAPα-FERL | 0.016 | 0.006 | 0.022 | 0.015 ± 0.004 |
| CAFs | BisG1-FAPα-FERL/DR4-FERR | 0.159 | 0.232 | 0.211 | 0.203 ± 0.02 |
|  | BisG1- FAPα-FERL/b12-FERR | 0.183 | 0.231 | 0.218 | 0.210 ± 0.01 |
|  | IgG1-FAPα-FERL | N/A | N/A | N/A | N/A |

N/A = EC$_{50}$ not calculated because the incomplete dose-response curves (plateau not reached)/too few points to calculate EC$_{50}$ b. Superior Monovalent Binding of FAPα Clone Compared to FAP5 Clone Binding of FAPα-targeting monoclonal antibody clones, IgG1-FAPα-FEAL and IgG1-FAP5-FEAL, and bispecific antibodies carrying a binding arm derived from the two FAPα-binding clones (BisG1-FAPα-FEAL/b12-FEAR and BisG1-FAP5-FEAL/b12-FEAR) to human lung fibroblasts, which endogenously express FAPα, was compared and analyzed by flow cytometry. IgG1-b12-FEAR was used as negative control.

The binding assay and analysis were performed as detailed in section a, with the following differences: 20,000 fibroblasts/well were seeded; no viability stain was performed; the primary antibody dilutions tested (10-0.0001 μg/mL final concentration, serial five-fold dilutions using FACS buffer).

Results

Figure 1C:
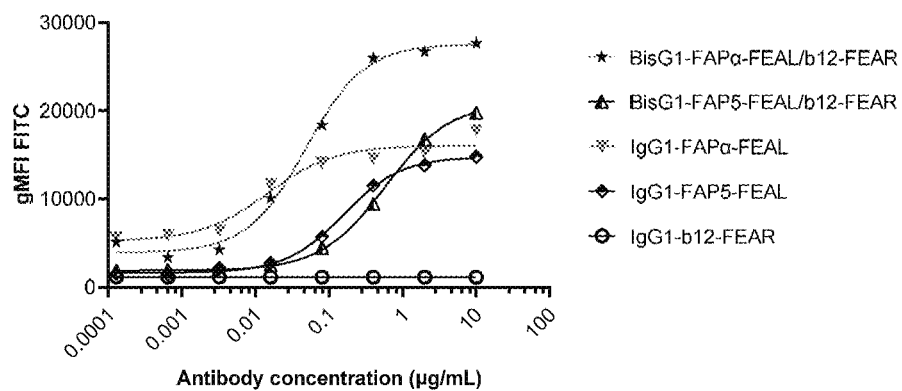
(FIG. 1C) Binding of two FAPα targeting antibody clones, FAPα-FEAL and FAP5 (antibodies BisG1-FAPα-FEAL/b12-FEAR, BisG1-FAP5-FEAL/b12-FEAR, IgG1-FAPα-FEAL and IgG1-FAP5-FEAL) and IgG1-b12-FEAR to human lung fibroblasts was assessed via flow cytometry. Data shown are gMFI values as determined by flow cytometry, for one representative experiment out of two.

All antibodies containing a FAPα-binding Fab arm showed dose-dependent binding to human FAPα on human lung fibroblasts (FIG. 1C and Table 2). The apparent affinity (EC$_{50}$) of monovalent and bivalent antibodies carrying FAPα-binding domains derived from the FAPα-FEAL clone were superior (as indicated by lower EC$_{50}$) to those carrying FAPα-binding domains from the FAP5 clone. Additionally, lower maximum binding was confirmed for bivalent antibody IgG1-FAPα-FEAL versus monovalent antibody BisG1-FAPα-FEAL/b12-FEAR in contrast to FAP5, where binding was found to be more similar for the monovalent versus bivalent formats. No binding was observed for the negative control IgG1-b12-FEAR.

TABLE 2

EC$_{50}$ values (μg/mL) of FAPα clone to human lung fibroblasts: comparison with prior art FAP5 clone.

| Target cells | Antibody | EC$_{50}$ (μg/mL) n = 1 | n = 2 |
|---|---|---|---|
| Human lung fibroblasts | BisG1-FAPα-FEAL/b12-FEAR | 0.048 | 0.044 |
|  | BisG1-FAP5-FEAL/b12-FEAR | 0.58 | 0.62 |
|  | IgG1-FAPα-FEAL | 0.014 | N/A |
|  | IgG1-FAP5-FEAL | 0.15 | 0.20 |

N/A = EC$_{50}$ not calculated because the incomplete dose-response curves (plateau not reached)/too few points to calculate EC$_{50}$

Example 3: Binding of DR4-Specific Antibodies to Cell Surface Expressed DR4 a. Efficient Monovalent and Bivalent Binding of the Anti-DR4 Antibodies to Multiple DR4-Expressing Tumor Cell Lines.

Binding of BisG1-FAPα-FERL/DR4-FERR, BisG1-b12-FERL/DR4-FERR and IgG1-DR4-FERR to cell surface expressed human DR4 was analyzed by flow cytometry using six human cancer cell lines derived from colorectal adenocarcinoma (DLD-1, HCT-15), non-small cell lung carcinoma (A549), colon cancer (HCT-116), triple negative breast cancer (MDA-MB-231) and pancreatic ductal adenocarcinoma (PANC-1), which endogenously express DR4. IgG-b12 was included as negative control.

The cancer cell lines (DLD-1: ATCC®, Cat #CCL-221; HCT-15: ATCC®, Cat #CCL-225; HCT-116: ATCC®, Cat #CCL-247; A549: ATCC®, Cat #CCL-185; MDA-MB-231: ATCC®, Cat #HTB-26; PANC-1: ATCC®, Cat #CRL-1469) were detached from cell culture flasks using trypsin solution (Gibco, Cat #25300-054), washed with PBS (GE Healthcare, Cat #SH3A3830.03), counted, and resuspended at the desired concentration.

The binding assay was performed as detailed in Example 2, section a, except for the use of IgG1-b12 antibody, for which only the three highest concentrations were tested. Data were processed using FlowJo_v10.8.1; gMFI was determined and visualized using GraphPad Prism.

Results

DR4-specific antibodies displayed dose-dependent binding to all human DR4-expressing cancer cell lines (FIG. 2A-F); the average EC$_{50}$ values from three independent experiments are shown in Table 3. As observed with binding to FAPα, maximal binding capacity for all cell lines was higher for the monovalent antibody variants compared to the bivalent antibody variants. The bivalent IgG1-DR4-FERR antibody showed a lower EC$_{50}$ compared to the monovalent antibody BisG1-FAPα-FERL/DR4-FERR for all cell lines. Strong binding of both monovalent and bivalent binding formats to DR4 is observed.

BisG1-b12-FERL/DR4-FERR showed similar binding and average EC$_{50}$ compared to BisG1-FAPα-FERL/DR4-FERR, whereas the negative control antibody IgG1-b12 did not show binding, confirming that the observed binding depends on the DR4-specific arm.

TABLE 3

EC$_{50}$ values of DR4-specific arm binding to DR4-expressing cell lines.

| Target cells | Antibody | EC$_{50}$ (µg/mL) of lead DR4 clone | | | |
|---|---|---|---|---|---|
| | | n = 1 | n = 2 | n = 3 | Average ± SEM |
| DLD-1 | BisG1-FAPα-FERL/DR4-FERR | 0.75 | 0.73 | 0.67 | 0.72 ± 0.02 |
| | BisG1-b12-FERL/DR4-FERR | 0.85 | 0.68 | 0.64 | 0.72 ± 0.06 |
| | IgG1-DR4-FERR | 0.33 | 0.22 | 0.23 | 0.26 ± 0.03 |
| PANC-1 | BisG1-FAPα-FERL/DR4-FERR | 1.80 | 1.89 | 1.40 | 1.70 ± 0.15 |
| | BisG1-b12-FERL/DR4-FERR | 1.35 | 2.12 | 1.44 | 1.63 ± 0.24 |
| | IgG1-DR4-FERR | 0.68 | 0.40 | 0.39 | 0.49 ± 0.09 |
| A549 | BisG1-FAPα-FERL/DR4-FERR | 0.86 | 0.93 | 0.87 | 0.89 ± 0.02 |
| | BisG1-b12-FERL/DR4-FERR | 0.89 | 0.68 | 0.78 | 0.78 ± 0.06 |
| | IgG1-DR4-FERR | 0.51 | 0.26 | 0.21 | 0.32 ± 0.09 |
| HCT-15 | BisG1-FAPα-FERL/DR4-FERR | 0.59 | 0.69 | 0.68 | 0.65 ± 0.03 |
| | BisG1-b12-FERL/DR4-FERR | 0.59 | 0.57 | 0.53 | 0.56 ± 0.01 |
| | IgG1-DR4-FERR | 0.18 | 0.17 | 0.15 | 0.17 ± 0.44 |
| HCT-116 | BisG1-FAPα-FERL/DR4-FERR | 0.48 | 0.55 | 0.53 | 0.52 ± 0.02 |
| | BisG1-b12-FERL/DR4-FERR | 0.51 | 0.65 | 0.55 | 0.57 ± 0.04 |
| | IgG1-DR4-FERR | 0.22 | 0.16 | 0.11 | 0.16 ± 0.03 |
| MDA-MB-231 | BisG1-FAPα-FERL/DR4-FERR | 1.12 | 1.24 | * | 1.18 ± 0.06 |
| | BisG1-b12-FERL/DR4-FERR | 1.14 | 1.00 | 0.92 | 1.02 ± 0.06 |
| | IgG1-DR4-FERR | 0.33 | 0.27 | 0.37 | 0.32 ± 0.03 |

* = technical error precluded binding assessment b. Monovalent Binding of chCTB007 and T1014A04 Antibodies to Cell Surface Expressed DR4 is Reduced Compared to Bivalent Binding.

Binding of DR4-specific antibodies BisG1-b12-FEAL/DR4-T1014A04-FEAR, BisG1-b12-FEAL/DR4-chCTB007-FEAR, IgG1-DR4-chCTB007-FEAR and IgG1-DR4-T1014A04-FEAR to cell surface expressed human DR4 was analyzed by flow cytometry using the human cancer cell line OPM-2 (DSMZ, Cat #ACC 50), which endogenously expresses DR4. IgG1-b12 was used as negative control.

The binding assay was performed as detailed in Example 2, section a, except for the following amendments: viability stain and Fc Block were not added; the antibody concentration series (10-0.0001 µg/mL final concentration, serial four-fold dilutions in FACS buffer); the secondary antibody used: R-Phycoerythrin (PE)-labeled polyclonal antibody goat anti-human IgG1 (Jackson Immuno Research, Cat #109-116-098, diluted 1:500 in FACS buffer); full concentration curve of negative control antibody was included; the flow cytometer iQue® Plus was used.

Furthermore, binding of DR4-specific antibodies IgG1-DR4-FERR, BisG1-b12-FERL/DR4-FERR, BisG1-FAPα-FERL/DR4-FERR, IgG1-DR4-chCTB007-FEAR, BisG1-b12-FEAL/DR4-chCTB007-FEAR, IgG1-DR4-T1014A04-FEAR and BisG1-b12-FEAL/DR4-T1014A04-FEAR to cell surface expressed human DR4 was analyzed by flow cytometry using the human cancer cell line MDA-MB-231, which endogenously expresses DR4. BisG1-b12-FERL/b12-FERR was used as a negative control.

The binding assay was performed as detailed in Example 2, section a, except for the following amendment: full concentration curve of negative control antibody was included.

Results

Figure 2A:
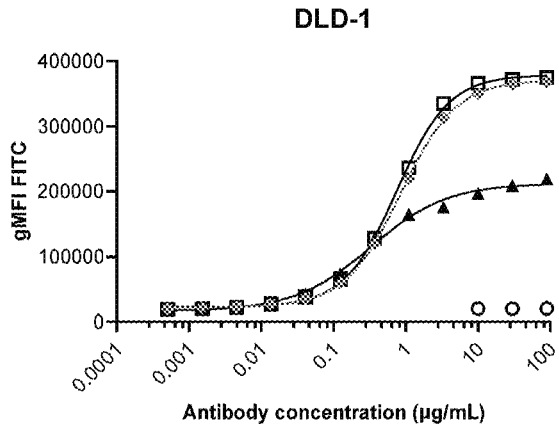
FIGS. 2A-2H: Binding of DR4-specific antibodies to cell surface expressed DR4.
Figure 2B:
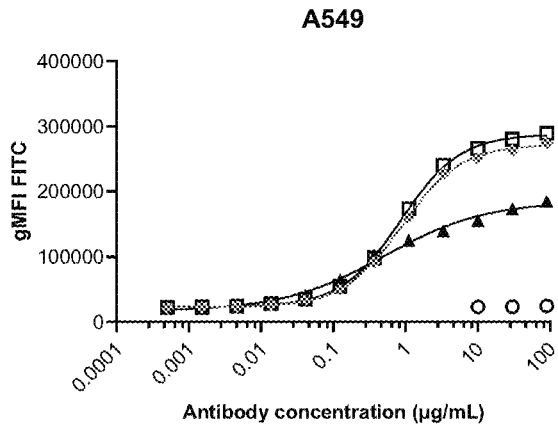
Figure 2C:
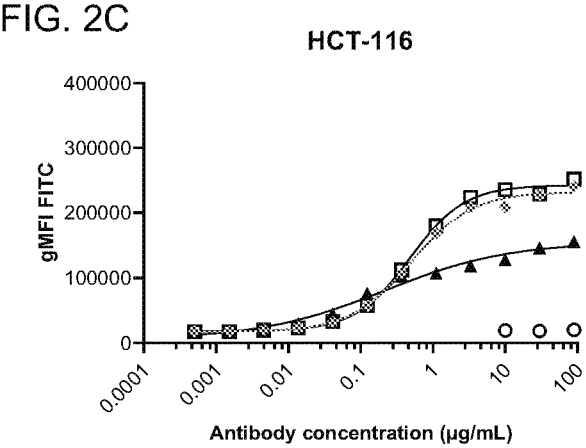
Figure 2D:
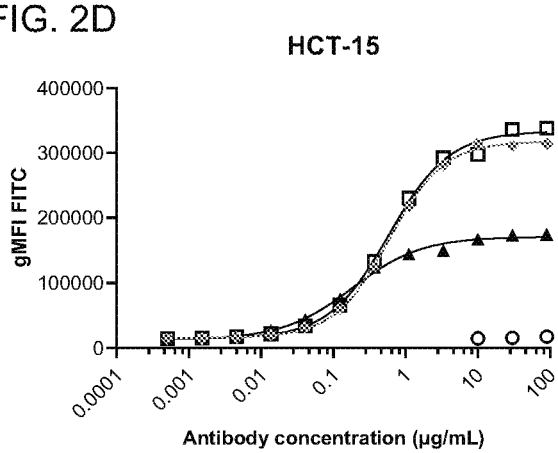
Figure 2E:
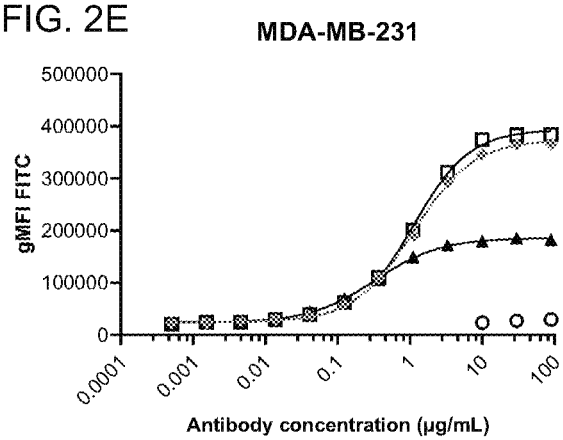
Figure 2F:
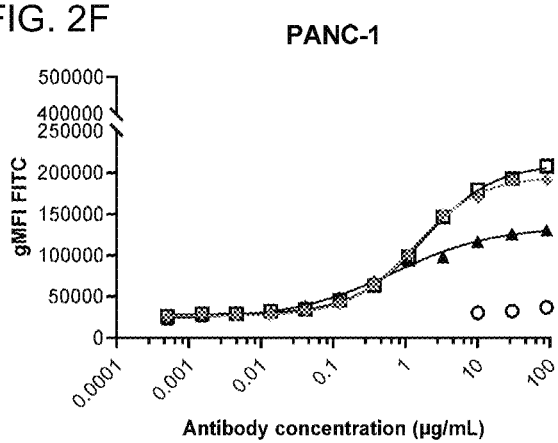
Figure 2G:
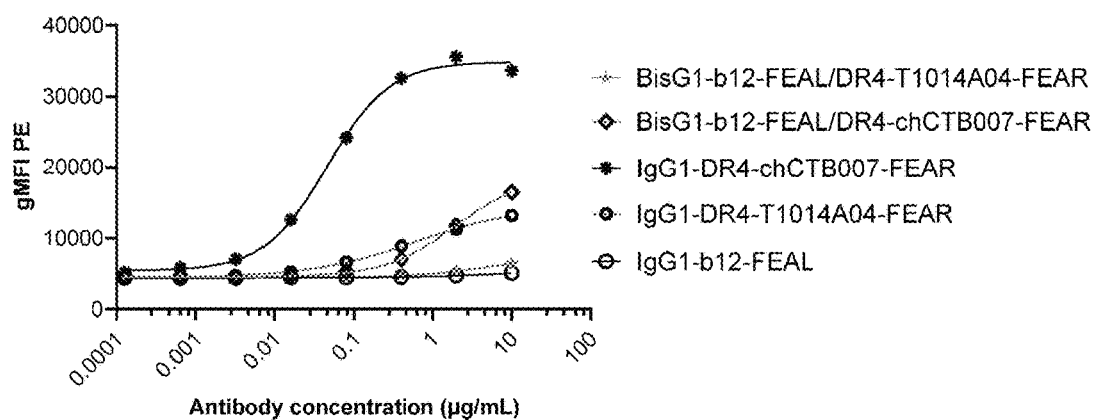

IgG1-DR4-T1014A04-FEAR and IgG1-DR4-chCTB007-FEAR showed dose-dependent binding to human DR4 expressed by human tumor cell line OPM-2 (FIG. 2G). Reduced binding of IgG1-DR4-T1014A04-FEAR compared to IgG-DR4-chCTBMx7 was observed. In addition, low binding of the monovalent binding variant BisGa-b12-FEAL/DR4-chCTBON7-FEAR was observed, while no/low binding of the monovalent binding variant BisG1-b12-FEAL/DR4-T1014AD4-FEAR was detected.

Figure 2H:
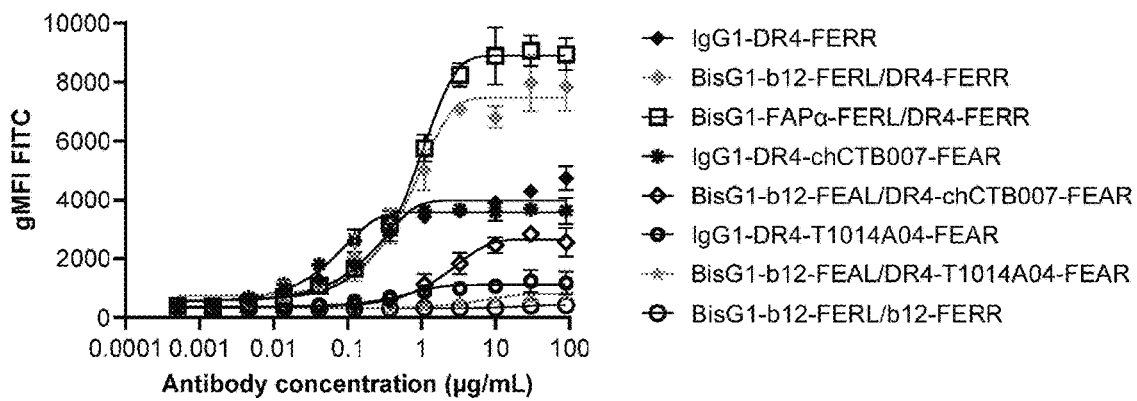
Figure 3A:
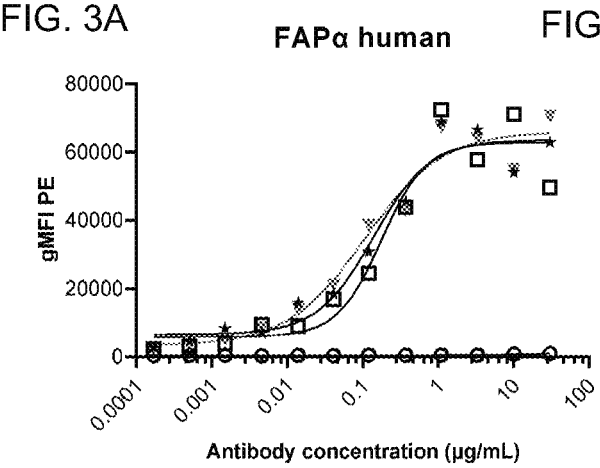
FIGS. 3A-3F: Species cross reactivity to FAPα orthologs. The antibodies BisG1-FAPα-FERL/DR4-FERR, BisG1-FAPα-FEAL/b12-FEAR, IgG1-FAPα-FERL and IgG1-b12 were tested.
Figure 3B:
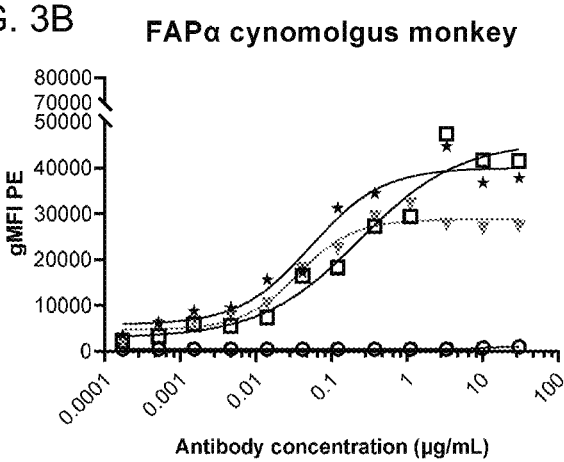
Figure 3C:
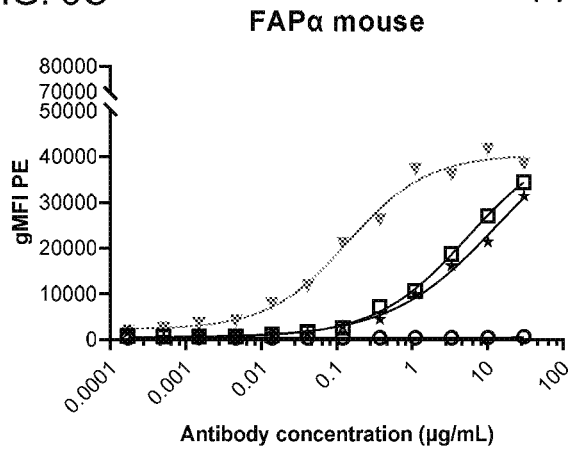
Figure 3D:
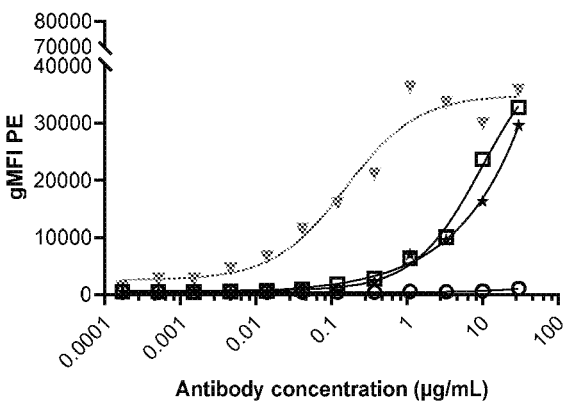
Figure 3E:
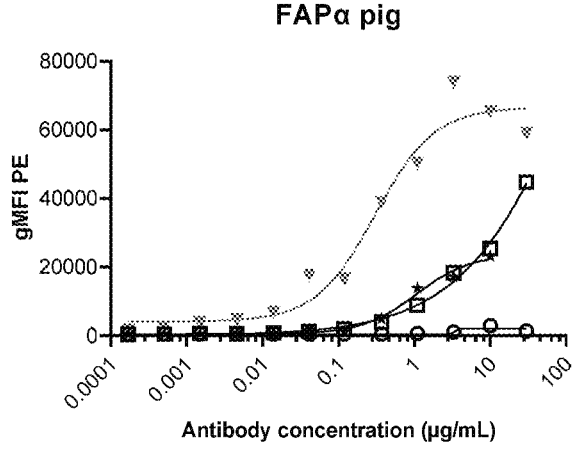
Figure 3F:
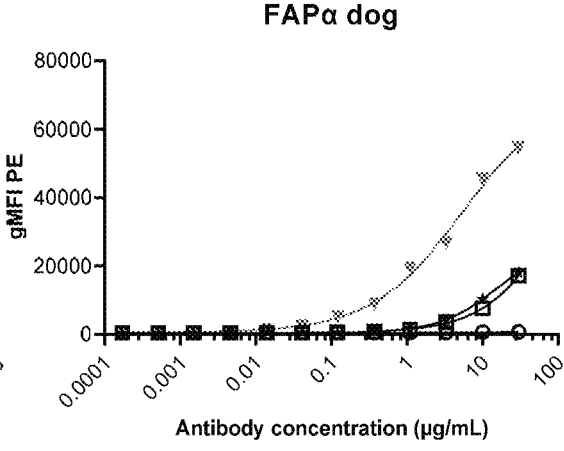

IgG1-DR4-FERR showed dose-dependent binding to human DR4 expressed by human tumor cell line MDA-MB-231 with similar apparent affinity and max MFI as IgG1-DR4-chCTB007-FEAR but higher apparent affinity and max MFI compared to IgG-DR4-T1014A04-FEAR. Monovalent binding of BisG1-b12-FERL/DR4-FERR and BisG1-FAPα-FERL/DR4-FERR to DR4 expressed by MDA-MB-231 cells was stronger (higher apparent affinity and max MFI) compared to BisG1-b12-FEAL/DR4-chCTB007-FEAR and BisG1-b12-FEAL/DR4-T1014A04-FEAR (FIG. 2H, Table 4).

TABLE 4

EC$_{50}$ values of bivalent and monovalent DR4-binding antibodies

| | | EC$_{50}$ (µg/mL) of DR4-binding antibodies | | | Max MFI (at 90 µg/mL) of DR4-binding antibodies | | |
|---|---|---|---|---|---|---|---|
| Antibody | | N = 1 | N = 2 | Average ± SEM | N = 1 | N = 2 | Average ± SEM |
| Bivalent antibody binding | IgG1-DR4-FERR | 0.24 | 0.26 | 0.25 ± 0.01 | 4977.5 | 4291 | 4634.25 ± 485.43 |
| | IgG1-DR4-chCTB007-FEAR | 0.04 | 0.08 | 0.06 ± 0.02 | 3750 | 3484.5 | 3617.25 ± 187.74 |

TABLE 4-continued

EC$_{50}$ values of bivalent and monovalent DR4-binding antibodies

| | Antibody | EC$_{50}$ (µg/mL) of DR4-binding antibodies | | | Max MFI (at 90 µg/mL) of DR4-binding antibodies | | |
|---|---|---|---|---|---|---|---|
| | | N = 1 | N = 2 | Average ± SEM | N = 1 | N = 2 | Average ± SEM |
| | IgG1-DR4-T1014A04-FEAR | 0.45 | 2.04 | 1.25 ± 0.8 | 953 | 1612 | 1282.5 ± 465.98 |
| Monovalent antibody binding | BisG1-b12-FERL/DR4-FERR | 0.39 | 0.95 | 0.67 ± 0.28 | 7840 | 7840.5 | 7840.250 ± 0.35 |
| | BisG1-FAPα-FERL/DR4-FERR | 0.71 | 0.72 | 0.72 ± 0.01 | 9381.5 | 8507 | 8944.250 ± 618.37 |
| | BisG1-b12-FEAL/DR4-chCTB007-FEAR | 1.61 | 2.68 | 2.14 ± 0.54 | 2949 | 2156.5 | 2552.75 ± 560.38 |
| | BisG1-b12-FEAL/DR4-T1014A04-FEAR | 4.33 | 6.36 | 5.35 ± 1.02 | 637.5 | 949.5 | 793.500 ± 220.62 |

Example 4: Species Cross Reactivity to FAPα Orthologs

Binding of BisG1-FAPα-FERL/DR4-FERR, BisG1-FAPα-FEAL/b12-FEAR and IgG1-FAPα-FERL to FAPα of species commonly used for nonclinical toxicology studies was assessed by flow cytometry using Expi293F cells transiently expressing FAPα from different animal species. IgG1-b12 was included as negative control.

Expi293F suspension cells (Thermo Fisher Scientific, Cat #A14527) were transiently transfected with mammalian expression vector pSB encoding full length human (UniProt ID Q12884, SEQ ID NO: 33), cynomolgus monkey (Macaca fascicularis, UniProt ID A0A2K5VGF4, SEQ ID NO: 39), dog (Canis familiaris, UniProt ID A0A8C0NKP1, SEQ ID NO: 37), pig (Sus scrofa, UniProt ID K7GQN2, SEQ ID NO: 38), rat (Rattus norvegicus, UniProt ID Q8R492, SEQ ID NO: 36), or mouse (Mus musculus, UniProt ID P97321, SEQ ID NO: 35) FAPα orthologs using ExpiFectamine™ 293 transfection reagent (Thermo Fisher Scientific, Cat #A14525), Opti-MEM™ Reduced Serum Medium, GlutaMAX™ Supplement (Thermo Fisher Scientific, Cat #51985026) and transfection enhancers 1 and 2 (Thermo Fisher Scientific, Cat #A14525), according to the manufacturer's instructions.

Expi293F cells expressing recombinant FAPα from various species (human, cynomolgus monkey, dog, pig, rat or mouse) were seeded (20,000 cells/well) in 96-Well round bottom plates (Greiner Bio-one, Cat #650101). Antibody dilutions were prepared using FACS buffer, consisting of PBS (Capricorn Scientific, Cat #PBS-10XA, diluted to 1×PBS in distilled water)+1% BSA (Roche, Cat #10735086001)+0.02% Sodium Azide (Bio-World, Cat #41920044-3). Plates were centrifuged, supernatant was removed, and cells were resuspended in 100 µL of antibody dilutions (concentration range 30-0.00017 µg/mL with three-fold serial dilutions using FACS buffer) of BisG1-FAPα-FERL/DR4-FERR, BisG1-FAPα-FEAL/b12-FEAR, IgG1-FAPα-FERL and IgG1-b12 and incubated for 30 min at 4° C. Cells were washed with FACS buffer and resuspended in 50 µL of PE-conjugated goat-anti-human IgG (Jackson ImmunoResearch, Cat #106-116-098; diluted 1:400 in FACS buffer). After 30 min incubation at 4° C., cells were washed with FACS buffer and resuspended in FACS buffer supplemented with TO-PRO®-3 Iodide viability marker (Invitrogen, Cat #T3605, diluted 1:4,000). Antibody binding to viable cells (gMFI of PE on TO-PRO®-3 negative cells) was analyzed by flow cytometry on a FACS Celesta® and FACS_Diva software (first two experiments) or iQue® 3 and FlowJo software (last experiment). gMFI was determined and visualized using GraphPad Prism. Binding curves were analyzed using nonlinear regression analysis. The concentration (µg/mL) at which 50% of the maximal effect was observed (EC$_{50}$) was derived from the fitted curves.

Results

BisG1-FAPα-FERL/DR4-FERR displayed dose-dependent binding to all species tested (FIG. 3A-F). The apparent affinity for human and cynomolgus monkey FAPα was comparable (FIG. 3A-B), with average EC$_{50}$ values of 0.24±0.04 µg/mL and 0.25 t 0.055 µg/mL, respectively (Table 5). All tested antibodies showed reduced binding to FAPα from mouse, rat, dog and pig compared to human (FIG. 3C-F); hence, the EC$_{50}$ for these species could not be calculated.

BisG1-FAPα-FEAL/b12-FEAR and BisG1-FAPα-FERL/DR4-FERR showed comparable dose-dependent binding profiles, indicating that binding is FAPα-specific. Bivalent binding with the IgG1-FAPα-FERL antibody showed higher binding than monovalent binding for most species except for human (similar binding) and cynomolgus monkey (lower maximal binding). No BisG1-FAPα-FERL/DR4-FERR binding was observed to untransfected control cells (data not shown), nor was binding of IgG1-b12 to FAPα of any of the tested species observed (FIG. 3A-F).

In summary, BisG1-FAPα-FERL/DR4-FERR and IgG1-FAPα-FERL showed cross-reactivity with all species tested, with highest and comparable binding to human and cynomolgus monkey FAPα.

TABLE 5

EC$_{50}$ values of FAPα-specific arm binding to human and cynomolgus monkey FAPα transiently expressed on Expi293F cells.

| Species | Antibody | EC$_{50}$ (µg/mL) | | | |
|---|---|---|---|---|---|
| | | n = 1 | n = 2 | n = 3 | Average ± SEM |
| Human | BisG1-FAPα-FERL/DR4-FERR | 0.18 | 0.32 | 0.23 | 0.24 ± 0.04 |
| | BisG1-FAPα-FEAL/b12-FEAR | 0.14 | 0.16 | 0.61 | 0.30 ± 0.15 |
| | IgG1-FAPα-FERL | 0.11 | 0.12 | 0.32 | 0.18 ± 0.06 |
| Cynomolgus monkey | BisG1-FAPα-FERL/DR4-FERR | 0.24 | 0.36 | 0.16 | 0.25 ± 0.05 |
| | BisG1-FAPα-FEAL/b12-FEAR | 0.05 | 0.16 | 0.35 | 0.19 ± 0.08 |
| | IgG1-FAPα-FERL | 0.03 | 0.11 | 0.16 | 0.10 ± 0.03 |

EC$_{50}$ = concentration at which 50% of the maximal binding was observed.

Example 5: Binding Affinity of FAPα Clone to Recombinant Human and Cynomolgus Monkey FAPα

The binding affinity of BisG1-FAPα-FERL/DR4-FERR, BisG1-FAPα-FERL/b12-FERR and control BisG1-b12-FERL/DR4-FERR to recombinant human and cynomolgus monkey FAPα proteins was determined using label-free biolayer interferometry on an Octet® HTX instrument (Sartorius).

Experiments were carried out while shaking at 1,000 RPM at 30° C. Amine Reactive 2nd Generation (AR2G) biosensors (Sartorius, Cat #18-5092) were activated by reaction with 20 mM EDC (N-(3-Dimethylaminopropyl)-N'-ethylcarbodiimide hydrochloride) (Sigma-Aldrich, Cat #03449) and 10 mM s-NHS (N-hydroxysulfosuccinimide sodium salt) (Sigma-Aldrich, Cat #56485) for 300 s. The activated AR2G sensors were loaded with 2.5 µg/mL His-tagged recombinant Human FAPα (Acro Biosystems, Cat #FAP-H5244-100 µg) in 10 mM Sodium Acetate pH 5.0 (Sartorius, Cat #18-1069) or 2.5 µg/mL His-tagged recombinant Cynomolgus FAPα (Acro Biosystems, Cat #FAP-C52H3-100 µg) in 10 mM Sodium Acetate pH 5.0 for 600 s and quenched with 1 M ethanolamine pH 8.5 (Sartorius Cat #18-1071) for 300 s. After a baseline measurement in Sample Diluent (1000 s; Sartorius, Cat #18-1104), the association (100 s) and dissociation (4,000 s) of functionally monovalent antibody was determined using a concentration range of 0.78-800 nM with two-fold dilution steps in Sample Diluent. The molecular mass of the antibodies used for the calculations was calculated from the sequences.

Data were acquired using Data Acquisition Software v12 (Sartorius) and analyzed with Data Analysis Software v12 (Sartorius). Antibody data traces were corrected by subtraction of reference sensors, which were incubated with Sample Diluent instead of antibody.

The Y-axis was aligned to the last 10 s of the baseline; Interstep Correction alignment to dissociation and Savitzky-Golay filtering were applied. Data traces with a response <0.05 nm were excluded from analysis. Data traces with a concentration higher than 100 nM were also excluded for antibodies with a K$_D$ value lower than 50 nM. The data were fitted with the 1:1 Global Full fit model using a window of interest for the association of 100 s and dissociation time set 4,000 s.

Results

BisG1-FAPα-FERL/DR4-FERR showed comparable, picomolar K$_D$ values for human and cynomolgus monkey FAPα (Table 6). The bispecific antibody with a non-binding control arm BisG1-FAPα-FERL/b12-FERR confirmed FAPα-specific binding with comparable affinity for human and cynomolgus monkey FAPα (Table 6) as BisG1-FAPα-FERL/DR4-FERR. Control antibody BisG1-b12-FERL/DR4-FERR showed no binding (data not shown).

TABLE 6

Binding affinity of BisG1-FAPα-FERL/DR4-FERR and BisG1-FAPα-FERL/b12-FERR antibodies to immobilized His-tagged recombinant Human and Cynomolgus FAPα protein.

| Sample ID | Species | | K$_D$ (pM) | k$_a$ (1/Ms) | k$_d$ (1/s) |
|---|---|---|---|---|---|
| BisG1-FAPα-FERL/DR4-FERR | Human | Average | 26 | 1.10E+06 | 3.00E−05 |
| | | stdev | 4 | 4.10E+05 | 1.40E−05 |
| | Cynomolgus monkey | Average | 37 | 7.70E+05 | 2.80E−05 |
| | | Stdev | 3 | 9.50E+04 | 1.60E−06 |
| BisG1-FAPα-FERL/b12-FERR | Human | Average | 17 | 1.20E+06 | 2.10E−05 |
| | | Stdev | 0 | 4.50E+05 | 8.20E−06 |
| | Cynomolgus monkey | Average | 34 | 7.50E+05 | 2.50E−05 |
| | | Stdev | 2 | 6.60E+04 | 2.40E−06 |

Results show the average and standard deviation (stdev) of three experiments.

Example 6: Binding Competition Between Anti-FAPα Antibodies to Recombinant Human FAPα in a BLI-Based Classical Sandwich Cross-Block Assay Antibody cross-block analysis (epitope binning) was performed using bio-layer interferometry (BLI) on an Octet® HTX instrument (FortéBio) to determine the binding competition to recombinant human FAPα between IgG1-FAPα-

F405L and benchmark FAPα-specific antibodies IgG1-FAP-ESC11-F405L and IgG1-FAP5. IgG1-b12 was included as a negative control.

Sandwich cross-block experiments were carried out while shaking at 1,000 RPM at 30° C. Amine Reactive biosensors (AR2G) (FortéBio, Cat #18-5092) were activated for 300 s with a solution of 20 mM EDC (N-(3-Dimethylaminopropyl)-N'-ethylcarbodiimide hydrochloride) (FortéBio, Cat. #18-1033) and 10 mM s-NHS (N-Hydroxysulfosuccinimide sodium salt) (FortéBio, Cat. #18-1067). The activated AR2G sensors were loaded with 10 μg/mL of the first antibody in 10 mM Sodium Acetate pH 6.0 (FortéBio, cat. no. 18-1070) for 600 s and quenched with 1 M ethanolamine pH 8.5 (FortéBio, Cat. #18-1071) for 300 s. After a baseline measurement in Sample Diluent (30 s; FortéBio, Cat. #18-1048), the AR2G biosensors containing immobilized antibodies were loaded for 200 s with His-tagged recombinant human FAPα (R&D Systems, Cat #3715-SE, 100 nM in Sample Diluent) for 200 s. The theoretical molecular mass of His-tagged recombinant human FAPα protein based on the amino acid sequence (86 kDa) was used for calculations. The association (200 s) of a second antibody (5 μg/mL in Sample Diluent) was determined. Sensors were regenerated by exposure to 10 mM glycine pH 2.5 (Riedl-deHaen, Cat. #15527) for 5 s, followed by neutralization in Sample Diluent for 5 s; both steps were repeated twice. Subsequently, the sensors containing immobilized first antibody were used again, starting with the baseline step.

Data were acquired using Data Acquisition Software v9 (FortéBio) and analyzed with Data Analysis HT Software v9 (FortéBio). The Y-axis was aligned to the start of the association step and Savitzky-Golay filtering was applied. The association responses of the second antibodies were plotted in a matrix format. Per immobilized antibody, the responses were corrected by subtraction of the average response of two reference sensors that were incubated with Sample Diluent instead of second antibody, to correct for the dissociation of His-tagged recombinant human FAPα protein from the immobilized first antibody. In general, a cutoff of 0.21 nm, based on the general response for self-block, was used to distinguish between blocking (<0.21 nm) and nonblocking (>0.21 nm) antibody pairs.

Results

Sandwich cross-block experiments using BLI showed that IgG1-FAPα-F405L did not bind to FAPα simultaneously with the benchmark antibody IgG1-FAP-ESC11-F405L (responses below cutoff, Table 7), indicating these antibodies block each other's binding in this particular assay setup. IgG1-FAP5 antibody could bind FAPα simultaneously with IgG1-FAPα-F405L antibody or IgG1-FAP-ESC11-F405L antibody (responses above cutoff of 0.21 nm), suggesting that the benchmark IgG1-FAP5 antibody targets a different epitope on FAPα than IgG1-FAPα-F405L. Negative control antibody IgG1-b12 showed no binding.

TABLE 7

Binding competition to recombinant human FAPα in a BLI-based sandwich cross-block assay.

| Immobilized Ab ↓ | IgG1-FAPα-F405L | IgG1-FAP-ESC11-F405L | IgG1-FAP5 |
|---|---|---|---|
| IgG1-FAPα-F405L | 0.13 | 0.11 | 0.34 |
| IgG1-FAP-ESC11-F405L | 0.10 | 0.08 | 0.58 |
| IgG1-FAP5 | 0.49 | 0.46 | 0.10 |

The first column on the left indicates the first (immobilized) antibody and the first row on the top indicates the second antibody. The numbers in the matrix indicate the response of the second antibody. Responses above cutoff of 0.21 nm are nonblocking antibody pairs. Responses below cutoff of 0.21 nm are blocking pairs.

Example 7: Species Cross Reactivity to DR4 or Mouse/Rat DR

Binding of BisG1-FAPα-FERL/DR4-FERR, BisG1-DR4-FEAL/b12-FEAR and IgG1-DR4-FERR to DR4 of various species commonly used for nonclinical toxicology studies was assessed by flow cytometry using ExpiCHO-S™ cells transiently expressing DR4 from different animal species. In contrast to other species, rodents only express one DR which has highest homology with human DR5. Therefore, ExpiCHO-S™ cells transiently expressing rat and mouse DR protein were used instead. All DR constructs lack the intracellular DD to avoid apoptosis of transfected cells upon DR(4) activation. IgG1-b12 was used as negative control.

ExpiCHO-S™ cells (Life Technologies, Cat #EXX8120-3605-036) were transiently transfected with mammalian expression vector pSB encoding human (UniProt ID: O00220 lacking aa 365-448 [DD deletion]; SEQ ID NO: 40), cynomolgus monkey (Macaca fascicularis; Uniprot ID: O15309893.2 lacking aa 370-457 [DD deletion]; SEQ ID NO: 41), rabbit (Oryctolagus cuniculus; UniProt ID: O17195576.1 lacking aa 331-418 [DD deletion]; SEQ ID NO: 46), dog (Canis familiaris; UniProt ID: 038280584.1 lacking aa 350-433 [DD deletion]; SEQ ID NO: 44), pig (Sus scrofa; UniProt ID: 005670488.1 lacking aa 336-423 [DD deletion]; SEQ ID NO: 45) DR4 protein with C-terminal HA-tag coupled to a snorkel-domain, or rat (Rattus norvegicus; UniProt ID: B8YBG7 lacking aa 254-323 [DD deletion]; SEQ ID NO: 43) and mouse (Mus musculus; UniProt ID: Q9QZM4 lacking aa 273-356 [DD deletion]; SEQ ID NO: 42) DR protein with C-terminal HA-tag coupled to a snorkel-domain, using ExpiFectamine™ CHO transfection reagent (Thermo Fisher Scientific, Cat #A29131), OptiPro™ Serum Free Medium (Thermo Fisher Scientific, Cat #12309019) and ExpiFectamineCHO™ Enhancer (Thermo Fisher Scientific, Cat #A29131), according to the manufacturer's instructions.

The binding assay was performed as described in Example 4, except for the following amendment: 50,000 cells/well were seeded. Binding curves were analyzed using nonlinear regression analysis (four-parameter dose-response curve fits) in GraphPad Prism.

Results

The BisG1-FAPα-FERL/DR4-FERR and BisG1-DR4-FEAL/b12-FEAR antibodies, which can bind only monovalently, displayed binding to ExpiCHO-S™ cells transfected with human DR4 and cynomolgus monkey DR4 (FIG. 4A-B). The apparent affinity of BisG1-FAPα-FERL/DR4-FERR to human DR4 was considerably higher: the average $EC_{50}$±SEM for binding to human DR4 was 0.50±0.26 μg/mL for BisG1-FAPα-FERL/DR4-FERR (Table 8), while the average $EC_{50}$ for cynomolgus monkey DR4 could not be calculated as the plateau was not reached. The monoclonal antibody (bivalent binding, IgG1-DR4-FERR) also showed higher apparent affinity for human DR4 (average $EC_{50}$ t SEM 0.14 t 0.09 µg/mL) compared to cynomolgus monkey DR4 (average $EC_{50}$ t SEM 1.84 t 0.45 µg/mL). BisG1-FAPα-FERL/DR4-FERR and BisG1-DR4-FEAL/b12-FEAR showed comparable dose-dependent binding and $EC_{50}$ confirming that the observed binding is via the DR4-specific arm and not via the FAPα-specific arm.

No binding to DR4 from rabbit, dog, pig, or to mouse/rat DR was observed for BisG1-FAPα-FERL/DR4-FERR or IgG1-DR4-FERR (FIG. 4C-G).

IgG1-b12, used as a negative control, did not show binding to DR4 of any of the tested species (FIG. 4A-G).

In conclusion, the DR4-specific antibody clone used for generation of bispecific antibody BisG1-FAPα-FERL/DR4-FERR (and of BisG1-DR4-FEAL/b12-FEAR) showed cross-reactivity to cynomolgus monkey DR4. However, the apparent affinity to cynomolgus DR4 is lower compared to the apparent affinity to human DR4. No binding was observed to DR4 (or mouse/rat DR) of other species (FIG. 4C-G).

monkey DR4 protein was determined using label-free biolayer interferometry on an Octet® HTX instrument (Sartorius).

The protocol detailed in Example 5 was used with the following differences: anti-Penta-HIS biosensors (Sartorius, Cat #18-5120) were used; the sensors were preconditioned by exposure to 10 mM glycine (Sigma-Aldrich, Cat #15527) buffer pH 1.5 for 5s, followed by neutralization in Sample Diluent (Sartorius, Cat #18-1104) for 5s; both steps were repeated 2 times; the sensors were loaded with 50 nM human DR4HsECD-FcHisCtag (SEQ ID NO: 66), or cynomolgus DR4MfECD-FcHisCtag (SEQ ID NO: 67), for 600 s; the dissociation time was 1,000s; The window of interest for the dissociation time was set at 100 s for the cynomolgus antigen and at 1,000 s for the human antigen.

Results

BisG1-FAPα-FERL/DR4-FERR showed considerably higher binding affinity for human compared to cynomolgus

TABLE 8

$EC_{50}$ values of DR4-specific arm binding to human and cynomolgus monkey DR4 transiently expressed on ExpiCHO-S ™ cells.

| Species | Antibody | $EC_{50}$ (µg/mL) | | | |
|---|---|---|---|---|---|
| | | n = 1 | n = 2 | n = 3 | Average ± SEM |
| Human | BisG1-FAPα-FERL/DR4-FERR | 1.00 | 0.38 | 0.11 | 0.50 ± 0.26 |
| | BisG1-DR4-FEAL/b12-FEAR | 1.02 | 1.23 | — | 0.32 ± 0.10 |
| | IgG1-DR4-FERR | 0.33 | 0.06 | 0.04 | 0.14 ± 0.09 |
| Cynomolgus monkey | BisG1-FAPα-FERL/DR4-FERR | N/A | N/A | N/A | N/A |
| | BisG1-DR4-FEAL/b12-FEAR | N/A | N/A | — | N/A |
| | IgG1-DR4-FERR | 2.57 | 1.94 | 1.01 | 1.84 ± 0.45 |

$EC_{50}$ = concentration (µg/mL) at which 50% of the maximal binding was observed;
N/A = $EC_{50}$ not calculated because the incomplete dose-response curves (plateau not reached);
— = assay not performed Example 8: Binding Affinity of DR4 Clone to Recombinant Human and Cynomolgus Monkey DR4

The binding affinity of BisG1-FAPα-FERL/DR4-FERR, BisG1-b12-FERL/DR4-FERR and control BisG1-FAPα-FERL/b12-FERR to recombinant human and cynomolgus monkey DR4 (Table 9). The bispecific antibody with the nonbinding control arm BisG1-b12-FERL/DR4-FERR confirmed DR4-specific binding with comparable nanomolar $K_D$ values (Table 9). Negative control antibody BisG1-FAPα-FERL/b12-FERR showed no binding (data not shown).

TABLE 9

Summary tables are shown for binding of the BisG1-FAPα-FERL/DR4-FERR and BisG1-b12-FERL/DR4-FERR to human and cynomolgus monkey DR4.

| Sample ID | Species | | $K_D$ (nM) | $k_a$ (1/Ms) | $k_d$ (1/s) |
|---|---|---|---|---|---|
| BisG1-FAPα-FERL/DR4-FERR | Human | Average | 0.39 | 3.20E+05 | 1.20E−04 |
| | | stdev | 0.02 | 1.50E+04 | 3.40E−06 |
| | Cynomolgus monkey | Average | 290 | 2.80E+04 | 8.00E−03 |
| | | stdev | 20 | 1.80E+03 | 1.10E−04 |
| BisG1-b12-FERL/DR4-FERR | Human | Average | 0.32 | 3.30E+05 | 1.00E−04 |
| | | stdev | 0.01 | 5.70E+03 | 2.30E−06 |
| | Cynomolgus monkey | Average | 260 | 3.10E+04 | 8.20E−03 |
| | | stdev | 15 | 1.30E+03 | 1.20E−04 |

Results show the average and stdev from three experiments.

Example 9: DR4, DR5 and FAPα Surface Expression Quantification and Assessment of Fibroblast Cell Death a. Surface Expression Pattern of FAPα and DR4 on Fibroblasts Supports Trans-Binding of BisG1-FAPα-FERL/DR4-FERR.

The proposed mechanism of action of BisG1-FAPα-FERL/DR4-FERR is trans-binding of FAPα, expressed on CAFs in the TME, and DR4, expressed on the tumor cells, resulting in DR4 transactivation-mediated tumor cell death. If cis-binding of BisG1-FAPα-FERL/DR4-FERR to fibroblasts was to take place, this could potentially reduce the antitumor activity by directly targeting the fibroblasts instead of tumor cells. In Example 2, efficient FAPα binding to lung fibroblasts and CAFs by BisG1-FAPα-FERL/DR4-FERR and IgG1-FAPα-FERL was shown.

Expression of human FAPα, DR4 and DR5 was assessed on human lung fibroblasts and CAFs by semiquantitative analysis using indirect immunofluorescence staining (Qifi assay). The following primary antibodies were used: mouse anti-human DR4 (Biolegend, Cat #307202), mouse anti-human DR5 (antibody from Diaclone, Cat #854.860.000 for human lung fibroblasts and antibody from Invitrogen, Cat #14-9908-82 for CAFs) and mouse anti-human FAPα (US-Biological, Cat #F4208-57E). Human lung fibroblasts were cultured in MEM medium (Lonza, Cat #M5650) supplemented with 10% fetal bovine serum (FBS, ATCC®, Cat #30-2020), 1% L-glutamine (Lonza, Cat #BE17-605E) and 1% Penicillin/Streptomycin (Pen/Strep, Lonza, Cat #DE17-603E). CAFs were cultured in DMEM high glucose medium (Sigma-Aldrich, Cat #D6429) supplemented with 50 U/mL Penicillin/Streptomycin, 2 mM GlutaMAX™ and 10% FBS (Bodinco B V, Cat #5067V20002)

Cell viability was checked with AO/PI (Nexcelom, Cat #CS2-0106). Human lung fibroblasts and CAFs (50,000 cells/well) were seeded in 96-Well round bottom plates (Greiner Bio-one, Cat #650101). Antibody dilutions were prepared using FACS buffer, consisting of PBS (Lonza, Cat #BE17-517Q) supplemented with 1% BSA (Roche, Cat #10735086001) and 0.02% Sodium Azide (Bio-World, Cat #41920044-3). For experiments using CAFs, the following step was performed: plates were centrifuged, supernatant was removed and cells were resuspended in 50 μL of human Fc Block (BD, Cat #564220, diluted 1:100 in FACS buffer) and 50 μL of viability stain TO-PRO®-3 Iodide (Thermo Fisher, Cat #T3605, diluted 1: 25,000 in FACS buffer), and incubated for 15 min at 4° C. Plates were washed once with FACS buffer. Plates containing either human lung fibroblasts or CAFs were centrifuged, supernatant was removed, cells were resuspended in 50 μL of the primary antibodies (final concentration of 10 μg/mL of FACS buffer) and incubated for 30 min at 4° C. Cells were washed three times with FACS buffer and resuspended in 50 μL of FITC-labeled polyclonal antibody goat anti-mouse IgG1 (Dako, Cat #F047902-2, diluted 1:50 for experiments using CAFs and 1:100 for experiments using human lung fibroblast, in FACS buffer). In parallel, 15 μL of human set-up Qifi beads (Biocytex, Cat #CP010) and 15 μL of calibration Qifi beads (Dako, Cat #K0078) were added to empty wells. After 30 min incubation at 4° C., cells were washed twice with FACS buffer and resuspended in FACS buffer. All samples were analyzed on an iQue® flow cytometer (Sartorius) or a FACSCelesta™ flow cytometer (BD biosciences) and data were processed using FlowJo_v10.8.1 (FlowJo LLC). Data were analyzed with GraphPad Prism.

For the Qifi assay, the primary antibody was used at saturating concentrations, where the number of bound primary antibody molecules corresponds to the number of antigenic sites present on the cell surface. The FITC-conjugated secondary antibody was also used at saturating concentration, to correlate the fluorescence intensity with the number of bound primary antibody molecules on the cells and on the beads. The recorded fluorescence values from the calibration beads, with a well-defined number of IgG monoclonal antibodies per bead, are used to generate the standard curve using GraphPad Prism software. The software then used the standard curve equation to calculate the specific antibody binding capacity (sABC, which corresponds to the mean number of accessible antigen or molecule sites per cell) for the antibody-stained cells.

Results

Figure 5A:
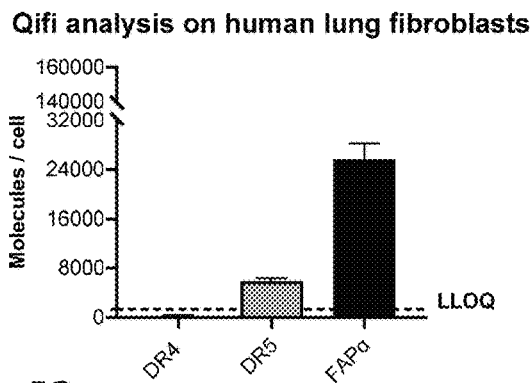
FIGS. 5A-5E: DR4, DR5 and FAPα surface expression quantification and assessment of fibroblast cell death.
Figure 5B:
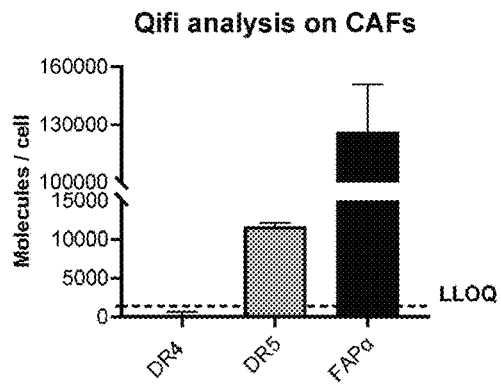

Human lung fibroblasts expressed high levels of human FAPα and low levels of DR5 (25,387±2,564 and 5,841±479 molecules/cell, respectively; mean±SEM of two independent experiments) (FIG. 5A). DR4 expression was below the lower limit of quantification (LLOQ, dashed line, FIG. 5A). Similar results were observed for CAFs (FIG. 5B): high FAPα expression (109,759±25,397 molecules/cell, mean±SEM of three independent experiments), low DR5 expression (11,610±502 molecules/cell, mean t SEM of two independent experiments) and DR4 expression below the LLOQ. In conclusion, binding data from example 2 and these results suggest that BisG1-FAPα-FERL/DR4-FERR will only target CAFs with the FAPα arm, while DR4 activation on fibroblasts as a consequence of simultaneous binding to DR4 and FAPα is unlikely.

b. BisG1-FAPα-FEAL/DR4-FEAR does not Induce Fibroblast Cell Death.

Next, the capacity of BisG1-FAPα-FEAL/DR4-FEAR, BisG1-FAPα-FEAL/b12-FEAR and BisG1-b12-FEAL/DR4-FEAR to induce death of human lung fibroblasts and CAFs was assessed. IgG1-b12-FEAR (negative control), IgG1-FAPα-FEAL and RG7386 were also tested.

Human lung fibroblasts were detached using trypsin/EDTA (Lonza, Cat #17-161E) and viability was checked using AO/PI (Nexcelom, Cat #CS2-0106-25 ml). 100 μL containing 5,000 cells/well was added to 96-Well flat bottom plates (Greiner bio-one, Cat #655180) and incubated at 37° C., 5% $CO_2$ for 24 h before adding 50 μL/well of antibody dilutions (10-0.0000256 μg/mL, five-fold dilutions using FACS buffer). After 72 h at 37° C., 5% $CO_2$, 15 μL/well of Cell-Titer Glo (Promega, Cat #G7571) was added; plates were further incubated for 1.5 h at 37° C., 5% $CO_2$, before transferring 100 μL supernatant to a 96-Well white Opti-Plate™ (Perkin Elmer, Cat #6005299). Luminescence (viability readout) was measured on the EnVision® instrument. Data were analyzed and visualized using GraphPad Prism. The percentage of viable cells, normalized to condition without antibodies, was plotted against antibody concentration.

A follow-up experiment with human lung fibroblasts was performed applying the following differences: cell viability was checked with trypan blue (Sigma, Cat #T8154-100 ml); 96-Well flat bottom plates were from Falcon® (Cat #353072); cells were incubated for 3 h before adding the antibody serial dilutions (1-0.000002 μg/mL, five-fold serial dilutions using M0130 medium). The M0130 medium, consisting of RPMI (Gibco, Cat #A10491-01) supplemented with 10% heat inactivated donor bovine serum (Gibco, Cat #20371-030) was used to dilute reagents. As positive control for killing, 3 µM of Staurosporine/well was added, while the antibody IgG1-b12 was used as negative control for killing; next, 50 µL/well of 100 nM Cytotox Green (Essenbio, Cat #4633, diluted in M0130) was added and plates were incubated in the Incucyte for 72 h (at 37° C., 5% $CO_2$), with images taken every 3 h. Data were generated and processed using the Incucyte software 2021B. Data were analyzed and visualized using GraphPad Prism. Data were fitted with a nonlinear four-parameter logistic curve. For each condition at each timepoint, the Incucyte software calculated the number of Cytotox Green-positive dead cells, which were plotted against time.

For the experiment with CAFs, cells were detached using trypsin (Lonza, Cat #BE02-007E) and counted using trypan blue (Fluka, Cat #93590). 100 µL containing 10,000 CAFs/well were seeded on a collagen (Ibidi, Cat #50204) monolayer (7.5 µg/mL collagen in 17.5 mM acetic acid from VWR, Cat #30010.292) in 96-Well plates and incubated at 37° C., 5% $CO_2$ for 24 h before adding 12 µL/well of BisG1-FAPα-FEAL/DR4-FEAR antibody dilutions (20-0.05 µg/mL, four-fold dilutions using FACS buffer). After 72 h at 37° C., 5% $CO_2$ cell viability was assessed by adding 80 µL/well of prewarmed CellTiter-Glo™ 3D (Promega, Cat #G9681) to each well. After 30 min (of which the first 15 min on gentle agitation), luminescence was read using Spectramax plate reader (Molecular Devices). Data were processed and visualized using GraphPad Prism. Data were fitted with a nonlinear four-parameter logistic curve. The graph shows the % viable tumor cells t SEM of technical duplicates, normalized to condition without antibody and plotted against the antibody concentration.

Results

Figure 5C:
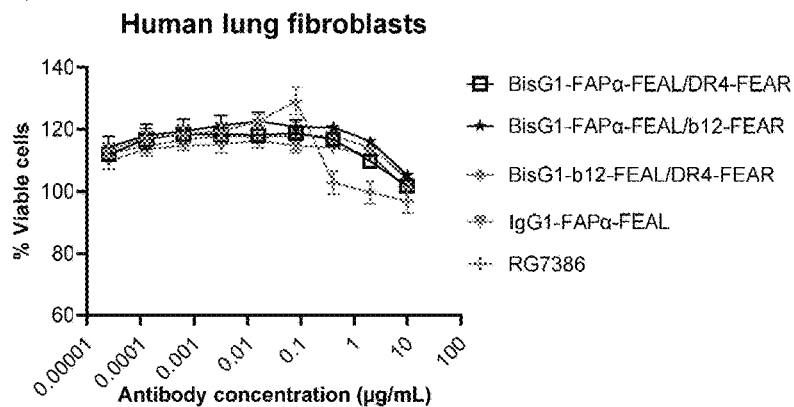
Figure 5D:
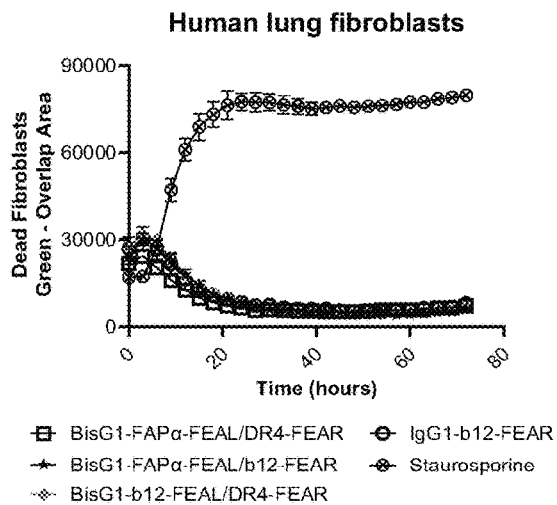
Figure 5E:
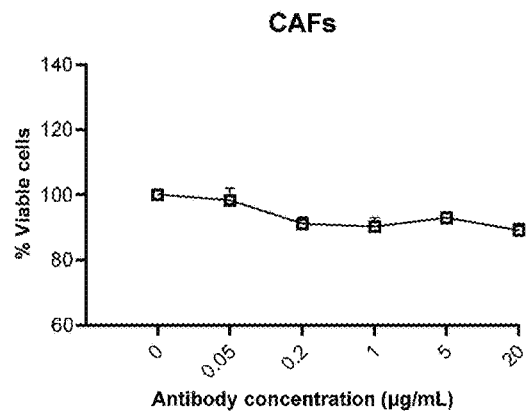

In two separate experiments with human lung fibroblasts, BisG1-FAPα-FEAL/DR4-FEAR, IgG1-FAPα-FEAL, BisG1-FAPα-FEAL/b12-FEAR or BisG1-b12-FEAL/DR4-FEAR did not alter lung fibroblast viability when compared to negative control IgG1-b12-FEAR (FIGS. 5C-D). However, treatment with high concentrations of RG7386 showed a decline in fibroblast viability (FIG. 5C). CAFs viability was also unaffected by treatment with BisG1-FAPα-FEAL/DR4-FEAR (FIG. 5E). These results show that BisG1-FAPα-FEAL/DR4-FEAR antibody does not induce fibroblast cell death.

Example 10: Transactivation Potential of BisG1-FAPα-FEAL/DR4-FEAR a. Comparison Between FAPα-Binding Clones in a Bispecific Format to Induce DR4 Transactivation-Mediated Cell Death.

The capacity of BisG1-FAPα-FEAL/DR4-FEAR and BisG1-FAP5-FEAL/DR4-FEAR to induce DR4 transactivation-mediated cell death of DR4-expressing human cancer cell line MDA-MB-231 in the presence of human lung fibroblasts was assessed. BisG1-FAPα-FEAL/b12-FEAR, BisG1-FAP5-FEAL/b12-FEAR and BisG1-b12-FEAL/DR4-FEAR were used as negative controls.

The in vitro viability assays were performed using the human cancer cell line MDA-MB-231 (breast cancer, ATCC®, Cat #HTB26) cultured in the presence of human lung fibroblast. MDA-MB-231 cells (cultured in M0089 medium consisting of DMEM with high glucose and HEPES [N'-2-Hydroxyethylpiperazine-N'-2 ethanesulphonic acid] from Lonza, Cat #BE12-709F supplemented with 10% donor bovine serum with iron from Life Technologies, Cat #20371, 1% L-glutamine from Lonza, Cat #BE17-605E, 1% 100 mM Sodium Pyruvate from Lonza, Cat #BE13-115E and 1% of 100× Non-essential aminoacid solution from Life Technologies, Cat #11140) were incubated with 0.3 µM CytoLight Rapid Red (Essen Bio, Cat #4706, stock 1 µM) for 20 min at 37° C. and washed three times with culture medium M0130 (RPMI from Gibco, Cat #A10491-01, supplemented with 10% heat-inactivated donor bovine serum from Gibco, Cat #20371-030). MDA-MB-231 cell viability was checked with trypan blue (Sigma-Aldrich, Cat #T8154-100 ml). Cells (5,000 CytoLight Rapid Red labeled cells/well and 2,500 human lung fibroblasts/well) were seeded in 96-Well flat bottom plates (Falcon, Cat #353072) in M0130 medium and incubated at 370C, 5% $CO_2$ for 24 hours before adding the antibody serial dilutions (1000-0.00051 ng/mL final concentration, five-fold serial dilutions using M0130 medium). For the negative control antibodies (BisG1-FAPα-FEAL/b12-FEAR, BisG1-FAP5-FEAL/b12-FEAR and BisG1-b12-FEAL/DR4-FEAR), a fixed concentration of 1000 ng/mL was added, and 1 µM final concentration of Staurosporine (Sigma, Cat #S6942, diluted in M0130 medium) was used as a positive control for killing. Next, 50 µL/well of 100 nM Cytotox Green (Essen Bio, Cat #4633, diluted in M0130 medium) was added before incubating the coculture plates in the Incucyte© (Essenbio) for 72 h at 370C, 5% $CO_2$, with imaging performed every 4 h. Data were generated and processed using the Incucyte software 2021B. Data were analyzed and visualized using GraphPad Prism. Data were fitted with a nonlinear four-parameter logistic curve. For each condition, the Incucyte software calculated the signal corresponding to the number of Cytotox Green-positive dead cells (Overlap Object Area, $µm^2$/Image) and the signal corresponding to the number of total cells (Red Object Area, $µm^2$/Image) for each timepoint. Viable tumor cells were calculated by subtracting the signal of dead cells to the signal of total cells. Next, the area under the curve (AUC) was calculated using GraphPad Prism and plotted against the antibody concentration.

Results

In cocultures of MDA-MB-231 cells and human lung fibroblasts BisG1-FAPα-FEAL/DR4-FEAR and BisG1-FAP5-FEAL/DR4-FEAR induced dose-dependent cell death (FIG. 6A). BisG1-FAPα-FEAL/DR4-FEAR induced maximum DR4-dependent MDA-MB-231 cell death at lower concentrations than BisG1-FAP5-FEAL/DR4-FEAR (Table 10). As expected, the control bispecific antibodies BisG1-FAPα-FEAL/b12-FEAR, BisG1-FAP5-FEAL/b12-FEAR and BisG1-b12-FEAL/DR4-FEAR did not elicit cell death.

TABLE 10 viability of MDA-MB-231 cells treated with different concentrations
of BisG1-FAPα-FEAL/DR4-FEAR or BisG1-FAP5-FEAL/DR4-FEAR

| | Sample ID | |
|---|---|---|
| Concentration antibody (ng/mL) | BisG1-FAPα-FEAL/DR4-FEAR (mean ± SEM of $\mu m^2$/image) | BisG1-FAP5-FEAL/DR4-FEAR (mean ± SEM of $\mu m^2$/image) |
| 0.00051 | 172,809 ± 1,315 | 167,370 ± 2,629 |
| 0.00256 | 171,166 ± 2,001 | 170,445 ± 4,928 |
| 0.0128 | 163,914 ± 5,134 | 167,805 ± 365 |
| 0.064 | 165,243 ± 2,873 | 170,128 ± 2,228 |
| 0.32 | 154,470 ± 6,283 | 153,561 ± 12,643 |
| 1.6 | 144,137 ± 12,007 | 168,597 ± 6,059 |
| 8 | 126,521 ± 16,500 | 173,446 ± 6,235 |
| 40 | 116,390 ± 15,247 | 149,673 ± 5,495 |
| 200 | 113,562 ± 12,384 | 139,466 ± 9,261 |
| 1000 | 120,288 ± 23,683 | 128,458 ± 15,925 |

Results are shown as mean ± SEM (of μm2/image) from one experiment.

b. BisG1-FAPα-FERL/DR4-FERR Induces DR4 Transactivation-Mediated Cell Death Only in the Presence of FAPα-Expressing Cells.

The capacity of the BisG1-FAPα-FERL/DR4-FERR to induce DR4 transactivation-mediated cell death of DR4-expressing human cancer cells in the presence and absence of FAPα-expressing cells was assessed. BisG1-b12-FERR/b12-FERL antibody was used as negative control. RG7386 was included in experiments with cancer cells only, while control antibodies BisG1-b12-FERL/DR4-FERR and BisG1-FAPα-FERL/b12-FERR were included in coculture experiments.

For coculture experiments, the cancer cells were cultured in the presence of cell line NIH/3T3 (mouse fibroblasts, ATCC©, Cat #CRL-1658) which was transfected to express FAPα mature polypeptide (SEQ ID NO: 33) as follows: on the day of transfection, the NIH/3T3 cells were harvested using 0.5% trypsin/EDTA (Gibco, Cat #25300-062) and viability was measured using Vicell-BLU® instrument (Beckman Coulter). A total of 1 million cells was transferred to 15 mL tubes (Greiner Bio-one, Cat #188271), washed with Hanks' Balanced Salt Solution (HBSS, Gibco, Cat #14175-053) and resuspended in 100 μL 4D-Nucleofector® solution (500 μL of supplement 1 mixed with 2.25 mL SG Cell Line Solution, both reagents from the SG Cell Line Solution box, Lonza, Cat #PBC3-02250) and transferred to a cuvette (Lonza, Cat #PCK-2005) containing 4.7 μL of pGENPGK-FAP-puro plasmid DNA. The pGENPGK-FAP-puro expression vector (size approximately: 7,000 bp) contained the following main elements: full length human FAP, with expression driven by a phosphoglycerate kinase (PGK) promoter; the puromycin selection marker, with expression driven by a simian virus 40 (SV40) promoter; a kozak sequence upstream the PGK promoter, and the ampicillin selection marker, with expression driven by a Beta-lactamase (BLA) promoter. Electroporation was performed using the 4D-Nucleofector® instrument (X unit, Lonza). Next, 400 μL of M0057-05 medium consisting of DMEM High glucose and HEPES (Lonza, Cat #BE12-709F) supplemented with 10% heat-inactivated donor bovine serum with iron (DBSI, from Life Technologies, Cat #20371) and 1% of 200 mM L-Glutamine (Life Technologies, Cat #25030-081) was added to the cuvette. After 10 minutes of incubation at 37° C., 5% $CO_2$ the cuvette content was transferred with a Pasteur pipette (from Lonza kit Cat #V4XC-3024) to a 24-Well plate (Cellstar, Cat #662 160) already containing 500 μL/well of M0057-05 medium. The plate was stored in the incubator (37° C., 5% $CO_2$) to allow the cells to recover and expand. After 72 h, medium was replaced with 1 mL/well of medium consisting of 3.5 μL puromycin (stock solution 10 mg/mL from Sigma, Cat #P9620) added to 20 mL of a 1:1 mixture of fresh M0057-05 medium and M0057-05 medium collected from a flask containing untransfected, 100% confluent NIH/3T3 cells. The medium replacement step was repeated every four days until enough cells were available to assess transfection efficiency (FAPα expression) via flow cytometry.

To measure FAPα expression, 10,000 NIH/3T3-FAPα cells/well (round bottom 96-Well plates) were seeded, centrifuged, and resuspended in 20 μL/well of IgG1-FAPα-FERL primary antibody (stock concentration of 5 mg/mL diluted 1:4 with FACS buffer). After 20 minutes of incubation at 4° C. in the dark, cells were washed twice with FACS buffer and resuspended in 20 μL of secondary FITC-labeled polyclonal antibody goat anti-mouse IgG1 (diluted 1:4 with FACS buffer), followed by an additional 20 min incubation step (4° C. in the dark). Cells were washed twice with FACS buffer and resuspended in FACS buffer before readout using CellStream™ (Luminex). FAPα expression, measured in gMFI, was comparable to the expression measured for the positive control (HEK293F cells transiently expressing FAPα) (data not shown).

The in vitro viability assays were performed using two human cancer cell lines: DLD-1 (colorectal adenocarcinoma, ATCC®, Cat #CCL221, cultured in M0130 medium), and MDA-MB-231 (cultured in M0089 medium). The cells were harvested using trypsin (Gibco, Cat #25300-054) and cell viability was measured using AO/PI (Nexcelom, Cat #CS2-0106). 50 μL of 6,600 cancer cells/well, with or without 50 μL of 3,300 NIH/3T3-FAPα cells/well were seeded into 96-Well plates (Perkin Elmer, Cat #6005680); cells were incubated for 4 h (370C, 5% $CO_2$) to allow them to adhere to the plate before adding 50 μL/well of the antibody concentration series (14.4-0.000007 μg/mL final concentration, eight-fold serially diluted in M0130 medium); 50 μL/well of Phenylarsine oxide (PAO, from Sigma-Aldrich, Cat #P3075, stock concentration of 50 mg/mL was diluted 1:1,000 with FACS buffer) was used as positive control for killing. Plates were incubated (370C, 5% $CO_2$) for 72 h before viability readout. For viability readout, 20 μL/well of cell CellTiter-Glo™ 3D (Promega, Cat #G755A) was added and plates were incubated for 1.5 h (370C, 5% $CO_2$) before luminescence readout using EnVision. The percentage of live cells is calculated with the following formula: ([signal sample−signal PAO control]−[signal fibroblast cells only−signal PAO control])/([signal cancer cells only−signal PAO control]−[signal fibroblast cells−signal PAO control]). Data were analyzed and visualized using GraphPad Prism. Data were fitted with a nonlinear four-parameter logistic curve. The percentage of viable cells (in duplicate) is plotted against the antibody concentration.

Results

In monocultures of MDA-MB-231 and DLD-1 cancer cells, viability following treatment with BisG1-FAPα-FERL/DR4-FERR was comparable to control BisG1-b12-FERL/b12-FERR. On the other hand, treatment with the highest concentration of RG7386 showed a reduction in cancer cell viability (FIG. 6B-C; Table 11). Both MDA-MB-231 and DLD-1 cancer cells express DR5 (data not shown).

TABLE 11

% viable cells treated with top concentration (14,400 ng/mL) of antibodies

| Cell ID | % viable cells | | |
|---|---|---|---|
| | BisG1-FAPα-FERL/DR4-FERR | BisG1-b12-FERL/b12-FERR | RG7386 |
| MDA-MB-231 | 92 ± 3.3 | 100.4 ± 1.5 | 75 ± 1.2 |
| DLD-1 | 96 ± 3.5 | 91 ± 1.0 | 70.6 ± 5.9 |

Results are shown as mean ± SEM of technical duplicates from one representative experiment.

Figure 6E:
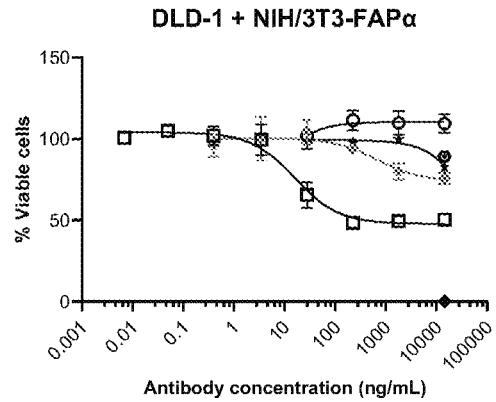

In cocultures of cancer cells and NIH/3T3-FAPα effector cells, BisG1-FAPα-FERL/DR4-FERR induced dose-dependent cell death (FIGS. 6D-E; Table 12 for top four concentrations). As expected, BisG1-b12-FERL/DR4-FERR, BisG1-FAPα-FERL/b12-FERR and BisG1-b12-FERL/b12-FERR (all containing at least one nonbinding control Fab arm) did not elicit substantial tumor cell death. Thus, DR4 transactivation-mediated cancer cell death depends on the targeting of DR4 and FAPα with a bispecific antibody.

TABLE 12

% viable cells treated with top four concentrations of BisG1-FAPα-FERL/DR4-FERR or BisG1-b12-FERL/b12-FERR

| Concentration | % viable cells | | | |
|---|---|---|---|---|
| | MDA-MB-231 | | DLD-1 | |
| antibody (ng/mL) | BisG1-FAPα-FERL/DR4-FERR | BisG1-b12-FERL/b12-FERR | BisG1-FAPα-FERL/DR4-FERR | BisG1-b12-FERL/b12-FERR |
| 28 | 75.6 ± 8.9 | 95.6 ± 5.3 | 65 ± 7.8 | 101.7 ± 0.9 |
| 225 | 51.8 ± 0.2 | 104.4 ± 11.5 | 48.6 ± 0.3 | 111.3 ± 6.2 |
| 1800 | 48.3 ± 1.2 | 107.1 ± 9 | 49.3 ± 3.6 | 109.7 ± 7.2 |
| 14400 | 46.1 ± 0.7 | 103 ± 0.9 | 50.3 ± 2.7 | 109.5 ± 5.7 |

Results are shown as mean ± SEM of technical duplicates from one representative experiment.

c. Caspase-8 Activation

To assess signaling downstream of DR4 transactivation, caspase-8 activation was assessed in cocultures of tumor cell lines with NIH/3T3-FAPα cells in presence or absence of BisG1-FAPα-FERL/DR4-FERR, RG7386, positive control recombinant human TRAIL (Biolegend, Cat #752906), and negative control antibody BisG1-b12-FERL/DR4-FERR.

DR4-expressing tumor cells (MDA-MB-231, A549, DLD-1 and SNU-1076 [head- and neck cancer; Creative Bioarray Cat #CSC-C9620L]) were harvested as described in Example 3. NIH-3T3-FAPα cells were harvested as described in Example 10, section b. Tumor cells and fibroblasts were seeded at a 2:1 ratio (13,300 tumor cells and 6,700 fibroblasts per well) in White Opaque 96-well Microplates (PerkinElmer, Cat #6005680) and incubated at 37° C. and 5% $CO_2$ overnight to allow the cells to adhere to the plate. Next, antibody concentration series (0.0003-100 nM with fivefold increments) were added. The samples were mixed on a plate shaker (300 RPM) for 2 min and plates were incubated at 37° C. and 5% $CO_2$ for 5 h.

Activation of the extrinsic apoptosis pathway was determined by measuring caspase-8 activation using the homogeneous Caspase-Glo® 8 Luminescent Assay (Promega, Cat #G8202). The plates were first left at RT for 30 min. Then 100 μL/well Caspase-Glo® 8 Reagent from the kit was added, mixed on a plate shaker (300 RPM) for 2 min and incubated protected from light at room temperature for 1 h. Luminescence was measured on an EnVision® Multiplate Reader. Luminescence data was processed with GraphPad Prism software to generate dose-response curves using non-linear regression analysis (sigmoidal dose-response with variable slope).

Results

Figure 7A:
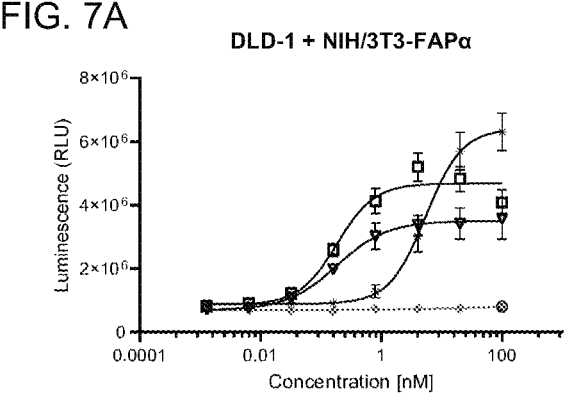
Figure 7B:
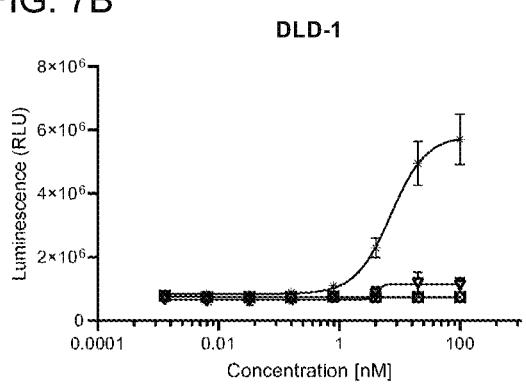
Figure 7C:
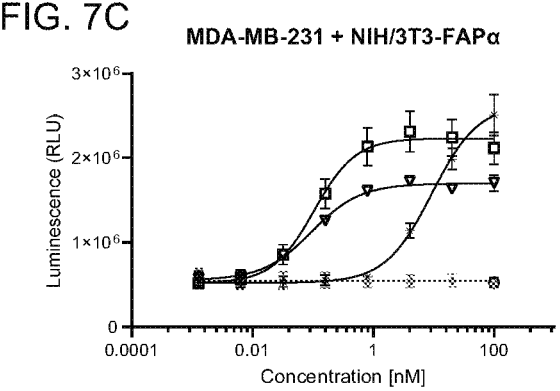
Figure 7D:
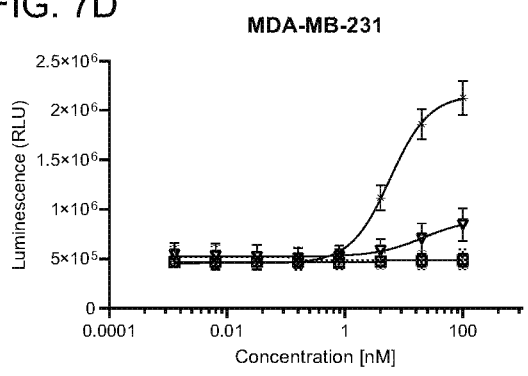
Figure 7E:
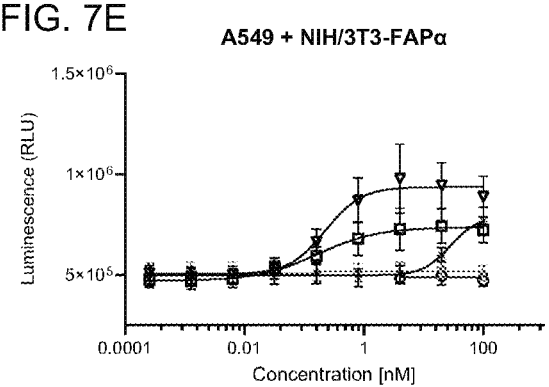
Figure 7F:
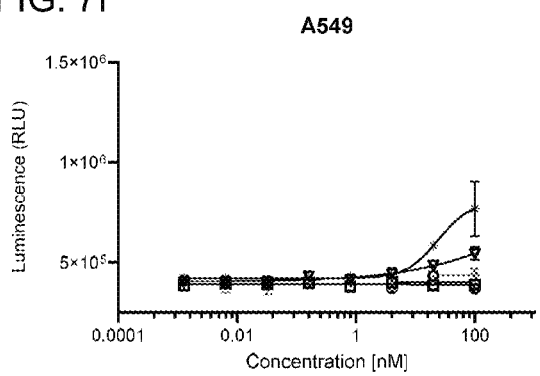
Figure 7G:
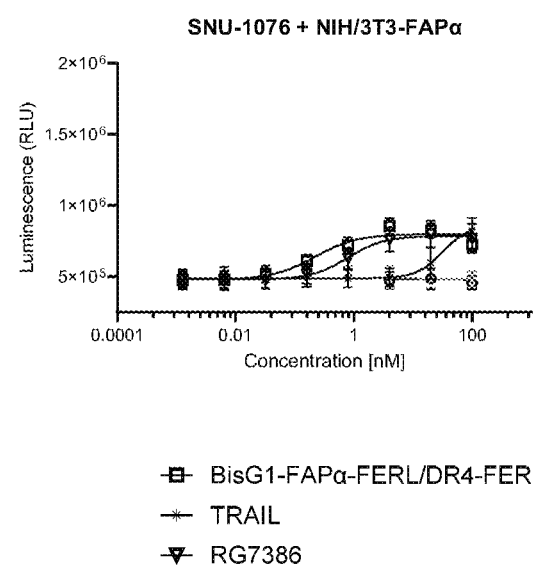
Figure 7H:
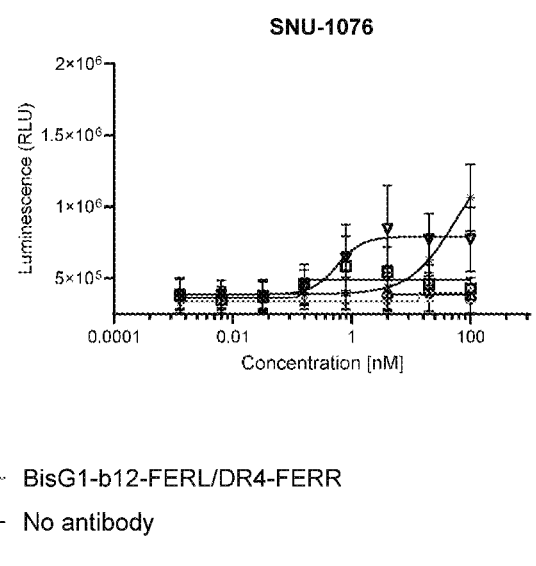

Dose-dependent caspase-8 activation was observed for BisG1-FAPα-FERL/DR4-FERR in cocultures of DLD-1, MDA-MB-231, A549 and SNU-1076 tumor cells with NIH/3T3-FAPα cells (FIG. 7A, C, E, G), but not in monocultures (FIG. 7B, D, F, H). These data suggest that BisG1-FAPα-FERL/DR4-FERR-induced cytotoxicity is mediated by caspase-8 activation. Maximum observed caspase-8 activation levels were comparable for BisG1-FAPα-FERL/DR4-FERR and TRAIL, included as a positive control. Moreover, dose-dependent caspase-8 activation was observed for RG7386 in all tumor cell lines. (FIG. 7).

Lack of BisG1-FAPα-FERL/DR4-FERR-induced caspase-8 activation in tumor cell monocultures or in cocultures in presence of BisG1-b12-FERL/DR4-FERR show that caspase-8 activation by BisG1-FAPα-FERL/DR4-FERR is conditional and dependent on binding of both DR4 and FAPα. In contrast, the unconditional agonist TRAIL induced caspase-8 activation also in tumor cell monocultures, independent of the presence of FAPα. Limited caspase-8 activation was furthermore observed in tumor cell monocultures with RG7386 (potentially due to its ability to bivalently bind DR5) but not BisG1-FAPα-FERL/DR4-FERR (FIG. 7A-H).

In summary, BisG1-FAPα-FERL/DR4-FERR shows effective caspase activation in all tumor cell lines tested that is dependent on the presence of FAPα-expressing fibroblasts. This is in line with the conclusions of the transactivation-mediated cell death as shown in section a and b in this example.

Example 11: Targeted Cell Death of PDOs Via DR4 Transactivation in the Presence of CAFs The capacity of BisG1-FAPα-FEAL/DR4-FEAR to induce DR4 transactivation-mediated cell death via transbinding of CRC PDOs was explored in the presence and absence of CAFs. IgG1-FAPα-FEAL was used as negative control.

In vitro viability assays were performed using PDOs derived from three patients with CRC: Hub096 (primary tumor, ascending colon), p19B (primary tumor, ascending colon) and p18T (primary tumor, sigmoid). The PDOs were cultured in basement membrane extract (BME) matrix (Amsbio, Cat #3533-010-02) at a 2:1 ratio with PDO medium, consisting of Advanced DMEM/F12 medium (Gibco, Cat #12634-010) containing the following supplements: 10 mM N-2-hydroxyethylpiperazine-N-2-ethane sulfonic acid (HEPES) Buffer (Lonza, Cat #17737E), 50 U/mL Penicillin/Streptomycin (Gibco, Cat #15070-063), 2 mM GlutaMAX™ (Gibco, Cat #35050-038), 20% R-Spondin conditioned medium (293T-HA-Rspol-F cell line), 100 ng/mL Noggin conditioned medium (293T-mNoggin-Fc cell line), 1× B27 (Invitrogen, Cat #17504-044), 10 mM Nicotinamide (Sigma-Aldrich, Cat #N0636), 10 nM Prostaglandin E2 (Tocris, Cat #2296-10), 10 nM Gastrin (Sigma-Aldrich, Cat #G9145), 0.5 mM N-acetylcysteine (NAC, Sigma-Aldrich, Cat #A9165), 500 nM A83-01 (SignalChem, Cat #A09-900-05), 50 ng/mL of Human recombinant epidermal growth factor (EGF, Sigma-Aldrich, Cat #A9165), 10 µM SB202190 (p38 inhibitor, Gentaur, Cat #A1632) and 10 mM Y27632 (Rock kinase inhibitor, Abmole Bioscience, Cat #HY-10583). CAFs were cultured in CAF medium, consisting of DMEM high glucose medium (Sigma-Aldrich, Cat #D6429) supplemented with 50 U/mL Penicillin/Streptomycin, 2 mM GlutaMAX™ and 10% FBS (Bodinco B V, Cat #5067V20002).

CellTiter-Glo® Viability Assays with PDOs and CAFs

The day before the coculture experiment, CAFs were detached using trypsin (Lonza, Cat #BE02-007E) and counted using trypan blue (Fluka, Cat #93590). 10,000 CAFs/well were seeded on a collagen (Ibidi, Cat #50204) monolayer (7.5 µg/mL collagen in 17.5 mM acetic acid from VWR, Cat #30010.292) in 96-Well plates (Thermo Fisher Scientific, Cat #165306) and incubated at 37° C., 5% $CO_2$. The following day, the PDOs were collected and dissociated using TripLE™ Express (Gibco, Cat #12604021) for 5 min at 37° C. Cells were washed with PBS (Corning, Cat #21-0310CVR), counted using trypan blue and resuspended in 5% Matrigel® (Corning, Cat #354234) diluted in coculture medium consisting of Advanced DMEM/F12 supplemented with HEPES Buffer, penicillin/Streptomycin, GlutaMAX™, B27, EGF, Y27632, A83-01 and NAC (as aforementioned), 10 ng/mL Human insulin (Sigma-Aldrich, Cat #19278), 10 ng/mL Human fibroblast growth factor (FGF)-basic (Prepotech, Cat #100-18B) and 25 ng/mL Platelet-derived growth factor receptor (PDGFR) α/β (Sigma-Aldrich, Cat #p3326). 10,000 PDOs were added to empty wells or to the CAF monolayer and the plates were incubated for 4 h at 37° C., 5% $CO_2$ before adding 12 µL/well of the antibody concentration series (10-0.001 µg/mL, five-fold serial dilutions in coculture medium). All conditions were tested in technical duplicates. After 72 h at 37° C., 5% $CO_2$ cell viability was assessed by adding 80 µL/well of prewarmed CellTiter-Glo™ 3D (Promega, Cat #G9681) to each well. After 30 min (of which the first 15 min on gentle agitation), luminescence was read using Spectramax plate reader (Molecular Devices). Data were processed and visualized using GraphPad Prism. Data were fitted with a nonlinear four-parameter logistic curve. The graphs show the % viable tumor cells±SEM of duplicates, normalized to PDO only condition (without CAFs nor antibody), and plotted against the antibody concentration.

Annexin-V Viability Assay

The day before the start of the coculture experiment, CAFs were harvested as described for the CellTiter-Glo® assay, and incubated with cytoplasmic membrane dye CellBrite® Orange (Biotium, Cat #30022) at 37° C. and 5% $CO_2$ for 1.5-2 h. Next, the cells were washed three times with CAF medium and seeded at $4 \times 10^5$ cells/well in collagen-coated 6-well plates (Costar®, Cat #3506) (see CellTiter-Glo® assay description for coating procedure). The following day, PDO Hub096 cells were harvested as described for the CellTiter-Glo® assay, after which the single-cell suspension was incubated with cytoplasmic membrane dye CellBrite® Blue (Biotium, Cat #30024) at 37° C. and 5% $CO_2$ for 1.5-2 h. Next, the cells were washed, resuspended in PDO medium supplemented with 5% Matrigel® and seeded at $5 \times 10^5$ cells/well on top of the adherent CellBrite® Orange-labeled CAFs and incubated with antibody samples (0.1 µg/mL or 0.02 µg/mL) at 37° C. and 5% $CO_2$ overnight.

After overnight incubation, the cells were harvested using Trypsin, washed in cold PBS and gently resuspended in 200 µL Annexin-V-FITC master mix consisting of 125 µL Annexin-V-FITC (BD Pharmingen™, Cat #556419) and 2.5 mL 1×Binding buffer (BD Pharmingen, Cat #556454). Cells were incubated with the Annexin-V mix at room temperature in the dark for 30 min. Next, 400 µL 1×Binding Buffer was added to each tube and transferred to 5 mL FACS tubes (Falcon®, Cat #352008). Annexin-V positivity was measured by flow cytometry on a FACSCelesta™ Cell Analyzer (BD Biosciences) and was analyzed by gating on FITC+ cells in the CellBrite® Orange-positive CAF and CellBrite® Blue-positive PDO cell populations using FACSCelesta™ Cell Analyzer Software.

Results

BisG1-FAPα-FEAL/DR4-FEAR induced dose-dependent cell death in all three PDOs, however sensitivity to BisG1-FAPα-FEAL/DR4-FEAR varied between the tested PDOs. Cell death was observed only in the presence of CAFs. Treatment of PDO monocultures did not result in DR4 transactivation-mediated cell death, confirming that dual binding to DR4 and FAPα is required for the bispecific antibody to elicit cell death. Treatment with negative control IgG1-FAPα-FEAL antibody did not result in PDO cell death (FIG. 8A-C; Tables 13-15).

Figure 8A:
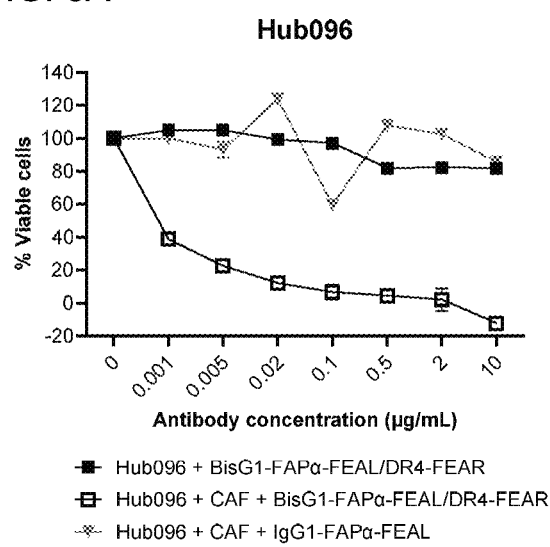
Figure 8B:
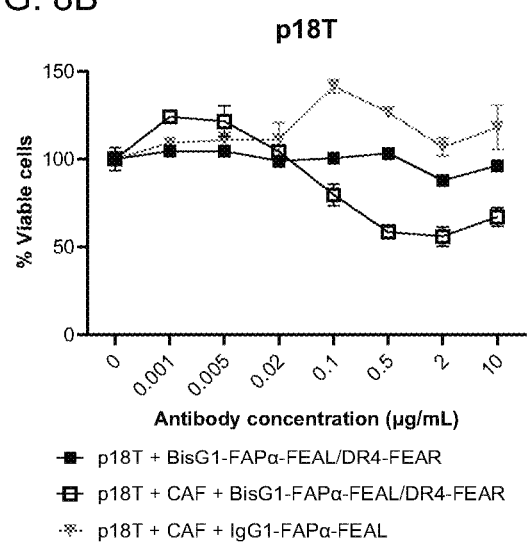
Figure 8C:
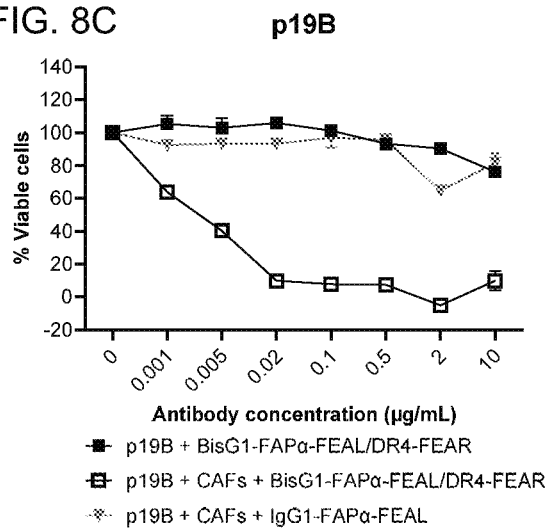
Figure 8D:
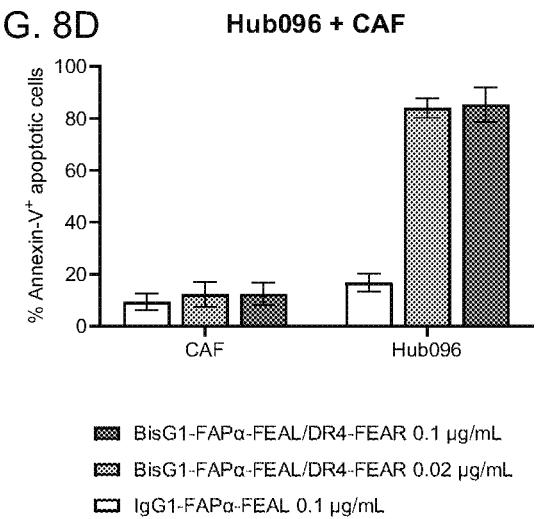

Cocultures of fluorescently labeled PDO line Hub096 with fluorescently labeled CAFs confirmed that BisG1-FAPα-FEAL/DR4-FEAR induced an apoptotic phenotype (as assessed by Annexin-V positivity) in PDO Hub096 only, without affecting the viability of the CAFs (FIG. 8D, Table 16).

TABLE 13

% Viable Hub096 PDO treated with different concentrations of BisG1-FAPα-FEAL/DR4-FEAR with or without CAFs

| Concentration antibody (μg/mL) | % Viable Hub096 + BisG1-FAPα-FEAL/DR4-FEAR | |
|---|---|---|
| | with CAFs | without CAFs |
| 0 | 99.9 ± 2.5 | 100 ± 0.6 |
| 0.001 | 38.6 ± 0.6 | 104.9 ± 0.9 |
| 0.005 | 22.3 ± 2.2 | 104.9 ± 0.3 |
| 0.02 | 11.4 ± 3 | 99.2 ± 0.1 |
| 0.1 | 4.8 ± 4.5 | 97 ± 2.3 |
| 0.5 | 1.6 ± 4.1 | 81.7 ± 0.5 |
| 2 | 2 ± 6.6 | 82.2 ± 0.4 |
| 10 | −11.7 ± 4.1 | 81.8 ± 0.8 |

Results are shown as mean ± SEM of technical duplicates from one experiment.

TABLE 14

% Viable p18T PDO treated with different concentrations of BisG1-FAPα-FEAL/DR4-FEAR with or without CAFs

| Concentration antibody (μg/mL) | % Viable p18T + BisG1-FAPα-FEAL/DR4-FEAR | |
|---|---|---|
| | with CAFs | without CAFs |
| 0 | 99.7 ± 6.7 | 99.9 ± 1.5 |
| 0.001 | 124.1 ± 1.4 | 104.5 ± 2.2 |
| 0.005 | 121.3 ± 8.8 | 104.6 ± 0.4 |
| 0.02 | 104.3 ± 0.9 | 98.8 ± 1.5 |
| 0.1 | 79.4 ± 6.2 | 100.5 ± 2.3 |
| 0.5 | 58.5 ± 0.1 | 103.3 ± 0.8 |
| 2 | 55.6 ± 5.3 | 87.8 ± 3.1 |
| 10 | 66.9 ± 5.3 | 96.4 ± 0.9 |

Results are shown as mean ± SEM of technical duplicates from one experiment.

TABLE 15

% Viable p19B PDO treated with different concentrations of BisG1-FAPα-FEAL/DR4-FEAR with or without CAFs

| Concentration antibody (μg/mL) | % Viable p19B + BisG1-FAPα-FEAL/DR4-FEAR | |
|---|---|---|
| | with CAFs | without CAFs |
| 0 | 99.9 ± 0.8 | 99.9 ± 2.2 |
| 0.001 | 63.7 ± 0.1 | 105.1 ± 5 |
| 0.005 | 40.1 ± 0.1 | 102.6 ± 5.9 |
| 0.02 | 8.9 ± 3.8 | 105.9 ± 2.2 |
| 0.1 | 7.7 ± 0.9 | 101.2 ± 2.2 |
| 0.5 | 7.3 ± 0.4 | 93.1 ± 1.4 |
| 2 | −5.2 ± 2.8 | 90.3 ± 1.6 |
| 10 | 7.8 ± 5.8 | 76 ± 0.4 |

Results are shown as mean ± SEM of technical duplicates from one experiment.

TABLE 16

% Annexin-V+ apoptotic cells treated with BisG1-FAPα-FEAL/DR4-FEAR or IgG1-FAPα-FEAL

| Antibody | CAFs | PDO-Hub096 |
|---|---|---|
| IgG1-FAPα-FEAL 0.1 μg/mL | 9.3 ± 3.3 | 16.8 ± 3.4 |
| BisG1-FAPα-FEAL/DR4-FEAR 0.02 μg/mL | 12.3 ± 4.9 | 84 ± 3.8 |
| BisG1-FAPα-FEAL/DR4-FEAR 0.1 μg/mL | 12.5 ± 4.2 | 85.3 ± 6.7 |

Results are shown as mean ± SD of two independent experiments.

Example 12: Assessment of BisG1-FAPα-FEAL/DR4-FEAR Antitumor Activity in Vivo a. Patient-Derived Tumor Tissues Express Different Levels of FAPα

To exhibit its mechanism of action, BisG1-FAPα-FEAL/DR4-FEAR requires both FAPα and DR4 expression in the TME to allow trans binding-dependent DR4 agonism leading to tumor cell death. For in vivo proof-of-concept studies, two patient-derived xenograft (PDX) models CTG-1234 (gastric) and CTG-1150 (pancreatic) with known DR4 mRNA expression (available via the vendor) were assessed for FAPα expression using immunohistochemistry (IHC) on formalin-fixed, paraffin-embedded (FFPE) tissue slides.

FFPE tissue of a patient-derived invasive ductal carcinoma (Avaden Biosciences) was used as positive control. Tissue sections were transferred to Superfrost Plus glass slides (Fisher Scientific; Cat #10149870) and were subjected, together with FFPE tissue slides from CTG-1234 and CTG-1150 (both from Champions Oncology), to IHC staining using the Ventana Discovery-Ultra (Roche) platform. Tissue staining was initiated with an incubation at 37° C. to warm up the slides, followed by a baking step (60° C. for 12 min). Next, three deparaffinization cycles were performed, each cycle consisting of incubation at 70° C. for 8 min and rinsing with EZ Prep (Roche, Cat #05279755001, diluted 1 in 10), coverslip application for 4 min, and EZ Prep application. After the third cycle, slides were washed again with EZ Prep and EZ Prep was added. Slides were incubated at 37° C. and washed before applying Discovery Cell Conditioner 1 (CC1; Roche, Cat #06414575001) reagent for antigen retrieval. Slides were incubated at 95° C. for 40 min. Next, slides were incubated for 16 min in CC Medium Coverslip (LCS; Roche, Cat #05264839001). Slides were placed at 37° C. and washed three times with Reaction Buffer (Roche, Cat #05353955001) before applying one drop of inhibitor CM (Roche, Cat #07017944001) and incubating for 8 min. Slides were washed twice with Reaction Buffer before adding the primary antibody rabbit anti-FAPα clone EPR20021 (reactive with both human and mouse FAPα: 5 μg/mL final concentration, Abcam, Cat #ab207178) or Rabbit IgG isotype control (5 μg/mL final concentration, Cell Signaling Technology, Cat #3900S). Slides were incubated for 32 min and washed twice before incubation with OmniMap anti-rabbit HRP-conjugated secondary antibody (Roche, Cat #05269679001) for 16 min. After three washing steps slides were incubated with ChromoMap 3,3'-diaminobenzidine (DAB) and ChromoMap $H_2O_2$ for 8 min followed by incubation with ChromoMap Copper for 4 min (all included in ChromoMap DAB kit from Roche, Cat #05266645001). Slides were washed twice, followed by incubation for 12 min with hematoxylin II (Roche, Cat #05277965001) and Bluing reagent (Roche, Cat #05266769001) for 8 min. Slides were washed three times and covered with a coverslip using Epredia™ ClearVue™ mounting medium (Fisher Scientific, Cat #23-425-401).

Immunostained FFPE tissue slides were scanned at 20× magnification with AxioScan slide scanner (Zeiss). For scoring of FAPα-positive PDX tumor tissues, image scans were analyzed in HALO software (Indica Labs) to quantify the proportion and IHC intensity of FAPα-positive tissue surface area by using the predesigned Area Quantification v2.4.2 image analysis algorithm.

Results

Figure 9A:
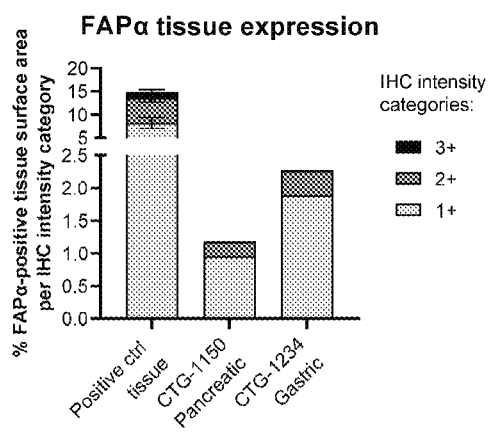

FAPα positivity was demonstrated for both PDX tissues (surface area with mostly low (1+) to moderate (2+) IHC intensity staining, FIG. 9A), indicating that both PDX models were deemed suitable for in vivo proof-of-concept studies.

b. Antitumor Activity in the Gastric PDX CTG-1234 Model

The ability of BisG1-FAPα-FEAL/DR4-FEAR to induce antitumor activity in a gastric cancer-derived PDX model was assessed in mice. BisG1-DR4-FEAL/b12-FEAR was used as a negative control.

Stock mice (Athymic Nude-Foxnlnu from Envigo) were bilaterally implanted with fragments from Champions TumorGraft® CTG-1234, originally derived from a human gastric cancer biopsy. After the tumors reached 1000-1500 mm$^3$, they were harvested, and the tumor fragments were implanted subcutaneously in the left flank of the female study mice (Athymic Nude-Foxnlnu from Envigo, aged 6 to 8 weeks at start of experiment).

Tumor growth was monitored twice a week using digital calipers, and the tumor volume (TV) was calculated using the formula 0.52×(length×width$^2$). The study was terminated when the mean tumor volume (MTV) of living mice (uncensored) in the control group reached 1500 mm$^3$.

When the TV reached approximately 200 mm$^3$, animals were matched by tumor size and assigned into control or treatment groups (n=8/group), and dosing was initiated on day 0. On treatment days, the mice were injected intravenously (IV) with BisG1-FAPα-FEAL/DR4-FEAR (0.5 mg/kg, 2 mg/kg or 8 mg/kg, one dose a week for three weeks [QW×3]) or with control BisG1-DR4-FEAL/b12-FEAR (8 mg/kg; QW×3) (Table 17).

The mice were monitored daily for clinical signs of illness and weighed twice weekly using a digital scale; data including individual and mean gram weights, mean percent weight change versus day 0 (% vD0) were recorded for each group. Animal deaths, if any, were recorded. Groups reporting a mean loss of % vD0>20 and/or >10% mortality were considered above the maximum tolerated dose (MTD) for that treatment on the evaluated regimen. Additional study toxicity endpoints were mice found moribund or displayed >20% net weight loss for a period lasting 7 days or if the mice displayed >30% net weight loss.

Inhibition of tumor growth (TGI) was determined by calculating the percent TGI (100%×[1-(final MTV−initial MTV of a treated group)/(final MTV−initial MTV of the control group)]). Tumor volumes of treatment groups for the duration of the study and at the completion of the study were compared to that of the control group. Mean tumor volumes at day 42 (last day all groups were complete) were used to analyze statistical differences of the various treatment groups (Mann-Whitney).

One additional end point used to evaluate efficacy was progression-free survival (PFS). Kaplan-Meier curves were analyzed using the Log-Rank (Mantel-Cox) test to assess statistically significant differences in PFS time (using a tumor size cut-off of 500 mm$^3$).

TABLE 17

Treatment groups and dosing regimen

| Treatment group | N per group | Treatment | Dose$^a$ | Dosing route | Dosing regimen |
|---|---|---|---|---|---|
| 1 | 8 | BisG1-DR4-FEAL/b12-FEAR | 8 mg/kg | IV | QW × 3$^a$ |
| 2 | 8 | BisG1-FAPα-FEAL/DR4-FEAR | 0.5 mg/kg | IV | QW × 3$^a$ |
| 3 | 8 | BisG1-FAPα-FEAL/DR4-FEAR | 2 mg/kg | IV | QW × 3$^a$ |
| 4 | 8 | BisG1-FAPα-FEAL/DR4-FEAR | 8 mg/kg | IV | QW × 3$^a$ |

$^a$QW × 3: one dose weekly for three weeks

Results

Figure 9B:
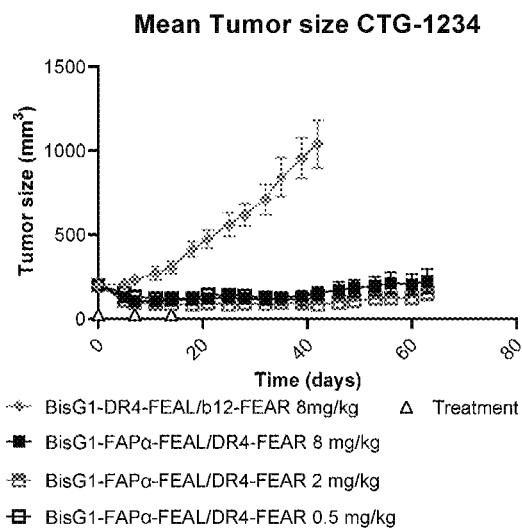
Figure 9C:
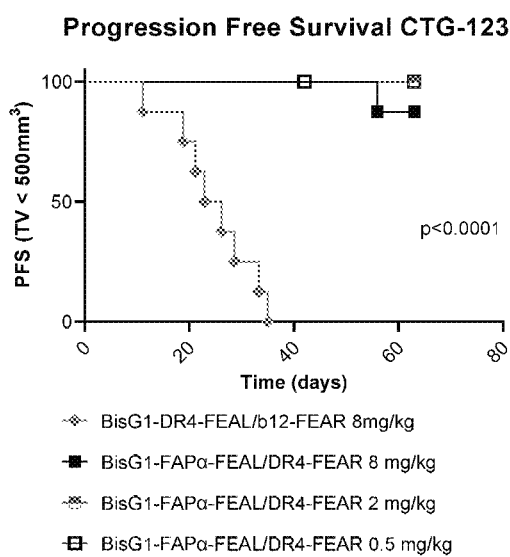
Figure 9D:
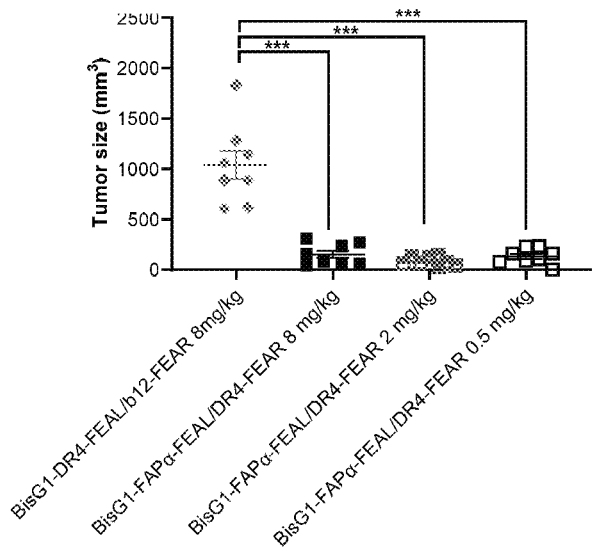
Figure 9E:
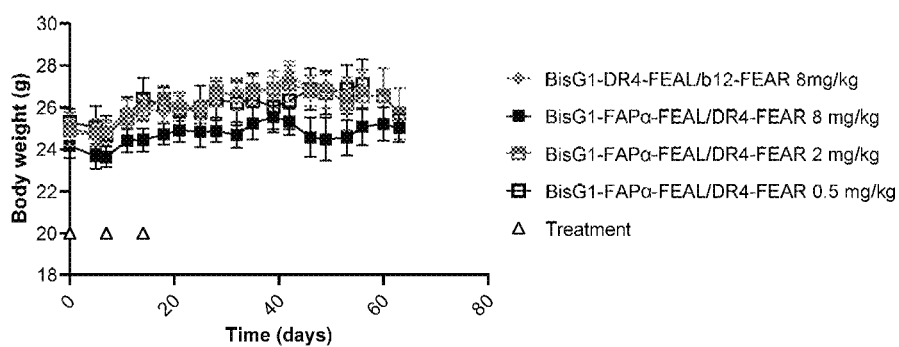
Figure 9F:
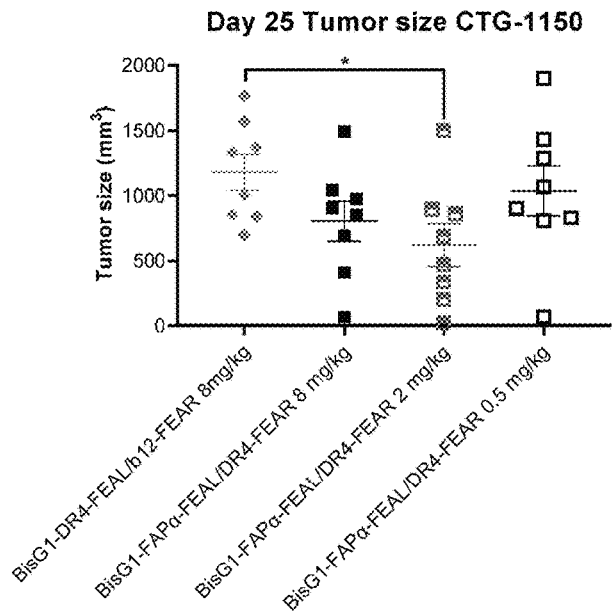

Rapid tumor outgrowth was observed in tumor-bearing mice treated with the negative control BisG1-DR4-FEAL/b12-FEAR (FIG. 9B). BisG1-FAPα-FEAL/DR4-FEAR, at all tested doses, significantly inhibited tumor growth of the gastric cancer PDX tumors in athymic nude mice (Table 18 and FIG. 9D, p=0.0002 for all tested doses). PFS in this model was significantly extended by BisG1-FAPα-FEAL/DR4-FEAR treatment even at the lowest dose of 0.5 mg/kg, indicating strong antitumor activity (p<0.0001; Mantel-Cox; FIG. 9C). Lastly, body weight measurements over time showed no changes compared to the negative control group, indicating that treatments were well-tolerated (FIG. 9E).

TABLE 18

Mean size (mm$^3$) of gastric tumor CTG-1234 for each treatment on day 42

| Treatment | Tumor size (mm$^3$) | p-value* |
|---|---|---|
| BisG1-DR4-FEAL/b12-FEAR 8 mg/kg | 1041 ± 140 | |
| BisG1-FAPα-FEAL/DR4-FEAR 0.5 mg/kg | 92 ± 28.2 | 0.0002 |
| BisG1-FAPα-FEAL/DR4-FEAR 2 mg/kg | 128 ± 16.2 | 0.0002 |
| BisG1-FAPα-FEAL/DR4-FEAR 8 mg/kg | 147 ± 37.8 | 0.0002 |

Results are shown as mean ± SEM of 8 measurements/treatment group.
*compared to treatment with BisG1-DR4-FEAL/b12-FEAR, Mann-Whitney test.

c. Antitumor Activity in the Pancreatic PDX CTG-1150 Model

A parallel experiment was conducted in which athymic nude mice were implanted with Champions TumorGraft® CTG-1150, originally derived from a human pancreatic cancer biopsy. The same treatment regimens, protocols and statistical tests as described in section b (and Table 17) were applied with the following differences: statistical comparison of tumor volumes was performed at day 25 (last day all groups were complete), and a tumor size cut-off of 1000 mm$^3$ for PFS was used.

Results

Figure 9G:
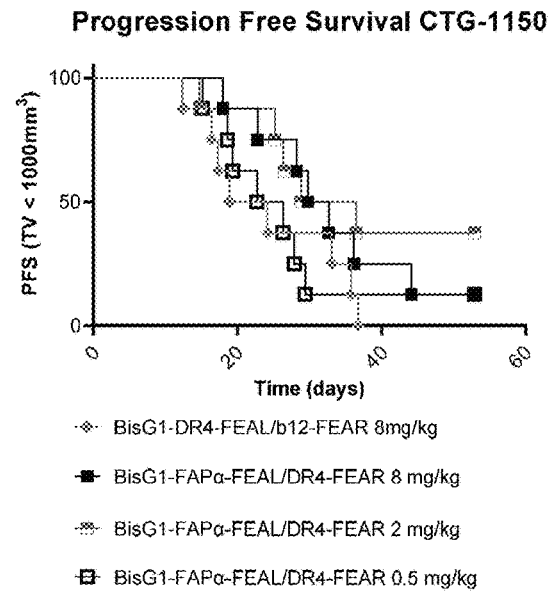
Figure 9H:
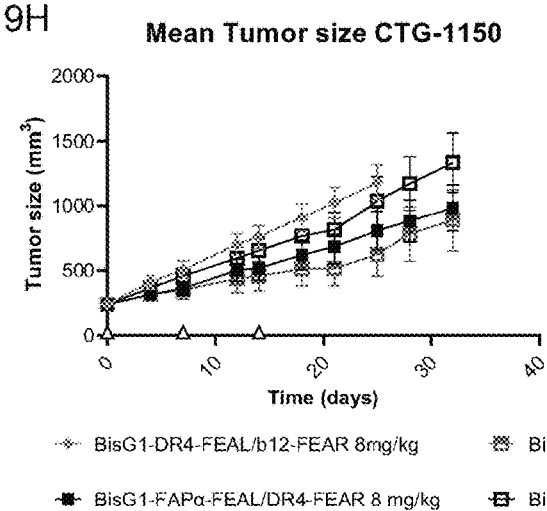
Figure 9I:
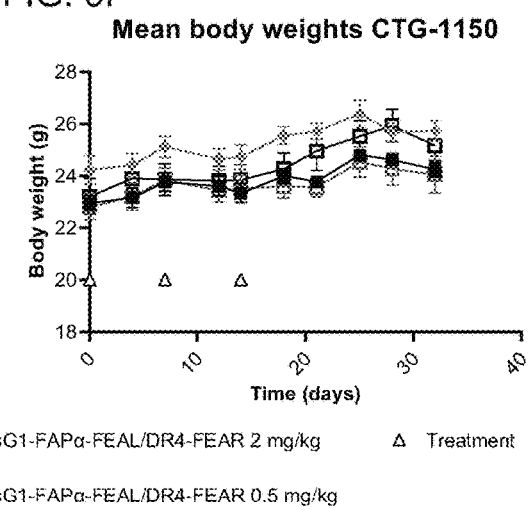

As observed in the gastric PDX model, rapid tumor outgrowth was observed in pancreatic PDX-bearing mice treated with BisG1-DR4-FEAL/b12-FEAR antibody (FIG. 9H). BisG1-FAPα-FEAL/DR4-FEAR, dosed at 2 mg/kg, significantly inhibited tumor growth of the pancreatic PDX model in athymic nude mice, when compared to the BisG1-DR4-FEAL/b12-FEAR control (Table 19 and FIG. 9F, p=0.038). BisG1-FAPα-FEAL/DR4-FEAR treatment did not extend PFS compared to BisG1-DR4-FEAL/b12-FEAR control (FIG. 9G). Lastly, body weight measurements over time showed no changes indicating that treatments were well-tolerated (FIG. 9I).

TABLE 19

Mean size (mm³) of pancreatic tumor CTG-1150 for each treatment on day 25

| Treatment | Tumor size (mm³) | p-value* |
|---|---|---|
| BisG1-DR4-FEAL/b12-FEAR 8 mg/kg | 1189 ± 136.6 | |
| BisG1-FAPα-FEAL/DR4-FEAR 0.5 mg/kg | 1041 ± 189.9 | 0.038 |
| BisG1-FAPα-FEAL/DR4-FEAR 2 mg/kg | 626 ± 166.6 | >0.05 |
| BisG1-FAPα-FEAL/DR4-FEAR 8 mg/kg | 801 ± 151.2 | >0.05 |

Results are shown as mean ± SEM of 8 measurements/treatment group.
*compared to treatment with BisG1-DR4-FEAL/b12-FEAR, Mann-Whitney test.

d. Antitumor Activity in the Gastric PDX CTG-1234 Follow-Up

The ability of BisG1-FAPα-FERL/DR4-FERR to induce antitumor activity at lower dose ranges, as well as in comparison to RG7386 was assessed in a gastric cancer-derived PDX model CTG-1234 in mice. BisG1-b12-FERL/DR4-FERR was used as a negative control, RG7386 was tested to compare antitumor efficacy between BisG1-FAPα-FERL/DR4-FERR and RG7386. Experimental procedures were as described in Example 12, section b, except for the following amendment: mice randomization to control and treatment groups occurred upon establishment of mean tumor volume (MTV) of approximately 270 mm² (Table 20).

TABLE 20

Treatment groups and dosing regimen

| Treatment group | N per group | Treatment | Dose[a] | Dosing route | Dosing regimen |
|---|---|---|---|---|---|
| 1 | 8 | BisG1-b12-FERL/DR4-FERR | 2 mg/kg | IV | QW × 3[a] |
| 2 | 8 | BisG1-FAPα-FERL/DR4-FERR | 2 mg/kg | IV | QW × 3[a] |
| 3 | 8 | BisG1-FAPα-FERL/DR4-FERR | 0.5 mg/kg | IV | QW × 3[a] |
| 4 | 8 | BisG1-FAPα-FERL/DR4-FERR | 0.1 mg/kg | IV | QW × 3[a] |
| 5 | 8 | RG7386 | 3.2 mg/kg[b] | IV | QW × 3[a] |
| 6 | 8 | RG7386 | 0.8 mg/kg[c] | IV | QW × 3[a] |
| 7 | 8 | RG7386 | 0.16 mg/kg[d] | IV | QW × 3[a] |

[a]QW × 3: one dose weekly for three weeks
[b-d]equimolar dose compared to BisG1-FAPα-FERL/DR4-FERR 2 mg/kg (b), 0.5 mg/kg (c), 0.1 mg/kg (d)

Results

BisG1-FAPα-FERL/DR4-FERR induced tumor regression and prolonged tumor suppression of CTG-1234 tumors. Pairwise analysis of the tumor volume (TV) on the last day that all groups were complete (Day 12) showed that treatment with 2.0 and 0.5 mg/kg BisG1-FAPα-FERL/DR4-FERR resulted in significantly smaller TV compared with 2.0 mg/kg BisG1-b12-FERL/DR4-FERR control antibody as well as equimolar dose levels of RG7386 (FIG. 10A-B, Table 21).

PFS was significantly extended in groups treated with 2.0 mg/kg BisG1-FAPα-FERL/DR4-FERR when compared with the BisG1-b12-FERL/DR4-FERR control group as well as RG7386-treated mice (FIG. 10C).

TABLE 21

Statistical analysis of tumor volume in PDX model CTG-1234 follow-up

| Table analyzed | Pairwise comparisons | | | |
|---|---|---|---|---|
| Treatment 1[b] | GEN1057 2.0 mg/kg | GEN1057 2.0 mg/kg | GEN1057 0.5 mg/kg | GEN1057 0.1 mg/kg |
| vs. | vs. | vs. | vs. | vs. |
| Treatment 2[b] | bsIgG1-ctrl-FERLxDR4-FERR 2.0 mg/kg | RG7386 surrogate 3.2 mg/mL | RG7386 surrogate 0.8 mg/kg | RG7386 surrogate 0.16 mg/kg |

TABLE 21-continued

Statistical analysis of tumor volume in PDX model CTG-1234 follow-up

| Table analyzed | Pairwise comparisons | | | |
|---|---|---|---|---|
| P value[a] | 0.0006 | 0.0011 | 0.007 | 0.645 |
| Treatment 1 (Median tumor volume) | 98 | 98 | 146.5 | 525 |
| Treatment 2 (Median tumor volume) | 617.5 | 304.5 | 852.5 | 738 |

[a]Mann-Whitney test; Two-tailed.
[b]n = 8

Example 13: Antitumor Activity in a Multiorgan Metastatic Mouse Model

The antitumor activity of BisG1-FAPα-FEAL/DR4-FEAR was investigated using a CRC PDO multiorgan metastasis mouse model with mouse fibroblasts as source of FAPα. IgG1-b12-FEAL was used as negative control.

Hub096 PDOs (described in Example 11) were transduced using lentivirus encoding Luciferase linked to the green fluorescent protein (GFP) gene (PLV-Luciferase-IRES-GFP lentiviral vector). The lentivirus encoding Luciferase linked to GFP was produced by human embryonic kidney (HEK) 293T cells following a calcium phosphate transfection protocol.

On the day of transfection, HEK293T cells were detached using trypsin (Lonza, Cat #BE02-007E), checked for viability using trypan blue (Fluka, Cat #93590) and seeded onto a 10 cm culture dish (Greiner, Cat #664160) in 9 mL of DMEM High glucose medium (Sigma-Aldrich, Cat #D6429) supplemented with 50 U/mL of penicillin/streptomycin (Gibco, Cat #15070-063), 2 mM GlutaMAX™ (Gibco, Cat #35050-038), and 10% heat inactivated FBS (Bodinco BV, ID 5067V20002) at a density to obtain around 60% confluency the following day. Cells were incubated for 24 h at 37° C. and 5% (vol/vol) $CO_2$ to adhere to the plate. The following day, the medium was washed off gently two times using PBS (Corning, Cat #21-0310CVR). Fresh DMEM High glucose medium (supplemented with 50 U/mL of penicillin/streptomycin, 2 mM GlutaMAX™ and 10% heat inactivated FBS) was added. 500 μL of 2× HEPES buffered saline (HBS), consisting of 280 mM Sodium Chloride (from Riedel-de-Haen, Cat #31434), 1.5 mM Sodium phosphate dibasic (Sigma, Cat #S0876), 12 mM (d)Glucose (Sigma, Cat #G8270), 10 mM Potassium Chloride (Riedel-de-Haen, Cat #31248) and 50 mM HEPES (Sigma, Cat #H3375), pH 7.05 was mixed with 50 μL of 3 M Calcium chloride-2-hydrate (Riedel-de-Haen, Cat #31307) and with 450 μL consisting of 20 μg plasmid DNA (10 μg of PLV-Luciferase-IRES-GFP, 5 μg of psPAX from Addgene [plasmid #12260], and 5 μg of pCMV-VSV-G [Addgene, plasmid #8454]) and demineralized water (Aqua B. Braun, Cat #0082479E). The 1 mL transfection mix was quickly added to the 10 cm culture dish, which was then incubated overnight at 37° C., 5% $CO_2$. The following day, the HEK293T cells were washed again two times with PBS and 6 mL of fresh DMEM High glucose medium supplemented with penicillin/streptomycin, GlutaMAX™, and heat inactivated 10% FBS were added to the 10 cm culture dish before an additional overnight incubation. The following day, Hub096 PDOs were dissociated using TrypLE™ Express Stable Trypsin-Like Enzyme (Gibco, Cat #12604021) and 1-2 million PDOs were plated on nonadherent 6-Well plates (Corning, Cat #3471) in 6 mL of lentivirus-containing medium (harvested from the virus-producing HEK293T cell culture plate and filtered through a 0.22 μm polyether sulfone filter from Sarstedt B. V., Cat #83.1826.001), supplemented with 6 μg/mL Polybrene® (Sigma-Aldrich, Cat #TR-1003), 0.5 mM N-acetylcysteine (Sigma-Aldrich, Cat #A9165), and 10 μM of ROCK-inhibitor Y-27632 (Abmole bioscience, Cat #HY-10583). The PDOs were incubated overnight 37° C., 5% $CO_2$. After 24 h incubation, PDOs were recovered in 15 mL tubes (Corning, Cat #430791), washed twice with PBS (Corning, Cat #21-031-CV) and resuspended in basement membrane extract (BME) matrix (Amsbio, Cat #3533-010-02) at a 2:1 ratio with PDO medium (refer to Example 11 for medium composition). PDOs were plated in 150 μL droplets (containing roughly 2,500-5,000 cells/drop) which were allowed to solidify at 37° C., 5% $CO_2$ before adding 2 mL/well of PDO medium and incubating at 37° C., 5% $CO_2$. After at least two passages to expand the cells, GFP-positive PDOs were sorted using Fluorescence Activated Cell Sorting (FACS) Aria II™ (BD Biosciences) machine.

The day before transplantation, the Hub096 PDOs were harvested, washed with PBS (Corning, Cat #21-031-CVR) and dissociated into single cells using TrypLE™ (Thermofisher, Cat #12604013). Next, cells were washed, resuspended in PDO medium and viability was measured with trypan blue. Cells were washed and resuspended in a pre-cooled solution of Rat Tail High Concentrated Type I Collagen (Corning, Cat #354249) mixed at a 4:1 ratio with 5× Neutralization buffer (1 g AlphaMEM powder 5× from Life Technologies, Cat #12000-014; 5 mL of 1 M HEPES pH 7.5 from Lonza, Cat #17737E; 1 g of Sodium bicarbonate from Sigma, Cat #31437). 10 μL droplets containing 300,000 single cells were added on prewarmed 6-Well plates (Corning, Cat #3506). Plates were incubated (37° C., 5% $CO_2$) for 40 to 60 min to allow droplets to solidify, before adding 2 mL/well of PDO medium. PDOs were allowed to recover overnight at 37° C., 5% $CO_2$.

For cecum transplantation, male study mice (NOD.Cg-Prkdc$^{scid}$Il2rg$^{scid}$Il2rg$^{tm1Wjl}$/SzJ NSG® from Charles River Laboratories, Strain #005557; aged 8 to 9 weeks at start of experiment) were treated with a subcutaneous injection of Carprofen (5 mg/kg, Rimady™) 30 min before surgery. To perform surgery, animals were sedated (isoflurane inhalation anesthesia: ~2% [vol/vol]isoflurane/$O_2$ mixture), the cecum was exteriorized through a midline abdominal incision and a single collagen drop containing the Luciferase-tagged PDOs was surgically transplanted in the cecal submucosa.

Mice were randomized into groups (n=9/group). Treatment was initiated on week 2 following cecum implantation and was performed once in week 2, 5 and 6, and twice a week in weeks 3 and 4. On treatment days, the mice were injected intraperitoneally with the antibodies (2 mg/kg in 200 µL of PBS).

The mice were monitored daily for clinical signs of illness and weighed once a week using a digital scale; data including individual and mean gram weights and mean percent weight change versus Day 0 (% vD0) were recorded for each group. Animal deaths, if any, were recorded. Study toxicity endpoints were reported mean loss of % vD0>20 and/or >15% net weight loss within two days; mice found moribund or displaying abnormal behavior and posture; appearance of combination of clinical symptoms that may indicate excessive tumor growth and metastases (large abdomen, ascites).

Prior to study termination, mice were injected intraperitoneally with 100 µL (1.25 mg) of luciferin (VivoGlo™ Luciferin, In Vivo Grade, Promega, Cat #P1041), and euthanized after 10 min. Individual organs (cecum, peritoneal wall, liver, lung, and brain) were collected and measured for tumor load using ex vivo bioluminescence imaging (BioLI). Data were analyzed using GraphPad Prism 9, where the BioLI measurement (cpm/cm$^2$, $Log_{10}$ scale) of the organs from each mouse was plotted for both treatment groups. BioLI differences are assessed by comparing the treatment group to the control group on log-transformed data using paired t-tests and unpaired nonparametric t-tests.

DR4 activation was furthermore assessed by cleaved caspase-3 IHC staining on FFPE sections from cecum, peritoneal wall, and liver tissues. After dissection and BioLI measurements, cecum, peritoneal wall, and liver tissues were fixed in 4% (w/v) formaldehyde (Added Pharma, Cat. #ROL.1642810), embedded in Surgipath Paraplast paraffin (Leica Biosystems, Cat. #39602012) in laser biopsy green cassettes (FA-Tech Diagnostics Europe B. V., Cat. #215-05-10LM) using the HistoCore Arcadia H (Leica Biosystems, Cat. #14039357258). Tissue blocks were cut into 4 µm serial sections parallel to the longitudinal axis of each tissue, using a microtome (Leica Biosystems, Cat. #RM2255), transferred on the surface of a water bath (KLINIPATH, Cat. #WB28040) and mounted on X-tra Slides (Leica Biosystems, Cat. #3800203AE). The slides were then dried on a slide warmer (Adamas Instruments B. V. Cat. #SW85). Hereafter, FFPE sections of cecum, peritoneal wall and liver tissues were deparaffinized with xylene (Klinipath, Cat. #4055-9005) and rehydrated with serial dilutions of ethanol (Klinipath, Cat. #4096-9005) and water. Endogenous peroxidase activity was blocked with 5% $H_2O_2$ (Merck, Cat. #1072091000) diluted in PBS (1.87 M of NaCl (Merck, Cat. #1064041000), 0.28 M of $NaH_2PO_4$ (Sigma-Aldrich, Cat. #7558-79-4), and 0.0366 M $NaH_2PO_4$ (Merck, Cat. #1063451000)) at RT for 20 min. Slides were incubated in boiling 10 mM citrate antigen retrieval buffer pH 6.0 (ThermoFisher Scientific, Cat. #36439) for 20 min. After cooling for 10 min, slides were washed with 0.05% Tween 20 buffer (VWR, Cat. #M147-1L) diluted in PBS and incubated with Cleaved Caspase-3 (CCASP3) antibody (Cell Signaling Technology, Cat. #9661, 1:300 in PBS supplemented with 1% BSA and 0.2% sodium azide) at RT for 1 h. Slides were washed three times with Tween 20 buffer and incubated with BrightVision+poly-HRP-conjugated Anti-Rabbit IgG (Immunologic, Cat. #VWRKDPVR110HRP) at RT for 30 min. After three wash steps with PBS, slides were incubated with 3,3'-Diaminobenzidine (DAB) $H_2O_2$ solution (0.03% DAB [Sigma-Aldrich, Cat. #91-95-2] and 0.03% $H_2O_2$ [Merck, cat. no. 7722-84-1] in 0.05M Tris™ HCl buffer pH 7.6 [Biosolve, Cat. #20092391]) at 37° C. for 10 min. Slides were washed with water, stained with hematoxylin (Merck, Cat. #HHS32; 1:4 in water) at RT for 30 s. After wash steps with water and subsequently with 96% ethanol, slides were air dried and mounted with cover slips using the ClearVue™ coverslipper (Thermo Scientific). The stained cecum, liver, and peritoneal wall slides were scanned using a NanoZoomer-XR digital slide scanner (Hamamatsu) at 40× magnification with a resolution of 0.25 µm/pixel, and QuPath software was used for automated recognition of background, tissue (hematoxylin) and CCASP3 staining (DAB-positive) areas. Manual outlining of each tumor region (excluding necrotic areas) was subsequently performed and annotated. The percentage CCASP3-positive tumor area was determined using QuPath's trained pixel classifier.

Results

Ex vivo BioLI measurements of tumor load in individual organs showed that, compared to IgG1-b12-FEAL antibody, BisG1-FAPα-FEAL/DR4-FEAR antibody significantly reduced tumor burden at the primary tumor site (caecum) and metastases in brain, liver, peritoneal wall and lungs (FIGS. 11A-E; Table 22) when using paired t-test. Using unpaired t-test (Mann-Whitney) demonstrated reduced tumor burden at the primary tumor site (cecum) and metastatic sites, reaching statistical significance in the metastatic sites including brain, liver, peritoneal wall and lungs (Table 22).

For mice treated with BisG1-FAPα-FEAL/DR4-FEAR, DR4 activation was observed at the primary tumor and metastatic sites, as demonstrated by a significant increased percentage of tumor area that stained positive for cleaved caspase-3 on FFPE sections from cecum and peritoneal wall tissues compared with IgG1-b12-FEAL (FIG. 11F, Table 23). Compared with cecum and peritoneal wall tissues, caspase-3 activity in the liver was low and not significantly increased by treatment with BisG1-FAPα-FEAL/DR4-FEAR.

TABLE 22

Tumor load (BioLI) in individual organs

| Organ | Tumor load (BioLI) per treatment group | | p-value[a] | p-value[b] |
|---|---|---|---|---|
| | BisG1-FAPα-FEAL/DR4-FEAR | IgG1-b12-FEAL | | |
| Cecum | $0.8 \times 10^7 \pm 0.25 \times 10^7$ | $2.4 \times 10^7 \pm 2.3 \times 10^7$ | 0.039 | 0.075 |
| Brain | $0.19 \times 10^5 \pm 0.12 \times 10^5$ | $2.5 \times 10^5 \pm 1.8 \times 10^5$ | 0.026 | 0.003 |
| Liver | $0.19 \times 10^6 \pm 0.12 \times 10^6$ | $4 \times 10^6 \pm 2.6 \times 10^6$ | 0.005 | 0.014 |
| Peritoneal wall | $0.2 \times 10^7 \pm 0.1 \times 10^7$ | $2.1 \times 10^7 \pm 1.3 \times 10^7$ | 0.012 | 0.003 |
| Lungs | $0.76 \times 10^5 \pm 0.67 \times 10^5$ | $4.3 \times 10^5 \pm 2.9 \times 10^5$ | 0.016 | 0.040 |

Results are shown as mean ± SEM of 9 measurements/treatment group. Statistical test:
[a]paired t-test;
[b]unpaired t-test.

TABLE 23

Tumor area scored positive for cleaved caspase-3

| Organ | BisG1-FAPα-FEAL/ DR4-FEAR | IgG1-b12-FEAL | p-value |
|---|---|---|---|
| Cecum | 13.7 ± 1.5 | 3 ± 0.3 | <0.0001 |
| Peritoneal wall | 4.8 ± 1.3 | 0.8 ± 0.1 | 0.0005 |
| Liver | 2.2 ± 0.4 | 0.9 ± 0.1 | 0.3 |

Results are shown as mean ± SEM of all sections analyzed per treatment group. Statistical test: unpaired t-test In this study, treatment of NSG mice transplanted with CRC-derived PDOs with BisG1-FAPα-FEAL/DR4-FEAR resulted in strong antitumor activity on the primary tumor and metastases compared to the negative control IgG1-b12-FEAL.

Example 14: Assessment of Hepatocyte Toxicity Using Human Liver Spheroids

TRAIL-R agonists have been shown to induce hepatotoxicity in some patients in clinical studies. For this reason, we developed a tumor-specific agonist (BisG1-FAPα-FEAL/DR4-FEAR) that should reduce the risk of hepatotoxicity. A hepatocyte toxicity assay was performed to assess the potential of BisG1-FAPα-FEAL/DR4-FEAR, ABBV-621-Fc fusion and RG7386 to induce hepatocyte toxicity in vitro. IgG1-b12-FEAR and IgG1-b12 were included as negative control.

The Drug Induced Liver Injury (DILI-Bio) Safety Assessment was performed using Human 3D InSight™ Human Liver Microtissues (InSphero©, Cat #MT-02-302-04), which are liver spheroids consisting of primary human hepatocytes and non-parenchymal liver cell types, such as Kupffer cells and liver endothelial cells. Two experiments were performed, in which viability of the liver spheroids was determined by measuring the release of lactic acid dehydrogenase (LDH) at day 4, an indicator of plasma membrane damage, and intracellular adenosine triphosphate (ATP) levels at day 6 and 7, an indicator of metabolically active cells.

The first experiment was performed according to the internal technical operation procedures (TOPs) ofIn-Sphero©. In brief, antibody dilutions (2 µg/mL, 10 µg/mL and 50 µg/mL final concentration using TOX microtissue culture medium fromInSphero©, Cat #CS-07-001-01) were added to 96-Well InSphero© Plates (Cat #MT-02-302-04). Plates were incubated at 37° C., 5% $CO_2$. Extracellular LDH release was measured with the bioluminescent LDH Release Toxicity Assay Kit (Promega, Cat #J2380) at day 4 of treatment, while intracellular ATP content was measured with the CellTiter-Glo® 2.0 Cell Viability Assay (Promega, Cat #G9243) at day 6 of the treatment.

The second experiment was performed as follows: InSphero© Plates were centrifuged to ensure that the microtissue was at the bottom of the well before adding the antibody dilutions (same as first experiment, diluted in TOX medium). The plates were incubated up to 7 days at 37° C., 5% $CO_2$. For LDH measurement, supernatant was collected after 4 days and used with the bioluminescent LDH Release Toxicity Assay (Promega, Cat #J2381) following the manufacturer's protocol. For ATP measurement, after 7 days supernatant was removed and 50 µL/well of CellTiter-Glo® 3D (Promega, Cat #G9681) reagent (diluted 1:1 in PBS from Hyclone GE Healthcare, Cat #SH3A3830.03) was added. After mixing, the entire volume was transferred to a 96-Well white OptiPlate™ (Perkin Elmer, Cat #6005299). After 30 min incubation at room temperature protected from light, bioluminescence was measured using the EnVision® (Perkin Elmer). For both experiments, data were analyzed using Microsoft Excel and GraphPad Prism. Data shown are mean t SEM of four technical replicates.

Results

Figure 12A:
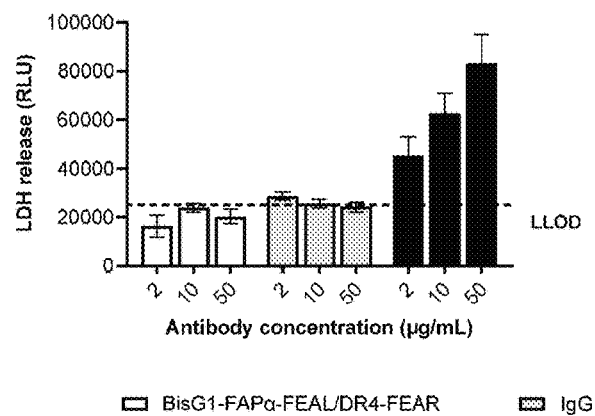

Treatment of the liver spheroids with ABBV-621-Fc fusion induced toxicity in hepatocytes, as shown by an increased release of LDH into the culture supernatant (FIG. 12A). Treatment with higher doses of RG7386 also induced substantial LDH release (FIG. 12C). In contrast, BisG1-FAPα-FEAL/DR4-FEAR did not induce toxicity in this liver spheroid model as the levels of LDH in the culture supernatant were below LLOD (dashed lines), similar to the negative control IgG1-b12-FEAR or IgG1-b12 (FIG. 12A/C).

Figure 12B:
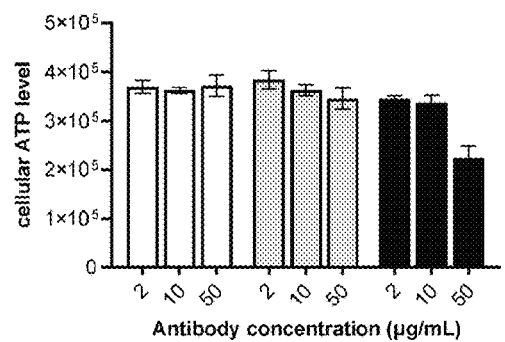
Figure 12C:
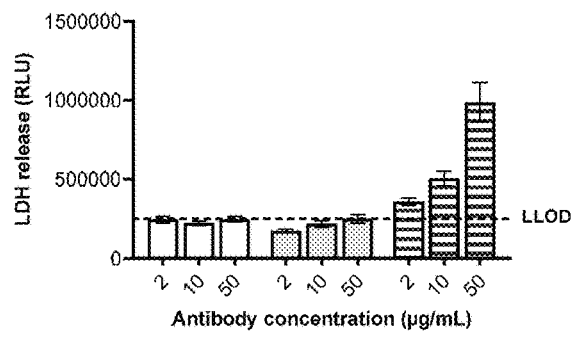
Figure 12D:
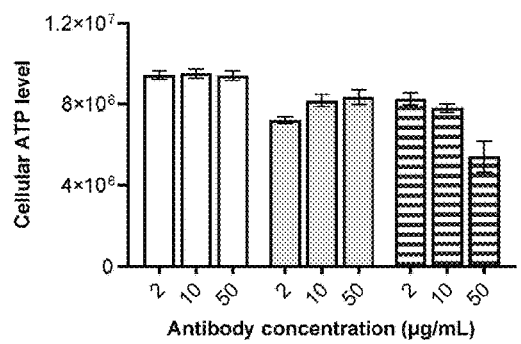

Cellular ATP levels of liver spheroids treated with lower dose of ABBV-621-Fc fusion and RG7386 were similar to those treated with BisG1-FAPα-FEAL/DR4-FEAR or control IgG1-b12-FEAR antibody (FIG. 12B). However, decreased cellular ATP levels were observed with treatment at the highest dose of ABBV-621-Fc fusion and RG7386 (FIG. 12B/D) indicating loss of hepatocyte viability.

In summary, the BisG1-FAPα-FEAL/DR4-FEAR antibody did not induce liver spheroid toxicity (measurements of viability indicators comparable to negative control IgG1-b12-FEAR/IgG1-b12). In contrast, ABBV-621-Fc fusion and RG7386 showed a dose-dependent toxicity.

Example 15: Cytoxicity in Cocultures with Reduced FAPα Availability

To investigate the relationship between FAPα expression levels and BisG1-FAPα-FERL/DR4-FERR-induced cytotoxicity, the role of the tumor cell to FAPα-expressing fibroblast ratio on BisG1-FAPα-FERL/DR4-FERR efficacy was explored.

Cytotoxicity in cocultures of tumor cells DLD-1 and MDA-MB-231 with different amounts of NIH/3T3-FAPα cells was assessed using CellTiter Glo assay. DR4-expressing tumor cells (MDA-MB-231 and DLD-1) were harvested as described in Example 3. NIH-3T3-FAPα cells were harvested as described in Example 10. Tumor cells and fibroblasts were seeded at indicated ratios (6,600 tumor cells and varying numbers [100-3,300 cell/well with twofold increments] of fibroblasts) in CELLSTAR® flat bottom 96-well plates (Greiner Bio, Cat. #655180) and incubated at 37° C. and 5% $CO_2$ for 4 h to allow the cells to adhere to the plate. In parallel, control wells were prepared with monocultures of tumor cells or NIH/3T3-FAPα cells. Next, supernatant was removed, and cells were incubated with antibody concentration series ($6.91 \times 10^{-6}$–14.5 µg/mL with eightfold increments) in RPMI 1640 (Gibco, Cat. #A1049101) with 10% DBSI (Gibco, Cat. #10371029) at 37° C. and 5% $CO_2$ for 72 h. Hereafter, the viability of cultured cells was assessed in a homogeneous CellTiter-Glo® Luminescent Cell Viability assay (Promega, Cat. #G7571) as described in Example 10, section a. The percentage viable tumor cells left was calculated and data were processed with GraphPad Prism software to generate fitted cell viability curves (nonlinear regression analysis with four-parameter logistic curve fit). The graphs show percentage viable tumor cells plotted against antibody concentration.

Cytotoxicity was furthermore assessed in cocultures of PDOs with CAFs transduced with FAPα shRNA or non-target shRNA. The different FAPα shRNA clones were produced by a calcium phosphatase transfection-based protocol for lentiviral vectors in HEK293T cells and used for transduction of CAFs. Lentiviral production in HEK293T cells was performed as described in Example 13, except for the following amendments: Transfection mix contained the following vectors: 15 pig MISSION® pLKO.1-puro-based plasmid (Sigma-Aldrich, Cat. #, #Scr: SHC016, #34: TRCN0000006802); 7.5 μg psPAX2 (Addgene, Plasmid #12260) and 7.5 pig pCMV-VSV-G (Addgene, plasmid #8454). After harvesting of the lentivirus-containing medium, transduction medium was filtered using 0.22 μm polyether sulfone filter (Sarstedt B. V. Cat. #83.1826.001) and supplemented with 3 μg/mL Polybrene® (Sigma-Aldrich Cat. #H9268). CAFs were harvested, counted and seeded in collagen-coated 6-well plates as described in Example 11, in lentivirus-containing filtered medium (2.5 mL/well) and incubated at 37° C. and 5% $CO_2$ to expand (2.5 mL/well). The transduced CAFs were harvested and resuspended in medium supplemented with 0.5 μg/mL puromycin dihydrochloride (Santa Cruz Biotechnology, cat. no. sc-108071A). To continue puromycin selection, medium was replaced with fresh medium and puromycin every 2-3 days. The CellTiter-Glo® viability assay was subsequently performed with PDOs and CAFs as described in Example 11.

Results

To investigate the relationship between FAPα expression level and BisG1-FAPα-FERL/DR4-FERR-induced cytotoxicity, the role of the tumor cell to FAPα-expressing fibroblast ratio on cytotoxicity was explored. DLD-1 or MDA-MB-231 tumor cell lines were cultured with different amounts of NIH-3T3-FAPα cells (2:1, 4:1, 8:1 and 64:1 of tumor cell to NIH-3T3-FAPα). Increasing the ratio of tumor cells versus fibroblasts (e.g. lower numbers of NIH/3T3-FAPα cells) resulted in reduced BisG1-FAPα-FERL/DR4-FERR-mediated cytotoxicity (FIG. 13A-B).

Moreover, the effect of BisG1-FAPα-FERL/DR4-FERR was studied in cocultures with fibroblasts with different levels of FAPα expression. CAFs were transduced with FAPα shRNA (CAF #34) or non-target shRNA (CAF #Scr). In cocultures of 4 PDO lines with CAFs engineered to express a lower level of surface FAPα (CAF #34), the maximal BisG1-FAPα-FERL/DR4-FERR-mediated cytotoxic effect was not affected in 1 PDO line, slightly reduced in 2 PDO lines, and completely lost in 1 PDO line (FIG. 14A-D). In all PDO lines a bell-shaped concentration response relation was observed in cocultures using engineered CAFs expressing reduced levels of FAPα. In conclusion, cytotoxicity mediated by BisG1-FAPα-FERL/DR4-FERR is dependent on FAPα density and expression level.

Example 16: Cytotoxicity and DR4 Transactivation in Presence of Soluble FAPα

Given that FAPα protein can be shed from the cell membrane and is found in human plasma (Xin et al., Front Oncol 2021 11:648187), the effect of soluble FAPα on BisG1-FAPα-FERL/DR4-FERR-mediated cytotoxicity was assessed. Cytotoxicity of BisG1-FAPα-FERL/DR4-FERR and control antibody BisG1-b12-FERL/DR4-FERR was assessed in DR4-expressing DLD-1 and MDA-MB-231 tumor cell monocultures as described in Example 15, except for the following amendments: Tumor cells were cultured in monocultures, and where indicated recombinant human FAPα (BioLegend®, Cat. #76908; at a fixed concentration of 29.4 nM) was added simultaneously with antibody samples.

Results

In tumor cell monocultures (DLD-1 and MDA-MB-231), the addition of recombinant human FAPα at a concentration of 29.4 nM, ie, corresponding to ten times the maximum concentration reported in human plasma did not induce BisG1-FAPα-FERL/DR4-FERR-mediated cytotoxicity (FIG. 15A-B). Thus, BisG1-FAPα-FERL/DR4-FERR-induced transactivation-mediated cell death required the presence of cell surface expressed FAPα.

Example 17: Effect on FAPα Enzymatic Activity In Vitro

The effect of BisG1-FAPα-FERL/DR4-FERR on FAPα dipeptidyl peptidase (DPP) activity was tested using a fluorogenic assay in which fluorogenic dipeptidyl peptidase substrate is incubated with a sample containing soluble FAPα.

As a readout for FAPα enzymatic activity, the fluorescent signal generated by release of 7-amino-4-methylcoumarin (AMC) from the dipeptidyl peptidase substrate can be measured using a fluorescence reader. FAPα dipeptidyl peptidase activity was tested using a FAP Fluorogenic Assay Kit (BPS Bioscience, Cat. #80210) according to manufacturer's instructions. Fluorogenic dipeptidyl peptidase substrate was incubated in presence of BisG1-FAPα-FERL/DR4-FERR, the nonbinding control antibody BisG1-b12-FERL/b12-FERR, or the chemical dipeptidyl peptidase inhibitor Talabostat (Cayman Chemical, Cat. #CAYM290075) as a positive control of enzyme inhibition, in presence of FAPα. The fluorescent signal generated by release of AMC from the dipeptidyl peptidase substrate was measured on an EnVision® Plate Reader (PerkinElmer). Blank values (DPP Assay Buffer only) were subtracted from sample values and AMC concentrations were interpolated from the standard curve by standard linear regression in GraphPad Prism after correcting for the sample dilution.

Results

BisG1-FAPα-FERL/DR4-FERR and the nonbinding control antibody BisG1-b12-FERL/b12-FERR did not affect FAPα dipeptidyl peptidase-mediated generation of fluorescent AMC. In contrast, clear dose-dependent inhibition of FAPα dipeptidyl peptidase activity was observed for the chemical dipeptidyl peptidase inhibitor Talabostat that was included as positive control (FIG. 16). Overall, these data show that BisG1-FAPα-FERL/DR4-FERR did not inhibit FAPα dipeptidyl peptidase activity in vitro.

Example 18: Fc Region Characterization

BisG1-FAPα-FERL/DR4-FERR was designed to have an inert Fc region to abrogate Fc-mediated effector functions such as ADCC, ADCP, and CDC. Therefore, the binding of the Fc region of BisG1-FAPα-FERL/DR4-FERR to complement component C1q and FcγRs, essential for Fc-mediated effector functions, and to FcRn, essential for the long serum half-life typical for IgG1 molecules, was assessed in vitro.

Binding of C1q to membrane-bound BisG1-FAPα-FERL/DR4-FERR was assessed by flow cytometry. MDA-MB-231 cells were harvested as described in Example 3, plated (50,000 cells/well) in round-bottom 96-well plates and incubated with a concentration range of BisG1-FAPα-FERL/DR4-FERR or IgG1-b12-FER control antibody (0.003-30 pig/mL in threefold increments) at 37° C. for 30 min. To assess C1q binding, normal human serum (NHS) (Sanquin, final concentration 20%) was added as a source of C1q and the mixture was incubated at 4° C. for 45 min. Cells were washed twice with FACS buffer (PBS [Lonza, Cat. #BE17-517Q] supplemented with 0.1% [w/v] BSA [Roche, Cat. #10735086001] and 0.02% [w/v] sodium azide [NaN3; bioWORLD, Cat. #41920044-3]) and subsequently incubated with FITC-conjugated rabbit anti-human C1q antibody (DAKO, Cat. #F0254; 1:100 in FACS buffer) at 4° C. for 30 min, protected from light. Within the same experiment, binding of the DR4-antibodies to the MDA-MB-231 cells was confirmed in parallel samples after the incubation with serial dilutions of the tested antibodies. To this end, cells were washed and incubated with R-PE AffiniPure F(ab')2 Fragment Goat Anti-Human IgG (Jackson ImmunoResearch (Cat. #109-116-098; 1:200 in FACS buffer) at 4° C. for 30 min. Next, all samples were then washed again with FACS buffer and resuspended in FACS buffer supplemented with viability marker TO-PRO™-3 Iodide (Invitrogen, Cat. #T3605; 1:20,000). C1q and antibody binding was analyzed by measuring fluorescence in flow cytometry on a BD LSRFortessa™ X-20 Cell Analyzer (BD Biosciences). Binding curves were analyzed using nonlinear regression analysis (sigmoidal three parameter dose-response curve) using GraphPad Prism software.

Binding of BisG1-FAPα-FERL/DR4-FERR to immobilized human His-tagged FcγRs and FcRn was analyzed by SPR using a Biacore™ 8K SPR system (Cytiva). To this end, anti-His antibodies were covalently immobilized on the surface of Biacore™ Series S Sensor Chip CM5 (Cytiva, Cat. #29104988) using the Amine Coupling Kit (Cytiva, Cat. #BR100050) and a His Capture Kit (Cytiva, Cat. #29234602) according to the manufacturer's instructions. To assess antibody binding to immobilized human FcγRs, aliquots of the recombinant His-tagged FcγR proteins (Table 24) were diluted in HBS EP+ Buffer pH 7.4 (Cytiva, Cat. #BR100669) and used to capture the FcγR proteins on the surface of the anti-His antibody-coated sensors using a flow rate of 10 μL/min and a contact time of 60 s. Captured levels ranged from 434 to 592 RU. After three start-up cycles of HBS-EP+ Buffer, concentration ranges of BisG1-FAPα-FERL/DR4-FERR or IgG1-b12 antibodies (Table 25) were injected to generate binding curves on FcγR-captured sensors (active surface). For each antibody sample, a parallel flow cell without captured FcγRs was included (reference surface), which was used for RU background correction.

Next, to assess antibody binding to immobilized human FcRn, aliquots of recombinant His-tagged FcRn protein (Table 24) were diluted in PBS-P+ Buffer pH 7.4 (Cytiva, Cat. #28995084) or pH 6.0, which was achieved by adding hydrochloric acid (Sigma-Aldrich, Cat. #30721-M) and were used to capture FcRn protein on the surface of the anti-His antibody-coated sensors using a flow rate of 10 μL/min and a contact time of 60 s. Captured levels ranged from 26 to 34 RU at pH 7.4, and 47 to 54 RU at pH 6.0. After three start-up cycles of PBS-P+ buffer pH 7.4 or pH 6.0, concentration ranges of BisG1-FAPα-FERL/DR4-FERR (31 to 500 nM in twofold increments in PBS-P+ Buffer pH 7.4 or pH 6.0) were injected to generate binding curves on FcRn-captured sensors (active surface). For each antibody sample, a parallel flow cell without captured FcRn was included (reference surface), which was used for RU background correction. At the end of each cycle, sensor surfaces were regenerated using 10 mM Glycine HCl pH 1.5 (Cytiva, Cat. #BR100354).

Biacore Insight Evaluation software (Cytiva) was used to generate sensorgrams (RU displayed in real time). All sensorgrams were subtracted by the signal of the third start-up cycle with buffer only (mock analyte). Then, double-referenced data were obtained for each antibody sample on a specific FcR-captured sensor (active surface) by correcting for background using the sensorgrams on the parallel sensor without immobilized FcR (reference surface). Graphs displaying double-referenced endpoint data (RU plateau versus postcapture baseline in sensorgrams) versus antibody concentrations for FcRn binding and graphs displaying FcγR binding response relative to IgG1-b12 versus antibody concentrations were generated in GraphPad Prism.

TABLE 24

Recombinant human FcR proteins

| Name | Description | Sino Biological cat. no. | Coating concentration in SPR |
|---|---|---|---|
| FcγRIa | CD64 Protein, Human, Recombinant (ECD, His Tag), HPLC-verified | 10256-H08S | 100 nM |
| FcγRIIa-H131 [a] | CD32A Protein, Human, Recombinant (167 His, His Tag), HPLC-verified | 10374-H08H1 | 89 nM |
| FcγRIIa-R131 [a] | CD32A Protein, Human, Recombinant (167 Arg, His & AVI Tag), Biotinylated, HPLC-verified | 10374-H27H-B | 78 nM |
| FcγRIIb | CD32B/Fcgr2b Protein, Human, Recombinant (His & AVI Tag), Biotinylated, HPLC-verified | 10259-H27H-B | 84 nM |
| FcγRIIIa-F158 [a] | CD16a Protein, Human, Recombinant (ECD, 176 Phe, His & AVI Tag) | 10389-H27H | 192 nM |

TABLE 24-continued

Recombinant human FcR proteins

| Name | Description | Sino Biological cat. no. | Coating concentration in SPR |
|---|---|---|---|
| FcγRIIIa-V158 [a] | CD16a Protein, Human, Recombinant (176 Val, His & AVI Tag) | 10389-H27H1 | 246 nM |
| FcRn | FCGRT & B2M Heterodimer Protein, Human, Recombinant (His Tag), Biotinylated | CT009-H08H-B | 5 nM |

[a] The polymorphisms in FcγRIIa and FcγRIIIa have been described in literature by two different annotations (with or without the signal peptide). Therefore, FcγRIIa residue 131 corresponds to residue 167 and FcγRIIIa residue 158 corresponds to residue 176.

TABLE 25

Antibody concentration ranges used for FCγR binding measurements

| | Antibody concentration range tested | | |
|---|---|---|---|
| FcγR | Start concentration (nM) | Lowest concentration (nM) | Fold dilution in HBS-EP+ Buffer pH 7.4 |
| FcγRIa | 3,000 | 0.02 | 1:3 |
| FcγRIIa-H131 [a] | 10,000 | 0.42 | 1:2.5 |
| FcγRIIa-R131 [a] | 10,000 | 0.42 | 1:2.5 |
| FcγRIIb | 10,000 | 4.9 | 1:2 |
| FcγRIIIa-F158 [a] | 10,000 | 0.42 | 1:2.5 |
| FcγRIIIa-V158 [a] | 10,000 | 0.06 | 1:3 |

[a] The polymorphisms in FcγRIIa and FcγRIIIa have been described in literature by two different annotations (with or without the signal peptide). Therefore, FcγRIIa residue 131 corresponds to residue 167 and FcγRIIIa residue 158 corresponds to residue 176.

Results

To confirm lack of complement binding to the Fc domain of BisG1-FAPα-FERL/DR4-FERR, binding of C1q to BisG1-FAPα-FERL/DR4-FERR bound to MDA-MB-231 cells was determined by flow cytometry. Even though BisG1-FAPα-FERL/DR4-FERR binding was detected on MDA-MB-231 cells (FIG. 17A), no binding of C1q was detected to cells incubated with BisG1-FAPα-FERL/DR4-FERR (FIG. 17B).

Next, to confirm lack of binding of FcγRs to the Fc domain of BisG1-FAPα-FERL/DR4-FERR, binding of BisG1-FAPα-FERL/DR4-FERR and a positive control antibody IgG1-b12 (with a wild-type Fc backbone) to immobilized human FcγRIa, FcγRIIa (polymorphic variants H131 and R131), FcγRIIb, and FcγRIIIa (polymorphic variants F158 and V158) was determined by SPR. Whereas binding to all tested FcγRs was observed for positive control antibody IgG1-b12, no binding was observed for BisG1-FAPα-FERL/DR4-FERR (FIG. 18).

Finally, to assess whether BisG1-FAPα-FERL/DR4-FERR retained the ability to bind FcRn, binding of BisG1-FAPα-FERL/DR4-FERR to immobilized FcRn was assessed in vitro at pH 6.0 and pH 7.4 by SPR. At pH 6.0, dose dependent binding of BisG1-FAPα-FERL/DR4-FERR to FcRn was observed (FIG. 19A), whereas no FcRn binding was observed at pH 7.4 (FIG. 19B).

In summary these data confirmed that the Fc domain of BisG1-FAPα-FERL/DR4-FERR was unable to bind C1q and FcγRs, and it is therefore considered unable to drive Fc-mediated effector functions. Further, these data confirm that binding of BisG1-FAPα-FERL/DR4-FERR to FcRn is preserved.

Example 19: Pharmacokinetics (PK) in Tumor-Free Mice

PK properties of BisG1-FAPα-FERL/DR4-FERR were determined in tumor-free immunodeficient C57BL/6 SCID mice expressing mouse or human FcRn.

11 to 12 weeks old female tumor-free (ie, non-tumor-bearing) C57BL/6 SCID (Female B6.Cg-Prkdc$^{scid}$/SzJ mice; The Jackson Laboratory, strain #001913) or hFcRn SCID mice (C57BL/6 SCID background with homozygous knock-out of the mouse FcRn α-chain [Fcgrt$^{tm1Dcr}$] and introduction of a human FcRn α-chain [FCGRT] transgene) were randomized (n=¾ per group) (Table 26) based on body weight. On the day of randomization (Day 0), each mouse received a single dose IV of 2 mg/kg BisG1-FAPα-FERL/DR4-FERR. Blood samples (40 μL) were collected using cheek vena puncture (after 10 min) or via the vena saphena (all other time points) in K$_2$EDTA Microvette® blood collection tubes (Sarstedt, Cat. #16.444) at the indicated time points (Table 26). Blood samples were centrifuged at 14,000×g at 4° C. for 10 min, plasma was collected and stored at <−65° C. until further use for analysis.

To assess PK properties, total human IgG concentrations were determined using an electrochemiluminescence immunoassay (ECLIA). Mouse plasma study samples were diluted 50× in assay buffer consisting of PBST (PBS [Lonza, Cat. #BE17-516Q] with 0.05% [w/v] Tween 20 [Sigma Aldrich, Cat. #P1379]) with 1% (w/v) Blocker-A (MSD, Cat. #R93AA-1). In some cases, study samples were further diluted 10× with 2% CD-1 (ICR) mouse pooled plasma (BioIVT, Cat. #MSEOOPLK2-0101232) in assay buffer to fit their measured concentration within the calibration range. Reference samples were prepared by serially diluting BisG1-FAPα-FERL/DR4-FERR with 2% mouse plasma in assay buffer (calibration range 0.156 to 20.0 μg/mL, anchor points 0.0781 and 40.0 μg/mL). Assay quality control (QC) samples were prepared by spiking different antibody concentrations of BisG1-FAPα-FERL/DR4-FERR in mouse pooled plasma to cover the range of the reference curve (concentrations 0.500, 1.75 and 15.0 μg/mL). Prior to assay performance, QC samples were diluted 50× in assay buffer, to have a final percentage of 2% mouse plasma in assay buffer, which is similar to the dilution of the study samples.

Human antibody concentrations in the mouse plasma samples were determined using a sandwich ECLIA method. MULTI-ARRAY™ Standard 96-well plates (MSD, Cat. #L15XA-3) were coated with 2 μg/mL chimeric mouse/llama anti-human IgG capture antibody (IgG2amm 1015-6A05) in PBS at 2 to 8° C. for 16 to 24 h. With wash steps in between, the coated plates were sequentially incubated at RT while shaking (300 RPM) with i) block buffer (PBST with 3% [w/v] Blocker-A) for 60 min, ii) study, reference and QC samples for 90 min, and iii) 0.25 µg/mL SULFO-tag-conjugated chimeric mouse/llama anti-human IgG detection antibody (IgG2amm-1015-4A01-ST) in assay buffer for 90 min. Finally, all plates were washed with PBST, and captured human antibodies were visualized by adding MSD GOLD Read Buffer A (MSD, Cat. #R92TG-2), applying an electrochemical stimulation at the electrode surfaces of the plate, and measuring light emission at 620 nm with a MESO QuickPlex® SQ 120MM Plate Imager. Standard curves were generated by applying a 1/Y2 weighted Five Parameter Logistic (5PL) curve fit using SoftMax® Pro software (Molecular Devices). The concentrations of the study samples were determined.

Noncompartmental analysis (NCA) was performed using the PKNCA package in the statistical programming language R (Denney et al., J Pharmacokinet Pharmacodyn 2015 42:11-107) to calculate PK parameters ($C_{max}$, $AUC_{0-tlast}$, $AUC_{0-inf}$, clearance, $t_{1/2}$ and $t_{max}$) for each animal. Animals were considered to have received (partial) extravascular injection when a markedly reduced $C_{max}$ and delayed $t_{max}$ were observed compared with what is expected based on the injected dose. The percentage $AUC_{0-inf}$ of the injected antibody in an animal considered misinjected was calculated relative to the mean $AUC_{0-inf}$ of all correctly dosed animals for that group. PK parameters were calculated for all individual animals and animals considered misinjected were excluded prior to calculation of mean PK parameters in each group. The predicted IgG concentration-time curves for wild-type human IgG1 in tumor-free hFcRn SCID mice were generated based on a two-compartment PK model with linear clearance described in literature (Betts et al., mAbs 2018 10:751-764). The lower limit of quantification (LLOQ) was 0.156 µg/mL; the upper limit of quantification (ULOQ) at 10× minimal required dilution was 200 µg/mL.

TABLE 26

Treatment groups and blood sampling

| Group | Mouse strain | n | Antibody | Dose | Dosing route | Dosing regimen | Blood sampling [a] |
|---|---|---|---|---|---|---|---|
| 1 | C57BL/6 SCID | 3 | BisG1-FAPα-FERL/DR4-FERR | 2 mg/kg | IV | single dose on t = 0 | 10 min, 5 h, 1 d, 2 d, 8 d, 15 d, 21 d |
| 2 | hFcRn SCID | 4 | BisG1-FAPα-FERL/DR4-FERR | 2 mg/kg | IV | single dose on t = 0 | 10 min, 5 h, 1 d, 2 d, 8 d, 15 d, 21 d |

[a] Blood was collected either from the left (l) or right (r) cheek vein at approximate time point 10 min (r) or saphenous vein at time points 5 h (r), 1 d (r), 2 d (l), 8 d (r), 14 d (l), and 21 d (r) post-injection.

Results

A total of three animals (two C57BL/6 SCID mice and one hFcRn SCID mouse) were considered to have received inadvertent extravascular injections and data from these animals were excluded prior to calculation of mean PK parameters in each group. Upon IV administration, BisG1-FAPα-FERL/DR4-FERR showed a linear PK profile generally consistent with predictions for a human IgG antibody in mice in absence of target binding, with maximum exposure at the earliest tested post-injection time point, followed by a two-phase decline (FIG. 20). BisG1-FAPα-FERL/DR4-FERR has low crossreactivity to mouse FAPα and expression of FAPα in tumor-free mice cannot be ruled out. However, the observed PK profiles are indicative of saturation of any target present. Maximum exposure, distribution and terminal elimination of BisG1-FAPα-FERL/DR4-FERR were observed to be typical for wild-type IgG1 in both C57BL/6 SCID and hFcRn SCID mice (FIG. 20).

In summary, in both C57BL/6 SCID and hFcRn SCID mice BisG1-FAPα-FERL/DR4-FERR showed PK properties generally consistent with those of wild-type human IgG1 in absence of target binding.

The invention claimed is:
1. A bispecific antibody comprising at least
   (i) a fibroblast activation protein alpha (FAPα) binding region comprising a heavy chain variable (VH) region and a light chain variable (VL) region, and
   (ii) a death receptor 4 (DR4) binding region comprising a VH region and a VL region,
   wherein the VH region of the FAPα binding region comprises the three complementarity determining regions, CDR1, CDR2, and CDR3, present within the amino acid sequence set forth in SEQ ID NO: 13, and the VL region of the FAPα binding region comprises the three complementarity determining regions, CDR1, CDR2, and CDR3, present within the amino acid sequence set forth in SEQ ID NO: 14.

2. The bispecific antibody of claim 1, wherein the VH region of the FAPα binding region comprises an amino acid sequence which is at least 90% identical to the amino acid sequence as set forth in SEQ ID NO: 13 and the VL region of the FAPα binding region comprises an amino acid sequence which is at least 90% identical to the amino acid sequence as set forth in SEQ ID NO: 14.

3. The bispecific antibody of claim 1, wherein the DR4 binding region comprises a heavy chain variable region (VH) comprising the three complementarity determining regions, CDR1, CDR2, and CDR3, present within the amino acid sequence set forth in SEQ ID NO: 15, and a light chain variable region (VL) comprising the three complementarity determining regions, CDR1, CDR2, and CDR3, present within the amino acid sequence set forth in SEQ ID NO: 16.

4. The bispecific antibody of claim 1, wherein the VH region of the DR4 binding region comprises an amino acid sequence which is at least 90% identical to the amino acid sequence as set forth in SEQ ID NO: 15, and the VL region of the DR4 binding region comprises an amino acid sequence which is at least 90% identical to the amino acid sequence as set forth in SEQ ID NO: 16.

5. The bispecific antibody of claim 1, wherein the antibody comprises:
   (i) a FAPα binding region comprising a heavy chain variable (VH) region and a light chain variable (VL) region, wherein the VH region comprises the CDR1, CDR2, and CDR3 sequences of SEQ ID NOs: 1, 2 and 3, respectively, and the VL region comprises the CDR1, CDR2 and CDR3 sequences of SEQ ID NO: 4, the sequence VAS, and SEQ ID NO: 6, respectively; and
   (ii) a DR4 binding region comprising a VH region and a VL region, wherein the VH comprises the CDR1, CDR2, and CDR3 sequences of SEQ ID NOs: 7, 8 and 9, respectively, and the VL region comprises the CDR1, CDR2 and CDR3 sequences of SEQ ID NO: 10, the sequence EVT, and SEQ ID NO: 12, respectively.

6. The bispecific antibody of claim 1, wherein the antibody comprises:
   (i) a FAPα binding region comprising a VH region comprising the amino acid sequence of SEQ ID NO: 13 and a VL region comprising the amino acid sequence of SEQ ID NO: 14; and
   (ii) a DR4 binding region comprising a VH region comprising the amino acid sequence of SEQ ID NO: 15 and a VL region comprising the amino acid sequence of SEQ ID NO: 16.

7. The bispecific antibody of claim 1, wherein the antibody comprises a first heavy chain and a second heavy chain, the first heavy chain comprises the VH region of the FAPα binding region and the second heavy chain comprises the VH region of the DR4 binding region,
   (i) wherein each of the first heavy chain and the second heavy chain comprises at least a hinge region, a CH2 region and a CH3 region, and
   (ii) wherein in the first heavy chain at least one of the amino acids in a position corresponding to a position selected from the group consisting of T366, L368, K370, D399, F405, Y407, and K409 in a human IgG1 heavy chain is substituted, and in the second heavy chain at least one of the amino acids in a position corresponding to a position selected from the group consisting of T366, L368, K370, D399, F405, Y407, and K409 in a human IgG1 heavy chain is substituted,
   wherein the amino acid positions are as defined by Eu numbering.

8. The bispecific antibody of claim 1, wherein the antibody comprises a first heavy chain and a second heavy chain, wherein in at least one of the first heavy chain and the second heavy chain one or more amino acids in the positions corresponding to L234, L235, G236, D265, N297, and P331 in a human IgG1 heavy chain are not L, L, G, D, N, and P, respectively, wherein the amino acid positions are as defined by Eu numbering.

9. The bispecific antibody of claim 1, wherein the antibody comprises a first heavy chain and a second heavy chain, wherein in at least one of the first heavy chain and the second heavy chain:
   (a) the positions corresponding to positions L234 and L235 in a human IgG1 heavy chain are F and E, respectively, in the first and/or second heavy chains;
   (b) the positions corresponding to positions L234, L235, and D265 in a human IgG1 heavy chain are F, E, and A, respectively, in the first and/or second heavy chains;
   (c) the positions corresponding to positions L234, L235, and G236 in a human IgG1 heavy chain are F, E, and R, respectively, in the first and/or second heavy chains; or
   (d) one of the first and second heavy chains comprises substitutions of the amino acids corresponding to the amino acids at positions L234, L235 and G236 to F, E and R, respectively, and the other heavy chain comprises substitutions of the amino acids corresponding to the amino acids at positions L234, L235 and D265 to F, E and A, respectively,
   wherein the amino acid positions are as defined by Eu numbering.

10. The bispecific antibody of claim 1, wherein the antibody comprises a first heavy chain and a second heavy chain, and wherein:
   (a) the positions corresponding to positions L234 and L235 in a human IgG1 heavy chain of both the first heavy chain and the second heavy chain are F and E, respectively, and wherein
      (i) the position corresponding to F405 in a human IgG1 heavy chain according to Eu numbering of the first heavy chain is L, and the position corresponding to K409 in a human IgG1 heavy chain according to Eu numbering of the second heavy chain is R, or
      (ii) the position corresponding to K409 in a human IgG1 heavy chain according to Eu numbering of the first heavy chain is R, and the position corresponding to F405 in a human IgG1 heavy chain according to Eu numbering of the second heavy chain is L;
   (b) the positions corresponding to positions L234, L235, and D265 in a human IgG1 heavy chain of both the first heavy chain and the second heavy chain are F, E, and A, respectively, and wherein (i) the position corresponding to F405 in a human IgG1 heavy chain according to Eu numbering of the first heavy chain is L, and the position corresponding to K409 in a human IgG1 heavy chain according to Eu numbering of the second heavy chain is R, or (ii) the position corresponding to K409 in a human IgG1 heavy chain according to Eu numbering of the first heavy chain is R, and the position corresponding to F405 in a human IgG1 heavy chain according to Eu numbering of the second heavy chain is L; or (c) the positions corresponding to positions L234, L235, and G236 in a human IgG1 heavy chain of both the first heavy chain and the second heavy chain are F, E, and R, respectively, and wherein (i) the position corresponding to F405 in a human IgG1 heavy chain according to Eu numbering of the first heavy chain is L, and the position corresponding to K409 in a human IgG1 heavy chain according to Eu numbering of the second heavy chain is R, or (ii) the position corresponding to K409 in a human IgG1 heavy chain according to Eu numbering of the first heavy chain is R, and the position corresponding to F405 in a human IgG1 heavy chain according to Eu numbering of the second heavy chain is L;

wherein the amino acid positions are as defined by Eu numbering.

11. The bispecific antibody of claim 1, wherein the antibody comprises a first heavy chain and a second heavy chain, and wherein both the first heavy chain and the second heavy chain comprise substitutions of the amino acids corresponding to the amino acids at positions L234, L235 and G236 to F, E and R, respectively and wherein (i) the position corresponding to F405 in a human IgG1 heavy chain according to Eu numbering of the first heavy chain is L, and the position corresponding to K409 in a human IgG1 heavy chain according to Eu numbering of the second heavy chain is R, or (ii) the position corresponding to K409 in a human IgG1 heavy chain according to Eu numbering of the first heavy chain is R, and the position corresponding to F405 in a human IgG1 heavy chain according to Eu numbering of the second heavy chain is L, wherein the amino acid positions are as defined by Eu numbering.

12. The bispecific antibody of claim 1, wherein the antibody comprises a kappa (κ) and/or a lambda (λ) light chain.

13. The bispecific antibody according to claim 1, wherein the antibody comprises two heavy chains and two light chains, wherein one heavy chain comprises a constant region as defined in SEQ ID NO: 26 and the other heavy chain comprises a constant region as defined in SEQ ID NO: 70, and wherein one light chain is a kappa light chain comprising a constant region as defined in SEQ ID NO: 27 and the other light chain is a lambda light chain comprising a constant region as defined in SEQ ID NO: 28.

14. The bispecific antibody of claim 1, wherein the antibody comprises a first heavy chain and a first light chain connected via disulfide bridges forming a first binding region that binds to FAPα, and a second heavy chain and a second light chain connected via disulfide bridges forming a second binding region that binds to DR4, wherein:

i) the first heavy chain comprises the amino acid sequence of SEQ ID NO: 17 and the first light chain comprises amino acid sequence of SEQ ID NO: 18; and ii) the second heavy chain comprises the amino acid sequence of SEQ ID NO: 19 and the second light chain comprises the amino acid sequence of SEQ ID NO: 20.

15. A nucleic acid construct, or a combination of nucleic acid constructs, comprising a nucleotide sequence encoding the bispecific antibody of claim 1.

16. An expression vector, or a combination of expression vectors, comprising the nucleic acid construct, or combination of nucleic acid constructs, of claim 15.

17. A recombinant host cell comprising the nucleic acid construct, or combination of nucleic acid constructs, of claim 15.

18. A pharmaceutical composition comprising the bispecific antibody of claim 1, and a pharmaceutically-acceptable carrier.

19. A method of treating cancer comprising administering to a subject in need thereof an effective amount of the bispecific antibody of claim 1.

20. The method of claim 19, wherein the cancer is a solid cancer.

21. The method of claim 19, wherein the cancer is colorectal cancer, breast cancer, pancreatic cancer, esophagogastric cancer, head and neck squamous cell carcinoma, cervical cancer, or lung cancer.

22. A method for producing a bispecific antibody which binds to fibroblast activation protein alpha (FAPα) and death receptor 4 (DR4), the method comprising:

(a) culturing the recombinant host cell of claim 17 under conditions wherein the antibody is produced; and (b) isolating the produced antibody from the culture.

23. A method for producing a bispecific antibody which binds to fibroblast activation protein alpha (FAPα) and death receptor 4 (DR4), the method comprising:

(a) providing a first antibody comprising the FAPα binding region and a second antibody comprising the DR4 binding region as defined in claim 1, wherein the first and second antibodies comprise an Fc region, and wherein the sequences of the first and second CH3 regions of the first and second antibodies are different and are such that the heterodimeric interaction between the first and second CH3 regions is stronger than each of the homodimeric interactions of the first and second CH3 regions;

(b) incubating the first antibody together with the second antibody under reducing conditions sufficient to allow the cysteines in the hinge regions to undergo disulfide-bond isomerization; and (c) obtaining the antibody comprising the first immunoglobulin heavy chain and the first immunoglobulin light chain of the first antibody and the second immunoglobulin heavy chain and the second immunoglobulin light chain of the second antibody.

24. A kit comprising the bispecific antibody of claim 1, and instructions for use.

25. The method of claim 20, wherein the solid cancer is a malignant solid tumor.

26. A bispecific antibody comprising at least (i) a fibroblast activation protein alpha (FAPα) binding region comprising a heavy chain variable (VH) region and a light chain variable (VL) region, and (ii) a death receptor 4 (DR4) binding region comprising a VH region and a VL region, wherein the DR4 binding region comprises a heavy chain variable region (VH) comprising the three complementarity determining regions, CDR1, CDR2, and CDR3, present within the amino acid sequence set forth in SEQ ID NO: 15, and a light chain variable region (VL) comprising the three complementarity determining regions, CDR1, CDR2, and CDR3, present within the amino acid sequence set forth in SEQ ID NO: 16.

27. The method of claim 21, wherein the cancer is colorectal cancer.

28. The method of claim 21, wherein the cancer is breast cancer.

29. The method of claim 21, wherein the cancer is pancreatic cancer.

30. The method of claim 21, wherein the cancer is esophagogastric cancer.

31. The method of claim 21, wherein the cancer is head and neck squamous cell carcinoma.

32. The method of claim 21, wherein the cancer is cervical cancer.

33. The method of claim 21, wherein the cancer is lung cancer.

34. The bispecific antibody of claim 1, wherein the antibody comprises:
   (i) a FAPα heavy chain comprising the amino acid sequence as set forth in SEQ ID NO: 17 and a FAPα light chain comprising the amino acid sequence as set forth in SEQ ID NO: 18, and
   (ii) a DR4 heavy chain comprising the amino acid sequence as set forth in SEQ ID NO: 19 and a DR4 light chain comprising the amino acid sequence as set forth in SEQ ID NO: 20.

\* \* \* \* \*

SEQUENCE LISTING

```
Sequence total quantity: 73
SEQ ID NO: 1            moltype = AA   length = 8
FEATURE                 Location/Qualifiers
source                  1..8
                        mol_type = protein
                        organism = synthetic construct
SEQUENCE: 1
GFTFSSYA                                                                 8

SEQ ID NO: 2            moltype = AA   length = 8
FEATURE                 Location/Qualifiers
```

```
source                  1..8
                        mol_type = protein
                        organism = synthetic construct
SEQUENCE: 2
ISGSGGGR                                                                    8

SEQ ID NO: 3            moltype = AA   length = 14
FEATURE                 Location/Qualifiers
source                  1..14
                        mol_type = protein
                        organism = synthetic construct
SEQUENCE: 3
AKEGYSSSGT YWDH                                                            14

SEQ ID NO: 4            moltype = AA   length = 6
FEATURE                 Location/Qualifiers
source                  1..6
                        mol_type = protein
                        organism = synthetic construct
SEQUENCE: 4
QGVSSW                                                                      6

SEQ ID NO: 5            moltype =     length =
SEQUENCE: 5
000

SEQ ID NO: 6            moltype = AA   length = 9
FEATURE                 Location/Qualifiers
source                  1..9
                        mol_type = protein
                        organism = synthetic construct
SEQUENCE: 6
QQANSFPPT                                                                   9

SEQ ID NO: 7            moltype = AA   length = 9
FEATURE                 Location/Qualifiers
source                  1..9
                        mol_type = protein
                        organism = synthetic construct
SEQUENCE: 7
GGSISSYSW                                                                   9

SEQ ID NO: 8            moltype = AA   length = 7
FEATURE                 Location/Qualifiers
source                  1..7
                        mol_type = protein
                        organism = synthetic construct
SEQUENCE: 8
LYHSGST                                                                     7

SEQ ID NO: 9            moltype = AA   length = 9
FEATURE                 Location/Qualifiers
source                  1..9
                        mol_type = protein
                        organism = synthetic construct
SEQUENCE: 9
VRGVATIDY                                                                   9

SEQ ID NO: 10           moltype = AA   length = 9
FEATURE                 Location/Qualifiers
source                  1..9
                        mol_type = protein
                        organism = synthetic construct
SEQUENCE: 10
SSDVGGYNF                                                                   9

SEQ ID NO: 11           moltype =     length =
SEQUENCE: 11
000

SEQ ID NO: 12           moltype = AA   length = 10
FEATURE                 Location/Qualifiers
source                  1..10
                        mol_type = protein
                        organism = synthetic construct
SEQUENCE: 12
SSYAGSNNVM                                                                 10

SEQ ID NO: 13           moltype = AA   length = 121
```

```
FEATURE              Location/Qualifiers
source               1..121
                     mol_type = protein
                     organism = synthetic construct
SEQUENCE: 13
EVQLLESGGG LVQPGGSPRL SCEASGFTFS SYALSWVRQA PGKGLEWVSA ISGSGGGRYY    60
ADSVKGRFTI SRDNSKNTLF LQMNSLRAED TAVYYCAKEG YSSSGTYWDH WGQGTLVTVS   120
S                                                                  121

SEQ ID NO: 14        moltype = AA  length = 107
FEATURE              Location/Qualifiers
source               1..107
                     mol_type = protein
                     organism = synthetic construct
SEQUENCE: 14
AIQMTQSPSS VSASVGDRVT ITCRASQGVS SWLAWYQQKP GRAPKLLIYV ASTLQSGVPS    60
RFSGSGSGTD FTLTINSLQP EDFATYYCQQ ANSFPPTFGQ GTRLEMK                107

SEQ ID NO: 15        moltype = AA  length = 116
FEATURE              Location/Qualifiers
source               1..116
                     mol_type = protein
                     organism = synthetic construct
SEQUENCE: 15
QVQLQESGPG LVKPSGTLSL TCAVSGGSIS SYSWWSWIRQ PPGKGLEWIG ELYHSGSTNY    60
NPSLKSRVTI SVDKSKNQFS LKLRSVTAAD TAVYYCVRGV ATIDYWGQGT LVTVSS       116

SEQ ID NO: 16        moltype = AA  length = 110
FEATURE              Location/Qualifiers
source               1..110
                     mol_type = protein
                     organism = synthetic construct
SEQUENCE: 16
QSALTQPPSA SGSPGQSVTI SCTGTSSDVG GYNFVSWYQQ DPGKAPKLLI YEVTKRPSGV    60
PDRFSGSKSG NTASLTVSGL QAEDEADYYC SSYAGSNNVM FGGGTKLTVL              110

SEQ ID NO: 17        moltype = AA  length = 450
FEATURE              Location/Qualifiers
source               1..450
                     mol_type = protein
                     organism = synthetic construct
SEQUENCE: 17
EVQLLESGGG LVQPGGSPRL SCEASGFTFS SYALSWVRQA PGKGLEWVSA ISGSGGGRYY    60
ADSVKGRFTI SRDNSKNTLF LQMNSLRAED TAVYYCAKEG YSSSGTYWDH WGQGTLVTVS   120
SASTKGPSVF PLAPSSKSTS GGTAALGCLV KDYFPEPVTV SWNSGALTSG VHTFPAVLQS   180
SGLYSLSSVV TVPSSSLGTQ TYICNVNHKP SNTKVDKRVE PKSCDKTHTC PPCPAPEFER   240
GPSVFLFPPK PKDTLMISRT PEVTCVVVDV SHEDPEVKFN WYVDGVEVHN AKTKPREEQY   300
NSTYRVVSVL TVLHQDWLNG KEYKCKVSNK ALPAPIEKTI SKAKGQPREP QVYTLPPSRE   360
EMTKNQVSLT CLVKGFYPSD IAVEWESNGQ PENNYKTTPP VLDSDGSFLL YSKLTVDKSR   420
WQQGNVFSCS VMHEALHNHY TQKSLSLSPG                                   450

SEQ ID NO: 18        moltype = AA  length = 214
FEATURE              Location/Qualifiers
source               1..214
                     mol_type = protein
                     organism = synthetic construct
SEQUENCE: 18
AIQMTQSPSS VSASVGDRVT ITCRASQGVS SWLAWYQQKP GRAPKLLIYV ASTLQSGVPS    60
RFSGSGSGTD FTLTINSLQP EDFATYYCQQ ANSFPPTFGQ GTRLEMKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                              214

SEQ ID NO: 19        moltype = AA  length = 445
FEATURE              Location/Qualifiers
source               1..445
                     mol_type = protein
                     organism = synthetic construct
SEQUENCE: 19
QVQLQESGPG LVKPSGTLSL TCAVSGGSIS SYSWWSWIRQ PPGKGLEWIG ELYHSGSTNY    60
NPSLKSRVTI SVDKSKNQFS LKLRSVTAAD TAVYYCVRGV ATIDYWGQGT LVTVSSASTK   120
GPSVFPLAPS SKSTSGGTAA LGCLVKDYFP EPVTVSWNSG ALTSGVHTFP AVLQSSGLYS   180
LSSVVTVPSS SLGTQTYICN VNHKPSNTKV DKRVEPKSCD KTHTCPPCPA PEFERGPSVF   240
LFPPKPKDTL MISRTPEVTC VVVDVSHEDP EVKFNWYVDG VEVHNAKTKP REEQYNSTYR   300
VVSVLTVLHQ DWLNGKEYKC KVSNKALPAP IEKTISKAKG QPREPQVYTL PPSREEMTKN   360
QVSLTCLVKG FYPSDIAVEW ESNGQPENNY KTTPPVLDSD GSFFLYSRLT VDKSRWQQGN   420
VFSCSVMHEA LHNHYTQKSL SLSPG                                        445

SEQ ID NO: 20        moltype = AA  length = 216
FEATURE              Location/Qualifiers
```

-continued

```
source                    1..216
                          mol_type = protein
                          organism = synthetic construct
SEQUENCE: 20
QSALTQPPSA SGSPGQSVTI SCTGTSSDVG GYNFVSWYQQ DPGKAPKLLI YEVTKRPSGV     60
PDRFSGSKSG NTASLTVSGL QAEDEADYYC SSYAGSNNVM FGGGTKLTVL GQPKAAPSVT    120
LFPPSSEELQ ANKATLVCLI SDFYPGAVTV AWKADSSPVK AGVETTTPSK QSNNKYAASS    180
YLSLTPEQWK SHRSYSCQVT HEGSTVEKTV APTECS                              216

SEQ ID NO: 21             moltype = AA  length = 329
FEATURE                   Location/Qualifiers
source                    1..329
                          mol_type = protein
                          organism = synthetic construct
SEQUENCE: 21
ASTKGPSVFP LAPSSKSTSG GTAALGCLVK DYFPEPVTVS WNSGALTSGV HTFPAVLQSS     60
GLYSLSSVVT VPSSSLGTQT YICNVNHKPS NTKVDKRVEP KSCDKTHTCP PCPAPELLGG    120
PSVFLFPPKP KDTLMISRTP EVTCVVVDVS HEDPEVKFNW YVDGVEVHNA KTKPREEQYN    180
STYRVVSVLT VLHQDWLNGK EYKCKVSNKA LPAPIEKTIS KAKGQPREPQ VYTLPPSREE    240
MTKNQVSLTC LVKGFYPSDI AVEWESNGQP ENNYKTTPPV LDSDGSFFLY SKLTVDKSRW    300
QQGNVFSCSV MHEALHNHYT QKSLSLSPG                                      329

SEQ ID NO: 22             moltype = AA  length = 329
FEATURE                   Location/Qualifiers
source                    1..329
                          mol_type = protein
                          organism = synthetic construct
SEQUENCE: 22
ASTKGPSVFP LAPSSKSTSG GTAALGCLVK DYFPEPVTVS WNSGALTSGV HTFPAVLQSS     60
GLYSLSSVVT VPSSSLGTQT YICNVNHKPS NTKVDKRVEP KSCDKTHTCP PCPAPEFEGG    120
PSVFLFPPKP KDTLMISRTP EVTCVVVDVS HEDPEVKFNW YVDGVEVHNA KTKPREEQYN    180
STYRVVSVLT VLHQDWLNGK EYKCKVSNKA LPAPIEKTIS KAKGQPREPQ VYTLPPSREE    240
MTKNQVSLTC LVKGFYPSDI AVEWESNGQP ENNYKTTPPV LDSDGSFFLY SKLTVDKSRW    300
QQGNVFSCSV MHEALHNHYT QKSLSLSPG                                      329

SEQ ID NO: 23             moltype = AA  length = 329
FEATURE                   Location/Qualifiers
source                    1..329
                          mol_type = protein
                          organism = synthetic construct
SEQUENCE: 23
ASTKGPSVFP LAPSSKSTSG GTAALGCLVK DYFPEPVTVS WNSGALTSGV HTFPAVLQSS     60
GLYSLSSVVT VPSSSLGTQT YICNVNHKPS NTKVDKRVEP KSCDKTHTCP PCPAPEFEGG    120
PSVFLFPPKP KDTLMISRTP EVTCVVVAVS HEDPEVKFNW YVDGVEVHNA KTKPREEQYN    180
STYRVVSVLT VLHQDWLNGK EYKCKVSNKA LPAPIEKTIS KAKGQPREPQ VYTLPPSREE    240
MTKNQVSLTC LVKGFYPSDI AVEWESNGQP ENNYKTTPPV LDSDGSFFLY SKLTVDKSRW    300
QQGNVFSCSV MHEALHNHYT QKSLSLSPG                                      329

SEQ ID NO: 24             moltype = AA  length = 329
FEATURE                   Location/Qualifiers
source                    1..329
                          mol_type = protein
                          organism = synthetic construct
SEQUENCE: 24
ASTKGPSVFP LAPSSKSTSG GTAALGCLVK DYFPEPVTVS WNSGALTSGV HTFPAVLQSS     60
GLYSLSSVVT VPSSSLGTQT YICNVNHKPS NTKVDKRVEP KSCDKTHTCP PCPAPELLGG    120
PSVFLFPPKP KDTLMISRTP EVTCVVVDVS HEDPEVKFNW YVDGVEVHNA KTKPREEQYN    180
STYRVVSVLT VLHQDWLNGK EYKCKVSNKA LPAPIEKTIS KAKGQPREPQ VYTLPPSREE    240
MTKNQVSLTC LVKGFYPSDI AVEWESNGQP ENNYKTTPPV LDSDGSFLLY SKLTVDKSRW    300
QQGNVFSCSV MHEALHNHYT QKSLSLSPG                                      329

SEQ ID NO: 25             moltype = AA  length = 329
FEATURE                   Location/Qualifiers
source                    1..329
                          mol_type = protein
                          organism = synthetic construct
SEQUENCE: 25
ASTKGPSVFP LAPSSKSTSG GTAALGCLVK DYFPEPVTVS WNSGALTSGV HTFPAVLQSS     60
GLYSLSSVVT VPSSSLGTQT YICNVNHKPS NTKVDKRVEP KSCDKTHTCP PCPAPELLGG    120
PSVFLFPPKP KDTLMISRTP EVTCVVVDVS HEDPEVKFNW YVDGVEVHNA KTKPREEQYN    180
STYRVVSVLT VLHQDWLNGK EYKCKVSNKA LPAPIEKTIS KAKGQPREPQ VYTLPPSREE    240
MTKNQVSLTC LVKGFYPSDI AVEWESNGQP ENNYKTTPPV LDSDGSFFLY SRLTVDKSRW    300
QQGNVFSCSV MHEALHNHYT QKSLSLSPG                                      329

SEQ ID NO: 26             moltype = AA  length = 329
FEATURE                   Location/Qualifiers
source                    1..329
                          mol_type = protein
                          organism = synthetic construct
```

```
SEQUENCE: 26
ASTKGPSVFP LAPSSKSTSG GTAALGCLVK DYFPEPVTVS WNSGALTSGV HTFPAVLQSS   60
GLYSLSSVVT VPSSSLGTQT YICNVNHKPS NTKVDKRVEP KSCDKTHTCP PCPAPEFERG  120
PSVFLFPPKP KDTLMISRTP EVTCVVVDVS HEDPEVKFNW YVDGVEVHNA KTKPREEQYN  180
STYRVVSVLT VLHQDWLNGK EYKCKVSNKA LPAPIEKTIS KAKGQPREPQ VYTLPPSREE  240
MTKNQVSLTC LVKGFYPSDI AVEWESNGQP ENNYKTTPPV LDSDGSFLLY SKLTVDKSRW  300
QQGNVFSCSV MHEALHNHYT QKSLSLSPG                                    329

SEQ ID NO: 27           moltype = AA  length = 107
FEATURE                 Location/Qualifiers
source                  1..107
                        mol_type = protein
                        organism = synthetic construct
SEQUENCE: 27
RTVAAPSVFI FPPSDEQLKS GTASVVCLLN NFYPREAKVQ WKVDNALQSG NSQESVTEQD   60
SKDSTYSLSS TLTLSKADYE KHKVYACEVT HQGLSSPVTK SFNRGEC                107

SEQ ID NO: 28           moltype = AA  length = 106
FEATURE                 Location/Qualifiers
source                  1..106
                        mol_type = protein
                        organism = synthetic construct
SEQUENCE: 28
GQPKAAPSVT LFPPSSEELQ ANKATLVCLI SDFYPGAVTV AWKADSSPVK AGVETTTPSK   60
QSNNKYAASS YLSLTPEQWK SHRSYSCQVT HEGSTVEKTV APTECS                 106

SEQ ID NO: 29           moltype = AA  length = 450
FEATURE                 Location/Qualifiers
source                  1..450
                        mol_type = protein
                        organism = synthetic construct
SEQUENCE: 29
EVQLLESGGG LVQPGGSPRL SCEASGFTFS SYALSWVRQA PGKGLEWVSA ISGSGGGRYY   60
ADSVKGRFTI SRDNSKNTLF LQMNSLRAED TAVYYCAKEG YSSSGTYWDH WGQGTLVTVS  120
SASTKGPSVF PLAPSSKSTS GGTAALGCLV KDYFPEPVTV SWNSGALTSG VHTFPAVLQS  180
SGLYSLSSVV TVPSSSLGTQ TYICNVNHKP SNTKVDKRVE PKSCDKTHTC PPCPAPEFEG  240
GPSVFLFPPK PKDTLMISRT PEVTCVVVAV SHEDPEVKFN WYVDGVEVHN AKTKPREEQY  300
NSTYRVVSVL TVLHQDWLNG KEYKCKVSNK ALPAPIEKTI SKAKGQPREP QVYTLPPSRE  360
EMTKNQVSLT CLVKGFYPSD IAVEWESNGQ PENNYKTTPP VLDSDGSFLL YSKLTVDKSR  420
WQQGNVFSCS VMHEALHNHY TQKSLSLSPG                                   450

SEQ ID NO: 30           moltype = AA  length = 445
FEATURE                 Location/Qualifiers
source                  1..445
                        mol_type = protein
                        organism = synthetic construct
SEQUENCE: 30
QVQLQESGPG LVKPSGTLSL TCAVSGGSIS SYSWWSWIRQ PPGKGLEWIG ELYHSGSTNY   60
NPSLKSRVTI SVDKSKNQFS LKLRSVTAAD TAVYYCVRGV ATIDYWGQGT LVTVSSASTK  120
GPSVFPLAPS SKSTSGGTAA LGCLVKDYFP EPVTVSWNSG ALTSGVHTFP AVLQSSGLYS  180
LSSVVTVPSS SLGTQTYICN VNHKPSNTKV DKRVEPKSCD KTHTCPPCPA PEFEGGPSVF  240
LFPPKPKDTL MISRTPEVTC VVVAVSHEDP EVKFNWYVDG VEVHNAKTKP REEQYNSTYR  300
VVSVLTVLHQ DWLNGKEYKC KVSNKALPAP IEKTISKAKG QPREPQVYTL PPSREEMTKN  360
QVSLTCLVKG FYPSDIAVEW ESNGQPENNY KTTPPVLDSD GSFFLYSRLT VDKSRWQQGN  420
VFSCSVMHEA LHNHYTQKSL SLSPG                                        445

SEQ ID NO: 31           moltype = AA  length = 450
FEATURE                 Location/Qualifiers
source                  1..450
                        mol_type = protein
                        organism = synthetic construct
SEQUENCE: 31
EVQLLESGGG LVQPGGSPRL SCEASGFTFS SYALSWVRQA PGKGLEWVSA ISGSGGGRYY   60
ADSVKGRFTI SRDNSKNTLF LQMNSLRAED TAVYYCAKEG YSSSGTYWDH WGQGTLVTVS  120
SASTKGPSVF PLAPSSKSTS GGTAALGCLV KDYFPEPVTV SWNSGALTSG VHTFPAVLQS  180
SGLYSLSSVV TVPSSSLGTQ TYICNVNHKP SNTKVDKRVE PKSCDKTHTC PPCPAPELLG  240
GPSVFLFPPK PKDTLMISRT PEVTCVVVDV SHEDPEVKFN WYVDGVEVHN AKTKPREEQY  300
NSTYRVVSVL TVLHQDWLNG KEYKCKVSNK ALPAPIEKTI SKAKGQPREP QVYTLPPSRE  360
EMTKNQVSLT CLVKGFYPSD IAVEWESNGQ PENNYKTTPP VLDSDGSFLL YSKLTVDKSR  420
WQQGNVFSCS VMHEALHNHY TQKSLSLSPG                                   450

SEQ ID NO: 32           moltype = AA  length = 445
FEATURE                 Location/Qualifiers
source                  1..445
                        mol_type = protein
                        organism = synthetic construct
SEQUENCE: 32
QVQLQESGPG LVKPSGTLSL TCAVSGGSIS SYSWWSWIRQ PPGKGLEWIG ELYHSGSTNY   60
NPSLKSRVTI SVDKSKNQFS LKLRSVTAAD TAVYYCVRGV ATIDYWGQGT LVTVSSASTK  120
```

```
GPSVFPPLAPS SKSTSGGTAA LGCLVKDYFP EPVTVSWNSG ALTSGVHTFP AVLQSSGLYS    180
LSSVVTVPSS SLGTQTYICN VNHKPSNTKV DKRVEPKSCD KTHTCPPCPA PEFEGGPSVF    240
LFPPKPKDTL MISRTPEVTC VVVAVSHEDP EVKFNWYVDG VEVHNAKTKP REEQYNSTYR    300
VVSVLTVLHQ DWLNGKEYKC KVSNKALPAP IEKTISKAKG QPREPQVYTL PPSREEMTKN    360
QVSLTCLVKG FYPSDIAVEW ESNGQPENNY KTTPPVLDSD GSFLLYSKLT VDKSRWQQGN    420
VFSCSVMHEA LHNHYTQKSL SLSPG                                         445

SEQ ID NO: 33           moltype = AA  length = 760
FEATURE                 Location/Qualifiers
source                  1..760
                        mol_type = protein
                        organism = Homo sapiens
SEQUENCE: 33
MKTWVKIVFG VATSAVLALL VMCIVLRPSR VHNSEENTMR ALTLKDILNG TFSYKTFFPN     60
WISGQEYLHQ SADNNIVLYN IETGQSYTIL SNRTMKSVNA SNYGLSPDRQ FVYLESDYSK    120
LWRYSYTATY YIYDLSNGEF VRGNELPRPI QYLCWSPVGS KLAYVYQNNI YLKQRPGDPP    180
FQITFNGREN KIFNGIPDWV YEEEMLATKY ALWWSPNGKF LAYAEFNDTD IPVIAYSYYG    240
DEQYPRTINI PYPKAGAKNP VVRIFIIDTT YPAYVGPQEV PVPAMIASSD YYFSWLTWVT    300
DERVCLQWLK RVQNVSVLSI CDFREDWQTW DCPKTQEHIE ESRTGWAGGF FVSTPVFSYD    360
AISYYKIFSD KDGYKHIHYI KDTVENAIQI TSGKWEAINI FRVTQDSLFY SSNEFEEYPG    420
RRNIYRISIG SYPPSKKCVT CHLRKERCQY YTASFSDYAK YYALVCYGPG IPISTLHDGR    480
TDQEIKILEE NKELENALKN IQLPKEEIKK LEVDEITLWY KMILPPQFDR SKKYPLLIQV    540
YGGPCSQSVR SVFAVNWISY LASKEGMVIA LVDGRGTAFQ GDKLLYAVYR KLGVYEVEDQ    600
ITAVRKFIEM GFIDEKRIAI WGWSYGGYVS SLALASGTGL FKCGIAVAPV SSWEYYASVY    660
TERFMGLPTK DDNLEHYKNS TVMARAEYFR NVDYLLIHGT ADDNVHFQNS AQIAKALVNA    720
QVDFQAMWYS DQNHGLSGLS TNHLYTHMTH FLKQCFSLSD                          760

SEQ ID NO: 34           moltype = AA  length = 735
FEATURE                 Location/Qualifiers
source                  1..735
                        mol_type = protein
                        organism = Homo sapiens
SEQUENCE: 34
LRPSRVHNSE ENTMRALTLK DILNGTFSYK TFFPNWISGQ EYLHQSADNN IVLYNIETGQ     60
SYTILSNRTM KSVNASNYGL SPDRQFVYLE SDYSKLWRYS YTATYYIYDL SNGEFVRGNE    120
LPRPIQYLCW SPVGSKLAYV YQNNIYLKQR PGDPPFQITF NGRENKIFNG IPDWVYEEEM    180
LATKYALWWS PNGKFLAYAE FNDTDIPVIA YSYYGDEQYP RTINIPYPKA GAKNPVVRIF    240
IIDTTYPAYV GPQEVPVPAM IASSDYYFSW LTWVTDERVC LQWLKRVQNV SVLSICDFRE    300
DWQTWDCPKT QEHIEESRTG WAGGFFVSTP VFSYDAISYY KIFSDKDGYK HIHYIKDTVE    360
NAIQITSGKW EAINIFRVTQ DSLFYSSNEF EEYPGRRNIY RISIGSYPPS KKCVTCHLRK    420
ERCQYYTASF SDYAKYYALV CYGPGIPIST LHDGRTDQEI KILEENKELE NALKNIQLPK    480
EEIKKLEVDE ITLWYKMILP PQFDRSKKYP LLIQVYGGPC SQSVRSVFAV NWISYLASKE    540
GMVIALVDGR GTAFQGDKLL YAVYRKLGVY EVEDQITAVR KFIEMGFIDE KRIAIWGWSY    600
GGYVSSLALA SGTGLFKCGI AVAPVSSWEY YASVYTERFM GLPTKDDNLE HYKNSTVMAR    660
AEYFRNVDYL LIHGTADDNV HFQNSAQIAK ALVNAQVDFQ AMWYSDQNHG LSGLSTNHLY    720
THMTHFLKQC FSLSD                                                    735

SEQ ID NO: 35           moltype = AA  length = 761
FEATURE                 Location/Qualifiers
source                  1..761
                        mol_type = protein
                        organism = Mus musculus
SEQUENCE: 35
MKTWLKTVFG VTTLAALALV VICIVLRPSR VYKPEGNTKR ALTLKDILNG TFSYKTYFPN     60
WISEQEYLHQ SEDDNIVFYN IETRESYIIL SNSTMKSVNA TDYGLSPDRQ FVYLESDYSK    120
LWRYSYTATY YIYDLQNGEF VRGYELPRPI QYLCWSPVGS KLAYVYQNNI YLKQRPGDPP    180
FQITYTGREN RIFNGIPDWV YEEEMLATKY ALWWSPDGKF LAYVEFNDSD IPIIAYSYYG    240
DGQYPRTINI PYPKAGAKNP VVRVFIVDTT YPHHVGPMEV PVPEMIASSD YYFSWLTWVS    300
SERVCLQWLK RVQNVSVLSI CDFREDWHAW ECPKNQEHIE ESRTGWAGGF FVSTPAFSGD    360
ATSYYKIFSD KDGYKHIHYI KDTVENAIQI TSGKWEAIYI FRVTQDSLFY SSNEFEGYPG    420
RRNIYRISIG NSPPSKKCVT CHLRKERCQY YTASFSYKAK YYALVCYGPG LPISTLHDGR    480
TDQEIQVLEE NKELENSLRN IQLPKVEIKK LKDGGLTFWY KMILPPQFDR SKKYPLLIQV    540
YGGPCSQSVK SVFAVNWITY LASKEGIVIA LVDGRGTAFQ GDKFLHAVYR KLGVYEVEDQ    600
LTAVRKFIEM GFIDEERIAI WGWSYGGYVS SLALASGTGL FKCGIAVAPV SSWEYYASIY    660
SERFMGLPTK DDNLEHYKNS TVMARAEYFR NVDYLLIHGT ADDNVHFQNS AQIAKALVNA    720
QVDFQAMWYS DQNHGISSGR SQNHLYTHMT HFLKQCFSLS D                       761

SEQ ID NO: 36           moltype = AA  length = 761
FEATURE                 Location/Qualifiers
source                  1..761
                        mol_type = protein
                        organism = Rattus norvegicus
SEQUENCE: 36
MKTWLKTVFG VTTLVALALV VICIVLRPSR VYSPEGNTGR SLTLKDILNG TFSYKTYFPN     60
WISEQEYLHQ SEDDNIVFYN IETRESYIIL SNSTMKSVNA TDYGLSPDRQ FIYLESDYSK    120
LWRYSYTATY YIYDLQNGEF VRGYELPRPI QYLCWSPVGS KLAYVYQNNI YLKQRPGDPP    180
FQITYTGREN RIFNGIPDWV YEEEMLATKY ALWWSPDGKY LAYVEFNDSD IPIIAYSYYG    240
DGQYPRTINI PYPKAGAKNP IVRVFIVDTI YPHHVGPIEV PVPEMIASSD YYFTWLTWVT    300
NERVCLQWLK RVQNVSVLSI CDFREDWHAW DCPKNQEHIE ESRTGWAGGF FVSTPAFSQD    360
```

```
AASYYKIFSD KDGYKHIHYI KDTVENAIQI TSGKWEAIYI FRVTQDSLFY SSNEFEGYPG    420
RRNIYRISIG NSPPSKKCVT CHLRKERCQY YTASFSYKAK YYALICYGPG LPISTLHDGR    480
TDQEIQVLEE NKELENALRN IQLPAVEIKK LEDGGMTFWY KMILPPQFDR SKKYPLLIQV    540
YGGPCSQSVK SVFSVNWITY LASKEGIVVA LVDGRGTAFQ GDKFLHAVYR KLGVYEVEDQ    600
LTAVRKFIEM GFIDEGRIAI WGWSYGGYVS SLALASGTGL FKCGIAVAPV SSWEYYASIY    660
TERFMGLPTK DDNLEHYKNS TVMARAEYFR NVDYLLIHGT ADDNVHFQNS AQIAKALVNA    720
QVDFQAMWYS DQNHGISSGR SQNHLYTHMT HFLKQCFSLS D                       761

SEQ ID NO: 37           moltype = AA   length = 760
FEATURE                 Location/Qualifiers
source                  1..760
                        mol_type = protein
                        organism = Canis lupus
SEQUENCE: 37
MKTWLKIVFG VATSAVLALL VMCIVLRPSR VHDSEGGTTR ALTLEDILNG TFTYKTFFPN    60
WISGQEYLHQ STDNDIVYYN IETGESYTIL SNATMKSVNA SNYGLSPDRQ FAYLESDYSK    120
LWRYSYTATY HIYNLNNGEF IRRNELPRPI QYLCWSPVGS KLAYVYQNNI YLKQRPEDPP    180
FQITYNGREN KIFNGIPDWV YEEEMLATKH ALWWSPNGKF LAYAEFNDTE IPVIAYSYYG    240
DEQYPRTINI PYPKAGAKNP VVRIFIIDTT YPQQTGPREV PVPAMIASSD YYFSWLTWVT    300
DERVCLQWLK RIQNVSVLSI CDFREGWQTW DCPKAQEHIE ESRTGWAGGF FVSTPVFSYD    360
AISYYKIFSD KDGYKHIHYI KDTVENAIQI TSGKWEAINI FRVTQDSLFY SSNEFEDYPG    420
RRNIYRISIG SSPPSKKCIT CHLRKERCQY YTASFSYDAK YYALICYGPG LPISTLHDGR    480
TDQEIKILEE NKELENALKN IQLPKEEIKK LEVDDITLWY KMMLPPRFDR SKKYPLLIQV    540
YGGPCSQSVK SVFSINWISY LASKEGIVIA LVDGRGTAYQ GDKLLYAVYR KLGVYEVEDQ    600
ITAVRKFIEM GFIDEKRIAI WGWSYGGYVS SLALASGTGL FKCGIAVAPV SSWEYYASIY    660
TERFMGLPTK NDNLEHYKNS TVMARAEYFR NVDYLLIHGT ADDNVHFQNS AQIAKALVNA    720
QVDFQAMWYS DQNHGIPGLS SKHLYTRMTH FLKQCFSLD                          760

SEQ ID NO: 38           moltype = AA   length = 760
FEATURE                 Location/Qualifiers
source                  1..760
                        mol_type = protein
                        organism = Sus scrofa
SEQUENCE: 38
MKTWLKIVFG VATSAVLALL VMCIVLRPSR VPNSEGSKTR ALTLKDILNG TFSYKTFFPN    60
WISGQEYLHQ STDDNVIFYN IETGESYTIL SNTTMKSVNA SSYGLSPDRQ FAYLESDYSK    120
LWRYSYTATY HIYDLRNGEF ITRNELPRPI QYLCWSPVGS KLAYVYQNNI YLKQRPEDPP    180
FQITYNGKEN KIFNGIPDWV YEEEMLATKY ALWWSPNGKF LAYAEFNDTE IPVIAYSYYG    240
DEQYPRTINI PYPKAGAKNP FVRIFIIDTS YPGHVGPREV PVPAMIASSD YYFSWFTWVT    300
DDRICLQWLK RIQNVSVLSI CDFREDWQTW NCPKTQEHIE ESRTGWAGGF FVSTPVFSYD    360
AISYYKIFSD KDGYKHIHYI KDSVENAIQI TSGKWEAINI FRVTQDSLFY SSNEFEGYPG    420
RRNIYRISIG SHPPSKKCVT CHLREKRCQY YTASFSDYAK YYALVCYGPG LPISTLHDGR    480
TDQEIKILEE NKDLEYALKN IRLPKEEIKK LDVDDITLWY KMILPPQFDR SKKYPLLIQV    540
YGGPCSQSVR SVFSIRWISY LASKEGIVIA LVDGRGTAFQ GDKLLYAVYR KLGVYEVEDQ    600
ITAVRKFIEM GFIDEKRIAI WGWSYGGYVS SLALASGTGL FKCGIAVAPV SSWEYYASIY    660
TERFMGLPTK DDNLEHYKNS TVMARAEYFR NVDYLLIHGT ADDNVHFQNS AQIAKALVNA    720
QVDFQAMWYS DQNHGISGLS TKHLYTHMTH FLKQCFSLPD                         760

SEQ ID NO: 39           moltype = AA   length = 760
FEATURE                 Location/Qualifiers
source                  1..760
                        mol_type = protein
                        organism = Macaca fascicularis
SEQUENCE: 39
MKTWVKIVFG VATSAVLALL VMCIVLRPPR VHNSEENTMR ALTLKDILNG TFSYKTFFPN    60
WISGQEYLHQ SADNNIVLYN IETGQSYTIL SNRTMKSVNA SNYGLSPDRQ FVYLESDYSK    120
LWRYSYTATY YIYDLSNGEF VRGNELPRPI QYLCWSPVGS KLAYVYQNNI YLKQRPGDPP    180
FQITFNGREN KIFNGIPDWV YEEEMLATKY ALWWSPNGKF LAYAEFNDTD IPVIAYSYYG    240
DEQYPRTINI PYPKAGAKNP FVRIFIIDTT YPAYVGPREV PVPAMIASSD YYFSWLTWVT    300
DERVCLQWLK RVQNVSVLSI CDFREDWQTW DCPKTQEHIE ESRTGWAGGF FVSTPVFSYD    360
AISYYKIFSD KDGYKHIHYI KDTVENAIQI TSGKWEAINI FRVTQDSLFY SSNEFEDYPG    420
RRNIYRISIG SYPPSKKCVT CHLRKERCQY YTASFSDYAK YYALVCYGPG IPISTLHDGR    480
TDQEIKILEE NKELENALKN IQLPKEEIKK LEVDEITLWY KMILPPQFDR SKKYPLLIQV    540
YGGPCSQSVR SVFAVNWISY LASKEGMVIA LVDGRGTAFQ GDKLLYAVYR KLGVYEVEDQ    600
ITAVRKFIEM GFIDEKRIAI WGWSYGGYVS SLALASGTGL FKCGIAVAPV SSWEYYASVY    660
TERFMGLPTK DDNLEHYKNS TVMARAEYFR NVDYLLIHGT ADDNVHFQNS AQIAKALVNA    720
QVDFQAMWYS DQNHGLSGLS TNHLYTHMTH FLKQCFSLSD                         760

SEQ ID NO: 40           moltype = AA   length = 453
FEATURE                 Location/Qualifiers
source                  1..453
                        mol_type = protein
                        organism = Homo sapiens
SEQUENCE: 40
MAPPPARVHL GAFLAVTPNP GSAASGTEAA AATPSKVWGS SAGRIEPRGG GRGALPTSMG    60
QHGPSARARA GRAPGPRPAR EASPRLRVHK TFKFVVVGVL LQVVPSSAAT IKLHDQSIGT    120
QQWEHSPLGE LCPPGSHRSE HPGACNRCTE GVGYTNASNN LFACLPCTAC KSDEEERSPC    180
TTTRNTACQC KPGTFRNDNS AEMCRKCSRG CPRGMVKVKD CTPWSDIECV HKESGNGHNI    240
WVILVVTLVV PLLLVAVLIV CCCIGSGCGG DPKCMDRVCF WRLGLLRGPG AEDNAHNEIL    300
```

```
SNADSLSTFV SEQQMESQEP ADLTGVTVQS PGEAQCLLGP AEAEGSQRRR LLVPANGADP      360
TETLVDSGKF IYLEDGTGSA VSLEGASSGS SGSGSQKKPR YEIRWKVVVI SAILALVVLT      420
VISLIILIML WGSDYKDDDD KGMQYPYDVP DYA                                   453

SEQ ID NO: 41              moltype = AA  length = 452
FEATURE                    Location/Qualifiers
source                     1..452
                           mol_type = protein
                           organism = Macaca fascicularis
SEQUENCE: 41
MAPPPAGVKL GAFLAVTPNP GSAASGTEAA TATPSKVWGS SAGRIEPRGG GRGALPTSMG       60
QQGPSAQARA GRVVGPRSAQ GASPGLRVHK TLKFVVVGVL LQVVPGSAAT IKVHDQSVGT      120
QQWEHSPLGE LCPPGSHRSE HSGACNQCTE GVGYTSASNN LFSCLPCTAC KSDEEERSAC      180
TRTRNTACQC KPGTFRNDDS AEMCRKCSTG CPRGKVKVKD CTPWSDIECV HNESGNGHNV      240
WAILIVIVVI LVVLLLLVAV LMFCRRIGSG CGGNPKCMHR VFLWCLGLLR GPGAEDNAHN      300
MILNHGDSLS TFISEQQMES QEPADLTGVT VQSPGEAQCL LGPAEPEGSQ RRRLLVPANG      360
ADPTETMMLI YVEDGTGSAV SLEGASSGSS GSGSQKKPRY EIRWKVVVIS AILALVVLTV      420
ISLIILIMLW GSDYKDDDDK GMQYPYDVPD YA                                   452

SEQ ID NO: 42              moltype = AA  length = 366
FEATURE                    Location/Qualifiers
source                     1..366
                           mol_type = protein
                           organism = Mus musculus
SEQUENCE: 42
MEPPGPSTPT ASAAARADHY TPGLRPLPKR RLLYSFALLL AVLQAVFVPV TANPAHNRPA       60
GLQRPEESPS RGPCLAGQYL SEGNCKPCRE GIDYTSHSNH SLDSCILCTV CKEDKVVETR      120
CNITTNTVCR CKPGTFEDKD SPEICQSCSN CTDGEEELTS CTPRENRKCV SKTAWASWHK      180
LGLWIGLLVP VVLLIGALLV WKTGAWRQWL LCIKRGCERD PESANSVHSS LLDRQTSSTT      240
NDSNHNTEPG KTQKTGKKLL VPVNGNDSAD DLVKSGRFTY QNAAAQPETG PGGSQCVGAS      300
SGSSSGSGSQ KPRYEIRWKV VVISAILALV VLTVISLIIL IMLWGSDYKD DDDKGMQYPY      360
DVPDYA                                                                366

SEQ ID NO: 43              moltype = AA  length = 335
FEATURE                    Location/Qualifiers
source                     1..335
                           mol_type = protein
                           organism = Rattus norvegicus
SEQUENCE: 43
MLQAFLLLSF FVPVTAKLAQ DRPADLQRLK QSPLECPAGQ YLSKEDGSCK ACIDGENYTS       60
GPNVLPSCLS CRVCKEDKVI KSRCVKARNT ECECKPGSFE DKDSTEICQT CSNCTDGEDE      120
VIPCTPKANR KCVPKNTQIP QHNLGLLIGL LASVISVVLF VAVIWKTKAW ESVCLFMARV      180
YPGCEQDHEN TVGLSLLDAQ TSRKTNGSHH NTEPDRTQSS PLGRKLLVLA NGNNPADALK      240
LIFERCSTEV PFNVKSGKFV YQNTTAGASS GSSSGSGSQK KPRYEIRWKV VISAILALVV      300
LTVISLIILI MLWGSDYKDD DDKGMQYPYD VPDYA                                335

SEQ ID NO: 44              moltype = AA  length = 427
FEATURE                    Location/Qualifiers
source                     1..427
                           mol_type = protein
                           organism = Canis lupus
SEQUENCE: 44
MGWSCIILFL VATATGVHSL PEWRVLGRAW AVCPLLLLLK VRVPMAAIVS DCMEYEYKPE       60
GLNLCCEKCP AGHYVSKHCD KNHGAGVCSP CEPGSYLPYR NGETNCRLCS RCREDQEVVS      120
PCTATRDQQC QCKPGYFCDS ENCVENCFRC QSCPDHVSSP CNATRDTVCN TQDTTDTSEK      180
KPEGGSLQMF VLVVITITII IVIVVVALIF LLVVYCKKKG MWLYQRLISL LKGRVDEQSS      240
TVEILFPSNP ENHQPALDIE TLLLKEGLEE SPRPRPLEET EEGIELQDVV VRESPPAPEQ      300
VVQTPALAVS VSQNQNEVFP SLKSLEQEYA KRYFVKDTSN EGTTRLYYEL GRHAETSDGA      360
SSGSSGSGSQ KKPRYEIRWK VVVISAILAL VVLTVISLII LIMLWGSDYK DDDDKGMQYP      420
YDVPDYA                                                               427

SEQ ID NO: 45              moltype = AA  length = 416
FEATURE                    Location/Qualifiers
source                     1..416
                           mol_type = protein
                           organism = Sus scrofa
SEQUENCE: 45
MGWSCIILFL VATATGVHSR WPGQRAPLNR TGQWGQSAPT TSGAQAGCAP SRQSWLQDPR       60
ALIFVVFGVL WLVTAASAMP TRQERVHQQF NVPQGWRRNF WELCPPGYHV SEDGKNCTSC      120
IHGVDFTIYW NVLPSCLPCT TCKSGEEEKT PCTATADTRC ECKPGTFREE NSPEFCQKCH      180
TRCPDGMVMA TPCTPSSDLK CMDQESGNSE LVVGIAVPCS ILLLAVVIAC LVCKCKVQGC      240
GLHRKFMDKV LFWRSHPSRG PGAQDNKLMC GDSLSTLLTK KEQEDQEQEK PADVTVQSSR      300
EAEHLLEPAA AEGSQVRRRL LVPADGGDPT VCLRQVFKES EAGAAVSGAS SGSSGSGSQK      360
KPRYEIRWKV VVISAILALV VLTVISLIIL IMLWGSDYKD DDDKGMQYPY DVPDYA         416

SEQ ID NO: 46              moltype = AA  length = 413
FEATURE                    Location/Qualifiers
source                     1..413
                           mol_type = protein
```

```
                    organism = Oryctolagus cuniculus
SEQUENCE: 46
MGWSCIILFL VATATGVHSI ACEPDEYLVE NYCCRFCPAG HFVSGLCSQN HSIGECEPCR      60
PGTFMAYPSS EASCSPCSPC RPDQEVVANC TLTSNTRCQC RPGHFYCDSE DCVENCFRCS     120
RCPKDKVTRR LCTPTRNTEC ADPTTGWWLL SLLAIPFVLV LILFIVRYCK SRGRSLGQAC     180
WGAKGLAGLS SPVPGVLRSL ARIFKRKSSE PGSHALGPLE PTEALLSAET KGSEMDPGRE     240
DALLVMEEET SASAPGAGPC PAPTGPGGSP EPQAAASGTS PTGPGQAPHP DPAARGARNR     300
TKAAASLEEL EQEYAEQYVL MDTSGPGISA LGKRHGGDTP HAASGASSGS SGSGSQKKPR     360
YEIRWKVVVI SAILALVVLT VISLIILIML WGSDYKDDDD KGMQYPYDVP DYA            413

SEQ ID NO: 47           moltype = AA   length = 446
FEATURE                 Location/Qualifiers
source                  1..446
                        mol_type = protein
                        organism = synthetic construct
SEQUENCE: 47
QVQLQQSGAE LARPGASVNL SCLASGYTFT NNGINWLKQR TGQGLEWIGE IYPRSTNTLY      60
NEKFKGKATL TADRSSNTAY MELRSLTSED SAVYFCARTL TAPFAFWGQG TLVTVSSAST     120
KGPSVFPLAP SSKSTSGGTA ALGCLVKDYF PEPVTVSWNS GALTSGVHTF PAVLQSSGLY     180
SLSSVVTVPS SSLGTQTYIC NVNHKPSNTK VDKRVEPKSC DKTHTCPPCP APEFEGGPSV     240
FLFPPKPKDT LMISRTPEVT CVVVAVSHED PEVKFNWYVD GVEVHNAKTK PREEQYNSTY     300
RVVSVLTVLH QDWLNGKEYK CKVSNKALPA PIEKTISKAK GQPREPQVYT LPPSREEMTK     360
NQVSLTCLVK GFYPSDIAVE WESNGQPENN YKTTPPVLDS DGSFLLYSKL TVDKSRWQQG     420
NVFSCSVMHE ALHNHYTQKS LSLSPG                                         446

SEQ ID NO: 48           moltype = AA   length = 213
FEATURE                 Location/Qualifiers
source                  1..213
                        mol_type = protein
                        organism = synthetic construct
SEQUENCE: 48
QIVLTQSPAI MSASPGELVT MTCSASSGVN FMHWYQQLSG TSPKRWIFDT SKLASGVPAR      60
FSGSGSGTSY SLTISSMEAE DAATYYCQQW SFNPPTFGGG TKLEIKRTVA APSVFIFPPS     120
DEQLKSGTAS VVCLLNNFYP REAKVQWKVD NALQSGNSQE SVTEQDSKDS TYSLSSTLTL     180
SKADYEKHKV YACEVTHQGL SSPVTKSFNR GEC                                  213

SEQ ID NO: 49           moltype = AA   length = 446
FEATURE                 Location/Qualifiers
source                  1..446
                        mol_type = protein
                        organism = synthetic construct
SEQUENCE: 49
QVQLQQSGAE LARPGASVNL SCLASGYTFT NNGINWLKQR TGQGLEWIGE IYPRSTNTLY      60
NEKFKGKATL TADRSSNTAY MELRSLTSED SAVYFCARTL TAPFAFWGQG TLVTVSSAST     120
KGPSVFPLAP SSKSTSGGTA ALGCLVKDYF PEPVTVSWNS GALTSGVHTF PAVLQSSGLY     180
SLSSVVTVPS SSLGTQTYIC NVNHKPSNTK VDKRVEPKSC DKTHTCPPCP APELLGGPSV     240
FLFPPKPKDT LMISRTPEVT CVVVDVSHED PEVKFNWYVD GVEVHNAKTK PREEQYNSTY     300
RVVSVLTVLH QDWLNGKEYK CKVSNKALPA PIEKTISKAK GQPREPQVYT LPPSREEMTK     360
NQVSLTCLVK GFYPSDIAVE WESNGQPENN YKTTPPVLDS DGSFFLYSKL TVDKSRWQQG     420
NVFSCSVMHE ALHNHYTQKS LSLSPG                                         446

SEQ ID NO: 50           moltype = AA   length = 458
FEATURE                 Location/Qualifiers
source                  1..458
                        mol_type = protein
                        organism = synthetic construct
SEQUENCE: 50
QVQLQESGPG LVKPSETLSL TCTVSGGSIS SNNYYWGWIR QTPGKGLEWI GSIYYSGSTN      60
YNPSLKSRVT ISVDTSKNQF SLKLSSVTAA DTAVYYCARG ARWQARPATR IDGVAFDIWG     120
QGTMVTVSSA STKGPSVFPL APSSKSTSGG TAALGCLVKD YFPEPVTVSW NSGALTSGVH     180
TFPAVLQSSG LYSLSSVVTV PSSSLGTQTY ICNVNHKPSN TKVDKRVEPK SCDKTHTCPP     240
CPAPELLGGP SVFLFPPKPK DTLMISRTPE VTCVVVDVSH EDPEVKFNWY VDGVEVHNAK     300
TKPREEQYNS TYRVVSVLTV LHQDWLNGKE YKCKVSNKAL PAPIEKTISK AKGQPREPQV     360
YTLPPSREEM TKNQVSLTCL VKGFYPSDIA VEWESNGQPE NNYKTTPPVL DSDGSFLLYS     420
KLTVDKSRWQ QGNVFSCSVM HEALHNHYTQ KSLSLSPG                            458

SEQ ID NO: 51           moltype = AA   length = 214
FEATURE                 Location/Qualifiers
source                  1..214
                        mol_type = protein
                        organism = synthetic construct
SEQUENCE: 51
ETTLTQSPGT LSLSPGERAT LSCRASQTVT RNYLAWYQQK PGQAPRLLMY GASNRAAGVP      60
DRFSGSGSGT DFTLTISRLE PEDFAVYYCQ QFGSPYTFGQ GTKVEIKRTV AAPSVFIFPP     120
SDEQLKSGTA SVVCLLNNFY PREAKVQWKV DNALQSGNSQ ESVTEQDSKD STYSLSSTLT     180
LSKADYEKHK VYACEVTHQG LSSPVTKSFN RGEC                                 214

SEQ ID NO: 52           moltype = AA   length = 447
FEATURE                 Location/Qualifiers
```

```
source                          1..447
                                mol_type = protein
                                organism = synthetic construct
SEQUENCE: 52
EVQLVQSGAD VKRPGASVKV SCKISGDSFN AYFIHWVRQA PGQGLEWMGW FNPDSGTADS        60
AQKFHGRVTM TRDTSSSTAF LELSRLRSDD TAVYYCVRQH RGNTFAPWGR GTMVTVSSAS       120
TKGPSVFPLA PSSKSTSGGT AALGCLVKDY FPEPVTVSWN SGALTSGVHT FPAVLQSSGL       180
YSLSSVVTVP SSSLGTQTYI CNVNHKPSNT KVDKRVEPKS CDKTHTCPPC PAPEFEGGPS       240
VPLFPPKPKD TLMISRTPEV TCVVVAVSHE DPEVKFNWYV DGVEVHNAKT KPREEQYNST       300
YRVVSVLTVL HQDWLNGKEY KCKVSNKALP APIEKTISKA KGQPREPQVY TLPPSREEMT       360
KNQVSLTCLV KGFYPSDIAV EWESNGQPEN NYKTTPPVLD SDGSFFLYSR LTVDKSRWQQ       420
GNVFSCSVMH EALHNHYTQK SLSLSPG                                          447

SEQ ID NO: 53                   moltype = AA  length = 216
FEATURE                         Location/Qualifiers
source                          1..216
                                mol_type = protein
                                organism = synthetic construct
SEQUENCE: 53
QSVLTQPPSA SGSPGQSVTI SCTGTTSDVG GYNYVSWYQQ HPGKAPKLMI YGVNQRPSGV        60
PDRFSGSKSG NTASLTVSGL QAEDEADYYC SSYAGSNNWV FGGGTKLTVL GQPKAAPSVT       120
LFPPSSEELQ ANKATLVCLI SDFYPGAVTV AWKADSSPVK AGVETTTPSK QSNNKYAASS       180
YLSLTPEQWK SHRSYSCQVT HEGSTVEKTV APTECS                                216

SEQ ID NO: 54                   moltype = AA  length = 448
FEATURE                         Location/Qualifiers
source                          1..448
                                mol_type = protein
                                organism = synthetic construct
SEQUENCE: 54
EVQLQQSGAE LVKPGASVKL SCTASGFNIK DTYMHWVKQR PEQGLEWIGR IDPANGNTKY        60
DPKFQGKATI TADTSSNTAY LQLSSLTSED TAVYYCAYYY VSNAWFTYWG QGTLVTVSAA       120
STKGPSVFPL APSSKSTSGG TAALGCLVKD YFPEPVTVSW NSGALTSGVH TFPAVLQSSG       180
LYSLSSVVTV PSSSLGTQTY ICNVNHKPSN TKVDKRVEPK SCDKTHTCPP CPAPEFEGGP       240
SVFLFPPKPK DTLMISRTPE VTCVVVAVSH EDPEVKFNWY VDGVEVHNAK TKPREEQYNS       300
TYRVVSVLTV LHQDWLNGKE YKCKVSNKAL PAPIEKTISK AKGQPREPQV YTLPPSREEM       360
TKNQVSLTCL VKGFYPSDIA VEWESNGQPE NNYKTTPPVL DSDGSFFLYS RLTVDKSRWQ       420
QGNVFSCSVM HEALHNHYTQ KSLSLSPG                                         448

SEQ ID NO: 55                   moltype = AA  length = 213
FEATURE                         Location/Qualifiers
source                          1..213
                                mol_type = protein
                                organism = synthetic construct
SEQUENCE: 55
DIQMTQSPAS LSVSVGETVT ITCRASENIY SNLEWYQQKQ GKSPQLLVYA ATNLADGVPS        60
RFSGSGSGTQ YSLKINSLQS EDFGSYYCQH FWGTWTFGGG TKLEIKRTVA APSVFIFPPS       120
DEQLKSGTAS VVCLLNNFYP REAKVQWKVD NALQSGNSQE SVTEQDSKDS TYSLSSTLTL       180
SKADYEKHKV YACEVTHQGL SSPVTKSFNR GEC                                    213

SEQ ID NO: 56                   moltype = AA  length = 456
FEATURE                         Location/Qualifiers
source                          1..456
                                mol_type = protein
                                organism = synthetic construct
SEQUENCE: 56
QVQLVQSGAE VKKPGASVKV SCQASGYRFS NFVIHWVRQA PGQRFEWMGW INPYNGNKEF        60
SAKFQDRVTF TADTSANTAY MELRSLRSAD TAVYYCARVG PYSWDDSPQD NYYMDVWGKG       120
TTVIVSSAST KGPSVPPLAP SSKSTSGGTA ALGCLVKDYF PEPVTVSWNS GALTSGVHTF       180
PAVLQSSGLY SLSSVVTVPS SSLGTQTYIC NVNHKPSNTK VDKRVEPKSC DKTHTCPPCP       240
APELLGGPSV FLFPPKPKDT LMISRTPEVT CVVVDVSHED PEVKFNWYVD GVEVHNAKTK       300
PREEQYNSTY RVVSVLTVLH QDWLNGKEYK CKVSNKALPA PIEKTISKAK GQPREPQVYT       360
LPPSREEMTK NQVSLTCLVK GFYPSDIAVE WESNGQPENN YKTTPPVLDS DGSFFLYSKL       420
TVDKSRWQQG NVFSCSVMHE ALHNHYTQKS LSLSPG                                456

SEQ ID NO: 57                   moltype = AA  length = 215
FEATURE                         Location/Qualifiers
source                          1..215
                                mol_type = protein
                                organism = synthetic construct
SEQUENCE: 57
EIVLTQSPGT LSLSPGERAT FSCRSSHSIR SRRVAWYQHK PGQAPRLVIH GVSNRASGIS        60
DRFSGSGSGT DFTLTITRVE PEDFALYYCQ VYGASSYTFG QGTKLERKRT VAAPSVFIFP       120
PSDEQLKSGT ASVVCLLNNF YPREAKVQWK VDNALQSGNS QESVTEQDSK DSTYSLSSTL       180
TLSKADYEKH KVYACEVTHQ GLSSPVTKSF NRGEC                                  215

SEQ ID NO: 58                   moltype = AA  length = 456
FEATURE                         Location/Qualifiers
source                          1..456
```

```
                            mol_type = protein
                            organism = synthetic construct
SEQUENCE: 58
QVQLVQSGAE VKKPGASVKV SCQASGYRFS NFVIHWVRQA PGQRFEWMGW INPYNGNKEF      60
SAKFQDRVTF TADTSANTAY MELRSLRSAD TAVYYCARVG PYSWDDSPQD NYYMDVWGKG     120
TTVIVSSAST KGPSVFPLAP SSKSTSGGTA ALGCLVKDYF PEPVTVSWNS GALTSGVHTF     180
PAVLQSSGLY SLSSVVTVPS SSLGTQTYIC NVNHKPSNTK VDKRVEPKSC DKTHTCPPCP     240
APEFEGGPSV FLFPPKPKDT LMISRTPEVT CVVVAVSHED PEVKFNWYVD GVEVHNAKTK     300
PREEQYNSTY RVVSVLTVLH QDWLNGKEYK CKVSNKALPA PIEKTISKAK GQPREPQVYT     360
LPPSREEMTK NQVSLTCLVK GFYPSDIAVE WESNGQPENN YKTTPPVLDS DGSFLLYSKL     420
TVDKSRWQQG NVFSCSVMHE ALHNHYTQKS LSLSPG                               456

SEQ ID NO: 59              moltype = AA  length = 456
FEATURE                    Location/Qualifiers
source                     1..456
                           mol_type = protein
                           organism = synthetic construct
SEQUENCE: 59
QVQLVQSGAE VKKPGASVKV SCQASGYRFS NFVIHWVRQA PGQRFEWMGW INPYNGNKEF      60
SAKFQDRVTF TADTSANTAY MELRSLRSAD TAVYYCARVG PYSWDDSPQD NYYMDVWGKG     120
TTVIVSSAST KGPSVFPLAP SSKSTSGGTA ALGCLVKDYF PEPVTVSWNS GALTSGVHTF     180
PAVLQSSGLY SLSSVVTVPS SSLGTQTYIC NVNHKPSNTK VDKRVEPKSC DKTHTCPPCP     240
APEFEGGPSV FLFPPKPKDT LMISRTPEVT CVVVAVSHED PEVKFNWYVD GVEVHNAKTK     300
PREEQYNSTY RVVSVLTVLH QDWLNGKEYK CKVSNKALPA PIEKTISKAK GQPREPQVYT     360
LPPSREEMTK NQVSLTCLVK GFYPSDIAVE WESNGQPENN YKTTPPVLDS DGSFFLYSRL     420
TVDKSRWQQG NVFSCSVMHE ALHNHYTQKS LSLSPG                               456

SEQ ID NO: 60              moltype = AA  length = 456
FEATURE                    Location/Qualifiers
source                     1..456
                           mol_type = protein
                           organism = synthetic construct
SEQUENCE: 60
QVQLVQSGAE VKKPGASVKV SCQASGYRFS NFVIHWVRQA PGQRFEWMGW INPYNGNKEF      60
SAKFQDRVTF TADTSANTAY MELRSLRSAD TAVYYCARVG PYSWDDSPQD NYYMDVWGKG     120
TTVIVSSAST KGPSVFPLAP SSKSTSGGTA ALGCLVKDYF PEPVTVSWNS GALTSGVHTF     180
PAVLQSSGLY SLSSVVTVPS SSLGTQTYIC NVNHKPSNTK VDKRVEPKSC DKTHTCPPCP     240
APEFERGPSV FLFPPKPKDT LMISRTPEVT CVVVDVSHED PEVKFNWYVD GVEVHNAKTK     300
PREEQYNSTY RVVSVLTVLH QDWLNGKEYK CKVSNKALPA PIEKTISKAK GQPREPQVYT     360
LPPSREEMTK NQVSLTCLVK GFYPSDIAVE WESNGQPENN YKTTPPVLDS DGSFLLYSKL     420
TVDKSRWQQG NVFSCSVMHE ALHNHYTQKS LSLSPG                               456

SEQ ID NO: 61              moltype = AA  length = 456
FEATURE                    Location/Qualifiers
source                     1..456
                           mol_type = protein
                           organism = synthetic construct
SEQUENCE: 61
QVQLVQSGAE VKKPGASVKV SCQASGYRFS NFVIHWVRQA PGQRFEWMGW INPYNGNKEF      60
SAKFQDRVTF TADTSANTAY MELRSLRSAD TAVYYCARVG PYSWDDSPQD NYYMDVWGKG     120
TTVIVSSAST KGPSVFPLAP SSKSTSGGTA ALGCLVKDYF PEPVTVSWNS GALTSGVHTF     180
PAVLQSSGLY SLSSVVTVPS SSLGTQTYIC NVNHKPSNTK VDKRVEPKSC DKTHTCPPCP     240
APEFERGPSV FLFPPKPKDT LMISRTPEVT CVVVDVSHED PEVKFNWYVD GVEVHNAKTK     300
PREEQYNSTY RVVSVLTVLH QDWLNGKEYK CKVSNKALPA PIEKTISKAK GQPREPQVYT     360
LPPSREEMTK NQVSLTCLVK GFYPSDIAVE WESNGQPENN YKTTPPVLDS DGSFFLYSRL     420
TVDKSRWQQG NVFSCSVMHE ALHNHYTQKS LSLSPG                               456

SEQ ID NO: 62              moltype = AA  length = 695
FEATURE                    Location/Qualifiers
source                     1..695
                           mol_type = protein
                           organism = synthetic construct
SEQUENCE: 62
EVQLVQSGGG VERPGGSLRL SCAASGFTFD DYAMSWVRQA PGKGLEWVSG INWQGGSTGY      60
ADSVKGRVTI SRDNAKNSLY LQMNSLRAED TAVYYCAKIL GAGRGWYFDY WGKGTTVTVS     120
SASTKGPSVF PLAPSSKSTS GGTAALGCLV KDYFPEPVTV SWNSGALTSG VHTFPAVLQS     180
SGLYSLSSVV TVPSSSLGTQ TYICNVNHKP SNTKVDKKVE PKSCDKTHTC PPCPAPELLG     240
GPSVFLFPPK PKDTLMISRT PEVTCVVVDV SHEDPEVKFN WYVDGVEVHN AKTKPREEQY     300
NSTYRVVSVL TVLHQDWLNG KEYKCKVSNK ALPAPIEKTI SKAKGQPREP QVYTLPPSRD     360
ELTKNQVSLT CLVKGFYPSD IAVEWESNGQ PENNYKTTPP VLDSDGSFFL YSKLTVDKSR     420
WQQGNVFSCS VMHEALHNHY TQKSLSLSPG KSGGGGSGGG GSGGGGSGGG GSEVQLLESG     480
GGLVQPGGSL RLSCAASGFT FSSHAMSWVR QAPGKGLEWV SAIWASGEQY YADSVKGRFT     540
ISRDNSKNTL YLQMNSLRAE DTAVYYCAKG WLGNFDYWGQ GTLVTVSSAS VAAPSVFIFP     600
PSDEQLKSGT ASVVCLLNNF YPREAKVQWK VDNALQSGNS QESVTEQDSK DSTYSLSSTL     660
TLSKADYEKH KVYACEVTHQ GLSSPVTKSF NRGEC                                695

SEQ ID NO: 63              moltype = AA  length = 214
FEATURE                    Location/Qualifiers
source                     1..214
```

```
                            mol_type = protein
                            organism = synthetic construct
SEQUENCE: 63
EIVLTQSPGT LSLSPGERAT LSCRASQSVS RSYLAWYQQK PGQAPRLLII GASTRATGIP      60
DRFSGSGSGT DFTLTISRLE PEDFAVYYCQ QGQVIPPTFG QGTKVEIKSS ASTKGPSVFP     120
LAPSSKSTSG GTAALGCLVK DYFPEPVTVS WNSGALTSGV HTFPAVLQSS GLYSLSSVVT     180
VPSSSLGTQT YICNVNHKPS NTKVDKKVEP KSCD                                 214

SEQ ID NO: 64               moltype = AA  length = 214
FEATURE                     Location/Qualifiers
source                      1..214
                            mol_type = protein
                            organism = synthetic construct
SEQUENCE: 64
SSELTQDPAV SVALGQTVRI TCSGDSLRSY YASWYQQKPG QAPVLVIYGA NNRPSGIPDR      60
FSGSSSGNTA SLTITGAQAE DEADYYCNSA DSSGNHVVFG GGTKLTVLGQ PKAAPSVTLF     120
PPSSEELQAN KATLVCLISD FYPGAVTVAW KADSSPVKAG VETTTPSKQS NNKYAASSYL     180
SLTPEQWKSH RSYSCQVTHE GSTVEKTVAP TECS                                 214

SEQ ID NO: 65               moltype = AA  length = 739
FEATURE                     Location/Qualifiers
source                      1..739
                            mol_type = protein
                            organism = synthetic construct
SEQUENCE: 65
QRVAAHITGT RGRSNTLSSP NSKNEKALGR KINSWESSRS GHSFLSNLHL RNGELVIHEK      60
GFYYIYSQTY FRFQEEIKEN TKNDKQMVQY IYKYTSYPDP ILLMKSARNS CWSKDAEYGL     120
YSIYQGGIFE LKENDRIFVS VTNEHLIDMD HEASFFGAFL VGGSGSGNGS RVAAHITGTR     180
GRSNTLSSPN SKNEKALGRK INSWESSRSG HSFLSNLHLR NGELVIHEKG FYYIYSQTYF     240
RPQEEIKENT KNDKQMVQYI YKYTSYPDPI LLMKSARNSC WSKDAEYGLY SIYQGGIFEL     300
KENDRIFVSV TNEHLIDMDH EASFFGAFLV GGSGSGNGSR VAAHITGTRG RSNTLSSPNS     360
KNEKALGRKI NSWESSRSGH SFLSNLHLRN GELVIHEKGF YYIYSQTYFR PQEEIKENTK     420
NDKQMVQYIY KYTSYPDPIL LMKSARNSCW SKDAEYGLYS IYQGGIFELK ENDRIFVSVT     480
NEHLIDMDHE ASFFGAFLVG GPGSSSSSSS GSCDKTHTCP PCPAPELLGG PSVFLFPPKP     540
KDTLMISRTP EVTCVVVDVS HEDPEVKFNW YVDGVEVHNA KTKPREEQYS STYRVVSVLT     600
VLHQDWLNGK EYKCKVSNKA LPAPIEKTIS KAKGQPREPQ VYTLPPSREE MTKNQVSLTC     660
LVKGFYPSDI AVEWESNGQP ENNYKTTPPV LDSDGSFFLY SKLTVDKSRW QQGNVFSCSV     720
MHEALHNHYT QKSLSLSPG                                                  739

SEQ ID NO: 66               moltype = AA  length = 482
FEATURE                     Location/Qualifiers
source                      1..482
                            mol_type = protein
                            organism = Homo sapiens
SEQUENCE: 66
MAPPPARVHL GAFLAVTPNP GSAASGTEAA AATPSKVWGS SAGRIEPRGG GRGALPTSMG      60
QHGPSARARA GRAPGPRPAR EASPRLRVHK TFKFVVVGVL LQVVPSSAAT IKLHDQSIGT     120
QQWEHSPLGE LCPPGSHRSE HPGACNRCTE GVGYTNASNN LFACLPCTAC KSDEEERSPC     180
TTTRNTACQC KPGTFRNDNS AEMCRKCSRG CPRGMVKVKD CTPWSDIECV HKESGNGHNP     240
KSCDKTHTCP PCPAPEAEGA PSVFLFPPKP KDTLMISRTP EVTCVVVDVS HEDPEVKFNW     300
YVDGVEVHNA KTKPREEQYN STYRVVSVLT VLHQDWLNGK EYKCKVSNKA LPAPIEKTIS     360
KAKGQPREPQ VYTLPPSREE MTKNQVSLTC LVKGFYPSDI AVEWESNGQP ENNYKTAPPV     420
LDSDGSFFLY SKLTVDKSRW QQGNVFSCSV MHEALHNHYT QKSLSLSPGK HHHHHHHEP     480
EA                                                                    482

SEQ ID NO: 67               moltype = AA  length = 482
FEATURE                     Location/Qualifiers
source                      1..482
                            mol_type = protein
                            organism = Macaca fascicularis
SEQUENCE: 67
MAPPPAGVKL GAFLAVTPNP GSAASGTEAA TATPSKVWGS SAGRIEPRGG GRGALPTSMG      60
QQGPSAQARA GRVVGPRSAQ GASPGLRVHK TLKFVVVGVL LQVVPGSAAT IKVHDQSIGT     120
QQWEHSPLGE LCPPGSHRSE HSGACNQCTE GVGYTSASNN LFSCLPCTAC KSDEEERSAC     180
TRTRNTACQC KPGTFRNDDS AEMCRKCSTG CPRGKVKVKD CTPWSDIECV HNESGNGHNP     240
KSCDKTHTCP PCPAPEAEGA PSVFLFPPKP KDTLMISRTP EVTCVVVDVS HEDPEVKFNW     300
YVDGVEVHNA KTKPREEQYN STYRVVSVLT VLHQDWLNGK EYKCKVSNKA LPAPIEKTIS     360
KAKGQPREPQ VYTLPPSREE MTKNQVSLTC LVKGFYPSDI AVEWESNGQP ENNYKTAPPV     420
LDSDGSFFLY SKLTVDKSRW QQGNVFSCSV MHEALHNHYT QKSLSLSPGK HHHHHHHEP     480
EA                                                                    482

SEQ ID NO: 68               moltype = AA  length = 468
FEATURE                     Location/Qualifiers
source                      1..468
                            mol_type = protein
                            organism = Homo sapiens
SEQUENCE: 68
MAPPPARVHL GAFLAVTPNP GSAASGTEAA AATPSKVWGS SAGRIEPRGG GRGALPTSMG      60
QHGPSARARA GRAPGPRPAR EASPRLRVHK TFKFVVVGVL LQVVPSSAAT IKLHDQSIGT     120
```

```
QQWEHSPLGE LCPPGSHRSE HPGACNRCTE GVGYTNASNN LFACLPCTAC KSDEEERSPC    180
TTTRNTACQC KPGTFRNDNS AEMCRKCSRG CPRGMVKVKD CTPWSDIECV HKESGNGHNI    240
WVILVVTLVV PLLLVAVLIV CCCIGSGCGG DPKCMDRVCF WRLGLLRGPG AEDNAHNEIL    300
SNADSLSTFV SEQQMESQEP ADLTGVTVQS PGEAQCLLGP AEAEGSQRRR LLVPANGADP    360
TETLMLFFDK FANIVPFDSW DQLMRQLDLT KNEIDVVRAG TAGPGDALYA MLMKWVNKTG    420
RNASIHTLLD ALERMEERHA REKIQDLLVD SGKFIYLEDG TGSAVSLE                 468

SEQ ID NO: 69           moltype = AA  length = 471
FEATURE                 Location/Qualifiers
source                  1..471
                        mol_type = protein
                        organism = Macaca fascicularis
SEQUENCE: 69
MAPPPAGVKL GAFLAVTPNP GSAASGTEAA TATPSKVWGS SAGRIEPRGG GRGALPTSMG     60
QQGPSAQARA GRVVGPRSAQ GASPGLRVHK TLKFVVVGVL LQVVPGSAAT IKVHDQSVGT    120
QQWEHSPLGE LCPPGSHRSE HSGACNQCTE GVGYTSASNN LFSCLPCTAC KSDEEERSAC    180
TRTRNTACQC KPGTFRNDDS AEMCRKCSTG CPRGKVKVKD CTPWSDIECV HNESGNGHNV    240
WAILIVIVVI LVVLLLLVAV LMFCRRIGSG CGGNPKCMHR VFLWCLGLLR GPGAEDNAHN    300
MILNHGDSLS TFISEQQMES QEPADLTGVT VQSPGEAQCL LGPAEPEGSQ RRRLLVPANG    360
ADPTETMMLF FDNFADIVPF NSWDQLMRQL GLTNNEIHMV RADTAGPGDA LYAMLMKWVN    420
KTGQDASIHT LLDALERIGE RHAKERIQDL LVDSGKFIYV EDGTGSAVSL E             471

SEQ ID NO: 70           moltype = AA  length = 329
FEATURE                 Location/Qualifiers
source                  1..329
                        mol_type = protein
                        organism = synthetic construct
SEQUENCE: 70
ASTKGPSVFP LAPSSKSTSG GTAALGCLVK DYFPEPVTVS WNSGALTSGV HTFPAVLQSS     60
GLYSLSSVVT VPSSSLGTQT YICNVNHKPS NTKVDKRVEP KSCDKTHTCP PCPAPEFERG    120
PSVFLFPPKP KDTLMISRTP EVTCVVVDVS HEDPEVKFNW YVDGVEVHNA KTKPREEQYN    180
STYRVVSVLT VLHQDWLNGK EYKCKVSNKA LPAPIEKTIS KAKGQPREPQ VYTLPPSREE    240
MTKNQVSLTC LVKGFYPSDI AVEWESNGQP ENNYKTTPPV LDSDGSFFLY SRLTVDKSRW    300
QQGNVFSCSV MHEALHNHYT QKSLSLSPG                                      329

SEQ ID NO: 71           moltype = AA  length = 329
FEATURE                 Location/Qualifiers
source                  1..329
                        mol_type = protein
                        organism = synthetic construct
SEQUENCE: 71
ASTKGPSVFP LAPSSKSTSG GTAALGCLVK DYFPEPVTVS WNSGALTSGV HTFPAVLQSS     60
GLYSLSSVVT VPSSSLGTQT YICNVNHKPS NTKVDKRVEP KSCDKTHTCP PCPAPEFEGG    120
PSVFLFPPKP KDTLMISRTP EVTCVVVAVS HEDPEVKFNW YVDGVEVHNA KTKPREEQYN    180
STYRVVSVLT VLHQDWLNGK EYKCKVSNKA LPAPIEKTIS KAKGQPREPQ VYTLPPSREE    240
MTKNQVSLTC LVKGFYPSDI AVEWESNGQP ENNYKTTPPV LDSDGSFLLY SKLTVDKSRW    300
QQGNVFSCSV MHEALHNHYT QKSLSLSPG                                      329

SEQ ID NO: 72           moltype = AA  length = 329
FEATURE                 Location/Qualifiers
source                  1..329
                        mol_type = protein
                        organism = synthetic construct
SEQUENCE: 72
ASTKGPSVFP LAPSSKSTSG GTAALGCLVK DYFPEPVTVS WNSGALTSGV HTFPAVLQSS     60
GLYSLSSVVT VPSSSLGTQT YICNVNHKPS NTKVDKRVEP KSCDKTHTCP PCPAPEFEGG    120
PSVFLFPPKP KDTLMISRTP EVTCVVVAVS HEDPEVKFNW YVDGVEVHNA KTKPREEQYN    180
STYRVVSVLT VLHQDWLNGK EYKCKVSNKA LPAPIEKTIS KAKGQPREPQ VYTLPPSREE    240
MTKNQVSLTC LVKGFYPSDI AVEWESNGQP ENNYKTTPPV LDSDGSFFLY SRLTVDKSRW    300
QQGNVFSCSV MHEALHNHYT QKSLSLSPG                                      329

SEQ ID NO: 73           moltype = AA  length = 456
FEATURE                 Location/Qualifiers
source                  1..456
                        mol_type = protein
                        organism = synthetic construct
SEQUENCE: 73
QVQLVQSGAE VKKPGASVKV SCQASGYRFS NFVIHWVRQA PGQRFEWMGW INPYNGNKEF     60
SAKFQDRVTF TADTSANTAY MELRSLRSAD TAVYYCARVG PYSWDDSPQD NYYMDVWGKG    120
TTVIVSSAST KGPSVFPLAP SSKSTSGGTA ALGCLVKDYF PEPVTVSWNS GALTSGVHTF    180
PAVLQSSGLY SLSSVVTVPS SSLGTQTYIC NVNHKPSNTK VDKRVEPKSC DKTHTCPPCP    240
APEFERGPSV FLFPPKPKDT LMISRTPEVT CVVVDVSHED PEVKFNWYVD GVEVHNAKTK    300
PREEQYNSTY RVVSVLTVLH QDWLNGKEYK CKVSNKALPA PIEKTISKAK GQPREPQVYT    360
LPPSREEMTK NQVSLTCLVK GFYPSDIAVE WESNGQPENN YKTTPPVLDS DGSFFLYSKL    420
TVDKSRWQQG NVFSCSVMHE ALHNHYTQKS LSLSPG                              456
```